(12) United States Patent
Hayashi et al.

(10) Patent No.: US 10,326,079 B2
(45) Date of Patent: Jun. 18, 2019

(54) ORGANIC ELECTROLUMINESCENT DEVICE

(71) Applicant: Hodogaya Chemical Co., Ltd., Tokyo (JP)

(72) Inventors: Shuichi Hayashi, Tokyo (JP); Shunji Mochizuki, Tokyo (JP); Takeshi Yamamoto, Tokyo (JP); Naoaki Kabasawa, Tokyo (JP)

(73) Assignee: Hodogaya Chemical Co., Ltd., Tokyo (JP)

( * ) Notice: Subject to any disclaimer, the term of this patent is extended or adjusted under 35 U.S.C. 154(b) by 0 days.

(21) Appl. No.: 15/569,569

(22) PCT Filed: Apr. 26, 2016

(86) PCT No.: PCT/JP2016/063081
§ 371 (c)(1),
(2) Date: Oct. 26, 2017

(87) PCT Pub. No.: WO2016/175211
PCT Pub. Date: Nov. 3, 2016

(65) Prior Publication Data
US 2018/0315928 A1 Nov. 1, 2018

(30) Foreign Application Priority Data

Apr. 27, 2015 (JP) .................. 2015-090281

(51) Int. Cl.
*H01L 51/00* (2006.01)
*H01L 51/50* (2006.01)
(Continued)

(52) U.S. Cl.
CPC ........ *H01L 51/0061* (2013.01); *C07C 211/54* (2013.01); *C09K 11/06* (2013.01);
(Continued)

(58) Field of Classification Search
None
See application file for complete search history.

(56) References Cited

U.S. PATENT DOCUMENTS 8,470,454 B2 6/2013 Kim et al.
8,652,654 B2 2/2014 Inoue et al.
(Continued)

FOREIGN PATENT DOCUMENTS

CN 102089288 A 6/2011
CN 103857671 A 6/2014
(Continued)

OTHER PUBLICATIONS

International Search Report dated Aug. 16, 2016, issued for PCT/JP2016/063081.
(Continued)

*Primary Examiner* — Su C Kim
*Assistant Examiner* — David S Wilbert
(74) *Attorney, Agent, or Firm* — Locke Lord LLP

(57) ABSTRACT

An organic electroluminescent device having low driving voltage, high luminous efficiency, and a long lifetime is provided by combining various materials for an organic electroluminescent device. In the organic electroluminescent device having at least an anode, a hole injection layer, a first hole transport layer, a second hole transport layer, a light emitting layer, an electron transport layer, and a cathode in this order, the hole injection layer includes an arylamine compound of the following general formula (1) and an electron acceptor.

[Chemical Formula 1]

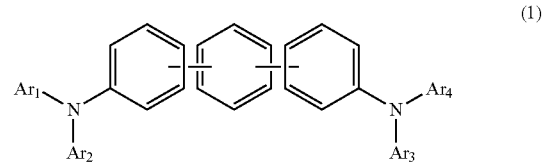

(1)

In the formula, $Ar_1$ to $Ar_4$ may be the same or different, and represent a substituted or unsubstituted aromatic hydrocar-
(Continued)

← 9 CATHODE
← 8 ELECTRON INJECTION LAYER
← 7 ELECTRON TRANSPORT LAYER
← 6 LIGHT EMITTING LAYER
← 5 SECOND HOLE TRANSPORT LAYER
← 4 FIRST HOLE TRANSPORT LAYER
← 3 HOLE INJECTION LAYER
← 2 TRANSPARENT ANODE
← 1 GLASS SUBSTRATE bon group, a substituted or unsubstituted aromatic heterocyclic group, or a substituted or unsubstituted condensed polycyclic aromatic group.

20 Claims, 1 Drawing Sheet

(51) Int. Cl.
*H01L 51/52* (2006.01)
*C07C 211/54* (2006.01)
*C09K 11/06* (2006.01)

(52) U.S. Cl.
CPC ........ *H01L 51/006* (2013.01); *H01L 51/0059* (2013.01); *H01L 51/0067* (2013.01); *H01L 51/0072* (2013.01); *H01L 51/50* (2013.01); *H01L 51/5024* (2013.01); *H01L 51/5064* (2013.01); *H01L 51/5092* (2013.01); *H01L 51/5096* (2013.01); *H01L 51/5206* (2013.01); *H01L 51/5221* (2013.01); *H01L 51/0052* (2013.01); *H01L 51/0085* (2013.01); *H01L 51/5056* (2013.01); *H01L 51/5072* (2013.01); *H01L 51/5088* (2013.01)

(56) References Cited

U.S. PATENT DOCUMENTS

| | | | |
|---|---|---|---|
| 8,865,323 B2 | 10/2014 | Inoue et al. | |
| 8,877,352 B2 | 11/2014 | Inoue et al. | |
| 8,940,414 B2 | 1/2015 | Inoue et al. | |
| 9,123,897 B2 | 9/2015 | Yokoyama et al. | |
| 9,318,705 B2 | 4/2016 | Bimstock et al. | |
| 2008/0203406 A1 | 8/2008 | He et al. | |
| 2009/0085474 A1* | 4/2009 | Shitagaki | H01L 51/5048 313/504 |
| 2011/0073852 A1* | 3/2011 | Yokoyama | C07D 471/04 257/40 |
| 2011/0156014 A1 | 6/2011 | Kim et al. | |
| 2011/0278555 A1* | 11/2011 | Inoue | C07D 209/82 257/40 |
| 2011/0279020 A1 | 11/2011 | Inoue et al. | |
| 2012/0138911 A1 | 6/2012 | Inoue et al. | |
| 2012/0138912 A1 | 6/2012 | Inoue et al. | |
| 2012/0223296 A1 | 9/2012 | Werner et al. | |
| 2013/0193414 A1 | 8/2013 | Werner et al. | |
| 2014/0332794 A1 | 11/2014 | Bimstock et al. | |
| 2014/0374721 A1 | 12/2014 | Yokoyama et al. | |
| 2015/0008423 A1 | 1/2015 | Inoue et al. | |
| 2015/0228912 A1 | 8/2015 | Inoue et al. | |
| 2016/0126464 A1 | 5/2016 | Yokoyama et al. | |
| 2017/0179398 A1 | 6/2017 | Yokoyama et al. | |
| 2018/0006235 A1 | 1/2018 | Yokoyama et al. | |

FOREIGN PATENT DOCUMENTS

| | | |
|---|---|---|
| CN | 107112429 A | 8/2017 |
| EP | 2423209 A1 | 2/2012 |
| EP | 2960958 A1 | 12/2015 |
| EP | 3244462 A1 | 11/2017 |
| JP | 2008-509565 A | 3/2008 |
| JP | 2014-040423 A | 3/2014 |
| JP | 2015-065457 A | 4/2015 |
| TW | 201342681 A | 10/2013 |
| WO | 2013/083712 A1 | 6/2013 |
| WO | 2014/129201 A1 | 8/2014 |
| WO | 2014/199567 A1 | 12/2014 |
| WO | 2016/006629 A1 | 1/2016 |

OTHER PUBLICATIONS

Supplementary European Search Report dated Nov. 20, 2018, issued for the corresponding European Patent Application No. 16786488.3.
Office Action dated Jan. 3, 2019, issued for the Corresponding Chinese Patent Application No. 201680024792.3 and Japanese tarnslation thereof.

* cited by examiner

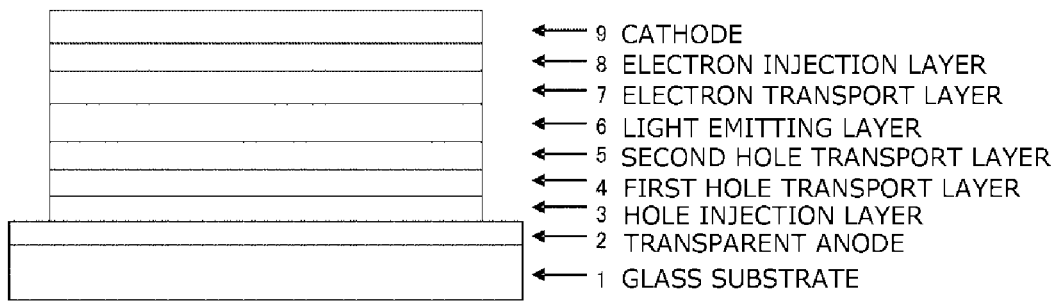

ORGANIC ELECTROLUMINESCENT DEVICE

TECHNICAL FIELD

The present invention relates to an organic electroluminescent device which is a preferred self-luminous device for various display devices. Specifically, this invention relates to organic electroluminescent devices (hereinafter referred to as organic EL devices) using specific arylamine compounds doped with an electron acceptor.

BACKGROUND ART

The organic EL device is a self-luminous device and has been actively studied for their brighter, superior visibility and the ability to display clearer images in comparison with liquid crystal devices.

In 1987, C. W. Tang and colleagues at Eastman Kodak developed a laminated structure device using materials assigned with different roles, realizing practical applications of an organic EL device with organic materials. These researchers laminated an electron-transporting phosphor and a hole-transporting organic substance, and injected both charges into a phosphor layer to cause emission in order to obtain a high luminance of 1,000 cd/m$^2$ or more at a voltage of 10 V or less (refer to PTLs 1 and 2, for example).

To date, various improvements have been made for practical applications of the organic EL device. Various roles of the laminated structure are further subdivided to provide an electroluminescence device that includes an anode, a hole injection layer, a hole transport layer, a light emitting layer, an electron transport layer, an electron injection layer, and a cathode successively formed on a substrate, and high efficiency and durability have been achieved by the electroluminescence device (refer to NPL 1, for example).

Further, there have been attempts to use triplet excitons for further improvements of luminous efficiency, and the use of a phosphorescence-emitting compound has been examined (refer to NPL 2, for example).

Devices that use light emission caused by thermally activated delayed fluorescence (TADF) have also been developed. In 2011, Adachi et al. at Kyushu University, National University Corporation realized 5.3% external quantum efficiency with a device using a thermally activated delayed fluorescent material (refer to NPL 3, for example).

The light emitting layer can be also fabricated by doping a charge-transporting compound generally called a host material, with a fluorescent compound, a phosphorescence-emitting compound, or a delayed fluorescent-emitting material. As described in the NPL, the selection of organic materials in an organic EL device greatly influences various device characteristics such as efficiency and durability (refer to NPL 2, for example).

In an organic EL device, charges injected from both electrodes recombine in a light emitting layer to cause emission. What is important here is how efficiently the hole and electron charges are transferred to the light emitting layer in order to form a device having excellent carrier balance. The probability of hole-electron recombination can be improved by improving hole injectability and electron blocking performance of blocking injected electrons from the cathode, and high luminous efficiency can be obtained by confining excitons generated in the light emitting layer. The role of a hole transport material is therefore important, and there is a need for a hole transport material that has high hole injectability, high hole mobility, high electron blocking performance, and high durability to electrons.

Heat resistance and amorphousness of the materials are also important with respect to the lifetime of the device. The materials with low heat resistance cause thermal decomposition even at a low temperature by heat generated during the drive of the device, which leads to the deterioration of the materials. The materials with low amorphousness cause crystallization of a thin film even in a short time and lead to the deterioration of the device.

The materials in use are therefore required to have characteristics of high heat resistance and satisfactory amorphousness.

N,N'-diphenyl-N,N'-di(α-naphthyl)benzidine (NPD) and various aromatic amine derivatives are known as the hole transport materials used for the organic EL device (refer to PTLs 1 and 2, for example). Although NPD has desirable hole transportability, its glass transition point (Tg), which is an index of heat resistance, is as low as 96° C., which causes the degradation of device characteristics by crystallization under a high-temperature condition (refer to NPL 4, for example). The aromatic amine derivatives described in the PTLs include a compound known to have an excellent hole mobility of 10$^{-3}$ cm$^2$/Vs or higher (refer to PTLs 1 and 2, for example). However, since the compound is insufficient in terms of electron blocking performance, some of the electrons pass through the light emitting layer, and improvements in luminous efficiency cannot be expected. For such a reason, a material with higher electron blocking performance, a more stable thin-film state and higher heat resistance is needed for higher efficiency. Although an aromatic amine derivative having high durability is reported (refer to PTL 3, for example), the derivative is used as a charge transporting material used in an electrophotographic photoconductor, and there is no example of using the derivative in the organic EL device.

Arylamine compounds having a substituted carbazole structure are proposed as compounds improved in the characteristics such as heat resistance and hole injectability (refer to PTLs 4 and 5, for example). Further, it is proposed that hole injectability can be improved by p-doping materials such as trisbromophenylamine hexachloroantimony, radialene derivatives, and F4-TCNQ into a material commonly used for the hole injection layer or the hole transport layer (refer to PTL 6 and NPL 5). However, while the devices using these compounds for the hole injection layer or the hole transport layer have been improved in lower driving voltage, heat resistance, luminous efficiency and the like, the improvements are still insufficient. Further lower driving voltage and higher luminous efficiency are therefore needed.

In order to improve characteristics of the organic EL device and to improve the yield of the device production, it has been desired to develop a device having high luminous efficiency, low driving voltage and a long lifetime by using in combination the materials that excel in hole and electron injection/transport performances, stability as a thin film and durability, permitting holes and electrons to be highly efficiently recombined together.

Further, in order to improve characteristics of the organic EL device, it has been desired to develop a device that maintains carrier balance and has high efficiency, low driving voltage and a long lifetime by using in combination the materials that excel in hole and electron injection/transport performances, stability as a thin film and durability.

CITATION LIST

Patent Literature

PTL 1: JP-A-8-048656
PTL 2: Japanese Patent No. 3194657
PTL 3: Japanese Patent No. 4943840
PTL 4: JP-A-2006-151979
PTL 5: WO2008/62636
PTL 6: WO2014/009310
PTL 7: WO2005/115970
PTL 8: JP-A-7-126615
PTL 9: JP-A-2005-108804
PTL 10: WO2011/059000
PTL 11: WO2003/060956
PTL 12: KR-A-2013-060157
PTL 13: WO2013/054764

Non Patent Literature

NPL 1: The Japan Society of Applied Physics, 9th Lecture Preprints, pp. 55 to 61 (2001)
NPL 2: The Japan Society of Applied Physics, 9th Lecture Preprints, pp. 23 to 31 (2001)
NPL 3: Appl. Phys. Let., 98, 083302 (2011)
NPL 4: Organic EL Symposium, the 3rd Regular presentation Preprints, pp. 13 to 14 (2006)
NPL 5: Appl. Phys. Let., 89, 253506 (2006)

SUMMARY OF INVENTION

Technical Problem

An object of the present invention is to provide an organic EL device having high efficiency, low driving voltage and a long lifetime, by combining various materials for an organic EL device, which are excellent, as materials for an organic EL device having high efficiency and high durability, in hole and electron injection/transport performances, electron blocking ability, stability in a thin-film state and durability, so as to allow the respective materials to effectively reveal their characteristics.

Physical properties of the organic EL device to be provided by the present invention include (1) low turn on voltage, (2) low actual driving voltage, (3) high luminous efficiency and high power efficiency, and (4) a long lifetime.

Solution to Problem

For achieving the object, the present inventors, who have focused attention on the fact that an arylamine material doped with an electron acceptor is excellent in hole injection and transport performances, stability and durability of a thin film thereof, have produced various organic EL devices by selecting a particular arylamine compound (having a particular structure), using the particular arylamine compound (having the particular structure) doped with an electron acceptor as a material for a hole injection layer so as to efficiently perform injection and transport of holes from an anode, and combining a particular arylamine compound (having a particular structure) that is not doped with an electron acceptor as a material for a hole transport layer, and earnestly evaluated the characteristics of the devices. The present inventors have also produced various organic EL devices by using a hole transport layer constituted by two layers including a first hole transport layer and a second hole transport layer, and selecting two kinds of particular arylamine compounds for these layers respectively to provide a combination of the material for the first hole transport layer and the material for the second hole transport layer capable of performing efficiently injection and transport of holes to a light emitting layer, and earnestly evaluated the characteristics of the devices. Furthermore, the present inventors have produced various organic EL devices by using a compound having an anthracene ring structure, a compound having a pyrimidine ring structure, or a compound having a benzotriazole ring structure, all of which having a particular structure, as a material for an electron transport layer, and combining the compound to provide a good carrier balance, and earnestly evaluated the characteristics of the devices. As a result, the present invention has been completed.

Specifically, according to the present invention, the following organic EL devices are provided.

1) An organic EL device having at least an anode, a hole injection layer, a first hole transport layer, a second hole transport layer, a light emitting layer, an electron transport layer, and a cathode in this order, wherein the hole injection layer includes an arylamine compound of the following general formula (1) and an electron acceptor.

[Chemical Formula 1]

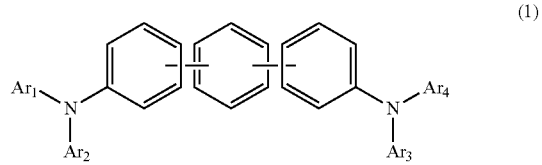

(1)

In the formula, $Ar_1$ to $Ar_4$ may be the same or different, and represent a substituted or unsubstituted aromatic hydrocarbon group, a substituted or unsubstituted aromatic heterocyclic group, or a substituted or unsubstituted condensed polycyclic aromatic group.)

2) The organic EL device of 1), wherein the electron acceptor is an electron acceptor selected from trisbromophenylaminehexachloroantimony, tetracyanoquinodimethane (TCNQ), 2,3,5,6-tetrafluoro-tetracyano-1,4-benzoquinodimethane (F4TCNQ), and a radialene derivative.

3) The organic EL device of 1), wherein the electron acceptor is a radialene derivative of the following general formula (2).

[Chemical Formula 2]

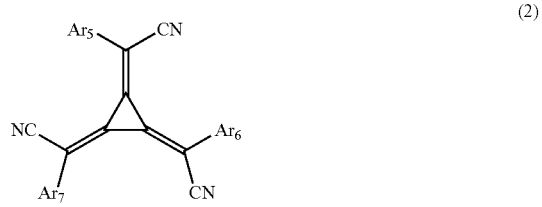

(2)

In the formula, $Ar_5$ to $Ar_7$ may be the same or different, and represent an aromatic hydrocarbon group, an aromatic heterocyclic group, or a condensed polycyclic aromatic group, having an electron acceptor group as a substituent.

4) The organic EL device of any one of 1) to 3), wherein the first hole transport layer or the second hole transport layer comprises only a hole transporting arylamine compound.

5) The organic EL device of any one of 1) to 3), wherein the first hole transport layer and the second hole transport layer comprise only a hole transporting arylamine compound.

6) The organic EL device of 4) or 5), wherein the first hole transport layer contains an arylamine compound having a structure in which two to six triphenylamine structures are joined within a molecule via a single bond or a divalent group that does not contain a heteroatom.

7) The organic EL device of 6), wherein the arylamine compound having a structure in which two to six triphenylamine structures are joined within a molecule via a single bond or a divalent group that does not contain a heteroatom is an arylamine compound of the following general formula (3).

[Chemical Formula 3]

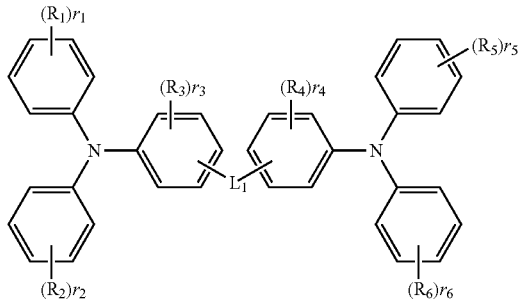

(3)

In the formula, $R_1$ to $R_6$ represent a deuterium atom, a fluorine atom, a chlorine atom, cyano, nitro, linear or branched alkyl of 1 to 6 carbon atoms that may have a substituent, cycloalkyl of 5 to 10 carbon atoms that may have a substituent, linear or branched alkenyl of 2 to 6 carbon atoms that may have a substituent, linear or branched alkyloxy of 1 to 6 carbon atoms that may have a substituent, cycloalkyloxy of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, or substituted or unsubstituted aryloxy; $r_1$ to $r_6$ may be the same or different, $r_1$, $r_2$, $r_5$, and $r_6$ representing an integer of 0 to 5, and $r_3$ and $r_4$ representing an integer of 0 to 4, where when $r_1$, $r_2$, $r_5$, and $r_6$ are an integer of 2 to 5, or when $r_3$ and $r_4$ are an integer of 2 to 4, $R_1$ to $R_6$, a plurality of which bind to the same benzene ring, may be the same or different and may bind to each other via a single bond, substituted or unsubstituted methylene, an oxygen atom, or a sulfur atom to form a ring; and $L_1$ represents a divalent linking group or a single bond.

8) The organic EL device of 6), wherein the arylamine compound having a structure in which two to six triphenylamine structures are joined within a molecule via a single bond or a divalent group that does not contain a heteroatom is an arylamine compound of the following general formula (4).

[Chemical Formula 4]

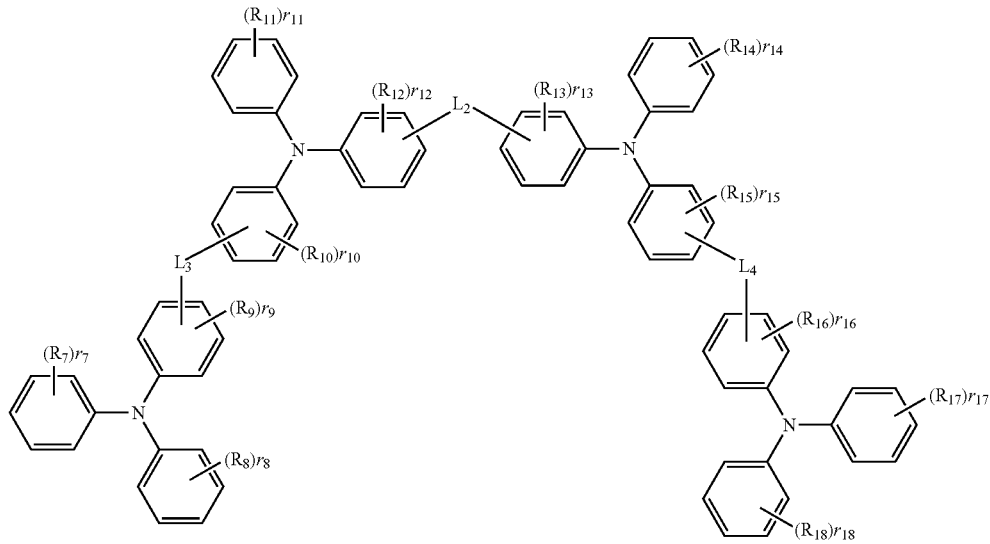

(4)

In the formula, $R_7$ to $R_{18}$ represent a deuterium atom, a fluorine atom, a chlorine atom, cyano, nitro, linear or branched alkyl of 1 to 6 carbon atoms that may have a substituent, cycloalkyl of 5 to 10 carbon atoms that may have a substituent, linear or branched alkenyl of 2 to 6 carbon atoms that may have a substituent, linear or branched alkyloxy of 1 to 6 carbon atoms that may have a substituent, cycloalkyloxy of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, or substituted or unsubstituted aryloxy; $r_7$ to $r_{18}$ may be the same or different, $r_7$, $r_8$, $r_{11}$, $r_{14}$, $r_{17}$, and $r_{18}$ representing an integer of 0 to 5, and $r_9$, $r_{10}$, $r_{12}$, $r_{13}$, $r_{15}$, and $r_{16}$ representing an integer of 0 to 4. where when $r_7$, $r_8$, $r_{11}$, $r_{14}$, $r_{17}$, and $r_{18}$ are an integer of 2 to 5, or when $r_9$, $r_{10}$, $r_{12}$, $r_{13}$, $r_{15}$, and $r_{16}$ are an integer of 2 to 4, $R_7$ to $R_{18}$, a plurality of which bind to the same benzene ring, may be the same or different and may bind to each other via a single bond, substituted or unsubstituted methylene, an oxygen atom, or a sulfur atom to form a ring; and $L_2$, $L_3$, and $L_4$ may be the same or different, and represent a divalent linking group or a single bond.

9) The organic EL device of 4) or 5), wherein the second hole transport layer comprises an arylamine compound of the general formula (5).

[Chemical Formula 5]

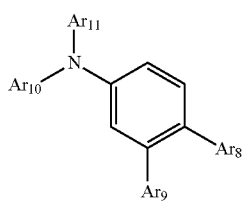

(5)

In the formula, $Ar_8$ to $Ar_{11}$ may be the same or different, and represent a substituted or unsubstituted aromatic hydrocarbon group, a substituted or unsubstituted aromatic heterocyclic group, or a substituted or unsubstituted condensed polycyclic aromatic group.

10) The organic EL device of any one of 1) to 9), wherein the electron transport layer comprises a compound having a LUMO level of 2.9 to 3.4 eV.

11) The organic EL device of any one of 1) to 9), wherein the electron transport layer comprises a compound having an anthracene ring structure of the following general formula (6).

[Chemical Formula 6]

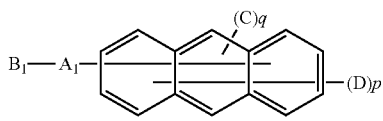

(6)

In the formula, wherein $A_1$ represents a divalent group of a substituted or unsubstituted aromatic hydrocarbon, a divalent group of a substituted or unsubstituted aromatic heterocyclic ring, a divalent group of a substituted or unsubstituted condensed polycyclic aromatic, or a single bond; $B_1$ represents a substituted or unsubstituted aromatic heterocyclic group; C represents a substituted or unsubstituted aromatic hydrocarbon group, a substituted or unsubstituted aromatic heterocyclic group, or a substituted or unsubstituted condensed polycyclic aromatic group; D may be the same or different, and represents a hydrogen atom, a deuterium atom, a fluorine atom, a chlorine atom, a cyano group, a trifluoromethyl group, a linear or branched alkyl group of 1 to 6 carbon atoms, a substituted or unsubstituted aromatic hydrocarbon group, a substituted or unsubstituted aromatic heterocyclic group, or a substituted or unsubstituted condensed polycyclic aromatic group; and while p and q maintain a relationship that the sum of p and q is 9, p represents 7 or 8, and q represents 1 or 2.

12) The organic EL device of any one of 1) to 9), wherein the electron transport layer comprises a compound having a pyrimidine ring structure of the following general formula (7).

[Chemical Formula 7]

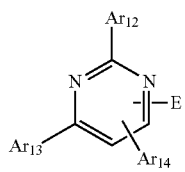

(7)

In the formula, $Ar_{12}$ represents a substituted or unsubstituted aromatic hydrocarbon group or a substituted or unsubstituted condensed polycyclic aromatic group; $Ar_{13}$ and $Ar_{14}$ may be the same or different, and represent a hydrogen atom, a substituted or unsubstituted aromatic hydrocarbon group, or a substituted or unsubstituted condensed polycyclic aromatic group; and E represents a monovalent group of the following structural formula (8), provided that $Ar_{13}$ and $Ar_{14}$ are not simultaneously a hydrogen atom.

[Chemical Formula 8]

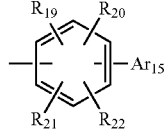

(8)

In the formula, $Ar_{15}$ represents a substituted or unsubstituted aromatic heterocyclic group; $R_{19}$ to $R_{22}$ may be the same or different, and represent a hydrogen atom, a deuterium atom, a fluorine atom, a chlorine atom, a cyano group, a trifluoromethyl group, a linear or branched alkyl group of 1 to 6 carbon atoms, a substituted or unsubstituted aromatic hydrocarbon group, a substituted or unsubstituted aromatic heterocyclic group, or a substituted or unsubstituted condensed polycyclic aromatic group.

13) The organic EL device of any one of 1) to 9), wherein the electron transport layer comprises a compound having a benzotriazole ring structure of the following general formula (9).

[Chemical Formula 9]

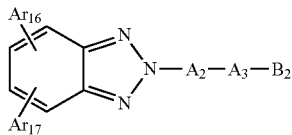

(9)

In the formula, $Ar_{16}$ represents a substituted or unsubstituted aromatic hydrocarbon group, a substituted or unsubstituted aromatic heterocyclic group, or a substituted or unsubstituted condensed polycyclic aromatic group; $Ar_{17}$ represents a hydrogen atom, a deuterium atom, a substituted or unsubstituted aromatic hydrocarbon group, a substituted or unsubstituted aromatic heterocyclic group, or a substituted or unsubstituted condensed polycyclic aromatic group; $A_2$ represents a divalent group of a substituted or unsubstituted aromatic hydrocarbon, a divalent group of a substituted or unsubstituted aromatic heterocyclic ring, a divalent group of a substituted or unsubstituted condensed polycyclic aromatic, or a single bond; $A_3$ represents a divalent group of a substituted or unsubstituted condensed polycyclic aromatic or a single bond; and $B_2$ represents a substituted or unsubstituted aromatic heterocyclic group.

14) The organic EL device of any one of 1) to 13), wherein the light emitting layer contains a phosphorescent light-emitting material.

15) The organic EL device of 14), wherein the phosphorescent light-emitting material is a metal complex that contains iridium or platinum.

16) The organic EL device of 14) or 15), wherein the phosphorescent light-emitting material is a red light emitting dopant.

17) The organic EL device of any one of 1) to 16), wherein the light emitting layer contains a quinazoline derivative.

18) The organic EL device of 17), wherein the light emitting layer contains a host material, which is a quinazoline derivative.

Specific examples of the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by $Ar_1$ to $Ar_4$ in the general formula (1) include a phenyl group, a biphenylyl group, a terphenylyl group, a naphthyl group, an anthracenyl group, a phenanthrenyl group, a fluorenyl group, an indenyl group, a pyrenyl group, a perylenyl group, a fluoranthenyl group, a triphenylenyl group, a pyridyl group, a pyrimidinyl group, a triazinyl group, a furyl group, a pyrrolyl group, a thienyl group, a quinolyl group, an isoquinolyl group, a benzofuranyl group, a benzothienyl group, an indolyl group, a carbazolyl group, a benzoxazolyl group, a benzothiazolyl group, a quinoxalinyl group, a benzoimidazolyl group, a pyrazolyl group, a dibenzofuranyl group, a dibenzothienyl group, a naphthyridinyl group, a phenanthrolinyl group, an acridinyl group, and a carbolinyl group.

Specific examples of the "substituent" in the "substituted aromatic hydrocarbon group", the "substituted aromatic heterocyclic group", or the "substituted condensed polycyclic aromatic group" represented by $Ar_1$ to $Ar_4$ in the general formula (1) include a deuterium atom, cyano, nitro; halogen atoms, such as a fluorine atom, a chlorine atom, a bromine atom, and an iodine atom; linear or branched alkyls of 1 to 6 carbon atoms, such as methyl, ethyl, n-propyl, isopropyl, n-butyl, isobutyl, tert-butyl, n-pentyl, isopentyl, neopentyl, and n-hexyl; linear or branched alkyloxys of 1 to 6 carbon atoms, such as methyloxy, ethyloxy, and propyloxy; alkenyls, such as vinyl and allyl; aryloxys, such as phenyloxy and tolyloxy; arylalkyloxys, such as benzyloxy and phenethyloxy; an aromatic hydrocarbon group or a condensed polycyclic aromatic group, such as phenyl, biphenylyl, terphenylyl, naphthyl, anthracenyl, phenanthrenyl, fluorenyl, indenyl, pyrenyl, perylenyl, fluoranthenyl, and triphenylenyl; an aromatic heterocyclic group, such as pyridyl, pyrimidinyl, triazinyl, thienyl, furyl, pyrrolyl, quinolyl, isoquinolyl, benzofuranyl, benzothienyl, indolyl, carbazolyl, benzoxazolyl, benzothiazolyl, quinoxalinyl, benzimidazolyl, pyrazolyl, dibenzofuranyl, dibenzothienyl, and carbolinyl; arylvinyls, such as styryl and naphthylvinyl; acyls, such as acetyl and benzoyl; and silyls, such as trimethylsilyl and triphenylsilyl. These substituents may be further substituted with the exemplified substituents above. These substituents may bind to each other via a single bond, substituted or unsubstituted methylene, an oxygen atom, or a sulfur atom to form a ring.

Examples of the "electron acceptor group" in the "aromatic hydrocarbon group, the aromatic heterocyclic group, or the condensed polycyclic aromatic group, having an electron acceptor group as a substitutent" represented by $Ar_5$ to $Ar_7$ in the general formula (2) include a fluorine atom, a chlorine atom, a bromine atom, a cyano group, a trifluoromethyl group, and a nitro group.

Examples of the "aromatic hydrocarbon group", the "aromatic heterocyclic group", or the "condensed polycyclic aromatic group" in the "aromatic hydrocarbon group, the aromatic heterocyclic group, or the condensed polycyclic aromatic group, having an electron acceptor group as a substitutent" represented by $Ar_5$ to $Ar_7$ in the general formula (2) include the same groups exemplified as the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by $Ar_1$ to $Ar_4$ in the above general formula (1).

Further, these groups may have a substituent other than the electron acceptor group, and specific examples of the substituent include a deuterium atom; aromatic hydrocarbon groups or condensed polycyclic aromatic groups such as a phenyl group, a biphenylyl group, a terphenylyl group, a naphthyl group, an anthracenyl group, a phenanthrenyl group, a fluorenyl group, an indenyl group, a pyrenyl group, a perylenyl group, a fluoranthenyl group, and a triphenylenyl group; and aromatic heterocyclic groups such as a pyridyl group, a pyrimidinyl group, a triazinyl group, a thienyl group, a furyl group, a pyrrolyl group, a quinolyl group, an isoquinolyl group, a benzofuranyl group, a benzothienyl group, an indolyl group, a carbazolyl group, a benzoxazolyl group, a benzothiazolyl group, a quinoxalinyl group, a benzoimidazolyl group, a pyrazolyl group, a dibenzofuranyl group, a dibenzothienyl group, and a carbolinyl group, and these substituents may be further substituted with a substituent exemplified above or an electron acceptor group. Then, these substituents may bind to each other via a single bond, a substituted or unsubstituted methylene group, an oxygen atom, or a sulfur atom to form a ring.

Specific examples of the "linear or branched alkyl of 1 to 6 carbon atoms", the "cycloalkyl of 5 to 10 carbon atoms", or the "linear or branched alkenyl of 2 to 6 carbon atoms" in the "linear or branched alkyl of 1 to 6 carbon atoms that may have a substituent", the "cycloalkyl of 5 to carbon atoms that may have a substituent", or the "linear or branched alkenyl of 2 to 6 carbon atoms that may have a substituent" represented by $R_1$ to $R_6$ in the general formula (3) include methyl, ethyl, n-propyl, isopropyl, n-butyl, isobutyl, tert-butyl, n-pentyl, isopentyl, neopentyl, n-hexyl, cyclopentyl, cyclohexyl, 1-adamantyl, 2-adamantyl, vinyl, allyl, isopropenyl, and 2-butenyl. These groups may bind to each other via a single bond, substituted or unsubstituted methylene, an oxygen atom, or a sulfur atom to form a ring.

Specific examples of the "substituent" in the "linear or branched alkyl of 1 to 6 carbon atoms that has a substituent", the "cycloalkyl of 5 to 10 carbon atoms that has a substituent", or the "linear or branched alkenyl of 2 to 6 carbon atoms that has a substituent" represented by $R_1$ to $R_6$ in the general formula (3) include a deuterium atom, cyano, nitro; halogen atoms, such as a fluorine atom, a chlorine atom, a bromine atom, and an iodine atom; linear or branched alkyloxys of 1 to 6 carbon atoms, such as methyloxy, ethyloxy, and propyloxy; alkenyls, such as vinyl and allyl; aryloxys, such as phenyloxy and tolyloxy; arylalkyloxys, such as benzyloxy and phenethyloxy; an aromatic hydrocarbon group or a condensed polycyclic aromatic group, such as phenyl, biphenylyl, terphenylyl, naphthyl, anthracenyl, phenanthrenyl, fluorenyl, indenyl, pyrenyl, perylenyl, fluoranthenyl, and triphenylenyl; and an aromatic heterocyclic group, such as pyridyl, pyrimidinyl, triazinyl, thienyl, furyl, pyrrolyl, quinolyl, isoquinolyl, benzofuranyl, benzothienyl, indolyl, carbazolyl, benzoxazolyl, benzothiazolyl, quinoxalinyl, benzimidazolyl, pyrazolyl, dibenzofuranyl, dibenzothienyl, and carbolinyl. These substituents may be further substituted with the exemplified substituents above. These substituents may bind to each other via a single bond, substituted or unsubstituted methylene, an oxygen atom, or a sulfur atom to form a ring.

Specific examples of the "linear or branched alkyloxy of 1 to 6 carbon atoms" or the "cycloalkyloxy of 5 to 10 carbon atoms" in the "linear or branched alkyloxy of 1 to 6 carbon atoms that may have a substituent" or the "cycloalkyloxy of 5 to 10 carbon atoms that may have a substituent" represented by $R_1$ to $R_6$ in the general formula (3) include methyloxy, ethyloxy, n-propyloxy, isopropyloxy, n-butyloxy, tert-butyloxy, n-pentyloxy, n-hexyloxy, cyclopentyloxy, cyclohexyloxy, cycloheptyloxy, cyclooctyloxy, 1-adamantyloxy, and 2-adamantyloxy. These groups may bind to each other via a single bond, substituted or unsubstituted methylene, an oxygen atom, or a sulfur atom to form a ring.

These groups may have a substituent. Examples of the substituent include the same groups exemplified as the "substituent" in the "linear or branched alkyl of 1 to 6 carbon atoms that has a substituent", the "cycloalkyl of 5 to 10 carbon atoms that has a substituent", or the "linear or branched alkenyl of 2 to 6 carbon atoms that has a substituent" represented by $R_1$ to $R_6$ in the general formula (3), and possible embodiments may also be the same embodiments as the exemplified embodiments.

Examples of the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by $R_1$ to $R_6$ in the general formula (3) include the same groups exemplified as the groups for the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by $Ar_1$ to $Ar_4$ in the general formula (1). These groups may bind to each other via a single bond, substituted or unsubstituted methylene, an oxygen atom, or a sulfur atom to form a ring.

These groups may have a substituent. Examples of the substituent include the same groups exemplified as the "substituent" in the "substituted aromatic hydrocarbon group", the "substituted aromatic heterocyclic group", or the "substituted condensed polycyclic aromatic group" represented by $Ar_1$ to $Ar_4$ in the general formula (1), and possible embodiments may also be the same embodiments as the exemplified embodiments.

Specific examples of the "aryloxy group" in the "substituted or unsubstituted aryloxy group" represented by $R_1$ to $R_6$ in the general formula (3) include phenyloxy, biphenylyloxy, terphenylyloxy, naphthyloxy, anthracenyloxy, phenanthrenyloxy, fluorenyloxy, indenyloxy, pyrenyloxy, and perylenyloxy. These groups may bind to each other via a single bond, substituted or unsubstituted methylene, an oxygen atom, or a sulfur atom to form a ring.

These groups may have a substituent. Examples of the substituent include the same groups exemplified as the "substituent" in the "substituted aromatic hydrocarbon group", the "substituted aromatic heterocyclic group", or the "substituted condensed polycyclic aromatic group" represented by $Ar_1$ to $Ar_4$ in the general formula (1), and possible embodiments may also be the same embodiments as the exemplified embodiments.

In the general formula (3), $r_1$ to $r_6$ may be the same or different, $r_1$, $r_2$, $r_5$, and $r_6$ representing an integer of 0 to 5, and $r_3$ and $r_4$ representing an integer of 0 to 4. When $r_1$, $r_2$, $r_5$, and $r_6$ are an integer of 2 to 5, or when $r_3$ and $r_4$ are an integer of 2 to 4, $R_1$ to $R_6$, a plurality of which bind to the same benzene ring, may be the same or different and may bind to each other via a single bond, substituted or unsubstituted methylene, an oxygen atom, or a sulfur atom to form a ring.

Examples of the "divalent linking group" represented by $L_1$ in the general formula (3) include "linear or branched alkylenes of 1 to 6 carbon atoms", such as methylene, ethylene, n-propylylene, isopropylylene, n-butylylene, isobutylylene, tert-butylylene, n-pentylylene, isopentylylene, neopentylylene, and n-hexylylene; "cycloalkylenes of 5 to 10 carbon atoms", such as cyclopentylylene, cyclohexylylene, and adamantylylene; "linear or branched alkenylenes of 2 to 6 carbon atoms", such as vinylene, arylene, isopropenylene, and butenylene; "divalent groups of aromatic hydrocarbons" that result from the removal of two hydrogen atoms from aromatic hydrocarbons, such as benzene, biphenyl, terphenyl, and tetrakisphenyl; and "divalent groups of condensed polycyclic aromatics" that result from the removal of two hydrogen atoms from condensed polycyclic aromatics, such as naphthalene, anthracene, acenaphthalene, fluorene, phenanthrene, indane, pyrene, and triphenylene.

These divalent groups may have a substituent. Examples of the substituent of the "linear or branched alkylene of 1 to 6 carbon atoms", the "cycloalkylene of 5 to 10 carbon atoms", or the "linear or branched alkenylene of 2 to 6 carbon atoms" include the same groups exemplified as the "substituent" in the "linear or branched alkyl of 1 to 6 carbon atoms that has a substituent", the "cycloalkyl of 5 to 10 carbon atoms that has a substituent", or the "linear or branched alkenyl of 2 to 6 carbon atoms that has a substituent" represented by $R_1$ to $R_6$ in the general formula (3), and examples of the substituent in the "divalent group of aromatic hydrocarbons" or the "divalent group of condensed polycyclic aromatics" include the same groups exemplified as the "substituent" in the "substituted aromatic hydrocarbon group", the "substituted aromatic heterocyclic group", or the "substituted condensed polycyclic aromatic group" represented by $Ar_1$ to $Ar_4$ in the general formula (1), and possible embodiments may also be the same embodiments as the exemplified embodiments.

Examples of the "linear or branched alkyl of 1 to 6 carbon atoms", the "cycloalkyl of 5 to 10 carbon atoms", or the "linear or branched alkenyl of 2 to 6 carbon atoms" in the "linear or branched alkyl of 1 to 6 carbon atoms that may have a substituent", the "cycloalkyl of 5 to 10 carbon atoms that may have a substituent", or the "linear or branched alkenyl of 2 to 6 carbon atoms that may have a substituent" represented by $R_7$ to $R_{18}$ in the general formula (4) include the same groups exemplified as the groups for the "linear or branched alkyl of 1 to 6 carbon atoms", the "cycloalkyl of 5 to 10 carbon atoms", or the "linear or branched alkenyl of 2 to 6 carbon atoms" in the "linear or branched alkyl of 1 to 6 carbon atoms that may have a substituent", the "cycloalkyl of 5 to 10 carbon atoms that may have a substituent", or the "linear or branched alkenyl of 2 to 6 carbon atoms that may have a substituent" represented by $R_1$ to $R_6$ in the general formula (3), and possible embodiments may also be the same embodiments as the exemplified embodiments.

Examples of the "linear or branched alkyloxy of 1 to 6 carbon atoms" or the "cycloalkyloxy of 5 to 10 carbon atoms" in the "linear or branched alkyloxy of 1 to 6 carbon atoms that may have a substituent" or the "cycloalkyloxy of to 10 carbon atoms that may have a substituent" represented by $R_7$ to $R_{18}$ in the general formula (4) include the same groups exemplified as the groups for the "linear or branched alkyloxy of 1 to 6 carbon atoms" or the "cycloalkyloxy of 5 to 10 carbon atoms" in the "linear or branched alkyloxy of 1 to 6 carbon atoms that may have a substituent" or the "cycloalkyloxy of 5 to 10 carbon atoms that may have a substituent" represented by $R_1$ to $R_6$ in the general formula (3), and possible embodiments may also be the same embodiments as the exemplified embodiments.

Examples of the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by $R_7$ to $R_{18}$ in the general formula (4) include the same groups exemplified as the groups for the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by $Ar_1$ to $Ar_4$ in the general formula (1). These groups may bind to each other via a single bond, substituted or unsubstituted methylene, an oxygen atom, or a sulfur atom to form a ring.

These groups may have a substituent, and examples of the substituent include the same substituents exemplified as the "substituent" in the "substituted aromatic hydrocarbon group", the "substituted aromatic heterocyclic group", or the "substituted condensed polycyclic aromatic group" represented by $Ar_1$ to $Ar_4$ in the general formula (1), and possible embodiments may also be the same embodiments as the exemplified embodiments.

Examples of the "aryloxy" in the "substituted or unsubstituted aryloxy" represented by $R_7$ to $R_{18}$ in the general formula (4) include the same groups exemplified as the groups for the "aryloxy" in the "substituted or unsubstituted aryloxy" represented by $R_1$ to $R_6$ in the general formula (3), and possible embodiments may also be the same embodiments as the exemplified embodiments.

In the general formula (4), $r_7$ to $r_{18}$ may be the same or different, $r_7$, $r_8$, $r_{11}$, $r_{14}$, $r_{17}$, and $r_{18}$ representing an integer of 0 to 5, and $r_9$, $r_{10}$, $r_{12}$, $r_{13}$, $r_{15}$ and $r_{16}$ representing an integer of 0 to 4. When $r_7$, $r_8$, $r_{11}$, $r_{14}$, $r_{17}$, and $r_{18}$ are each an integer of 2 to 5, or $r_9$, $r_{10}$, $r_{12}$, $r_{13}$, $r_{15}$ and $r_{16}$ are each an integer of 2 to 4, $R_7$ to $R_{18}$, a plurality of which bind to the same benzene ring, may be the same or different and may bind to each other via a single bond, substituted or unsubstituted methylene, an oxygen atom, or a sulfur atom to form a ring.

Examples of the "divalent linking group" represented by $L_2$, $L_3$, and $L_4$ in the general formula (4) include the same groups exemplified as the groups for the "divalent linking group" represented by $L_1$ in the general formula (3), and possible embodiments may also be the same embodiments as the exemplified embodiments.

Examples of the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by $Ar_8$ to $Ar_{17}$ in the general formula (5) include the same groups exemplified as the groups for the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by $Ar_1$ to $Ar_4$ in the general formula (1). These groups may bind to each other via a single bond, substituted or unsubstituted methylene, an oxygen atom, or a sulfur atom to form a ring.

These groups may have a substituent. Examples of the substituent include the same groups exemplified as the "substituent" in the "substituted aromatic hydrocarbon group", the "substituted aromatic heterocyclic group", or the "substituted condensed polycyclic aromatic group" represented by $Ar_1$ to $Ar_4$ in the general formula (1), and possible embodiments may also be the same embodiments as the exemplified embodiments.

Specific examples of the "aromatic hydrocarbon", the "aromatic heterocyclic ring", or the "condensed polycyclic aromatic" of the "substituted or unsubstituted aromatic hydrocarbon", the "substituted or unsubstituted aromatic heterocyclic ring", or the "substituted or unsubstituted condensed polycyclic aromatic" in the "divalent group of a substituted or unsubstituted aromatic hydrocarbon", the "divalent group of a substituted or unsubstituted aromatic heterocyclic ring", or the "divalent group of a substituted or unsubstituted condensed polycyclic aromatic" represented by $A_1$ in the general formula (6) include benzene, biphenyl, terphenyl, tetrakisphenyl, styrene, naphthalene, anthracene, acenaphthalene, fluorene, phenanthrene, indane, pyrene, triphenylene, pyridine, pyrimidine, triazine, pyrrole, furan, thiophene, quinoline, isoquinoline, benzofuran, benzothiophene, indoline, carbazole, carboline, benzoxazole, benzothiazole, quinoxaline, benzimidazole, pyrazole, dibenzofuran, dibenzothiophene, naphthyridine, phenanthroline, and acridine.

Then, the "divalent group of a substituted or unsubstituted aromatic hydrocarbon", the "divalent group of a substituted or unsubstituted aromatic heterocyclic ring", or the "divalent group of a substituted or unsubstituted condensed polycyclic aromatic" represented by $A_1$ in the general formula (6) represents a divalent group that results from the removal of two hydrogen atoms from the above "aromatic hydrocarbon", "aromatic heterocyclic ring", or "condensed polycyclic aromatic".

Further, these divalent groups may have a substituent, and examples of the substituent include the same substituents exemplified as the "substituent" in the "substituted aromatic hydrocarbon group", the "substituted aromatic heterocyclic group", or the "substituted condensed polycyclic aromatic group" represented by $Ar_1$ to $Ar_4$ in the above general formula (1), and possible embodiments may also be the same embodiments as the exemplified embodiments.

Specific examples of the "aromatic heterocyclic group" in the "substituted or unsubstituted aromatic heterocyclic group" represented by $B_1$ in the general formula (6) include a triazinyl group, a pyridyl group, a pyrimidinyl group, a furyl group, a pyrrolyl group, a thienyl group, a quinolyl group, an isoquinolyl group, a benzofuranyl group, a benzothienyl group, an indolyl group, a carbazolyl group, a benzoxazolyl group, a benzothiazolyl group, a quinoxalinyl group, a benzoimidazolyl group, a pyrazolyl group, a dibenzofuranyl group, a dibenzothienyl group, a naphthyridinyl group, a phenanthrolinyl group, an acridinyl group, and a carbolinyl group.

Specific examples of the "substituent" in the "substituted aromatic heterocyclic group" represented by $B_1$ in the general formula (6) include a deuterium atom, a cyano group, a nitro group; halogen atoms such as a fluorine atom, a chlorine atom, a bromine atom, and an iodine atom; linear or branched alkyl groups of 1 to 6 carbon atoms such as a methyl group, an ethyl group, an n-propyl group, an isopropyl group, an n-butyl group, an isobutyl group, a tert-butyl group, an n-pentyl group, an isopentyl group, a neopentyl group, and an n-hexyl group; cycloalkyl groups of 5 to 10 carbon atoms such as a cyclopentyl group, a cyclohexyl group, a 1-adamantyl group, and a 2-adamantyl group; linear or branched alkyloxy groups of 1 to 6 carbon atoms such as a methyloxy group, an ethyloxy group, and a propyloxy group; cycloalkyloxy groups of 5 to 10 carbon atoms such as a cyclopentyloxy group, a cyclohexyloxy group, a 1-adamantyloxy group, and a 2-adamantyloxy group; alkenyl groups such as a vinyl group and an allyl group; aryloxy groups such as a phenyloxy group and a tolyloxy group; arylalkyloxy groups such as a benzyloxy group and a phenethyloxy group; aromatic hydrocarbon groups or condensed polycyclic aromatic groups such as a phenyl group, a biphenylyl group, a terphenylyl group, a naphthyl group, an anthracenyl group, a phenanthrenyl group, a fluorenyl group, an indenyl group, a pyrenyl group, a perylenyl group, a fluoranthenyl group, and a triphenylenyl group; aromatic heterocyclic groups such as a pyridyl group, a pyrimidinyl group, a triazinyl group, a thienyl group, a furyl group, a pyrrolyl group, a quinolyl group, an isoquinolyl group, a benzofuranyl group, a benzothienyl group, an indolyl group, a carbazolyl group, a benzoxazolyl group, a benzothiazolyl group, a quinoxalinyl group, a benzoimidazolyl group, a pyrazolyl group, a dibenzofuranyl group, a dibenzothienyl group, and a carbolinyl group; aryloxy groups such as a phenyloxy group, a biphenylyloxy group, a naphthyloxy group, an anthracenyloxy group, and a phenanthrenyloxy group; arylvinyl groups such as a styryl group and a naphthylvinyl group; acyl groups such as an acetyl group and a benzoyl group; and other groups, and these substituents may be further substituted with a substituent exemplified above. Further, these substituents may bind to each other via a single bond, a substituted or unsubstituted methylene group, an oxygen atom, or a sulfur atom to form a ring.

Examples of the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by C in the general formula (6) include the same groups exemplified as the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by $Ar_1$ to $Ar_4$ in the above general formula (1), and when a plurality of these groups bind to the same anthracene ring (when q is 2), these groups may be the same or different.

Further, these groups may have a substituent, and examples of the substituent include the same substituents exemplified as the "substituent" in the "substituted aromatic hydrocarbon group", the "substituted aromatic heterocyclic group", or the "substituted condensed polycyclic aromatic group" represented by $Ar_1$ to $Ar_4$ in the above general formula (1), and possible embodiments may also be the same embodiments as the exemplified embodiments.

Specific examples of the "linear or branched alkyl group of 1 to 6 carbon atoms" represented by D in the general formula (6) include a methyl group, an ethyl group, an n-propyl group, an isopropyl group, an n-butyl group, an isobutyl group, a tert-butyl group, an n-pentyl group, an isopentyl group, a neopentyl group, and an n-hexyl group.

Further, the plurality of D may be the same or different, and these groups may bind to each other via a single bond, a substituted or unsubstituted methylene group, an oxygen atom, or a sulfur atom to form a ring.

Examples of the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by D in the general formula (6) include the same groups exemplified as the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by $Ar_1$ to $Ar_4$ in the above general formula (1), and the plurality of D may be the same or different, and these groups may bind to each other via a single bond, a substituted or unsubstituted methylene group, an oxygen atom, or a sulfur atom to form a ring.

Further, these groups may have a substituent, and examples of the substituent include the same substituents exemplified as the "substituent" in the "substituted aromatic hydrocarbon group", the "substituted aromatic heterocyclic group", or the "substituted condensed polycyclic aromatic group" represented by $Ar_1$ to $Ar_4$ in the above general formula (1), and possible embodiments may also be the same embodiments as the exemplified embodiments.

Specific examples of the "aromatic hydrocarbon group" or the "condensed polycyclic aromatic group" in the "substituted or unsubstituted aromatic hydrocarbon group" or the "substituted or unsubstituted condensed polycyclic aromatic group" represented by $Ar_{12}$, $Ar_{13}$, and $Ar_{14}$ in the general formula (7) include groups such as a phenyl group, a biphenylyl group, a terphenylyl group, a tetrakisphenyl group, a styryl group, a naphthyl group, an anthracenyl group, an acenaphthenyl group, a phenanthrenyl group, a fluorenyl group, an indenyl group, a pyrenyl group, a perylenyl group, a fluoranthenyl group, and a triphenylenyl group.

Further, these groups may have a substituent, and examples of the substituent include the same substituents exemplified as the "substituent" in the "substituted aromatic hydrocarbon group", the "substituted aromatic heterocyclic group", or the "substituted condensed polycyclic aromatic group" represented by $Ar_1$ to $Ar_4$ in the above general formula (1), and possible embodiments may also be the same embodiments as the exemplified embodiments.

Specific examples of the "aromatic heterocyclic group" in the "substituted or unsubstituted aromatic heterocyclic group" represented by $Ar_{15}$ in the structural formula (8) include groups such as a triazinyl group, a pyridyl group, a pyrimidinyl group, a furyl group, a pyrrolyl group, a thienyl group, a quinolyl group, an isoquinolyl group, a benzofuranyl group, a benzothienyl group, an indolyl group, a carbazolyl group, a benzoxazolyl group, a benzothiazolyl group, a quinoxalinyl group, a benzoimidazolyl group, a pyrazolyl group, a dibenzofuranyl group, a dibenzothienyl group, a naphthyridinyl group, a phenanthrolinyl group, an acridinyl group, and a carbolinyl group.

Further, these groups may have a substituent, and examples of the substituent include the same substituents exemplified as the "substituent" in the "substituted aromatic hydrocarbon group", the "substituted aromatic heterocyclic group", or the "substituted condensed polycyclic aromatic group" represented by $Ar_1$ to $Ar_4$ in the above general formula (1), and possible embodiments may also be the same embodiments as the exemplified embodiments.

Specific examples of the "linear or branched alkyl group of 1 to 6 carbon atoms" represented by $R_{19}$ to $R_{22}$ in the structural formula (8) include a methyl group, an ethyl group, an n-propyl group, an i-propyl group, an n-butyl group, a 2-methylpropyl group, a tert-butyl group, an n-pentyl group, a 3-methylbutyl group, a tert-pentyl group, an n-hexyl group, an iso-hexyl group, and a tert-hexyl group.

Specific examples of the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by $R_{19}$ to $R_{22}$ in the structural formula (8) include groups such as a phenyl group, a biphenylyl group, a terphenylyl group, a tetrakisphenyl group, a styryl group, a naphthyl group, an anthracenyl group, an acenaphthenyl group, a phenanthrenyl group, a fluorenyl group, an indenyl group, a pyrenyl group, a perylenyl group, a fluoranthenyl group, a triphenylenyl group, a triazinyl group, a pyridyl group, a pyrimidinyl group, a furyl group, a pyrrolyl group, a thienyl group, a quinolyl group, an isoquinolyl group, a benzofuranyl group, a benzothienyl group, an indolyl group, a carbazolyl group, a benzoxazolyl group, a benzothiazolyl group, a quinoxalinyl group, a benzoimidazolyl group, a pyrazolyl group, a dibenzofuranyl group, a dibenzothienyl group, a naphthyridinyl group, a phenanthrolinyl group, an acridinyl group, and a carbolinyl group.

Further, these groups may have a substituent, and examples of the substituent include the same substituents exemplified as the "substituent" in the "substituted aromatic hydrocarbon group", the "substituted aromatic heterocyclic group", or the "substituted condensed polycyclic aromatic group" represented by $Ar_1$ to $Ar_4$ in the above general formula (1), and possible embodiments may also be the same embodiments as the exemplified embodiments.

Specific examples of the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by $Ar_{16}$ and $Ar_{17}$ in the general formula (9) include groups such as a phenyl group, a biphenylyl group, a terphenylyl group, a tetrakisphenyl group, a styryl group, a naphthyl group, an anthracenyl group, an acenaphthenyl group, a phenanthrenyl group, a fluorenyl group, an indenyl group, a pyrenyl group, a pyridyl group, a triazinyl group, a pyrimidinyl group, a furyl group, a pyrrolyl group, a thienyl group, a quinolyl group, an isoquinolyl group, a benzofuranyl group, a benzothienyl group, an indolyl group, a carbazolyl group, a benzoxazolyl group, a benzothiazolyl group, a quinoxalinyl group, a benzoimidazolyl group, a pyrazolyl group, a dibenzofuranyl group, a dibenzothienyl group, a naphthyridinyl group, a phenanthrolinyl group, and an acridinyl group.

Further, these groups may have a substituent, and examples of the substituent include the same substituents exemplified as the "substituent" in the "substituted aromatic hydrocarbon group", the "substituted aromatic heterocyclic group", or the "substituted condensed polycyclic aromatic group" represented by $Ar_1$ to $Ar_4$ in the above general formula (1), and possible embodiments may also be the same embodiments as the exemplified embodiments.

Specific examples of the "aromatic hydrocarbon", the "aromatic heterocyclic ring", or the "condensed polycyclic aromatic" of the "substituted or unsubstituted aromatic hydrocarbon", the "substituted or unsubstituted aromatic heterocyclic ring", or the "substituted or unsubstituted condensed polycyclic aromatic" in the "divalent group of a substituted or unsubstituted aromatic hydrocarbon", the "divalent group of a substituted or unsubstituted aromatic heterocyclic ring", or the "divalent group of a substituted or unsubstituted condensed polycyclic aromatic" represented by $A_2$ in the general formula (9) include benzene, biphenyl, terphenyl, tetrakisphenyl, styrene, naphthalene, anthracene, acenaphthalene, fluorene, phenanthrene, indane, pyrene, triphenylene, pyridine, bipyridine, pyrimidine, triazine, pyrrole, furan, thiophene, quinoline, isoquinoline, benzofuran, benzothiophene, indoline, carbazole, carboline, benzoxazole, benzothiazole, quinoxaline, benzimidazole, pyrazole, dibenzofuran, dibenzothiophene, naphthyridine, phenanthroline, and acridine.

Then, the "divalent group of a substituted or unsubstituted aromatic hydrocarbon", the "divalent group of a substituted or unsubstituted aromatic heterocyclic ring", or the "divalent group of a substituted or unsubstituted condensed polycyclic aromatic" represented by $A_2$ in the general formula (9) represents a divalent group that results from the removal of two hydrogen atoms from the above "aromatic hydrocarbon", "aromatic heterocyclic ring", or "condensed polycyclic aromatic".

Further, these divalent groups may have a substituent, and examples of the substituent include the same substituents exemplified as the "substituent" in the "substituted aromatic hydrocarbon group", the "substituted aromatic heterocyclic group", or the "substituted condensed polycyclic aromatic group" represented by $Ar_1$ to $Ar_4$ in the above general formula (1), and possible embodiments may also be the same embodiments as the exemplified embodiments.

Specific examples of the "condensed polycyclic aromatic" of the "substituted or unsubstituted condensed polycyclic aromatic" in the "divalent group of a substituted or unsubstituted condensed polycyclic aromatic" represented by $A_3$ in the general formula (9) include naphthalene, anthracene, acenaphthalene, fluorene, phenanthrene, indane, pyrene, and triphenylene.

Then, the "divalent group of a substituted or unsubstituted condensed polycyclic aromatic" represented by $A_3$ in the general formula (9) represents a divalent group that results from the removal of two hydrogen atoms from the above "condensed polycyclic aromatic".

Further, these divalent groups may have a substituent, and examples of the substituent include the same substituents exemplified as the "substituent" in the "substituted aromatic hydrocarbon group", the "substituted aromatic heterocyclic group", or the "substituted condensed polycyclic aromatic group" represented by $Ar_1$ to $Ar_4$ in the above general formula (1), and possible embodiments may also be the same embodiments as the exemplified embodiments.

Specific examples of the "aromatic heterocyclic group", in the "substituted or unsubstituted aromatic heterocyclic group" represented by $B_2$ in the general formula (9) include groups such as a pyridyl group, a bipyridyl group, a triazinyl group, a pyrimidinyl group, a furyl group, a pyrrolyl group, a thienyl group, a quinolyl group, an isoquinolyl group, a benzofuranyl group, a benzothienyl group, an indolyl group, a carbazolyl group, a carbolinyl group, a benzoxazolyl group, a benzothiazolyl group, a quinoxalinyl group, a benzoimidazolyl group, a pyrazolyl group, a dibenzofuranyl group, a dibenzothienyl group, a naphthyridinyl group, a phenanthrolinyl group, and an acridinyl group.

Further, these groups may have a substituent, and examples of the substituent include the same substituents exemplified as the "substituent" in the "substituted aromatic heterocyclic group" represented by $B_1$ in the above general formula (6), and possible embodiments may also be the same embodiments as the exemplified embodiments.

$Ar_1$ to $Ar_4$ in the general formula (1) are preferably the "substituted or unsubstituted aromatic hydrocarbon group", the "substituted or unsubstituted oxygen-containing aromatic heterocyclic group", or the "substituted or unsubstituted condensed polycyclic aromatic group", and more preferably phenyl, biphenylyl, terphenylyl, naphthyl, phenanthrenyl, fluorenyl, and dibenzofuranyl.

The "substituent" in the "substituted aromatic hydrocarbon group", the "substituted aromatic heterocyclic group", or the "substituted condensed polycyclic aromatic group" represented by $Ar_1$ to $Ar_4$ in the general formula (1) is preferably a deuterium atom, the "linear or branched alkyl of 1 to 6 carbon atoms that may have a substituent", the "linear or branched alkenyl of 2 to 6 carbon atoms that may have a substituent", the "substituted or unsubstituted aromatic hydrocarbon group", or the "substituted or unsubstituted condensed polycyclic aromatic group", and specifically is more preferably a deuterium atom, phenyl, biphenylyl, naphthyl, or vinyl. Embodiments where these groups bind to each other via a single bond to form a condensed aromatic ring are also preferred.

In the hole injection layer of the organic EL device of the present invention, examples of the electron acceptor doped in the arylamine compound represented by the above general formula (1) include trisbromophenylaminehexachloroantimony, tetracyanoquinodimethane (TCNQ), 2,3,5,6-tetrafluoro-tetracyano-1,4-benzoquinodimethane (F4TCNQ), and a radialene derivative (refers to JP-A-2011-100621, for example), and a radialene derivative represented by the above general formula (2) is preferably used.

$Ar_5$ to $Ar_7$ in the general formula (2) are preferably an "aromatic hydrocarbon group", a "condensed polycyclic aromatic group", or a pyridyl group, more preferably a phenyl group, a biphenylyl group, a terphenylyl group, a naphthyl group, a phenanthrenyl group, a fluorenyl group, or a pyridyl group, and the "electron acceptor group" is preferably a fluorine atom, a chlorine atom, a cyano group, or a trifluoromethyl group.

An embodiment in which $Ar_5$ to $Ar_7$ in the general formula (2) are at least partially, preferably completely substituted with an "electron acceptor group" is preferable.

$Ar_5$ to $Ar_7$ in the general formula (2) are preferably a phenyl group or a pyridyl group completely substituted with a fluorine atom, a chlorine atom, a cyano group, or a trifluoromethyl group such as a tetrafluoropyridyl group, a tetrafluoro-(trifluoromethyl)phenyl group, a cyano-tetrafluorophenyl group, dichloro-difluoro-(trifluoromethyl)phenyl group, or a pentafluorophenyl group.

$R_1$ to $R_6$ in the general formula (3) are preferably a deuterium atom, the "linear or branched alkyl of 1 to 6 carbon atoms that may have a substituent", the "linear or branched alkenyl of 2 to 6 carbon atoms that may have a substituent", the "substituted or unsubstituted aromatic hydrocarbon group", or the "substituted or unsubstituted condensed polycyclic aromatic group", further preferably a deuterium atom, phenyl, biphenylyl, naphthyl, or vinyl, and particularly preferably a deuterium atom, phenyl, or biphenylyl. It is also preferable that these groups bind to each other via a single bond to form a condensed aromatic ring.

$r_1$ to $r_6$ in the general formula (3) are each preferably an integer of 0 to 3, and further preferably an integer of 0 to 2.

The "divalent linking group" represented by $L_1$ in the general formula (3) is preferably methylene, the "cycloalkylene of 5 to 10 carbon atoms", the "divalent group of an aromatic hydrocarbon", or the "divalent group of condensed polycyclic aromatics", or a single bond, further preferably divalent groups represented by the following structural formulae (B) to (G), or a single bond, and particularly preferably a divalent group represented by the following structural formula (B) or (D).

In the following structural formula (B) in the general formula (3), n is preferably an integer of 1 to 3, and further preferably 2 or 3.

[Chemical Formula 10]

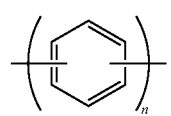

(B)

In the formula, n represents an integer of 1 to 4.

[Chemical Formula 11]

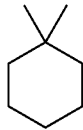
(C)

[Chemical Formula 12]

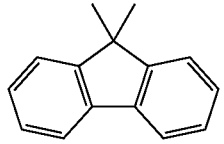
(D)

[Chemical Formula 13]

—CH$_2$—  (E)

[Chemical Formula 14]

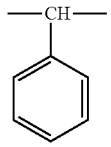
(F)

[Chemical Formula 15]

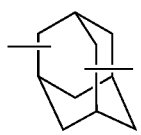
(G)

R$_7$ to R$_{18}$ in the general formula (4) are preferably a deuterium atom, the "linear or branched alkyl of 1 to 6 carbon atoms that may have a substituent", the "linear or branched alkenyl of 2 to 6 carbon atoms that may have a substituent", the "substituted or unsubstituted aromatic hydrocarbon group", or the "substituted or unsubstituted condensed polycyclic aromatic group", and further preferably a deuterium atom, phenyl, biphenylyl, naphthyl, or vinyl. It is also preferable that these groups bind to each other via a single bond to form a condensed aromatic ring. A deuterium atom, phenyl, and biphenylyl are particularly preferable.

r$_7$ to r$_{18}$ in the general formula (4) are preferably an integer of 0 to 3, and further preferably an integer of 0 to 2.

The "divalent linking groups" represented by L$_2$ to L$_4$ in the general formula (4) are preferably methylene, the "cycloalkylene of 5 to 10 carbon atoms", the "divalent group of an aromatic hydrocarbon", or the "divalent group of condensed polycyclic aromatics", or a single bond, further preferably divalent groups represented by the structural formulae (B) to (G), or a single bond, and still further preferably a divalent group represented by the structural formula (B) or (D), or a single bond.

In the structural formula (B) in the general formula (4), n is preferably 1 or 2, and further preferably 1.

Ar$_8$ in the general formula (5) is preferably the "substituted or unsubstituted aromatic hydrocarbon group", the "substituted or unsubstituted aromatic heterocyclic group", or the "substituted or unsubstituted condensed polycyclic aromatic group", and further preferably phenyl, biphenylyl, terphenylyl, naphthyl, phenanthrenyl, anthracenyl, fluorenyl, carbazolyl, indolyl, dibenzofuranyl, or dibenzothienyl.

Ar$_9$ in the general formula (5) is preferably the "substituted or unsubstituted aromatic hydrocarbon group" or the "substituted or unsubstituted condensed polycyclic aromatic group", further preferably phenyl, biphenylyl, terphenylyl, naphthyl, phenanthrenyl, anthracenyl, or fluorenyl, still further preferably phenyl, and particularly unsubstituted phenyl.

The arylamine compound of the general formula (5) is preferably an arylamine compound of the following general formula (5a) or the following general formula (5b).

[Chemical Formula 16]

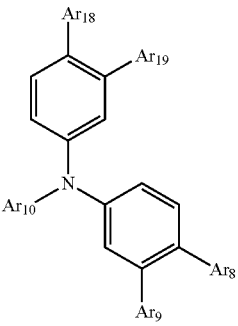
(5a)

In the formula, Ar$_8$ to Ar$_{10}$ have the same meanings as shown for the general formula (5). Ar$_{18}$ to Ar$_{19}$ may be the same or different, and represent a substituted or unsubstituted aromatic hydrocarbon group, a substituted or unsubstituted aromatic heterocyclic group, or a substituted or unsubstituted condensed polycyclic aromatic group.

[Chemical Formula 17]

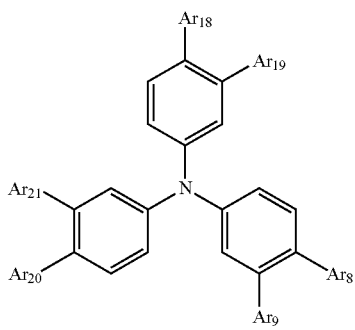
(5b)

In the formula, Ar$_8$ to Ar$_9$ have the same meanings as shown for the general formula (5). Ar$_{18}$ to Ar$_{21}$ may be the same or different, and represent a substituted or unsubstituted aromatic hydrocarbon group, a substituted or unsubstituted aromatic heterocyclic group, or a substituted or unsubstituted condensed polycyclic aromatic group.

Examples of the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by $Ar_{18}$ to $Ar_{21}$ in the general formula (5a) and the general formula (5b) include the same groups exemplified as the groups for the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by $Ar_1$ to $Ar_4$ in the general formula (1).

These groups may have a substituent, and examples of the substituent include the same substituents exemplified as the "substituent" in the "substituted aromatic hydrocarbon group", the "substituted aromatic heterocyclic group", or the "substituted condensed polycyclic aromatic group" represented by $Ar_1$ to $Ar_4$ in the general formula (1), and possible embodiments may also be the same embodiments as the exemplified embodiments.

In the general formula (5a), it is preferable that $Ar_8$ and $Ar_{18}$ are the same groups, and $Ar_9$ and $Ar_{19}$ are the same groups.

In the general formula (5b), it is preferable that $Ar_8$, $Ar_{18}$, and $Ar_{20}$ are the same groups, and $Ar_9$, $Ar_{19}$, and $Ar_{21}$ are the same groups.

The "substituent" in the "substituted aromatic hydrocarbon group", the "substituted aromatic heterocyclic group", or the "substituted condensed polycyclic aromatic group" represented by $Ar_8$ to $Ar_{17}$ in the general formula (5) is preferably a deuterium atom, a linear or branched alkyl of 1 to 6 carbon atoms that may have a substituent, a linear or branched alkenyl of 2 to 6 carbon atoms that may have a substituent, the "substituted or unsubstituted aromatic hydrocarbon group", or the "substituted or unsubstituted condensed polycyclic aromatic group", and further preferably a deuterium atom, phenyl, biphenylyl, naphthyl, or vinyl. It is also preferable that these groups bind to each other via a single bond to form a condensed aromatic ring.

The "aromatic heterocyclic group" in the "substituted or unsubstituted aromatic heterocyclic group" represented by $B_1$ in the general formula (6) is preferably a nitrogen-containing aromatic heterocyclic group, such as pyridyl, pyrimidinyl, pyrrolyl, quinolyl, isoquinolyl, indolyl, carbazolyl, benzoxazolyl, benzothiazolyl, quinoxalinyl, benzoimidazolyl, pyrazolyl, or carbolinyl, and further preferably pyridyl, pyrimidinyl, quinolyl, isoquinolyl, indolyl, pyrazolyl, benzoimidazolyl, or carbolinyl.

For p and q in the general formula (6), p represents 7 or 8, and q represents 1 or 2, while maintaining the relationship, in which the sum of p and q (p+q) is 9.

$A_1$ in the general formula (6) is preferably the "divalent group of a substituted or unsubstituted aromatic hydrocarbon" or the "divalent group of substituted or unsubstituted condensed polycyclic aromatics", and further preferably divalent groups that result from the removal of two hydrogen atoms from benzene, biphenyl, naphthalene, or phenanthrene.

The compound having an anthracene ring structure of the general formula (6) is preferably a compound having an anthracene ring structure of the following general formula (6a), the following general formula (6b), or the following general formula (6c).

[Chemical Formula 18]

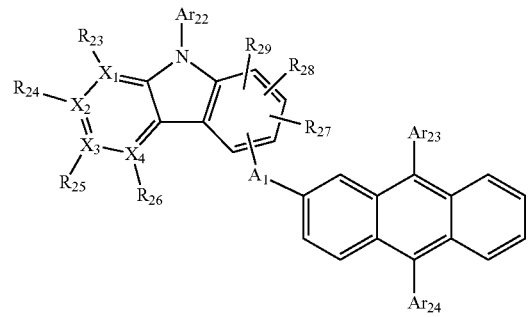

(6a)

In the formula, $A_1$ represents a divalent group of a substituted or unsubstituted aromatic hydrocarbon, a divalent group of a substituted or unsubstituted aromatic heterocyclic ring, a divalent group of substituted or unsubstituted condensed polycyclic aromatics, or a single bond. $Ar_{22}$, $Ar_{23}$, and $Ar_{24}$ may be the same or different, and represent a substituted or unsubstituted aromatic hydrocarbon group, a substituted or unsubstituted aromatic heterocyclic group, or a substituted or unsubstituted condensed polycyclic aromatic group. $R_{23}$ to $R_{29}$ may be the same or different, and represent a hydrogen atom, a deuterium atom, a fluorine atom, a chlorine atom, cyano, nitro, linear or branched alkyl of 1 to 6 carbon atoms that may have a substituent, cycloalkyl of 5 to 10 carbon atoms that may have a substituent, linear or branched alkenyl of 2 to 6 carbon atoms that may have a substituent, linear or branched alkyloxy of 1 to 6 carbon atoms that may have a substituent, cycloalkyloxy of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, or substituted or unsubstituted aryloxy, where these groups may bind to each other via a single bond, substituted or unsubstituted methylene, an oxygen atom, or a sulfur atom to form a ring. $X_1$, $X_2$, $X_3$, and $X_4$ represent a carbon atom or a nitrogen atom, and only one of $X_1$, $X_2$, $X_3$, and $X_4$ is a nitrogen atom. In this case, the nitrogen atom does not have the hydrogen atom or substituent for $R_{23}$ to $R_{26}$.

[Chemical Formula 19]

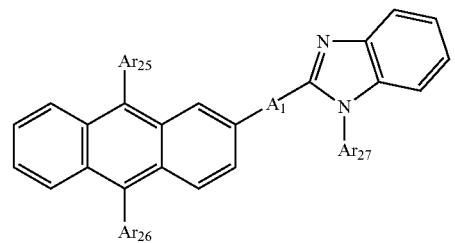

(6b)

In the formula, $A_1$ represents a divalent group of a substituted or unsubstituted aromatic hydrocarbon, a divalent group of a substituted or unsubstituted aromatic heterocyclic ring, a divalent group of substituted or unsubstituted condensed polycyclic aromatics, or a single bond. $Ar_{25}$, $Ar_{26}$, and $Ar_{27}$ may be the same or different, and represent a substituted or unsubstituted aromatic hydrocarbon group, a substituted or unsubstituted aromatic heterocyclic group, or a substituted or unsubstituted condensed polycyclic aromatic group.

[Chemical Formula 20]

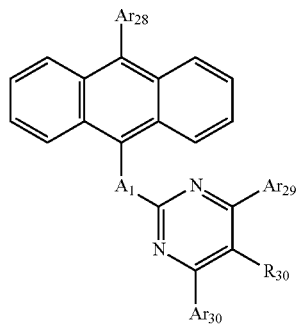

(6c)

In the formula, $A_1$ represents a divalent group of a substituted or unsubstituted aromatic hydrocarbon, a divalent group of a substituted or unsubstituted aromatic heterocyclic ring, a divalent group of substituted or unsubstituted condensed polycyclic aromatics, or a single bond. $Ar_{28}$, $Ar_{29}$, and $Ar_{30}$ may be the same or different, and represent a substituted or unsubstituted aromatic hydrocarbon group, a substituted or unsubstituted aromatic heterocyclic group, or a substituted or unsubstituted condensed polycyclic aromatic group. $R_{30}$ represents a hydrogen atom, a deuterium atom, a fluorine atom, a chlorine atom, cyano, nitro, linear or branched alkyl of 1 to 6 carbon atoms that may have a substituent, cycloalkyl of 5 to 10 carbon atoms that may have a substituent, linear or branched alkenyl of 2 to 6 carbon atoms that may have a substituent, linear or branched alkyloxy of 1 to 6 carbon atoms that may have a substituent, cycloalkyloxy of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, or substituted or unsubstituted aryloxy.

Examples of the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by $Ar_{22}$, $Ar_{23}$, and $Ar_{24}$ in the general formula (6a) include the same groups exemplified as the groups for the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by $Ar_1$ to $Ar_4$ in the general formula (1).

These groups may have a substituent. Examples of the substituent include the same groups exemplified as the "substituent" in the "substituted aromatic hydrocarbon group", the "substituted aromatic heterocyclic group", or the "substituted condensed polycyclic aromatic group" represented by $Ar_1$ to $Ar_4$ in the general formula (1), and possible embodiments may also be the same embodiments as the exemplified embodiments.

Specific examples of the "linear or branched alkyl of 1 to 6 carbon atoms", the "cycloalkyl of 5 to 10 carbon atoms", or the "linear or branched alkenyl of 2 to 6 carbon atoms" in the "linear or branched alkyl of 1 to 6 carbon atoms that may have a substituent", the "cycloalkyl of 5 to carbon atoms that may have a substituent", or the "linear or branched alkenyl of 2 to 6 carbon atoms that may have a substituent" represented by $R_{23}$ to $R_{29}$ in the general formula (6a) include methyl, ethyl, n-propyl, isopropyl, n-butyl, isobutyl, tert-butyl, n-pentyl, isopentyl, neopentyl, n-hexyl, cyclopentyl, cyclohexyl, 1-adamantyl, 2-adamantyl, vinyl, allyl, isopropenyl, and 2-butenyl. These groups may bind to each other via a single bond, substituted or unsubstituted methylene, an oxygen atom, or a sulfur atom to form a ring.

Specific examples of the "substituent" in the "linear or branched alkyl group of 1 to 6 carbon atoms that has a substituent", the "cycloalkyl group of 5 to 10 carbon atoms that has a substituent", or the "linear or branched alkenyl group of 2 to 6 carbon atoms that has a substituent" represented by $R_{23}$ to $R_{29}$ in the general formula (6a) include a deuterium atom, a cyano group, a nitro group; halogen atoms such as a fluorine atom, a chlorine atom, a bromine atom, and an iodine atom; linear or branched alkyloxy groups of 1 to 6 carbon atoms such as a methyloxy group, an ethyloxy group, and a propyloxy group; alkenyl groups such as a vinyl group and an allyl group; aryloxy groups such as a phenyloxy group and a tolyloxy group; arylalkyloxy groups such as a benzyloxy group and a phenethyloxy group; aromatic hydrocarbon groups or condensed polycyclic aromatic groups such as a phenyl group, a biphenylyl group, a terphenylyl group, a naphthyl group, an anthracenyl group, a phenanthrenyl group, a fluorenyl group, an indenyl group, a pyrenyl group, a perylenyl group, a fluoranthenyl group, and a triphenylenyl group; aromatic heterocyclic groups such as a pyridyl group, a pyrimidinyl group, a triazinyl group, a thienyl group, a furyl group, a pyrrolyl group, a quinolyl group, an isoquinolyl group, a benzofuranyl group, a benzothienyl group, an indolyl group, a carbazolyl group, a benzoxazolyl group, a benzothiazolyl group, a quinoxalinyl group, a benzoimidazolyl group, a pyrazolyl group, a dibenzofuranyl group, a dibenzothienyl group, and a carbolinyl group; and other groups, and these substituents may be further substituted with a substituent exemplified above. Further, these substituents may bind to each other via a single bond, a substituted or unsubstituted methylene group, an oxygen atom, or a sulfur atom to form a ring.

Specific examples of the "linear or branched alkyloxy group of 1 to 6 carbon atoms" or the "cycloalkyloxy group of 5 to 10 carbon atoms" in the "linear or branched alkyloxy group of 1 to 6 carbon atoms that may have a substituent" or the "cycloalkyloxy group of 5 to 10 carbon atoms that may have a substituent" represented by $R_{23}$ to $R_{29}$ in the general formula (6a) include a methyloxy group, an ethyloxy group, an n-propyloxy group, an isopropyloxy group, an n-butyloxy group, a tert-butyloxy group, an n-pentyloxy group, an n-hexyloxy group, a cyclopentyloxy group, a cyclohexyloxy group, a cycloheptyloxy group, a cyclooctyloxy group, a 1-adamantyloxy group, and a 2-adamantyloxy group, and these groups may bind to each other via a single bond, a substituted or unsubstituted methylene group, an oxygen atom, or a sulfur atom to form a ring.

Further, these groups may have a substituent, and examples of the substituent include the same substituents exemplified as the "substituent" in the "linear or branched alkyl group of 1 to 6 carbon atoms that has a substituent", the "cycloalkyl group of 5 to 10 carbon atoms that has a substituent", or the "linear or branched alkenyl group of 2 to 6 carbon atoms that has a substituent" represented by $R_{23}$ to $R_{29}$ in the above general formula (6a), and possible embodiments may also be the same embodiments as the exemplified embodiments.

Examples of the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by $R_{23}$ to $R_{29}$ in the general formula (6a) include the same groups exemplified as the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by $Ar_1$ to $Ar_4$ in the above general formula (1), and these groups may bind to each other via a single bond, a substituted or unsubstituted methylene group, an oxygen atom, or a sulfur atom to form a ring.

Further, these groups may have a substituent, and examples of the substituent include the same substituents exemplified as the "substituent" in the "substituted aromatic hydrocarbon group", the "substituted aromatic heterocyclic group", or the "substituted condensed polycyclic aromatic group" represented by $Ar_1$ to $Ar_4$ in the above general formula (1), and possible embodiments may also be the same embodiments.

Specific examples of the "aryloxy group" in the "substituted or unsubstituted aryloxy group" represented by $R_{23}$ to $R_{29}$ in the general formula (6a) include a phenyloxy group, a biphenylyloxy group, a terphenylyloxy group, a naphthyloxy group, an anthracenyloxy group, a phenanthrenyloxy group, a fluorenyloxy group, an indenyloxy group, a pyrenyloxy group, and a perylenyloxy group, and these groups may bind to each other via a single bond, a substituted or unsubstituted methylene group, an oxygen atom, or a sulfur atom to form a ring.

Further, these groups may have a substituent, and examples of the substituent include the same substituents exemplified as the "substituent" in the "substituted aromatic hydrocarbon group", the "substituted aromatic heterocyclic group", or the "substituted condensed polycyclic aromatic group" represented by $Ar_1$ to $Ar_4$ in the above general formula (1), and possible embodiments may also be the same embodiments.

In the general formula (6a), $X_1$, $X_2$, $X_3$, and $X_4$ represent a carbon atom or a nitrogen atom, and only one of $X_1$, $X_2$, $X_3$, and $X_4$ is a nitrogen atom, and the nitrogen atom in this case does not have a hydrogen atom or a substituent of $R_{23}$ to $R_{26}$. That is, it means that in the case where $X_1$ is a nitrogen atom, $R_{23}$, in the case where $X_2$ is a nitrogen atom, $R_{24}$, in the case where $X_3$ is a nitrogen atom, $R_{25}$, and in the case where $X_4$ is a nitrogen atom, $R_{26}$ is not present.

Examples of the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by $Ar_{25}$, $Ar_{26}$, and $Ar_{27}$ in the general formula (6b) include the same groups exemplified as the groups for the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by $Ar_1$ to $Ar_4$ in the general formula (1).

These groups may have a substituent. Examples of the substituent include the same groups exemplified as the "substituent" in the "substituted aromatic hydrocarbon group", the "substituted aromatic heterocyclic group", or the "substituted condensed polycyclic aromatic group" represented by $Ar_1$ to $Ar_4$ in the general formula (1), and possible embodiments may also be the same embodiments as the exemplified embodiments.

Examples of the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by $Ar_{28}$, $Ar_{29}$, and $Ar_{30}$ in the general formula (6c) include the same groups exemplified as the groups for the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by $Ar_1$ to $Ar_4$ in the general formula (1).

These groups may have a substituent. Examples of the substituent include the same groups exemplified as the "substituent" in the "substituted aromatic hydrocarbon group", the "substituted aromatic heterocyclic group", or the "substituted condensed polycyclic aromatic group" represented by $Ar_1$ to $Ar_4$ in the general formula (1), and possible embodiments may also be the same embodiments as the exemplified embodiments.

Examples of the "linear or branched alkyl of 1 to 6 carbon atoms", the "cycloalkyl of 5 to 10 carbon atoms", or the "linear or branched alkenyl of 2 to 6 carbon atoms" in the "linear or branched alkyl of 1 to 6 carbon atoms that may have a substituent", the "cycloalkyl of 5 to 10 carbon atoms that may have a substituent", or the "linear or branched alkenyl of 2 to 6 carbon atoms that may have a substituent" represented by $R_{30}$ in the general formula (6c) include the same groups exemplified as the groups for the "linear or branched alkyl of 1 to 6 carbon atoms", the "cycloalkyl of 5 to 10 carbon atoms", or the "linear or branched alkenyl of 2 to 6 carbon atoms" in the "linear or branched alkyl of 1 to 6 carbon atoms that may have a substituent", the "cycloalkyl of 5 to 10 carbon atoms that may have a substituent", or the "linear or branched alkenyl of 2 to 6 carbon atoms that may have a substituent" represented by $R_{23}$ to $R_{29}$ in the general formula (6a).

These groups may have a substituent. Examples of the substituent include the same groups exemplified as the "substituent" in the "linear or branched alkyl of 1 to 6 carbon atoms that has a substituent", the "cycloalkyl of 5 to 10 carbon atoms that has a substituent", or the "linear or branched alkenyl of 2 to 6 carbon atoms that has a substituent" represented by $R_{23}$ to $R_{29}$ in the general formula (6a), and possible embodiments may also be the same embodiments as the exemplified embodiments.

Examples of the "linear or branched alkyloxy of 1 to 6 carbon atoms" or the "cycloalkyloxy of 5 to 10 carbon atoms" in the "linear or branched alkyloxy of 1 to 6 carbon atoms that may have a substituent" or the "cycloalkyloxy of 5 to 10 carbon atoms that may have a substituent" represented by $R_{30}$ in the general formula (6c) include the same groups exemplified as the groups for the "linear or branched alkyloxy of 1 to 6 carbon atoms" or the "cycloalkyloxy of 5 to 10 carbon atoms" in the "linear or branched alkyloxy of 1 to 6 carbon atoms that may have a substituent" or the "cycloalkyloxy of 5 to 10 carbon atoms that may have a substituent" represented by $R_{23}$ to $R_{29}$ in the general formula (6a).

These groups may have a substituent. Examples of the substituent include the same groups exemplified as the "substituent" in the "linear or branched alkyl of 1 to 6 carbon atoms that has a substituent", the "cycloalkyl of 5 to 10 carbon atoms that has a substituent", or the "linear or branched alkenyl of 2 to 6 carbon atoms that has a substituent" represented by $R_{23}$ to $R_{29}$ in the general formula (6a), and possible embodiments may also be the same embodiments as the exemplified embodiments.

Examples of the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by $R_{30}$ in the general formula (6c) include the same groups exemplified as the groups for the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by $Ar_1$ to $Ar_4$ in the general formula (1).

These groups may have a substituent. Examples of the substituent include the same groups exemplified as the "substituent" in the "substituted aromatic hydrocarbon group", the "substituted aromatic heterocyclic group", or the "substituted condensed polycyclic aromatic group" represented by $Ar_1$ to $Ar_4$ in the general formula (1), and possible embodiments may also be the same embodiments as the exemplified embodiments.

Examples of the "aryloxy group" in the "substituted or unsubstituted aryloxy group" represented by $R_{30}$ in the general formula (6c) include the same groups exemplified as the groups for the "aryloxy group" in the "substituted or unsubstituted aryloxy group" represented by $R_{23}$ to $R_{29}$ in the general formula (6a).

These groups may have a substituent. Examples of the substituent include the same groups exemplified as the "substituent" in the "substituted aromatic hydrocarbon group", the "substituted aromatic heterocyclic group", or the "substituted condensed polycyclic aromatic group" represented by $Ar_1$ to $Ar_4$ in the general formula (1), and possible embodiments may also be the same embodiments as the exemplified embodiments.

$Ar_{12}$ in the general formula (7) is preferably phenyl, biphenylyl, naphthyl, anthracenyl, acenaphthenyl, phenanthrenyl, fluorenyl, indenyl, pyrenyl, perylenyl, fluoranthenyl, of triphenylenyl, and further preferably phenyl, biphenylyl, naphthyl, anthracenyl, phenanthrenyl, pyrenyl, fluoranthenyl, or triphenylenyl. The phenyl group preferably has a substituted or unsubstituted condensed polycyclic aromatic group as a substituent, and further preferably has a substituent selected from naphthyl, anthracenyl, phenanthrenyl, pyrenyl, fluoranthenyl, and triphenylenyl.

$Ar_{13}$ in the general formula (7) is preferably phenyl that has a substituent. The substituent of the phenyl in this case is preferably an aromatic hydrocarbon group, such as phenyl, biphenylyl, and terphenylyl, or a condensed polycyclic aromatic group, such as naphthyl, anthracenyl, acenaphthenyl, phenanthrenyl, fluorenyl, indenyl, pyrenyl, perylenyl, fluoranthenyl, and triphenylenyl, and further preferably phenyl, naphthyl, anthracenyl, phenanthrenyl, pyrenyl, fluoranthenyl, or triphenylenyl.

$Ar_{14}$ in the general formula (7) is preferably phenyl that has a substituent. The substituent of the phenyl in this case is preferably an aromatic hydrocarbon group, such as phenyl, biphenylyl, and terphenylyl, a condensed polycyclic aromatic group, such as naphthyl, anthracenyl, acenaphthenyl, phenanthrenyl, fluorenyl, indenyl, pyrenyl, perylenyl, fluoranthenyl, and triphenylenyl, and further preferably phenyl, naphthyl, anthracenyl, phenanthrenyl, pyrenyl, fluoranthenyl, or triphenylenyl.

In the general formula (7), it is preferable that $Ar_{12}$ and $Ar_{13}$ are not the same as each other from the viewpoint of thin film stability. When $Ar_{12}$ and $Ar_{13}$ are the same groups, the groups may have different substituents and may be substituted on different positions.

In the general formula (7), $Ar_{13}$ and $Ar_{14}$ may be the same groups, but there may be a possibility that the compound is easily crystallized due to the high symmetry of the entire molecule, and from the viewpoint of thin film stability, it is preferable that $Ar_{13}$ and $Ar_{14}$ are not the same as each other, and $Ar_{13}$ and $Ar_{14}$ are not simultaneously a hydrogen atom.

In the general formula (7), it is preferable that one of $Ar_{13}$ and $Ar_{14}$ is a hydrogen atom.

Example of the compound having a pyrimidine ring structure represented by the general formula (7) include compounds having a pyrimidine ring structure represented by the following general formula (7a) and general formula (7b) in which a bonding pattern of a substituent is different.

[Chemical Formula 21]

(7a)

In the formula, $Ar_{12}$, $Ar_{13}$, $Ar_{14}$, and E represent the same meanings as described in the above general formula (4).

[Chemical Formula 22]

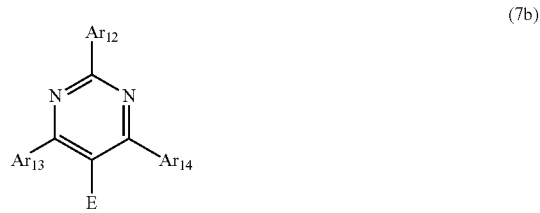

(7b)

In the formula, $Ar_{12}$, $Ar_{13}$, $Ar_{14}$, and E represent the same meanings as described in the above general formula (7).

$Ar_{15}$ in the structural formula (8) is preferably a nitrogen-containing heterocyclic group such as a triazinyl group, a pyridyl group, a pyrimidinyl group, a pyrrolyl group, a quinolyl group, an isoquinolyl group, an indolyl group, a carbazolyl group, a benzoxazolyl group, a benzothiazolyl group, a quinoxalinyl group, a benzoimidazolyl group, a pyrazolyl group, a naphthyridinyl group, a phenanthrolinyl group, an acridinyl group, or a carbolinyl group, more preferably a triazinyl group, a pyridyl group, a pyrimidinyl group, a quinolyl group, an isoquinolyl group, an indolyl group, a quinoxalinyl group, a benzoimidazolyl group, a naphthyridinyl group, a phenanthrolinyl group, or an acridinyl group, particularly preferably a pyridyl group, a pyrimidinyl group, a quinolyl group, an isoquinolyl group, an indolyl group, a quinoxalinyl group, a benzoimidazolyl group, a phenanthrolinyl group, or an acridinyl group.

In the structural formula (8), a bonding position of $Ar_{15}$ in the benzene ring is preferably a meta position with respect to a bonding position of the pyrimidine ring shown in the general formula (7) as shown in the following structural formula (8a) from the viewpoint of stability as a thin film.

[Chemical Formula 23]

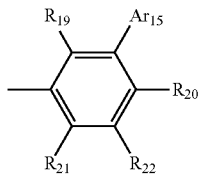

(8a)

In the formula, $Ar_{15}$, and $R_{19}$ to $R_{22}$ represent the same meanings as described in the above structural formula (8).

$Ar_{16}$ and $Ar_{17}$ in the general formula (9) are preferably the "substituted or unsubstituted aromatic hydrocarbon group", the "substituted or unsubstituted condensed polycyclic aromatic group", pyridyl, dibenzothienyl, carbazolyl, or dibenzofuranyl, further preferably phenyl, biphenylyl, terphenylyl, naphthyl, anthracenyl, phenanthrenyl, fluorenyl, indenyl, pyrenyl, pyridyl, carbazolyl, or dibenzofuranyl, and particularly preferably phenyl, biphenylyl, terphenylyl, naphthyl, anthracenyl, phenanthrenyl, or fluorenyl.

The substituent that these groups may have is preferably the "aromatic hydrocarbon group", the "aromatic heterocyclic group", and the "condensed polycyclic aromatic group", such as phenyl, biphenylyl, terphenylyl, tetrakisphenyl, styryl, naphthyl, anthracenyl, acenaphthenyl, phenanthrenyl, fluorenyl, indenyl, pyrenyl, pyridyl, triazinyl, pyrimidinyl, furyl, pyrrolyl, thienyl, quinolyl, isoquinolyl, benzofuranyl, benzothienyl, indolyl, carbazolyl, benzoxazolyl, benzothiazolyl, quinoxalinyl, benzoimidazolyl, pyrazolyl, dibenzofuranyl, dibenzothienyl, naphthyridinyl, phenanthrolinyl, or acridinyl, further preferably phenyl, biphenylyl, naphthyl, anthracenyl, phenanthrenyl, fluorenyl, pyrenyl, pyridyl, triazinyl, pyrimidinyl, quinolyl, isoquinolyl, indolyl, carbazolyl, quinoxalinyl, benzoimidazolyl, pyrazolyl, phenanthrolinyl, or acridinyl, and particularly preferably phenyl, naphthyl, anthracenyl, pyridyl, quinolyl, or isoquinolyl.

$A_2$ in the general formula (9) is preferably the "divalent group of a substituted or unsubstituted aromatic hydrocarbon", the "divalent group of substituted or unsubstituted condensed polycyclic aromatics", pyridylene, or bipyridylene, further preferably divalent groups that are derived from benzene, biphenyl, naphthalene, anthracene, fluorene, phenanthrene, pyrene, or pyridine, and particularly preferably divalent groups that are derived from benzene, naphthalene, or pyridine.

$A_3$ in the general formula (9) is preferably a single bond or divalent groups that are derived from naphthalene, anthracene, fluorene, phenanthrene, or pyrene, and further preferably a single bond or divalent groups that are derived from naphthalene or anthracene.

$B_2$ in the general formula (9) is preferably a nitrogen-containing aromatic heterocyclic group, such as pyridyl, bipyridyl, triazinyl, pyrimidinyl, pyrrolyl, quinolyl, isoquinolyl, indolyl, carbazolyl, carbolinyl, benzoxazolyl, benzothiazolyl, quinoxalinyl, benzoimidazolyl, pyrazolyl, naphthyridinyl, phenanthrolinyl, or acridinyl, further preferably pyridyl, bipyridyl, pyrimidinyl, quinolyl, isoquinolyl, indolyl, carbolinyl, quinoxalinyl, benzoimidazolyl, naphthyridinyl, or phenanthrolinyl, and particularly preferably pyridyl, quinolyl, or isoquinolyl.

In the general formula (9), when $A_2$ is a divalent group that results from the removal of two hydrogen atoms from substituted or unsubstituted benzene, and $A_3$ is a single bond, $B_2$ is preferably a nitrogen-containing aromatic heterocyclic group, such as pyridyl, bipyridyl, quinolyl, isoquinolyl, indolyl, carbazolyl, carbolinyl, benzoxazolyl, benzothiazolyl, quinoxalinyl, benzoimidazolyl, naphthyridinyl, phenanthrolinyl, or acridinyl, further preferably pyridyl, bipyridyl, quinolyl, isoquinolyl, indolyl, carbolinyl, quinoxalinyl, benzoimidazolyl, naphthyridinyl, or phenanthrolinyl, and particularly preferably pyridyl, bipyridyl, quinolyl, or isoquinolyl.

In the general formula (9), when $B_2$ is pyridyl or bipyridyl, and $A_3$ is a single bond, $A_2$ is further preferably divalent groups that result from the removal of two hydrogen atoms from benzene, biphenyl, naphthalene, anthracene, fluorene, phenanthrene, or pyrene, or a single bond, and particularly preferably divalent groups that results from the removal of two hydrogen atoms from benzene or biphenyl, or a single bond.

The arylamine compounds of the general formula (1), for preferred use in the organic EL device of the present invention, can be used as a constitutive material of a hole injection layer or a hole transport layer of an organic EL device. The arylamine compounds of the general formula (1) have high hole mobility and are therefore preferred compounds as material of a hole injection layer or a hole transport layer.

The radialene derivatives of the general formula (2) for preferred use in the organic EL device of the present invention are preferred compounds as a p-doping material into a material commonly used for a hole injection layer or a hole transport layer of an organic EL device.

The arylamine compound of general formula (3) having two triphenylamine structures in the molecule and the arylamine compound of general formula (4) having four triphenylamine structures in the molecule preferably used in the organic EL device of the present invention are a preferred compound as a constitutive material of a hole injection layer or a hole transport layer of an organic EL device.

The arylamine compound of general formula (5) preferably used in the organic EL device of the present invention can be used as a constitutive material of a hole transport layer or an electron blocking layer of an organic EL device. The compound has a high electron blocking performance, and is a preferred compound as a material of a layer adjacent to a light emitting layer on the side of an anode.

The compound of the general formula (6) having an anthracene ring structure preferably used in the organic EL device of the present invention is a preferred compound as a constitutive material of an electron transport layer of an organic EL device.

The compounds of the general formula (7) having a pyrimidine ring structure, for preferable use in the organic EL device of the present invention, are preferred compounds as a constitutive material of an electron transport layer of an organic EL device.

The compounds of the general formula (9) having a benzotriazole ring structure, for preferable use in the organic EL device of the present invention, are preferred compounds as a constitutive material of an electron transport layer of an organic EL device.

The organic EL device of the present invention combines the materials for an organic EL device excellent in hole injection/transport performances, and stability and durability as a thin film, taking the carrier balance into consideration. Therefore, as compared to the ordinary organic EL devices, the hole transport efficiency from the anode to the hole transport layer is improved (and furthermore the hole transport layer is constituted by two layers including the first hole transport layer and the second hole transport layer, for which two kinds of particular arylamine compounds (having particular structure) are selected respectively and combined), and thereby the luminous efficiency is improved, and the durability of the organic EL device is improved, while retaining the lower driving voltage.

Thus, an organic EL device having low driving voltage, high luminous efficiency, and a long lifetime can be attained.

Advantageous Effects of Invention

The organic EL device of the present invention can achieve an organic EL device having excellent hole injection and transport performances, low driving voltage, and high luminous efficiency by selecting a specific arylamine compound (having a specific structure) capable of effectively exhibiting hole injection and transport roles as a material of a hole injection layer and p-doping the compound with an electron acceptor so that holes can be efficiently injected and transported into a hole transport layer from an electrode, and thus, hole injection and transport efficiency into a light emitting layer can be improved.

An organic EL device having low driving voltage, high luminous efficiency, and a long lifetime can be achieved by selecting the two kinds of particular arylamine compounds (having the particular structures) without p-type doping as the materials of the first hole transport layer and the second hole transport layer, and combining the compounds for achieving elaborate carrier balance.

According to the present invention, luminous efficiency, particularly durability can be improved while maintaining low driving voltage of the conventional organic EL device.

BRIEF DESCRIPTION OF DRAWINGS

FIG. 1 is a diagram illustrating the configuration of the organic EL devices of Examples 15 to 22 and Comparative Examples 1 to 4.

DESCRIPTION OF EMBODIMENTS

The following presents specific examples of preferred compounds among the arylamine compounds of the general formula (1) preferably used in the organic EL device of the present invention. The present invention, however, is not restricted to these compounds.

[Chemical Formula 24]

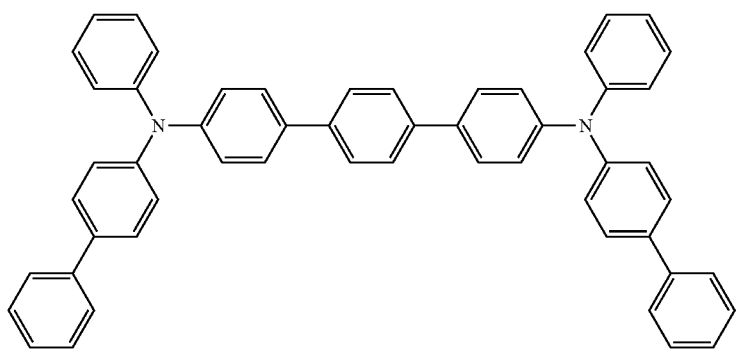

(1-1)

[Chemical Formula 25]

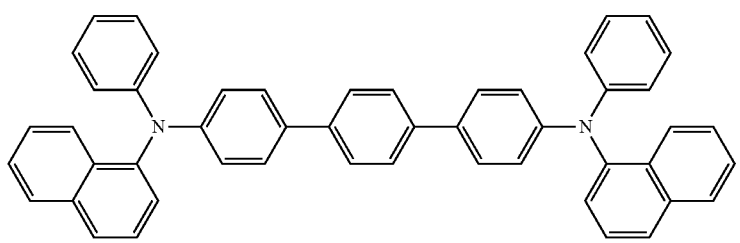

(1-2)

-continued
[Chemical Formula 26]
(1-3)
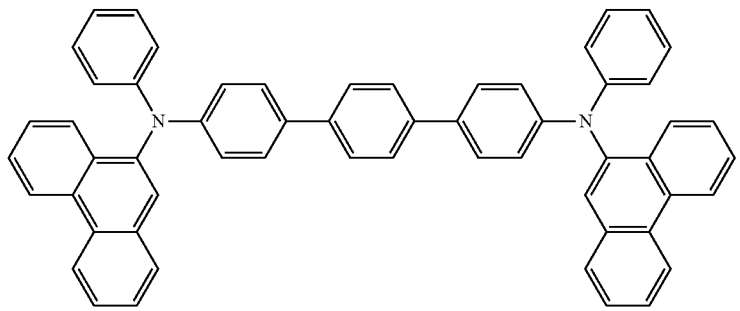
[Chemical Formula 27]
(1-4)
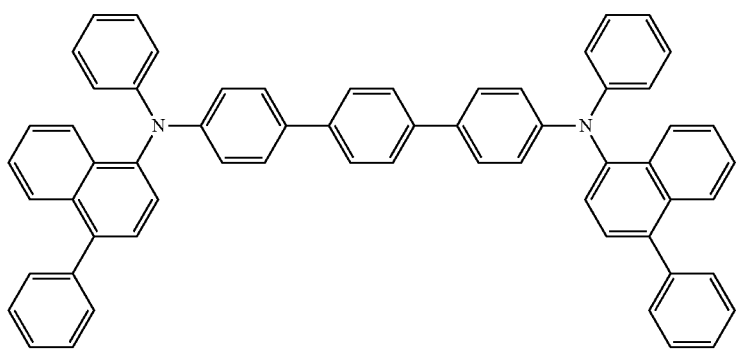
[Chemical Formula 28]
(1-5)
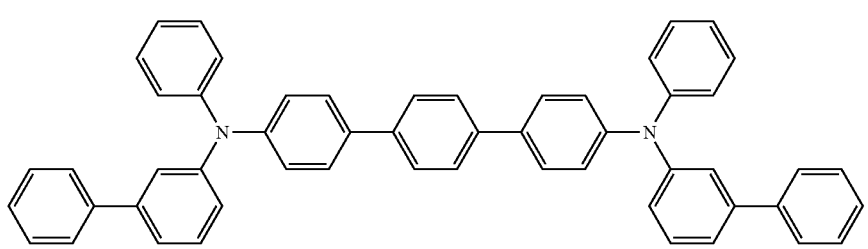
[Chemical Formula 29]
(1-6)
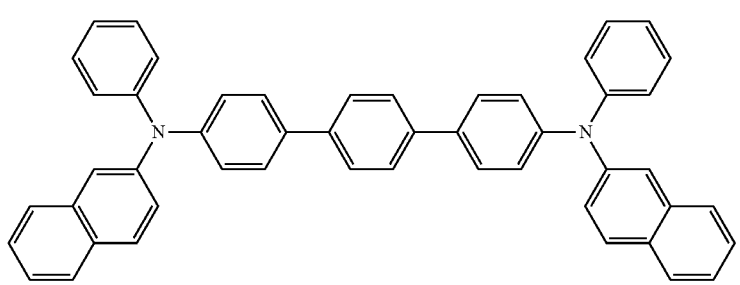
[Chemical Formula 30]
(1-7)
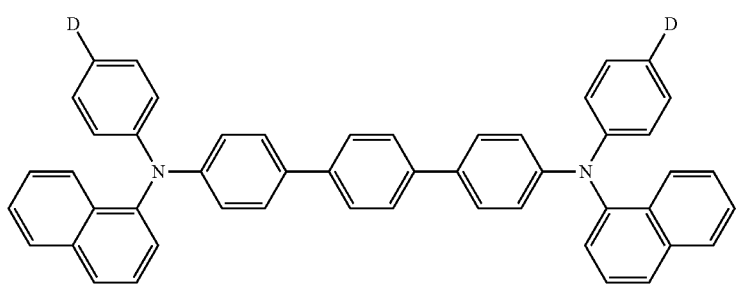

-continued
[Chemical Formula 31]
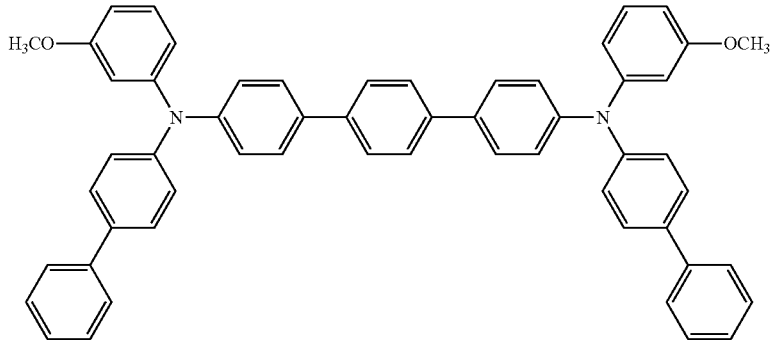
(1-8)
[Chemical Formula 32]
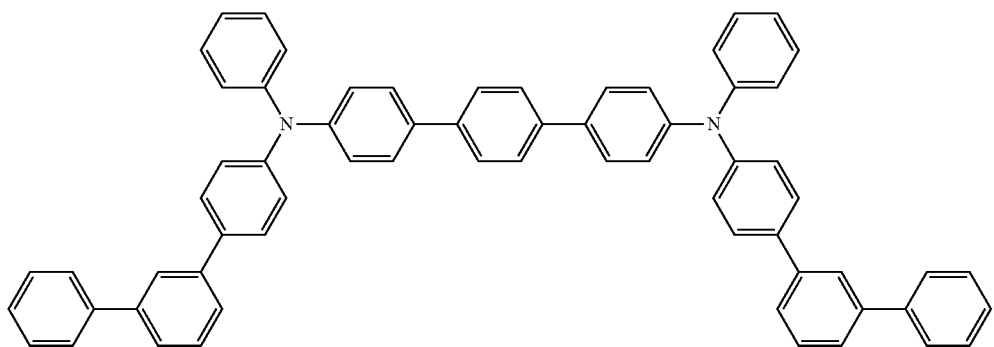
(1-9)
[Chemical Formula 33]
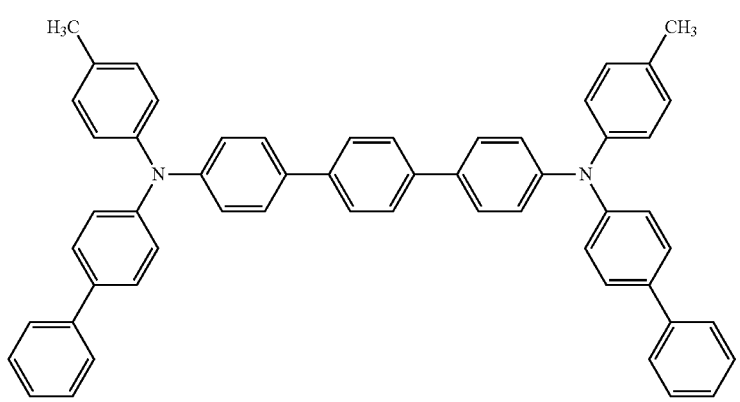
(1-10)
[Chemical Formula 34]
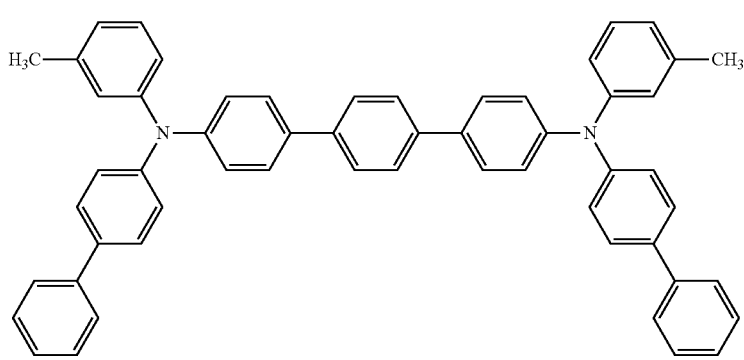
(1-11)

[Chemical Formula 35]
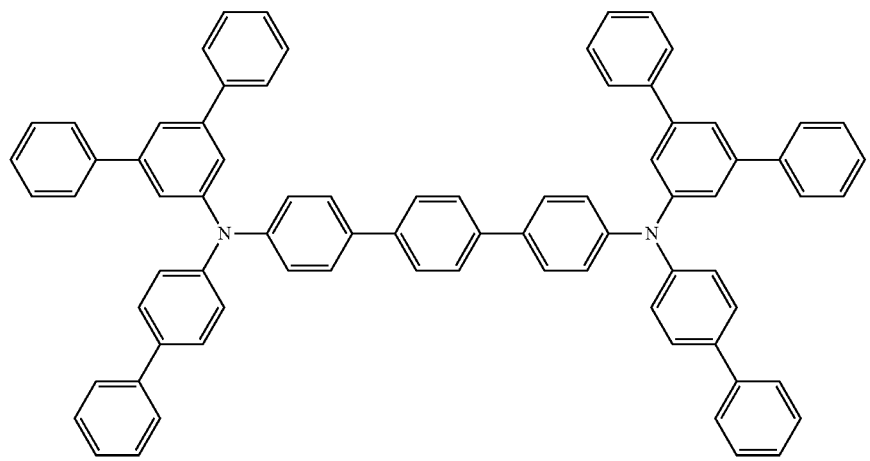
(1-12)
[Chemical Formula 36]
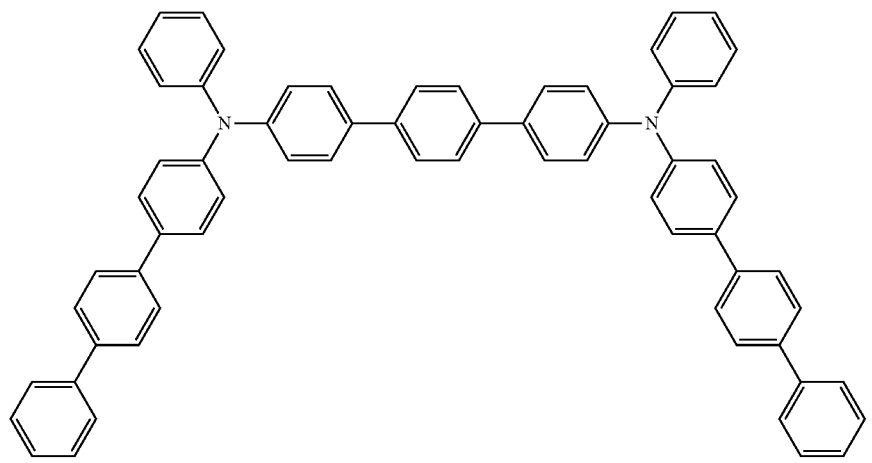
(1-13)
[Chemical Formula 37]
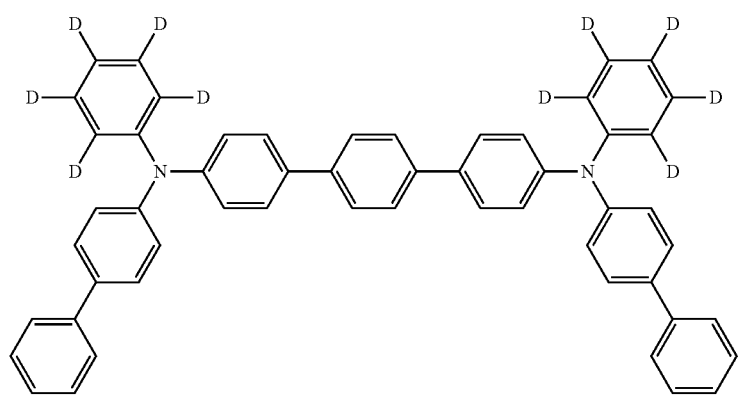
(1-14)

[Chemical Formula 38]
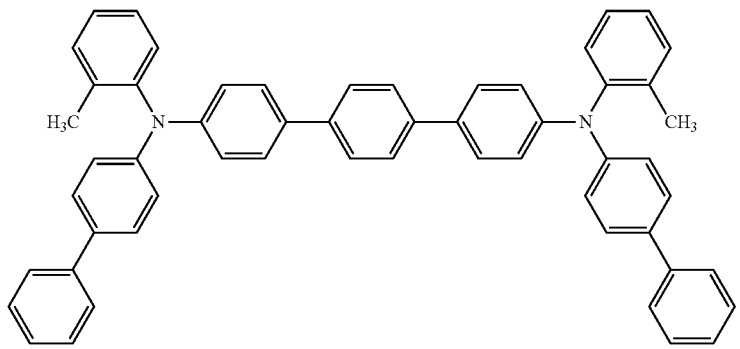
(1-15)
[Chemical Formula 39]
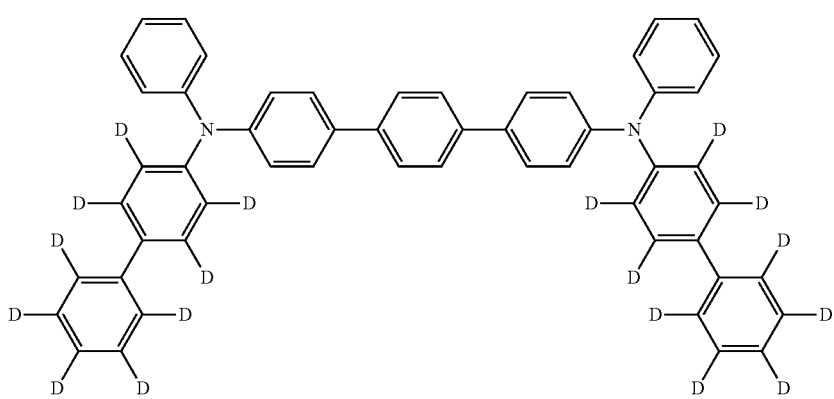
(1-16)
[Chemical Formula 40]
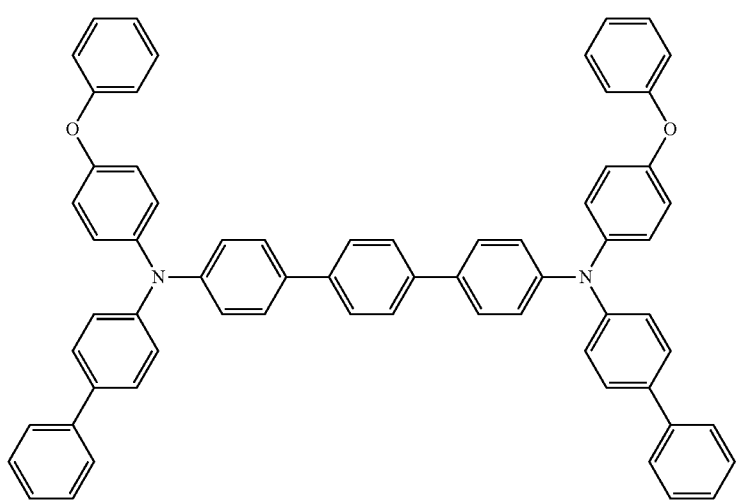
(1-17)

[Chemical Formula 41]
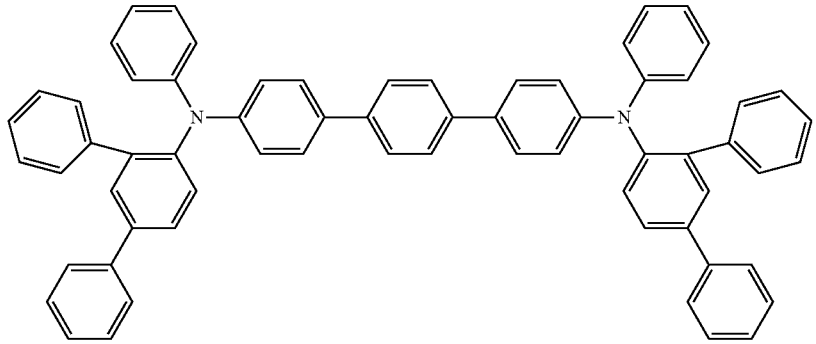
(1-18)
[Chemical Formula 42]
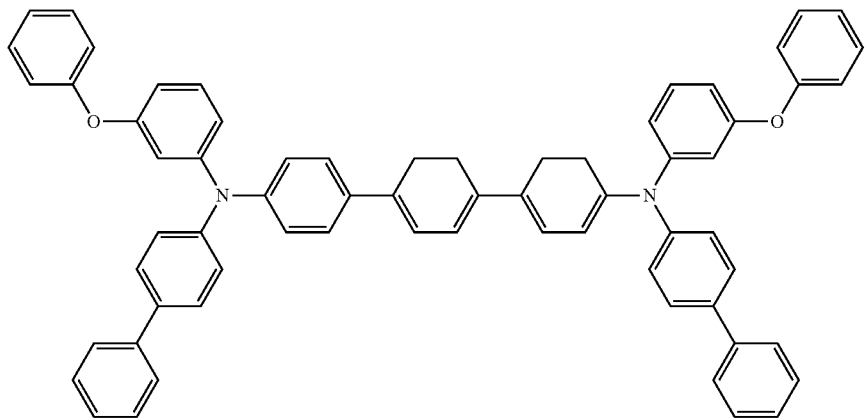
(1-19)
[Chemical Formula 43]
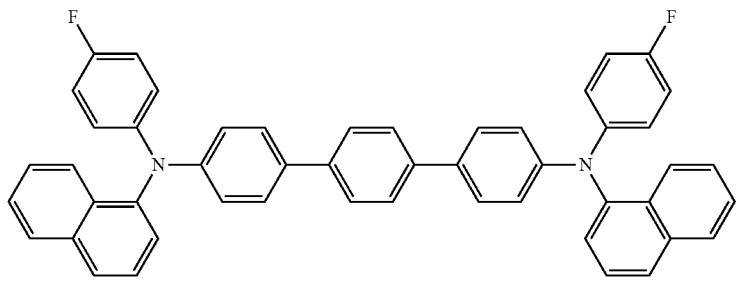
(1-20)

[Chemical Formula 44]
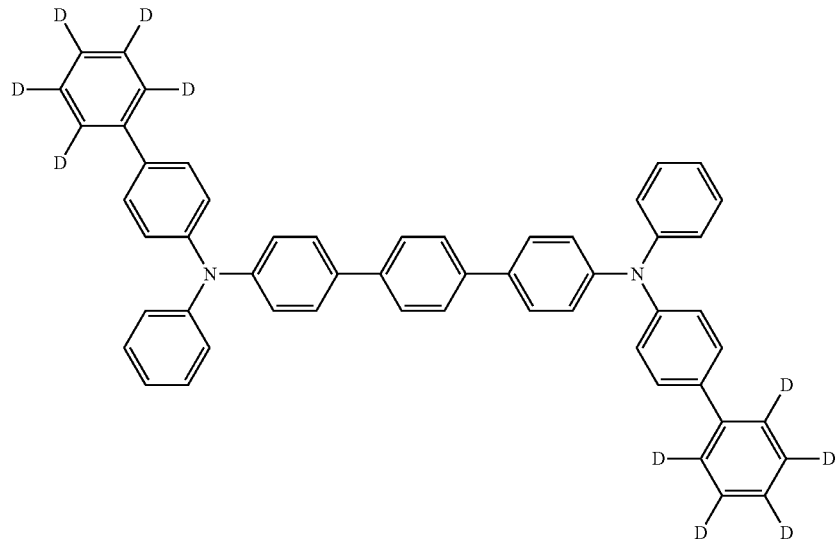
(1-21)
[Chemical Formula 45]
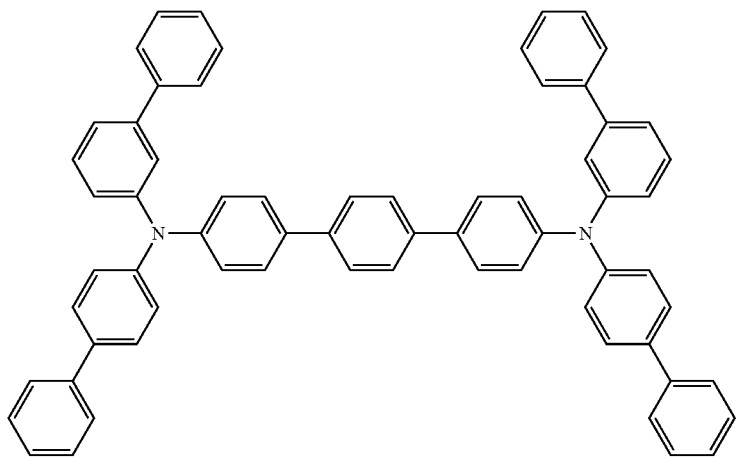
(1-22)
[Chemical Formula 46]
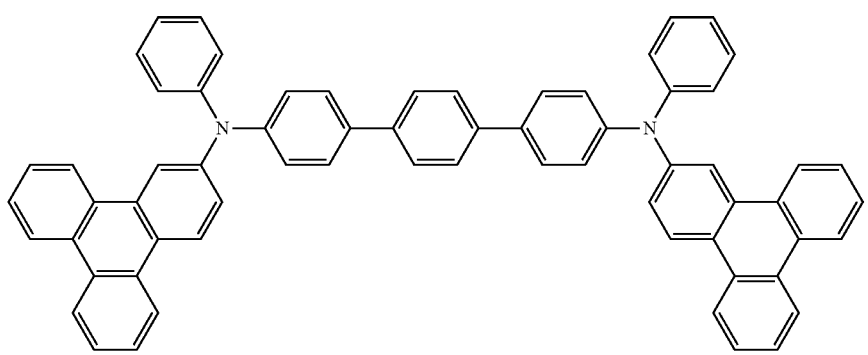
(1-23)

[Chemical Formula 47]
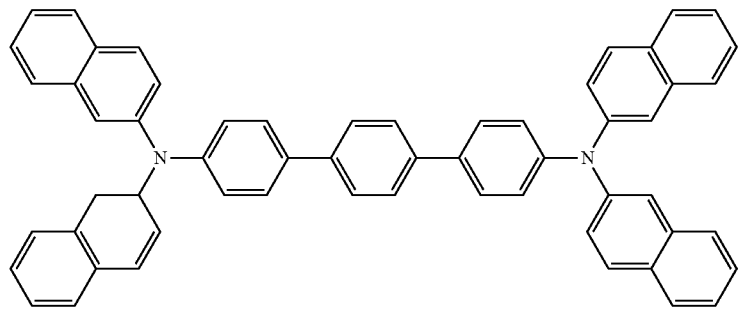
(1-24)
[Chemical Formula 48]
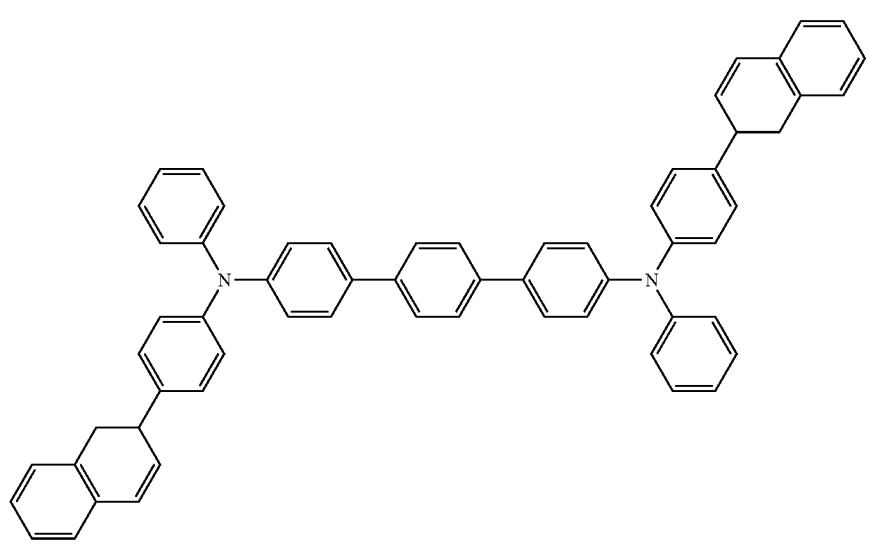
(1-25)
[Chemical Formula 49]
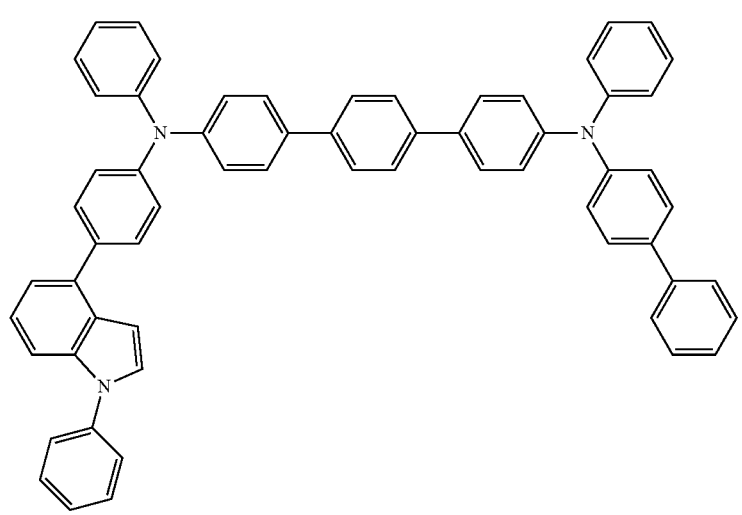
(1-26)

[Chemical Formula 50]
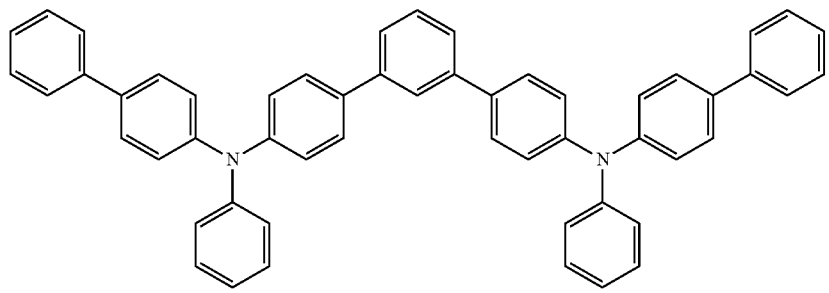
(1-27)
[Chemical Formula 51]
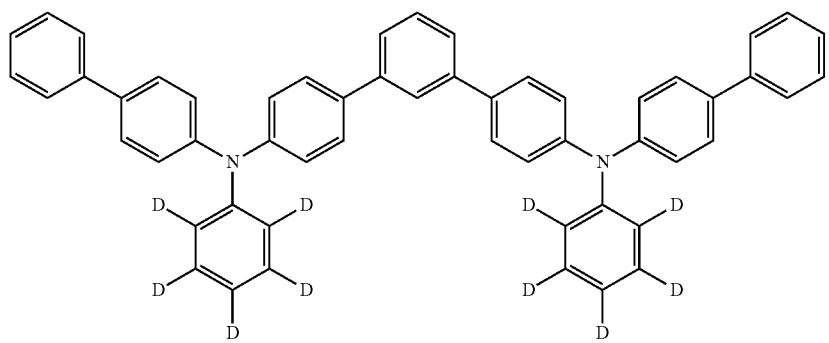
(1-28)
[Chemical Formula 52]
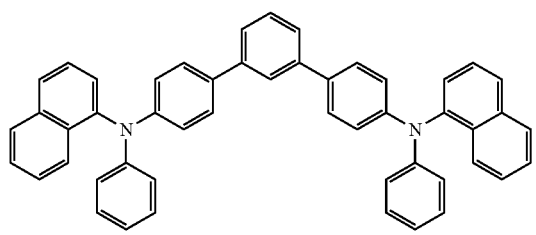
(1-29)
[Chemical Formula 53]
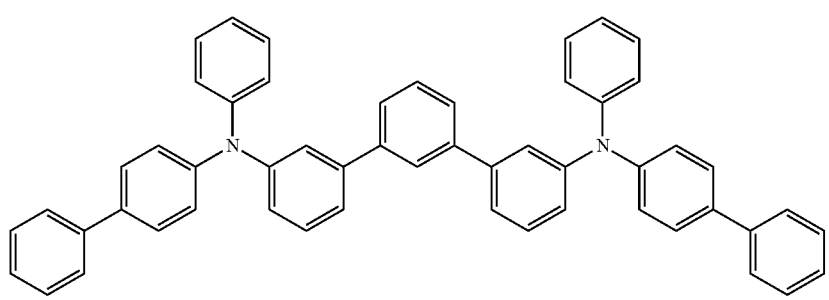
(1-30)

[Chemical Formula 54]
(1-31)
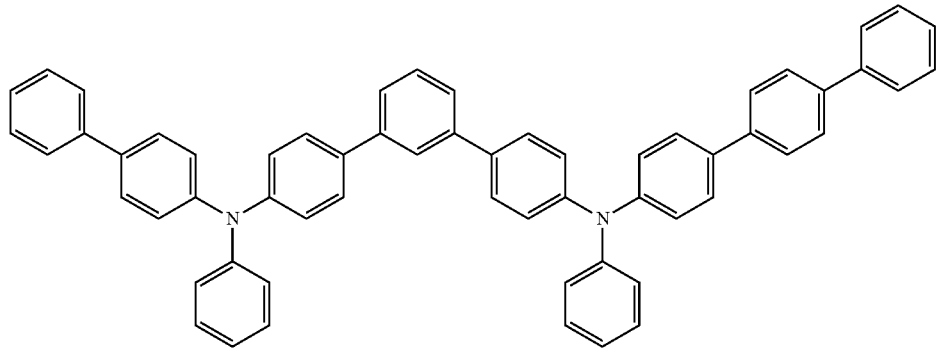
[Chemical Formula 55]
(1-32)
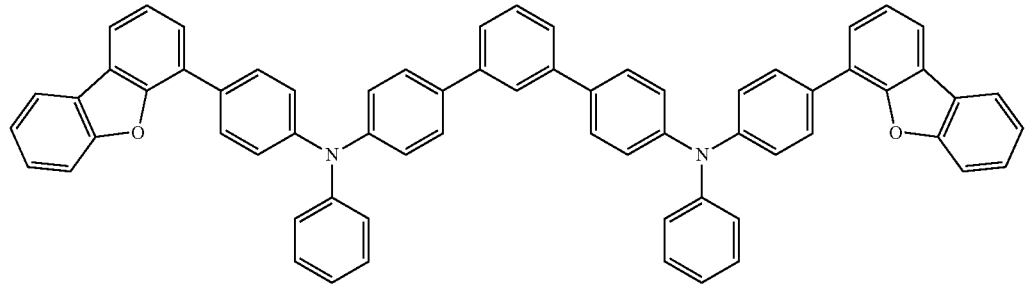
[Chemical Formula 56]
(1-33)
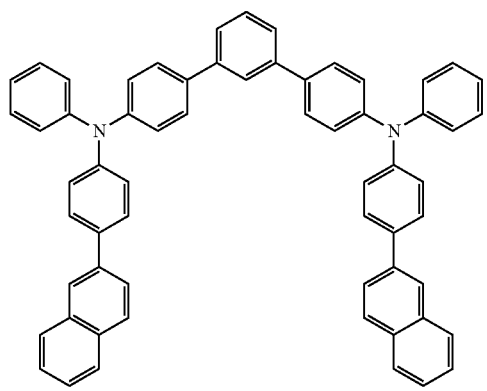
[Chemical Formula 57]
(1-34)
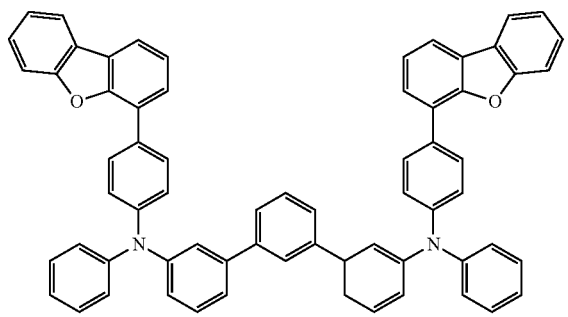
[Chemical Formula 58]
(1-35)
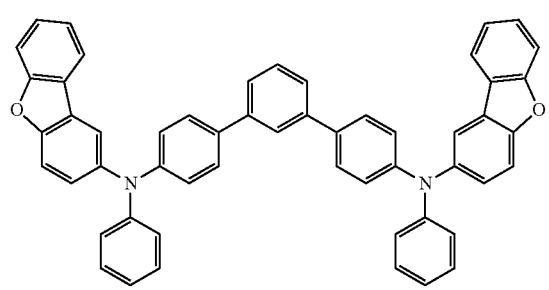

-continued
[Chemical Formula 59]
(1-36)
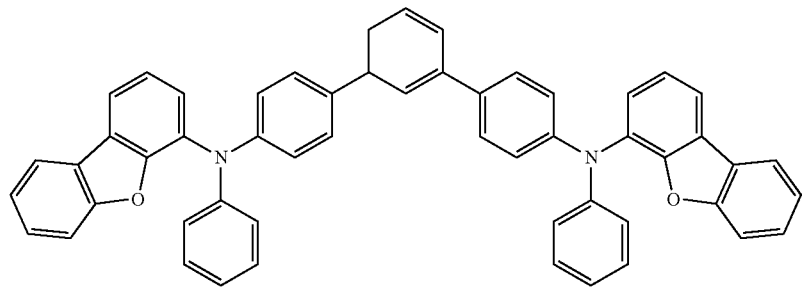
[Chemical Formula 60]
(1-37)
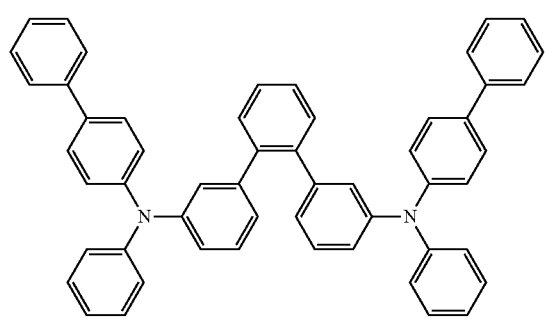
[Chemical Formula 61]
(1-38)
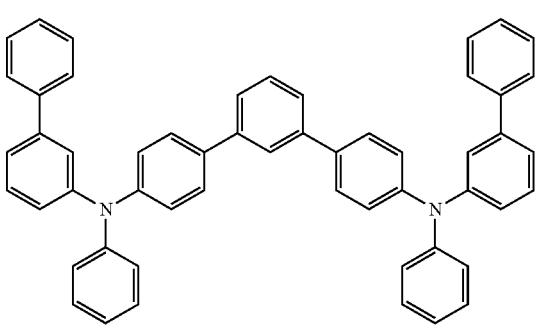
[Chemical Formula 62]
(1-39)
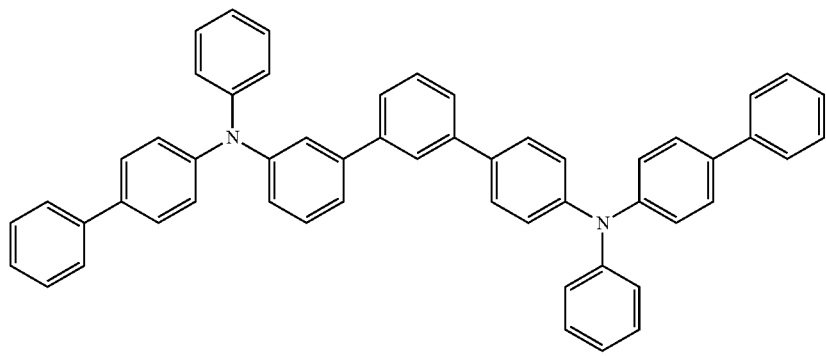
[Chemical Formula 63]
(1-40)
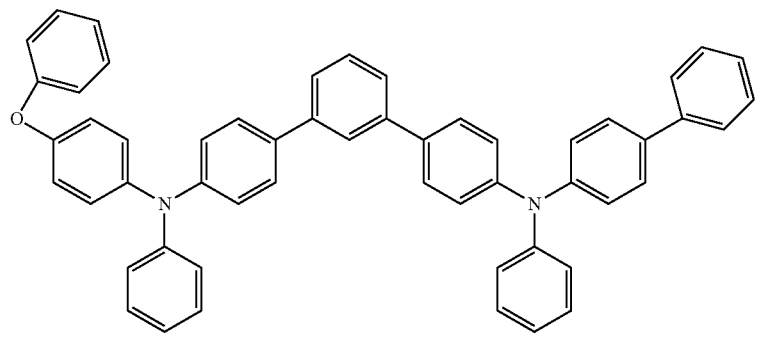

[Chemical Formula 64]
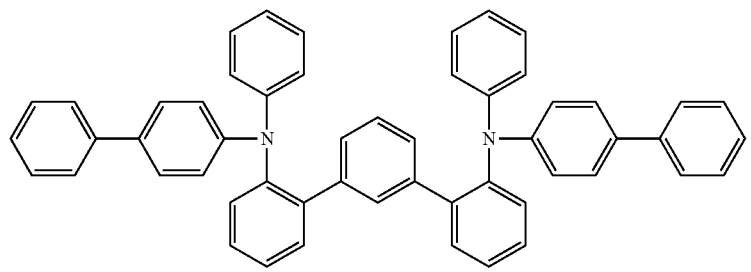
(1-41)
[Chemical Formula 65]
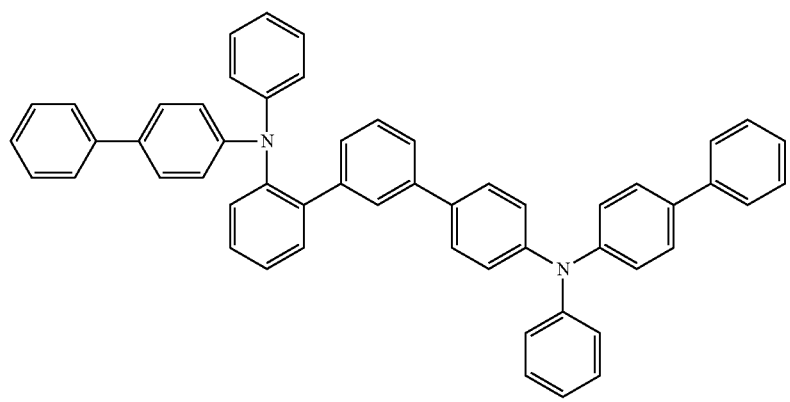
(1-42)
[Chemical Formula 66]
(1-43)
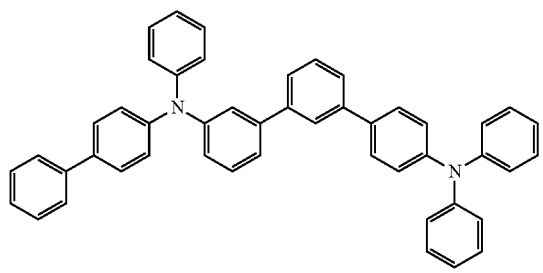
[Chemical Formula 67]
(1-44)
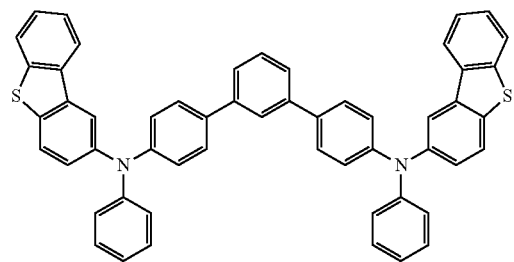
[Chemical Formula 68]
(1-45)
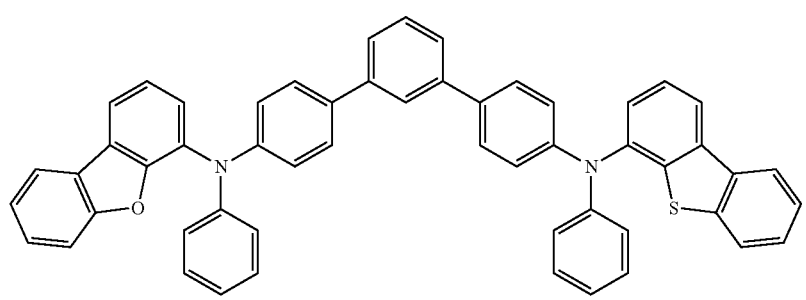

-continued
[Chemical Formula 69]
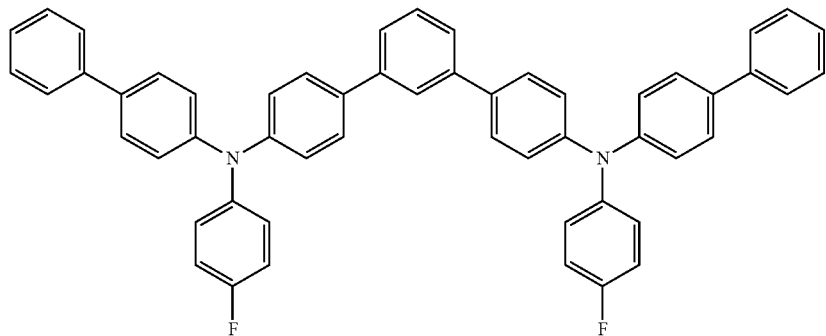
(1-46)
[Chemical Formula 70]
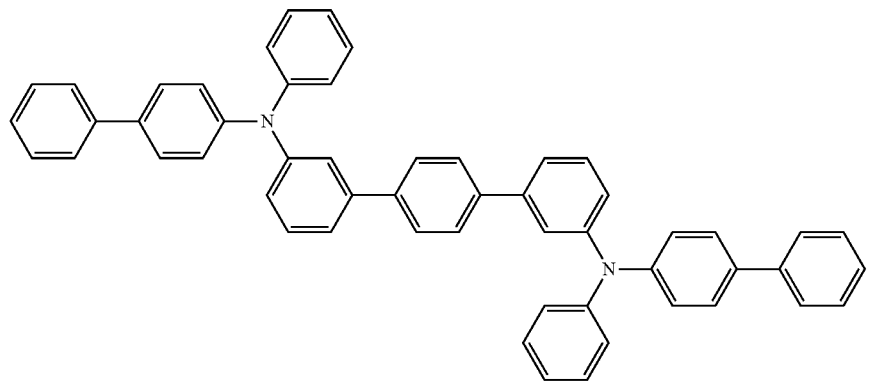
(1-47)
[Chemical Formula 71]
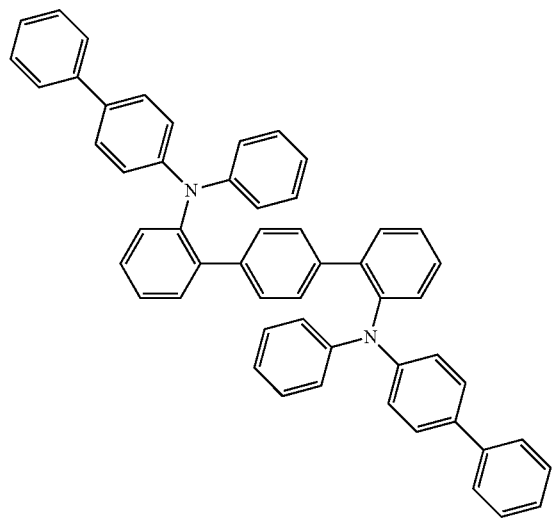
(1-48)

[Chemical Formula 72]
(1-49)
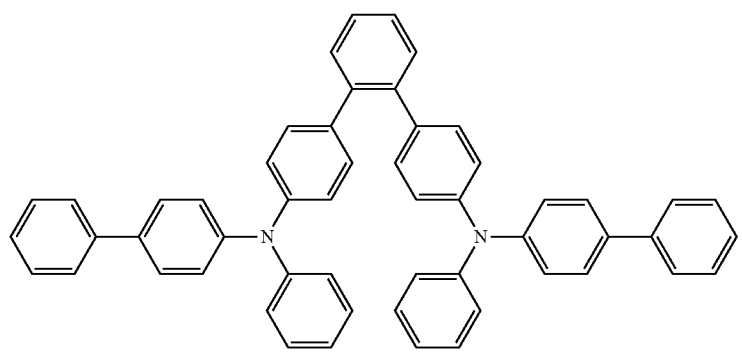
[Chemical Formula 73]
(1-50)
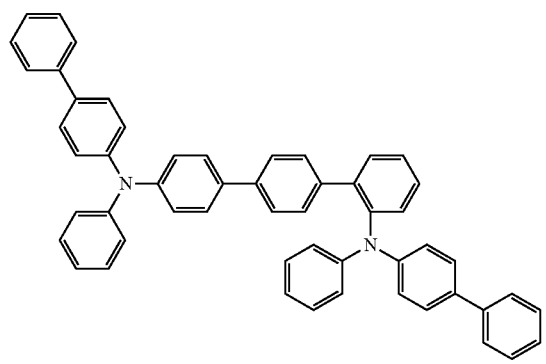
[Chemical Formula 74]
(1-51)
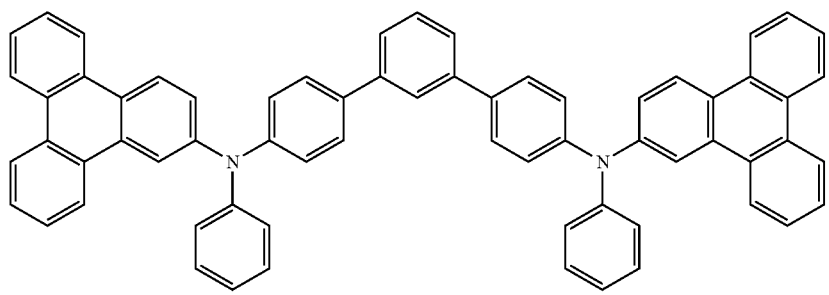
[Chemical Formula 75]
(1-52)
[Chemical Formula 76]
(1-53)
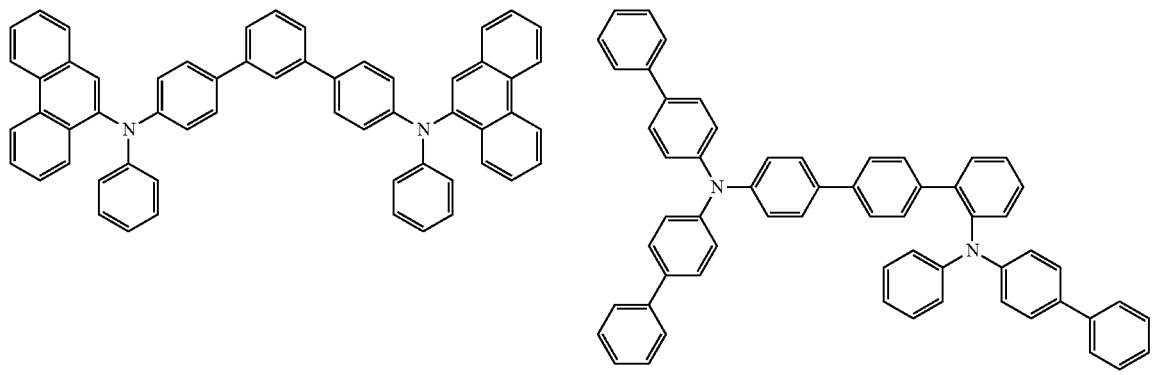

-continued
[Chemical Formula 77]
(1-54)
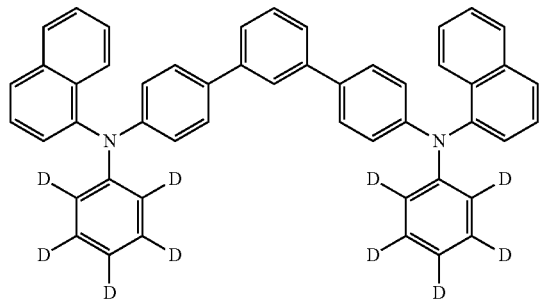
[Chemical Formula 78]
(1-55)
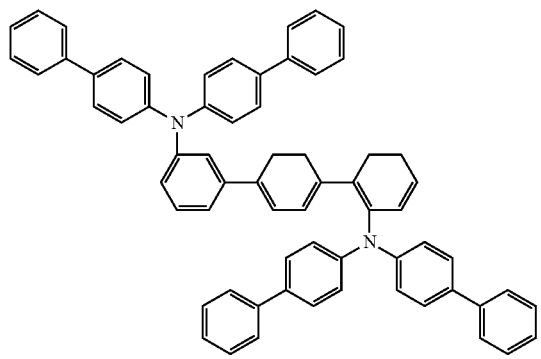
[Chemical Formula 79]
(1-56)
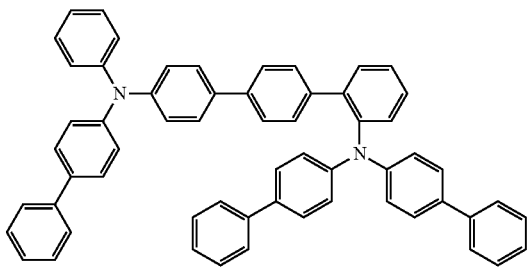
[Chemical Formula 80]
(1-57)
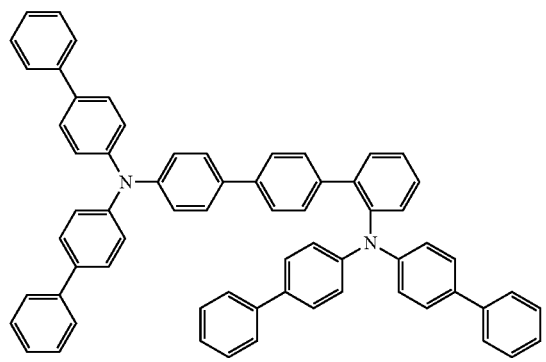
[Chemical Formula 81]
(1-58)
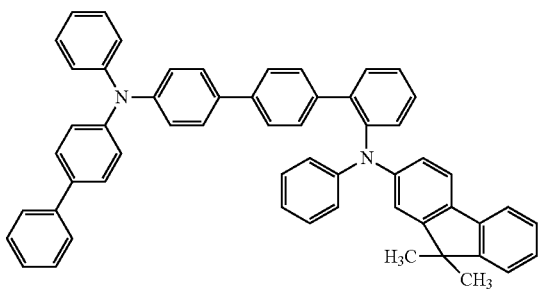
[Chemical Formula 82]
(1-59)
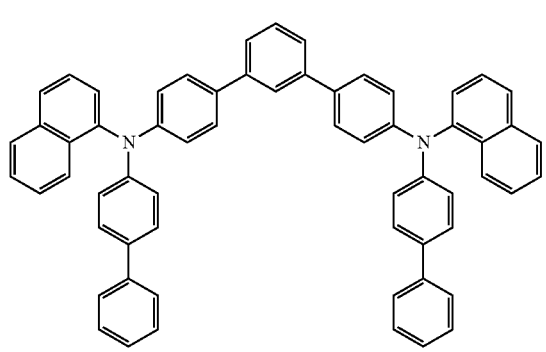

[Chemical Formula 83]
(1-60)
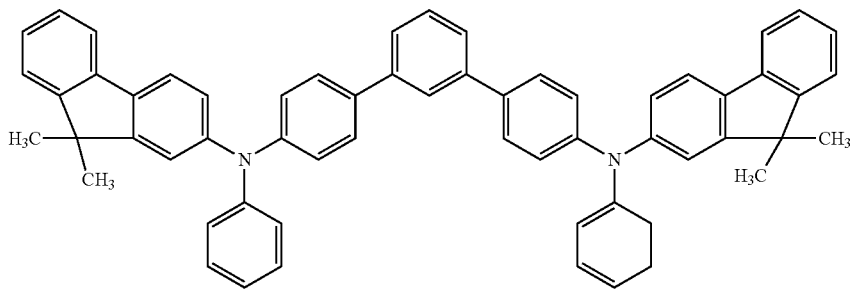
[Chemical Formula 84]
(1-61)
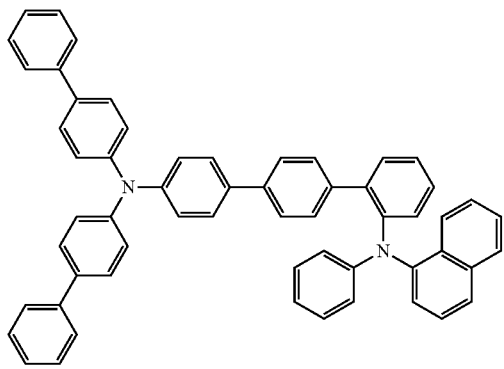
[Chemical Formula 85]
(1-62)
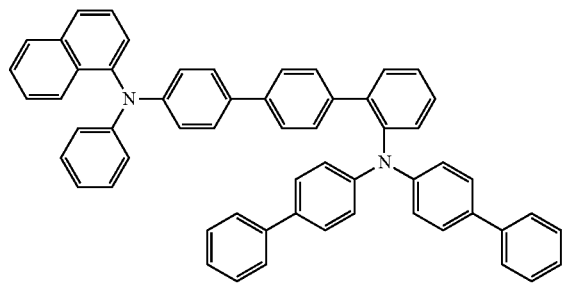
[Chemical Formula 86]
(1-63)
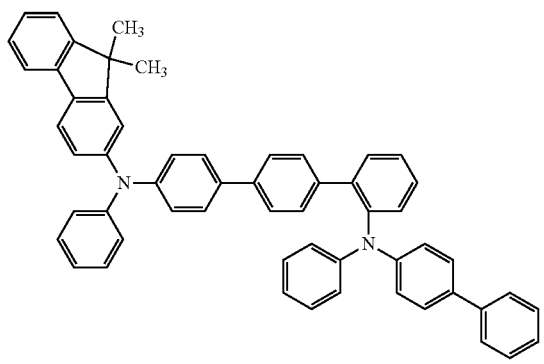
[Chemical Formula 87]
(1-64)
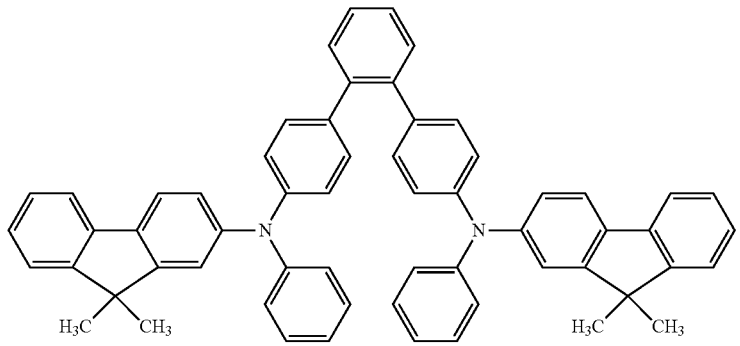

[Chemical Formula 88]
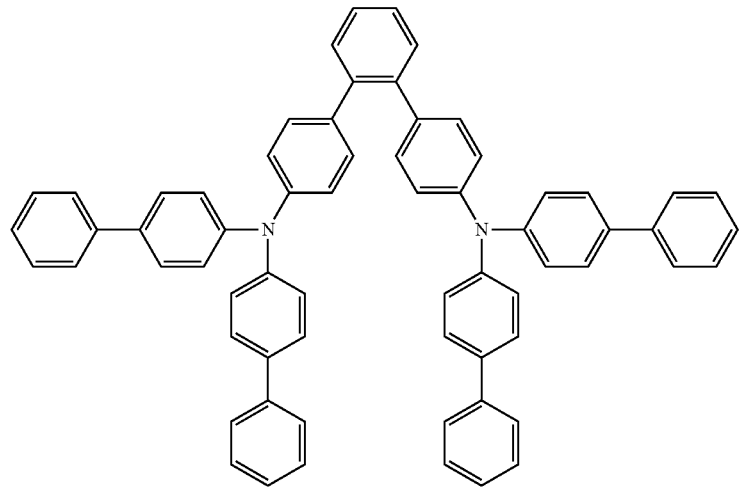
(1-65)
[Chemical Formula 89]
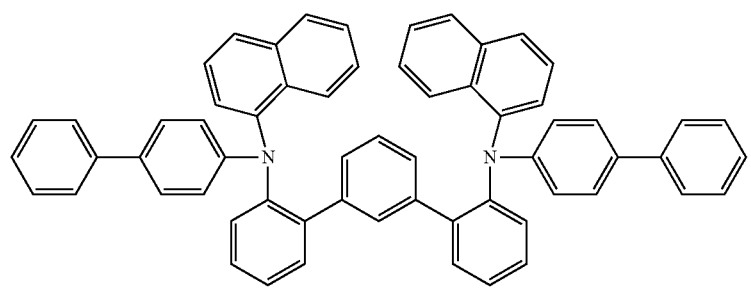
(1-66)
[Chemical Formula 90]
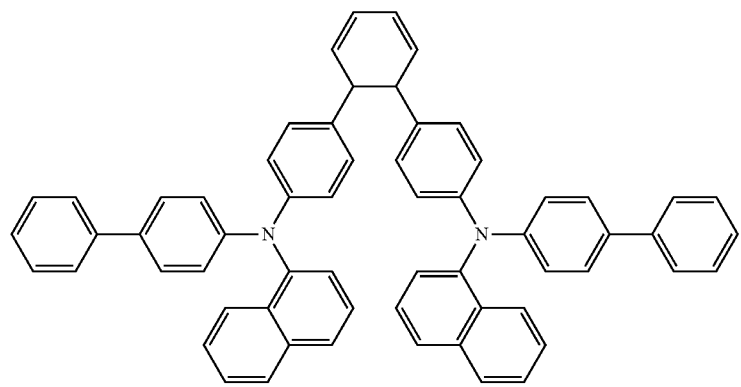
(1-67)

[Chemical Formula 91]
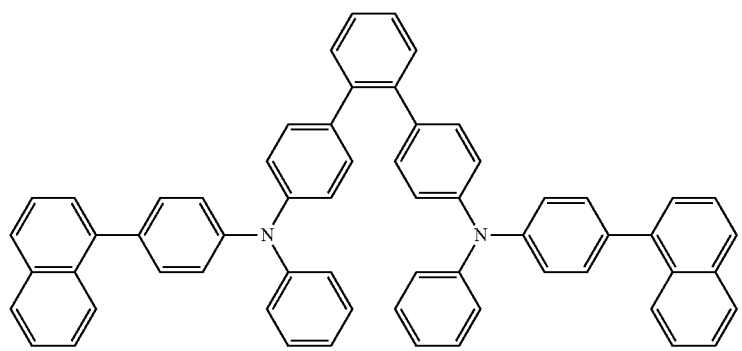
(1-68)
[Chemical Formula 92]
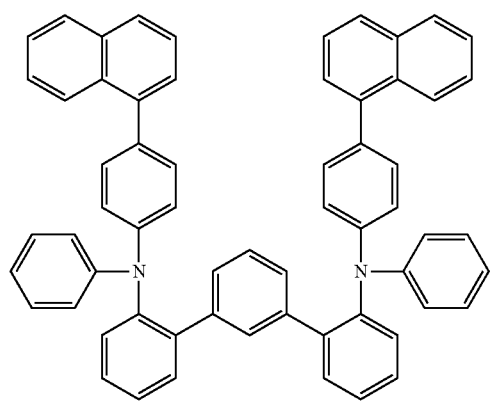
(1-69)
[Chemical Formula 93]
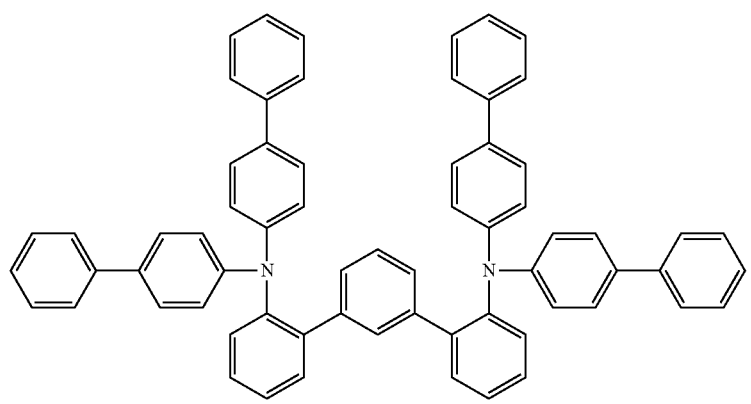
(1-70)
[Chemical Formula 94]
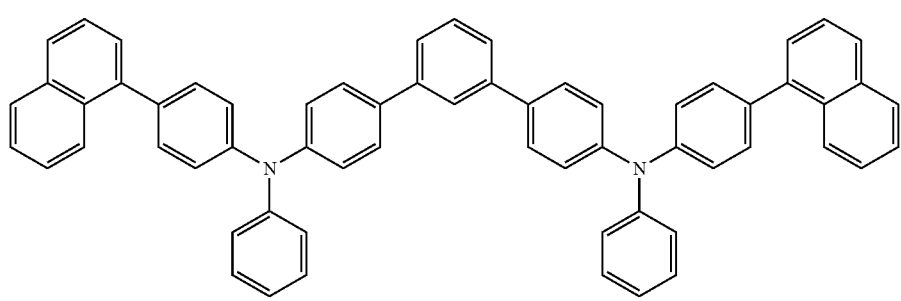
(1-71)

[Chemical Formula 95]
(1-72)
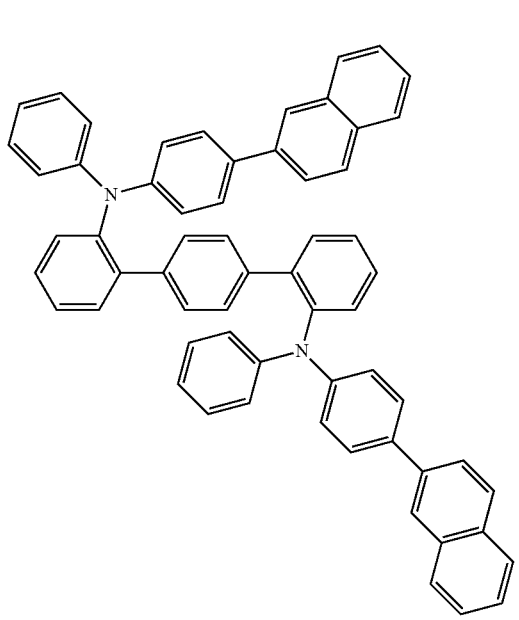
[Chemical Formula 96]
(1-73)
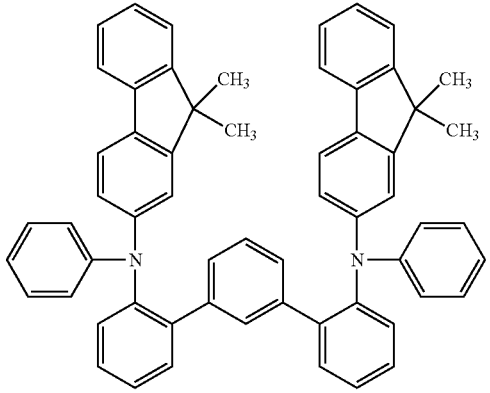
[Chemical Formula 97]
(1-74)
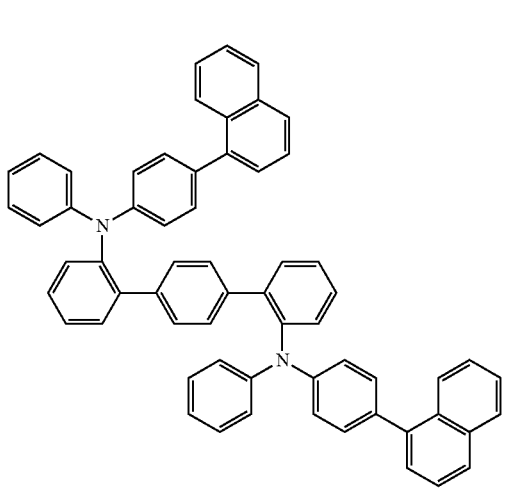
[Chemical Formula 98]
(1-75)
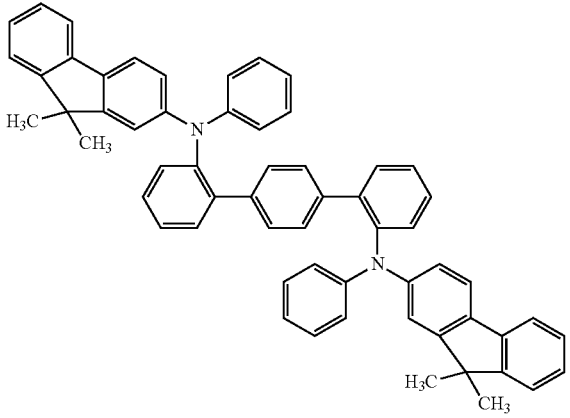
[Chemical Formula 99]
(1-76)
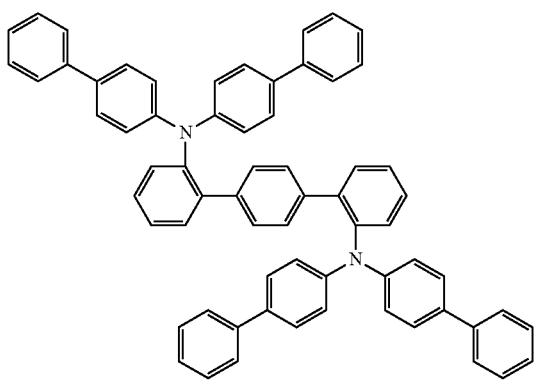
[Chemical Formula 100]
(1-77)
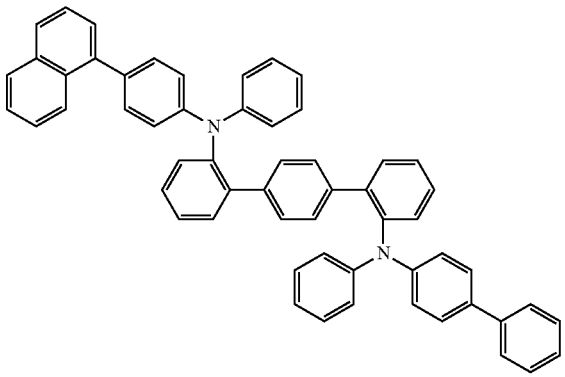

[Chemical Formula 101]
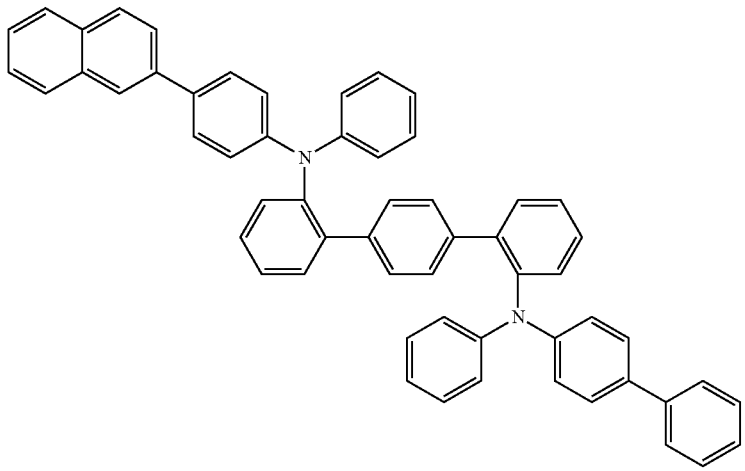
(1-78)
[Chemical Formula 102]
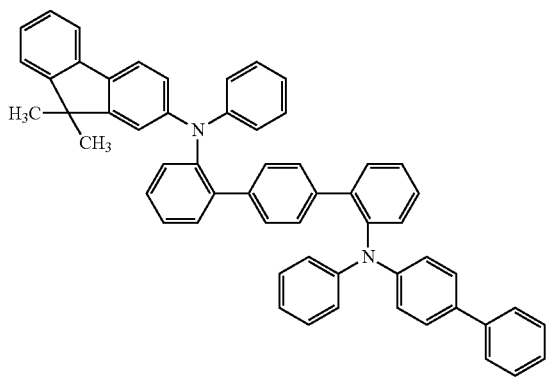
(1-79)
[Chemical Formula 103]
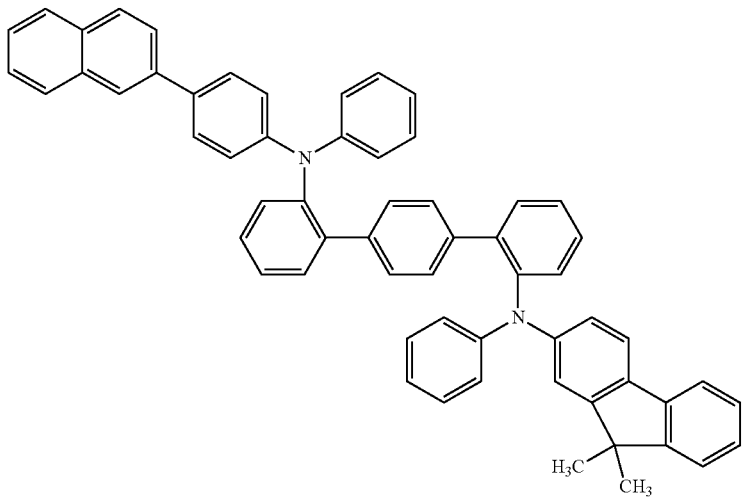
(1-80)

[Chemical Formula 104]
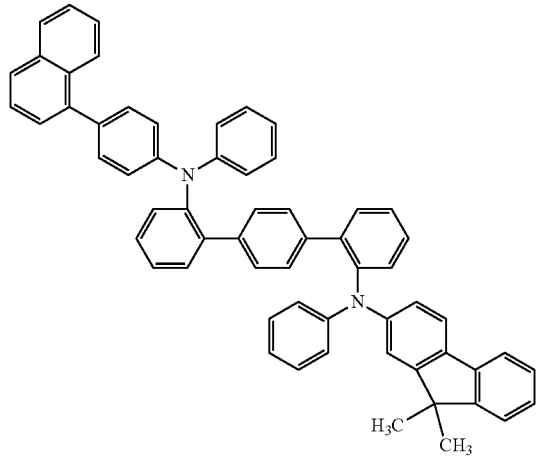
(1-81)
[Chemical Formula 105]
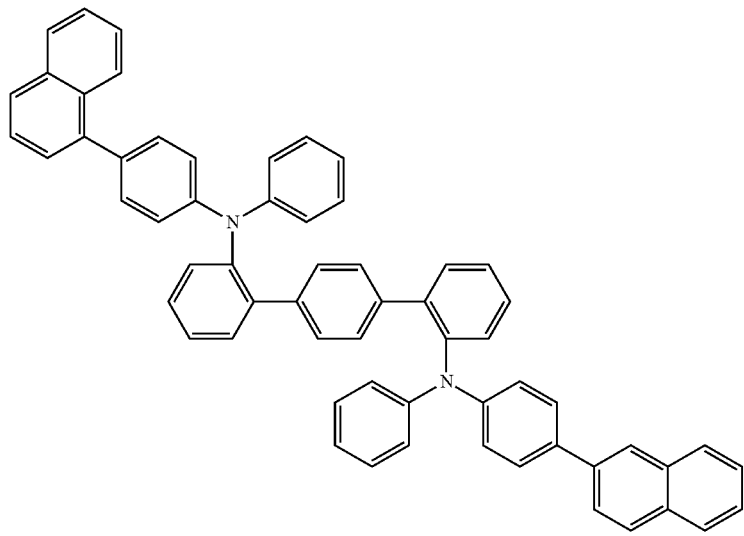
(1-82)
[Chemical Formula 106]
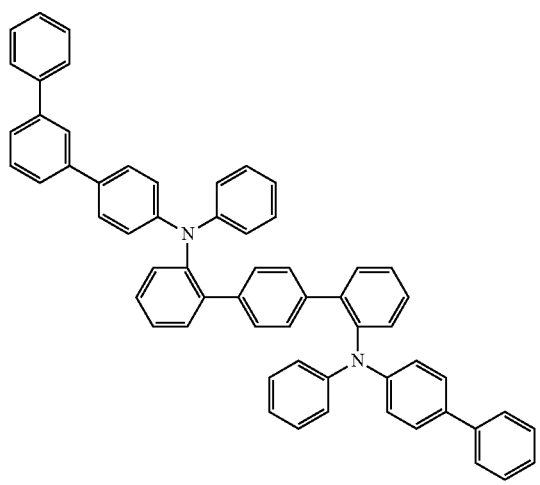
(1-83)

[Chemical Formula 107]
(1-84)
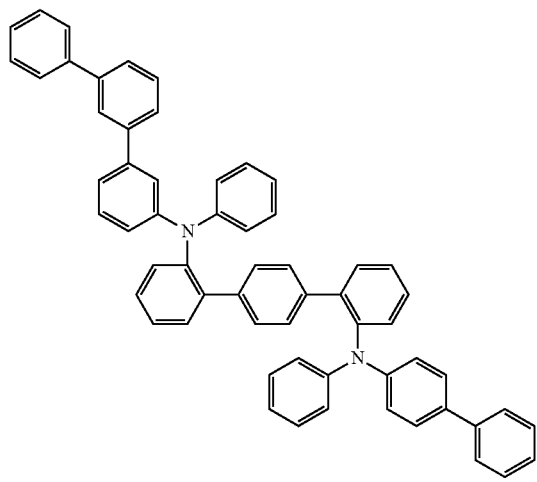
[Chemical Formula 108]
(1-85)
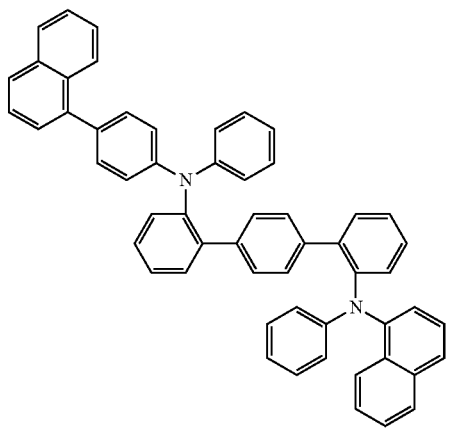
[Chemical Formula 109]
(1-86)
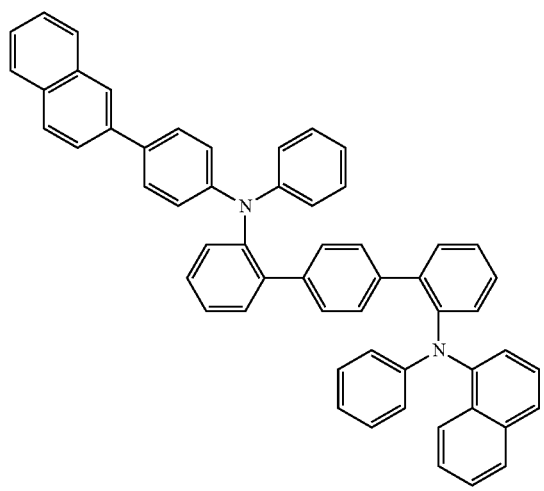
[Chemical Formula 110]
(1-87)
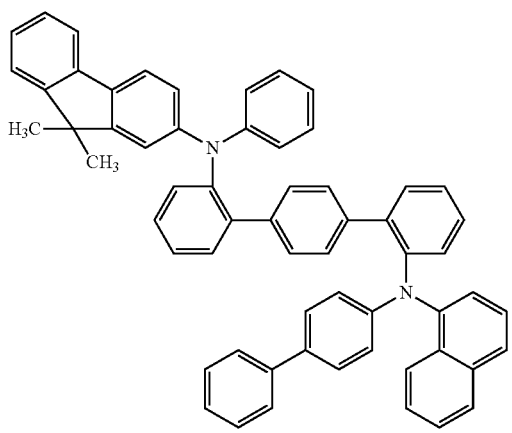
[Chemical Formula 111]
(1-88)
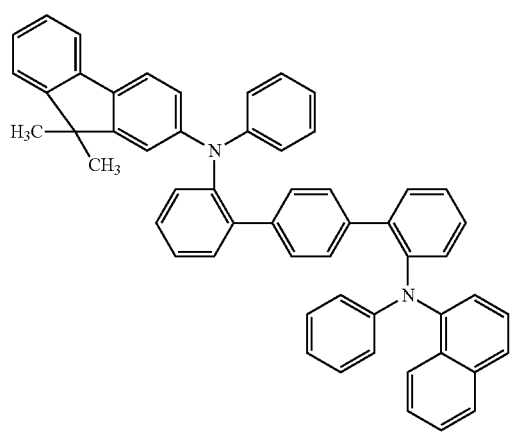
[Chemical Formula 112]
(1-89)
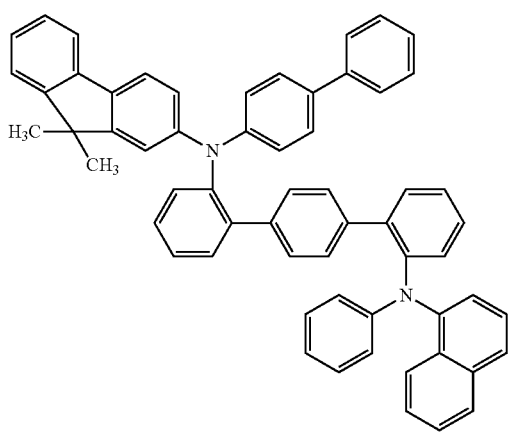

[Chemical Formula 113]

(1-90)

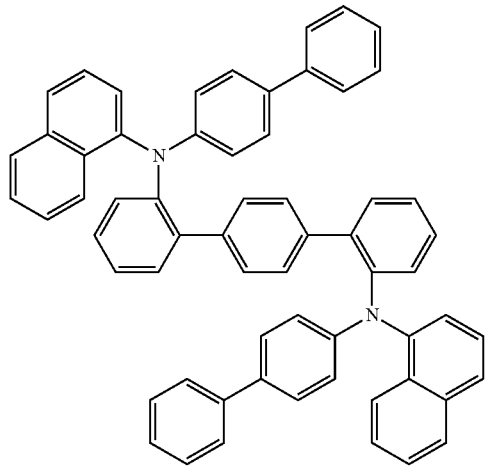

[Chemical Formula 114]

(1-91)

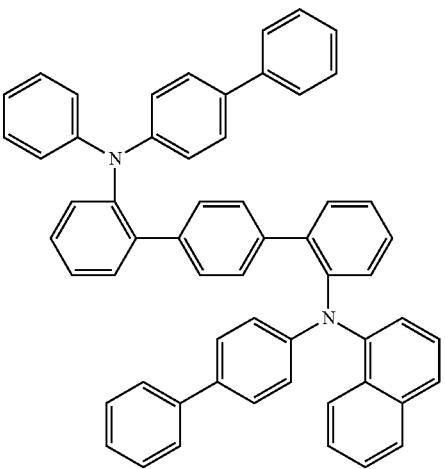

The arylamine compounds described above can be synthesized by a known method (refer to PTL 7, for example).

The following presents specific examples of preferred compounds among the arylamine compounds of the general formula (3) preferably used in the organic EL device of the present invention. The present invention, however, is not restricted to these compounds.

[Chemical Formula 115]

(3-1)

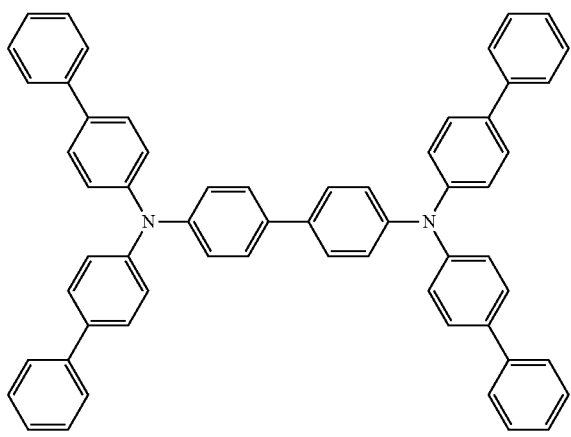

-continued

[Chemical Formula 116]

(3-2)

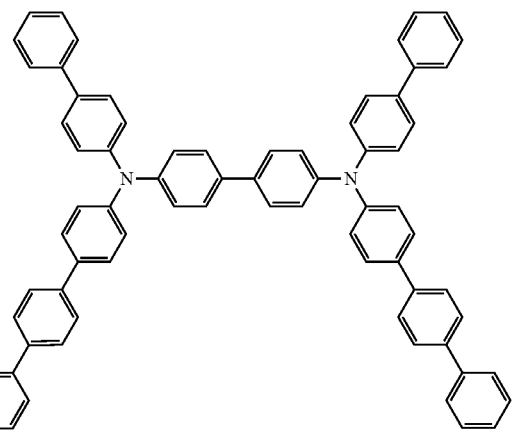

[Chemical Formula 117]

(3-3)

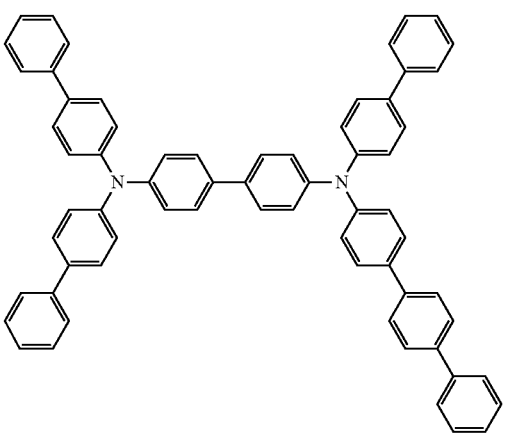

[Chemical Formula 118]
(3-4)
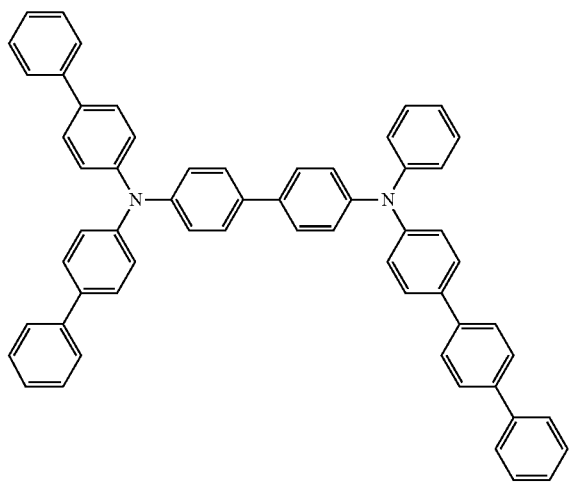
[Chemical Formula 119]
(3-5)
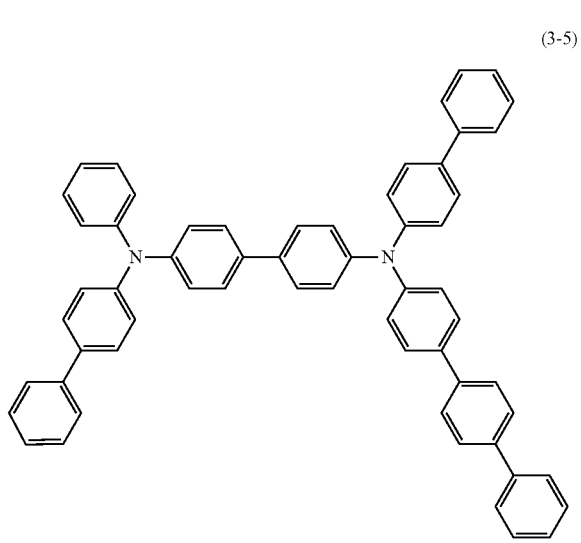
[Chemical Formula 120]
(3-6)
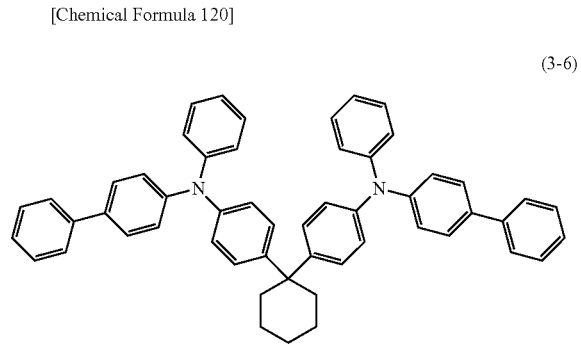
[Chemical Formula 121]
(3-7)
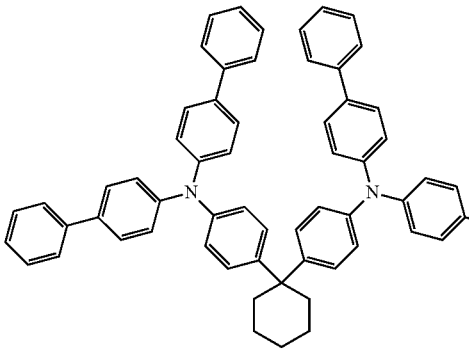
[Chemical Formula 122]
(3-8)
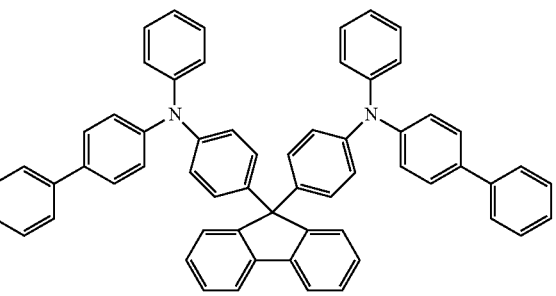
[Chemical Formula 123]
(3-9)
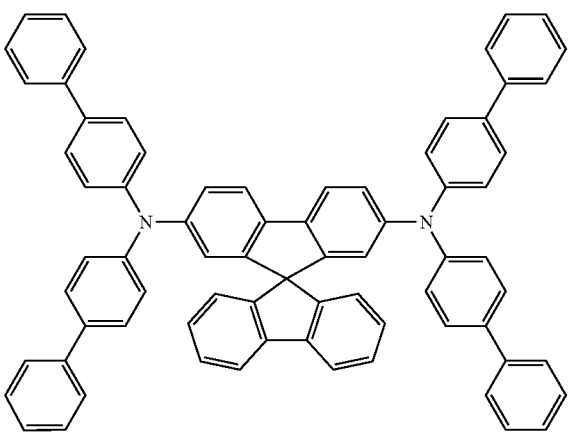

[Chemical Formula 124]
(3-10)
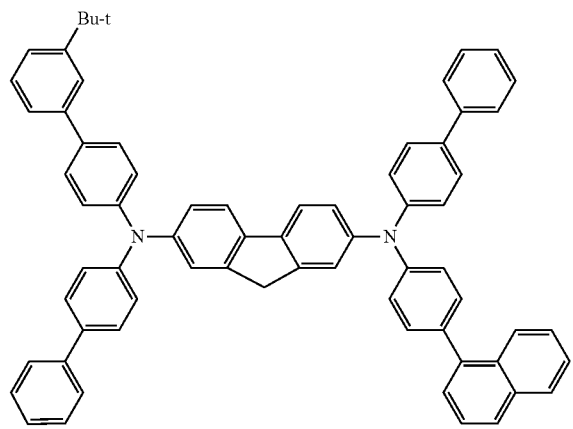
[Chemical Formula 125]
(3-11)
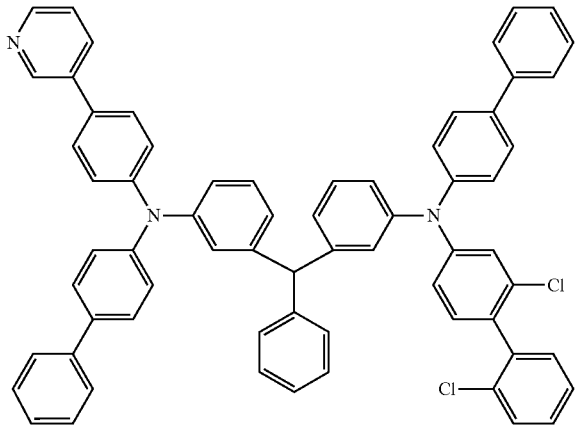
[Chemical Formula 126]
(3-12)
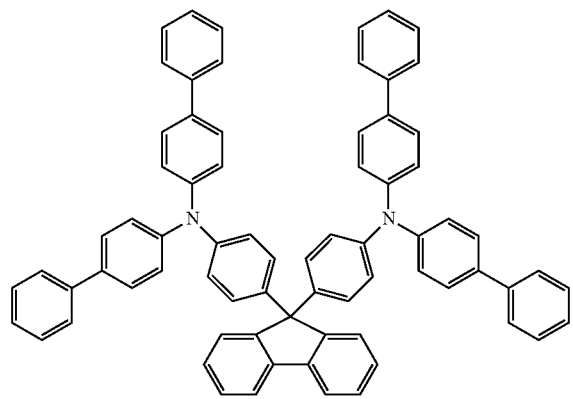
[Chemical Formula 127]
(3-13)
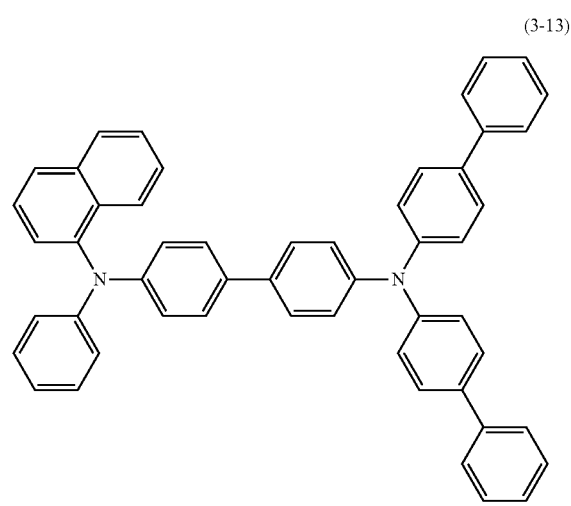
[Chemical Formula 128]
(3-14)
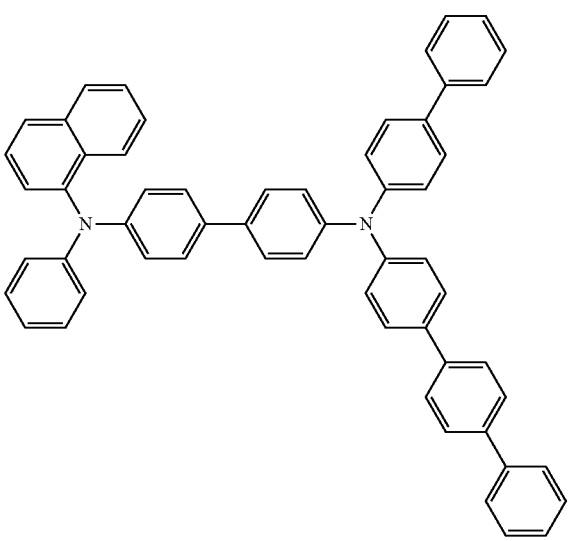
[Chemical Formula 129]
(3-15)
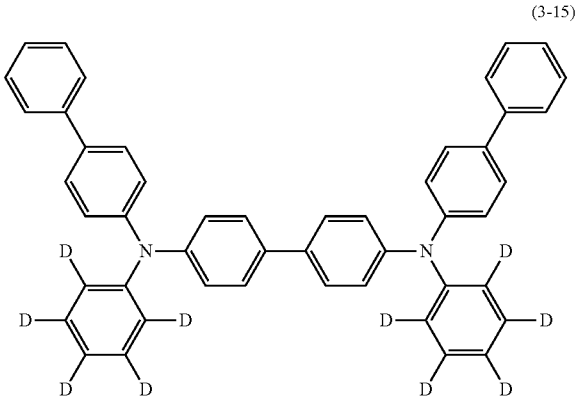

[Chemical Formula 130]
(3-16)
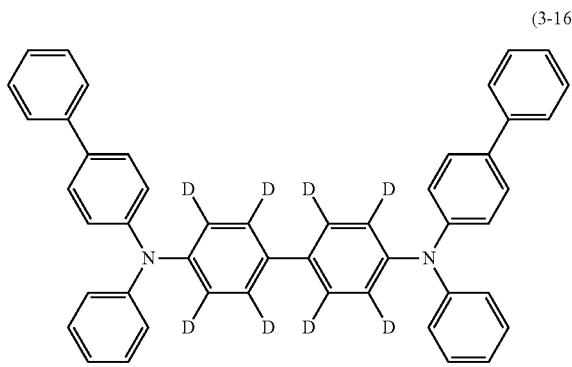
[Chemical Formula 131]
(3-17)
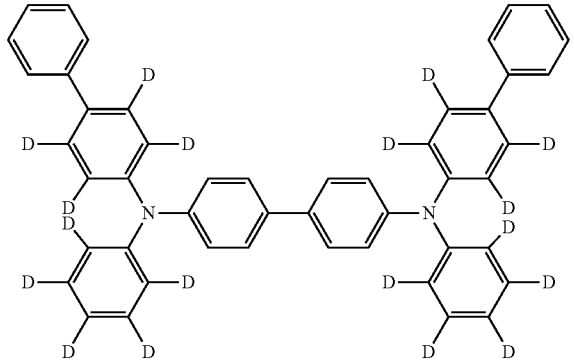
[Chemical Formula 132]
(3-18)
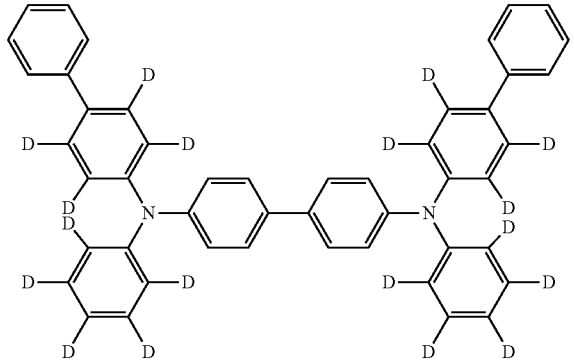
[Chemical Formula 133]
(3-19)
[Chemical Formula 134]
(3-20)
[Chemical Formula 135]
(3-21)
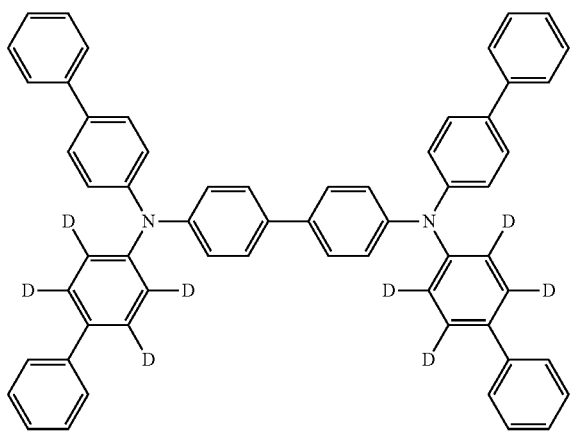

-continued

[Chemical Formula 136]

(3-22)

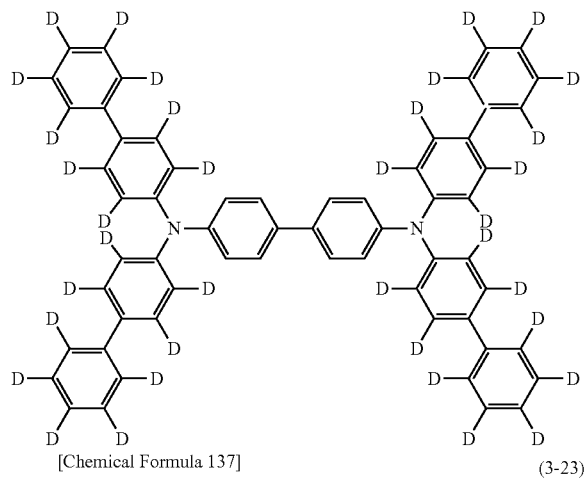

[Chemical Formula 137]

(3-23)

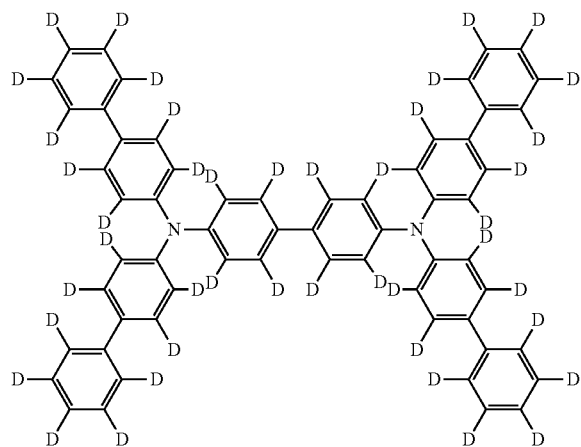

The following presents specific examples of preferred compounds of the arylamine compounds having two triphenylamine structures in the molecule among the arylamine compounds having a structure in which two to six triphenylamine structures in the molecule bind via a single bond or a divalent group that does not contain a heteroatom preferably used in the organic EL device of the present invention, in addition to the arylamine compounds of general formula (3). The present invention, however, is not restricted to these compounds.

[Chemical Formula 138]

(3'-1)

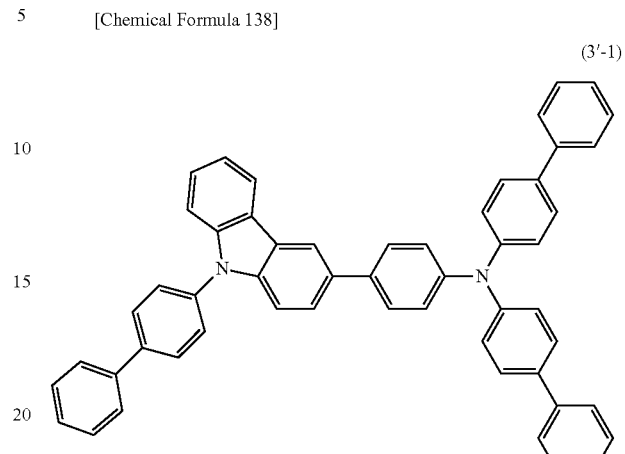

[Chemical Formula 139]

(3'-2)

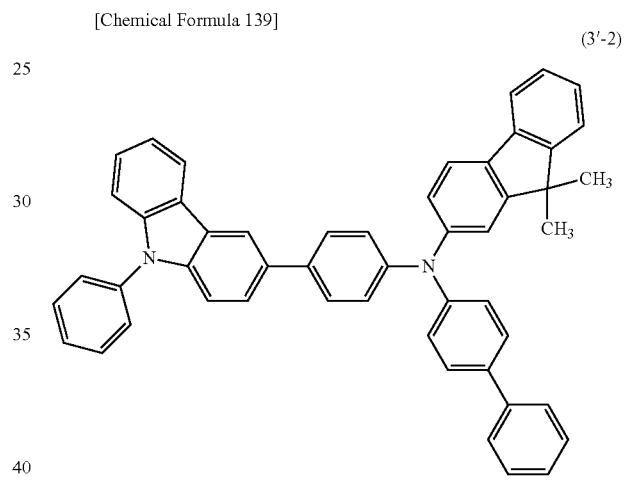

The following presents specific examples of preferred compounds among the arylamine compounds of the general formula (4) preferably used in the organic EL device of the present invention. The present invention, however, is not restricted to these compounds.

[Chemical Formula 140]

(4-1)

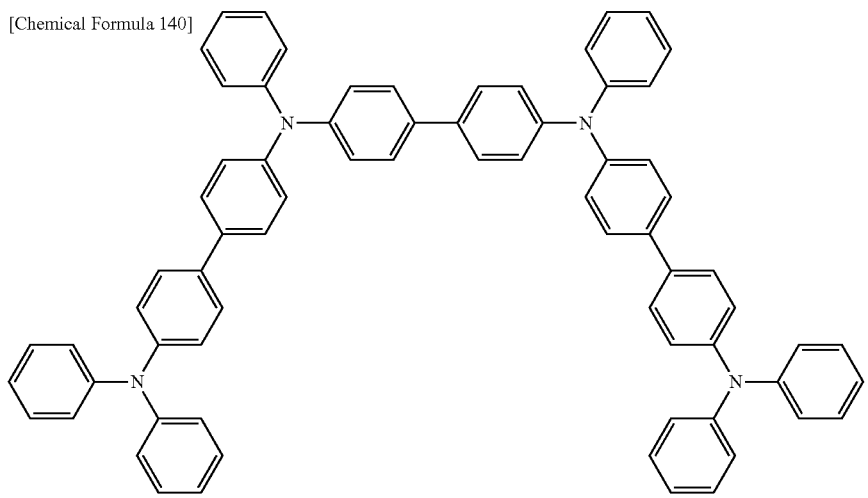

[Chemical Formula 141]
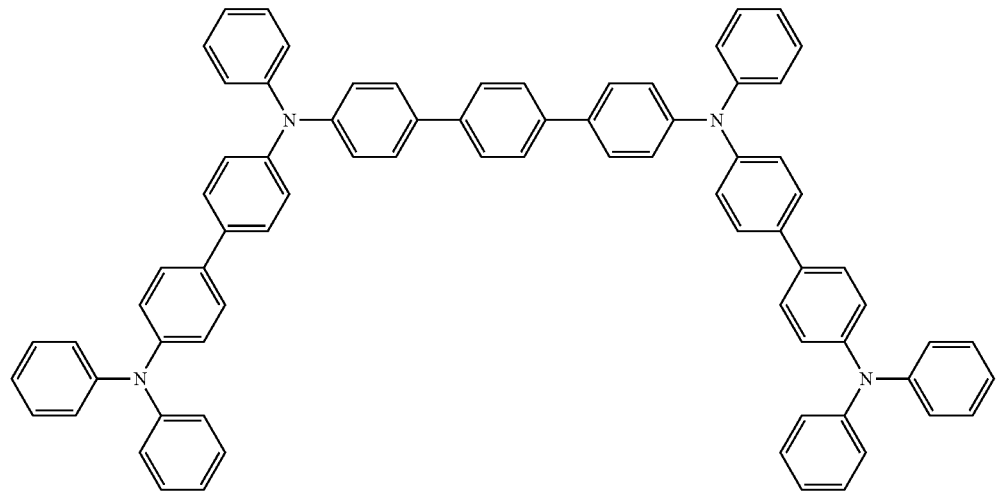
(4-2)
[Chemical Formula 142]
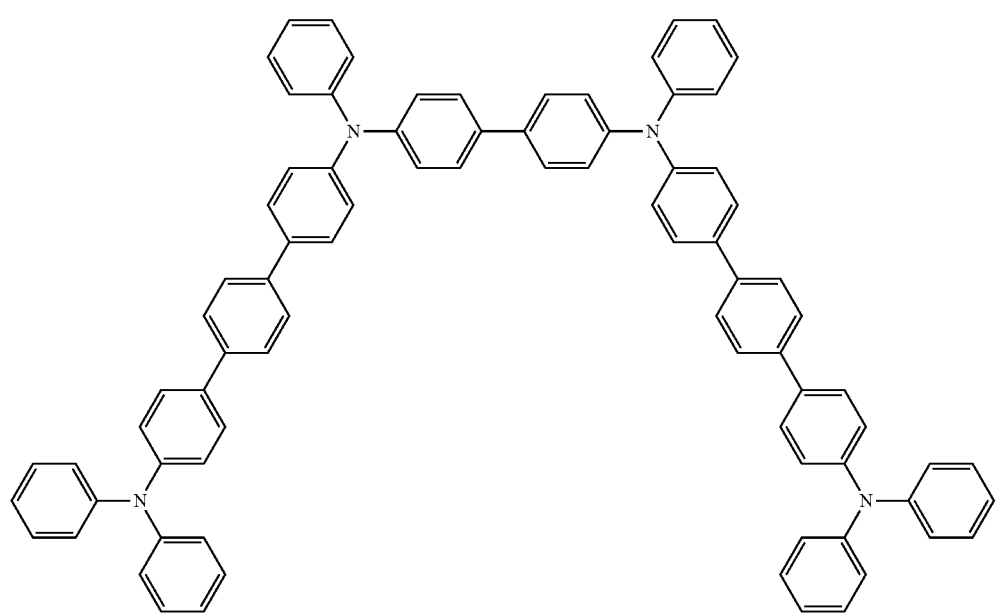
(4-3)

[Chemical Formula 143]
(4-4)
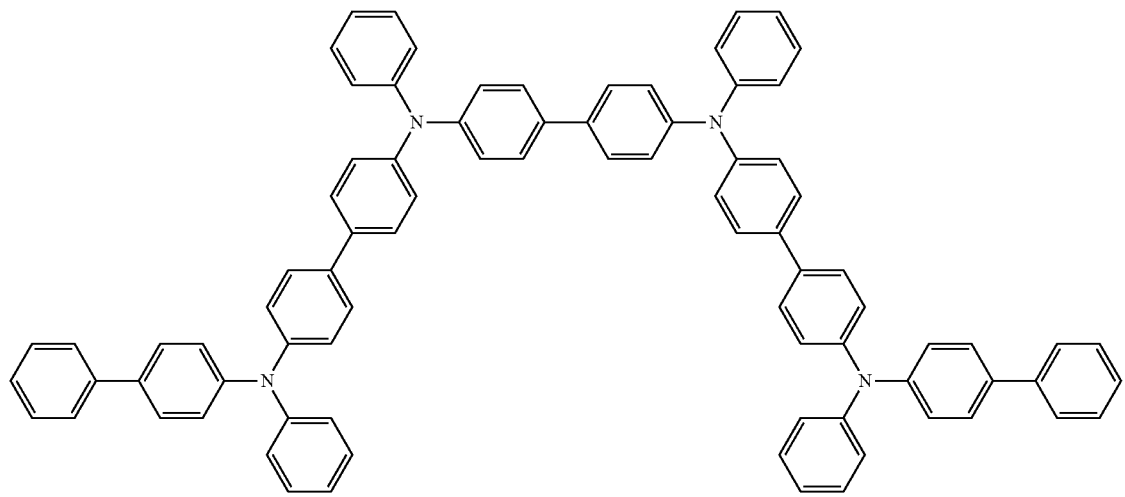
[Chemical Formula 144]
(4-5)
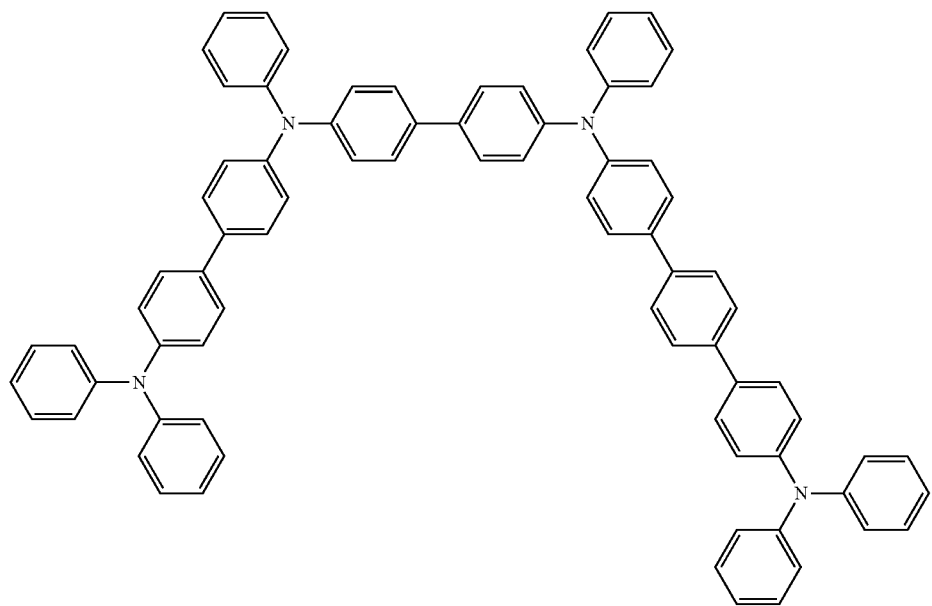

[Chemical Formula 145]
(4-6)
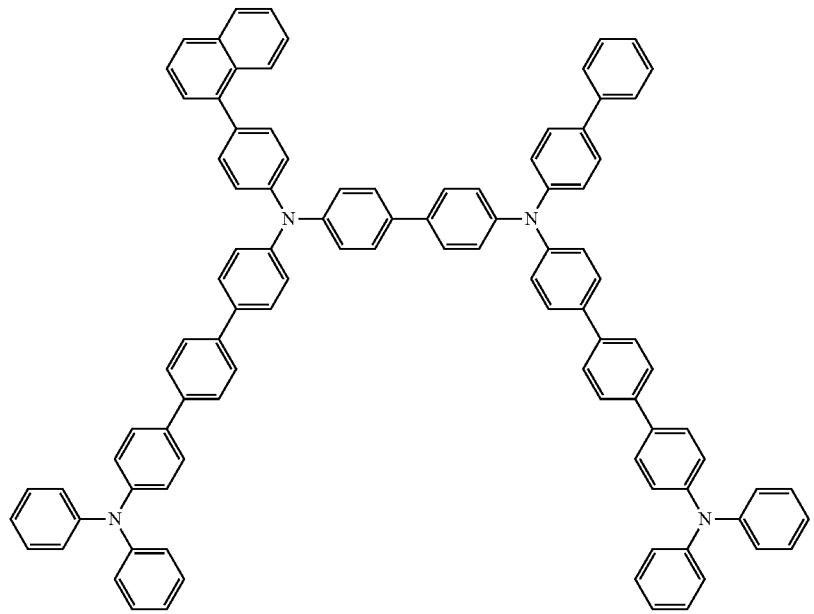
[Chemical Formula 146]
(4-7)
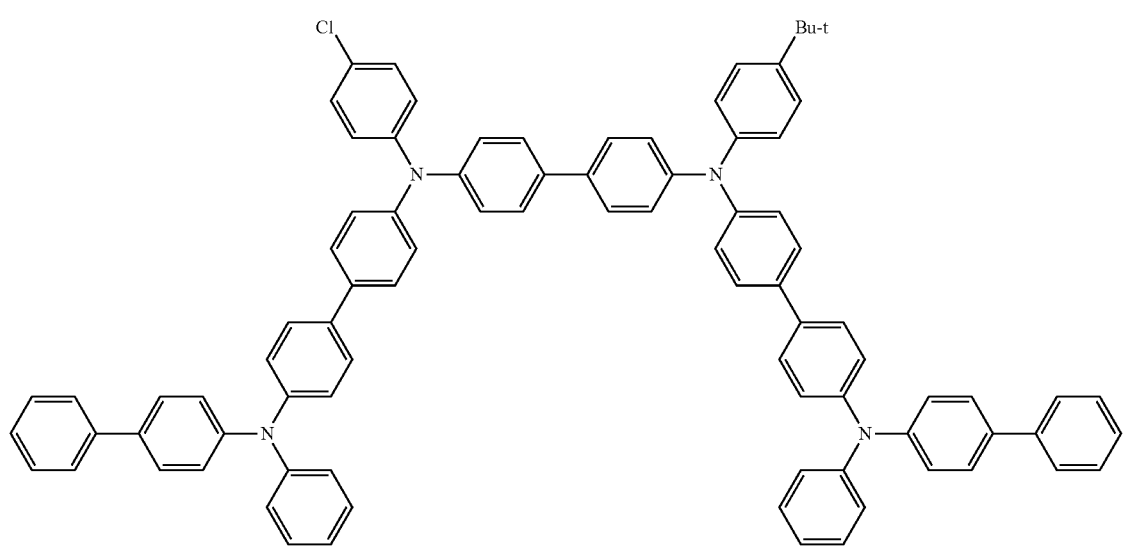

[Chemical Formula 147]
(4-8)
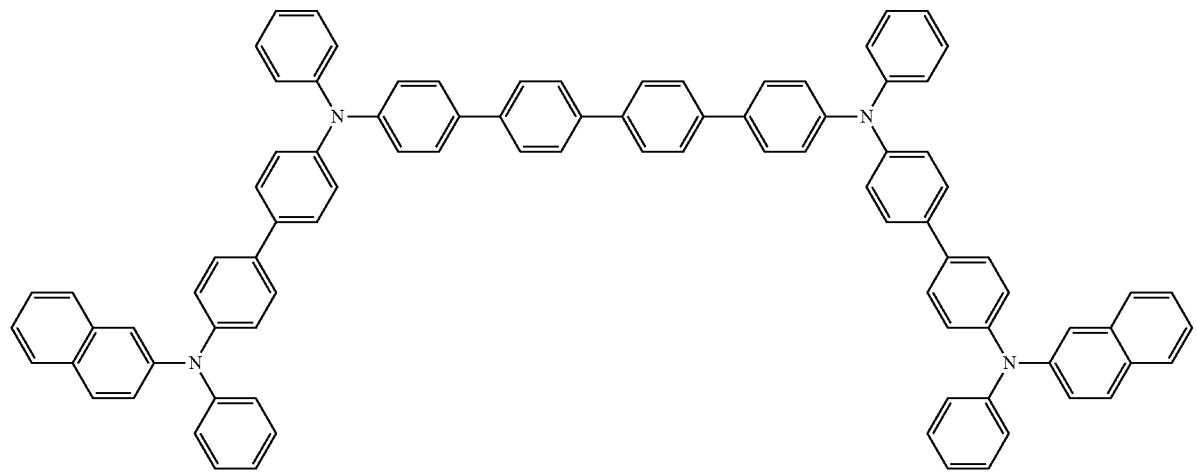
[Chemical Formula 148]
(4-9)
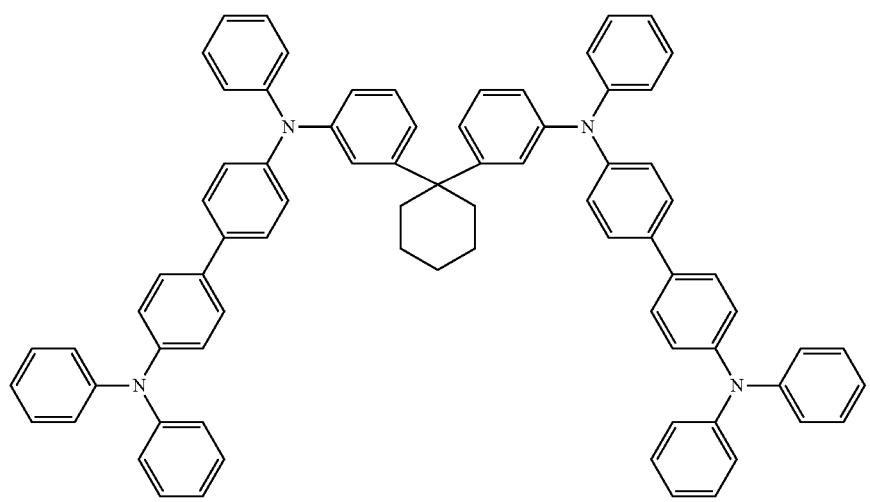
[Chemical Formula 149]
(4-10)
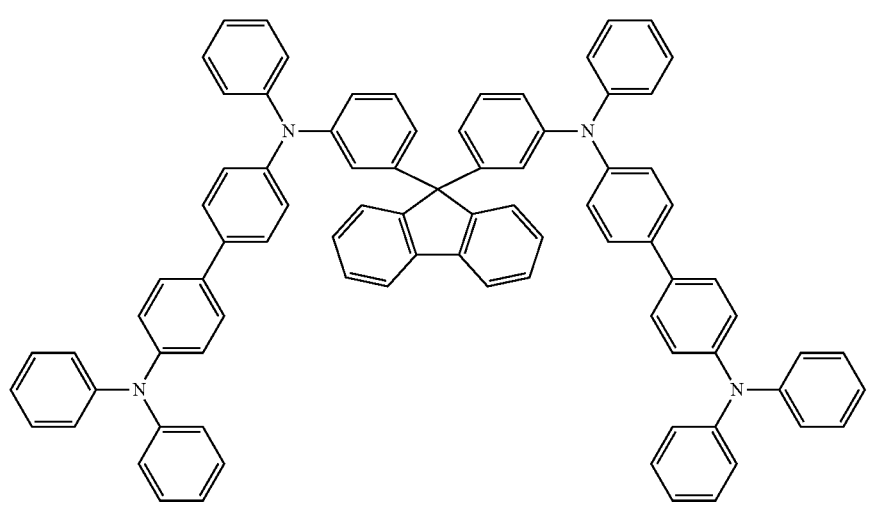

[Chemical Formula 150]
(4-11)
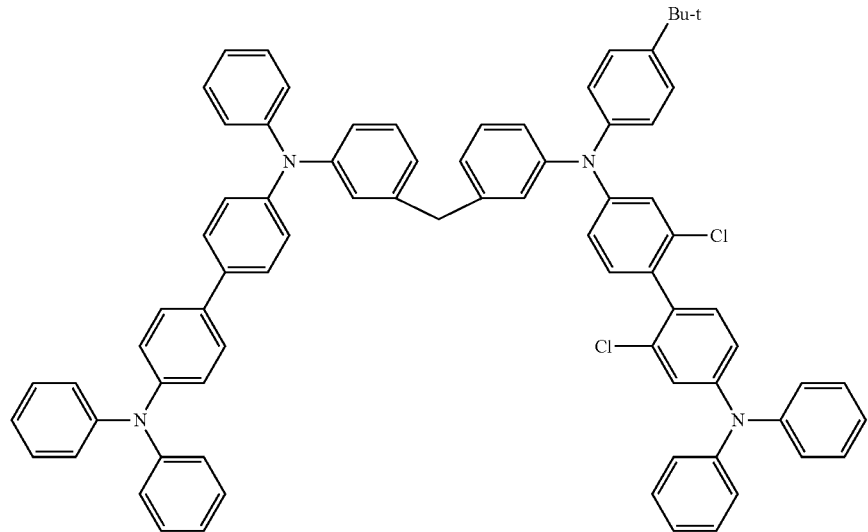
[Chemical Formula 151]
(4-12)
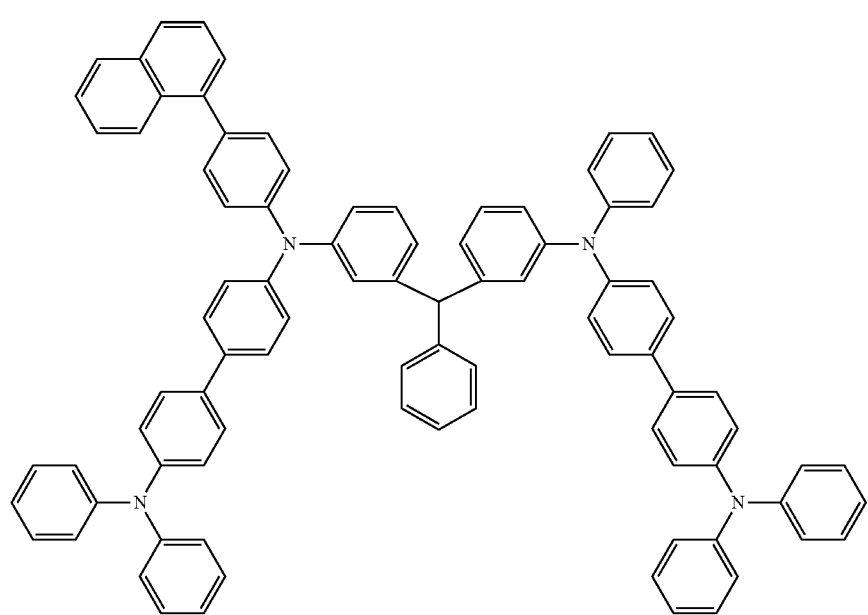

[Chemical Formula 152]
(4-13)
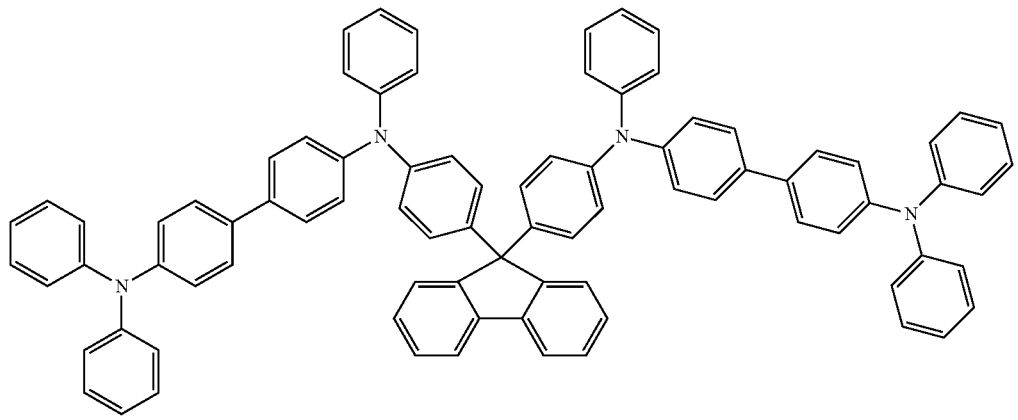
[Chemical Formula 153]
(4-14)
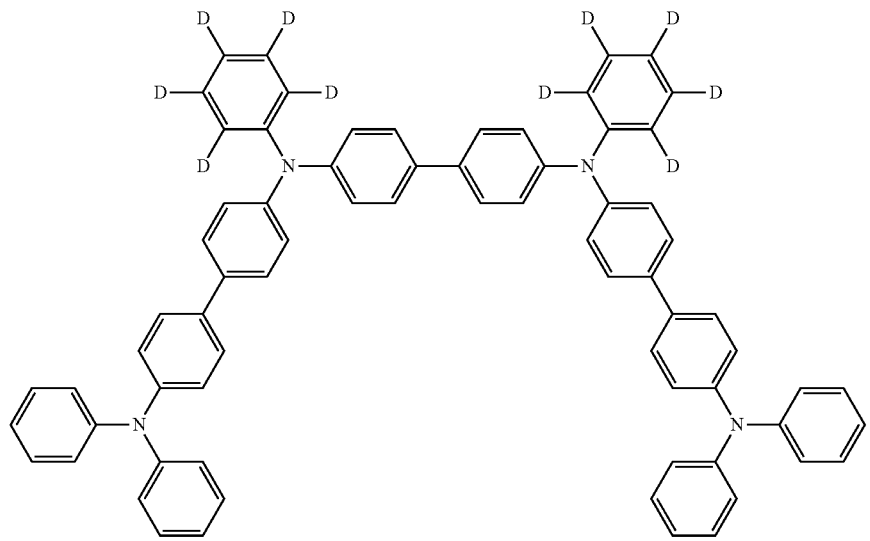
[Chemical Formula 154]
(4-15)
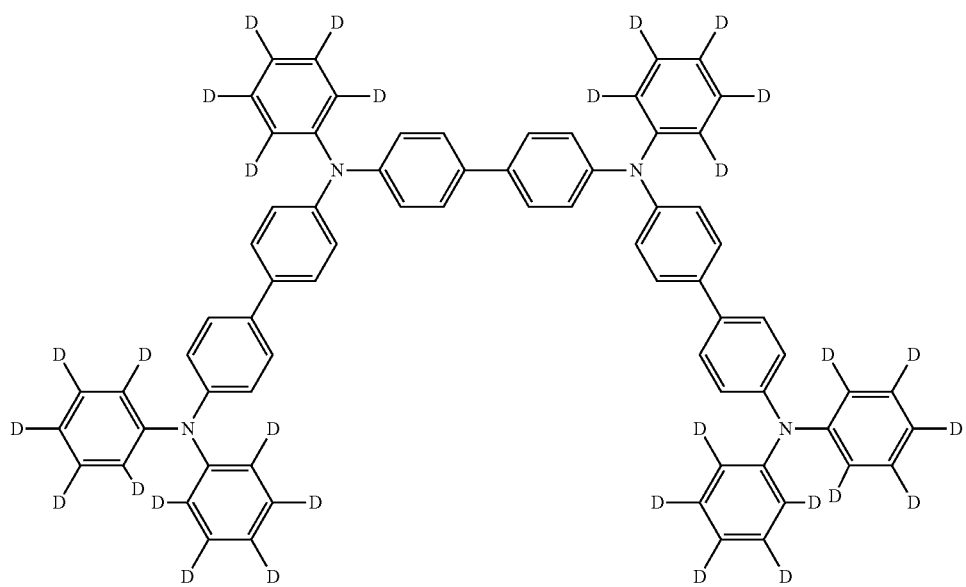

[Chemical Formula 155]

(4-16)

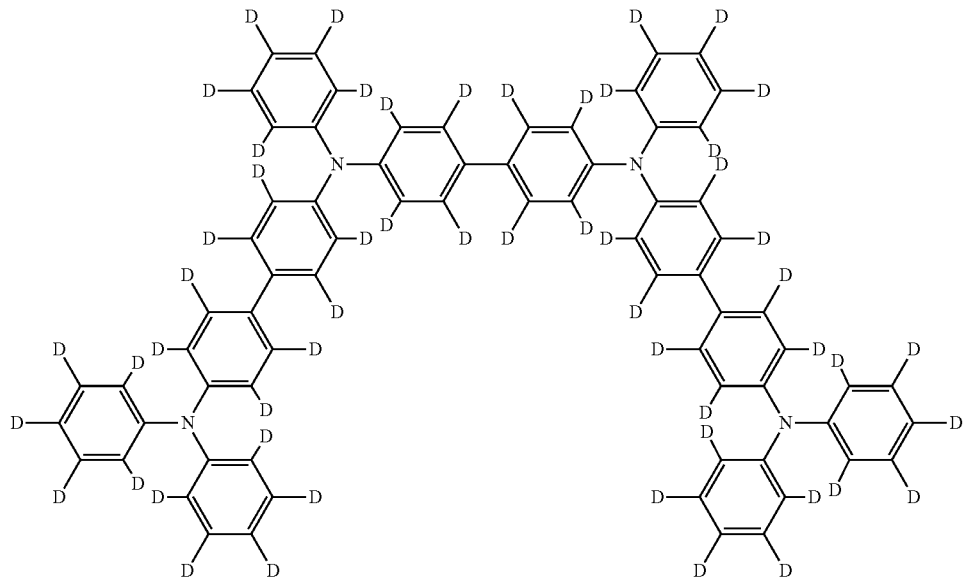

[Chemical Formula 156]

(4-17)

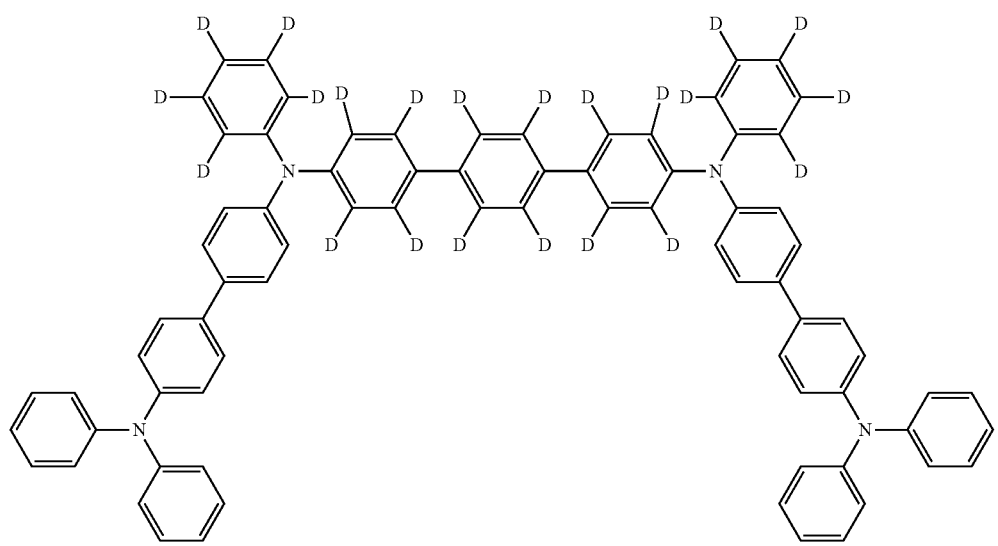

The arylamine compounds of the general formula (3) and the arylamine compounds of the general formula (4) can be synthesized by a known method (refer to Patent Documents 1 and 8 to 9, for example).

The following presents specific examples of preferred compounds among the arylamine compounds of the general formula (5) preferably used in the organic EL device of the present invention. The present invention, however, is not restricted to these compounds.

[Chemical Formula 157]
(5-1)
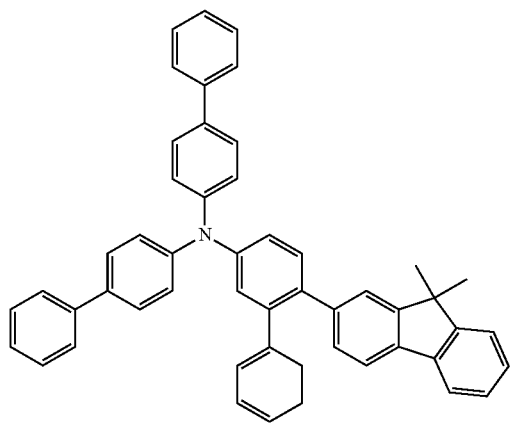
[Chemical Formula 158]
(5-2)
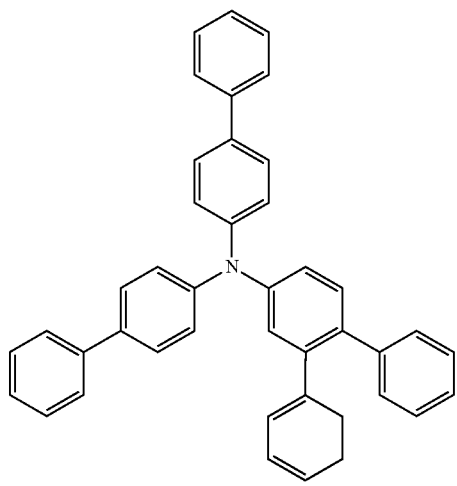
[Chemical Formula 159]
(5-3)
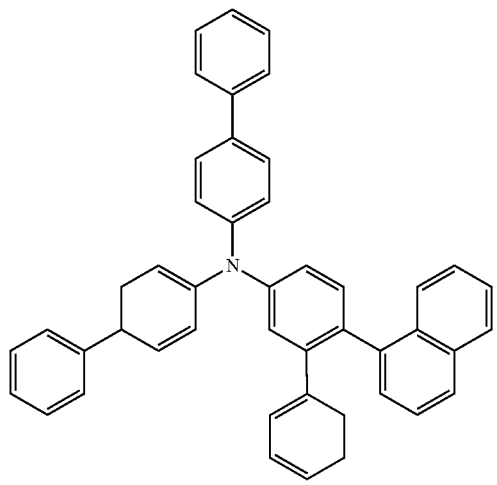
[Chemical Formula 160]
(5-4)
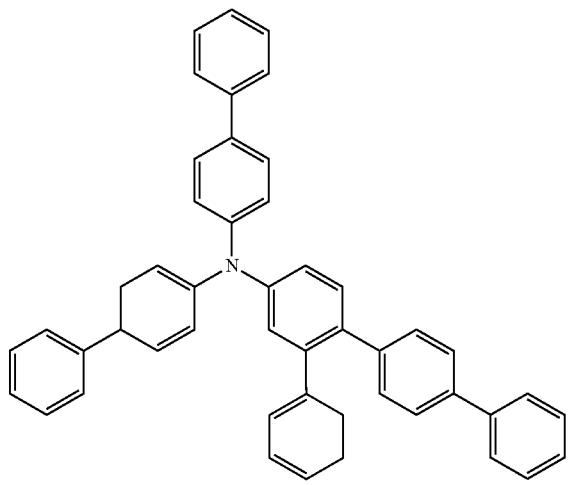
[Chemical Formula 161]
(5-5)
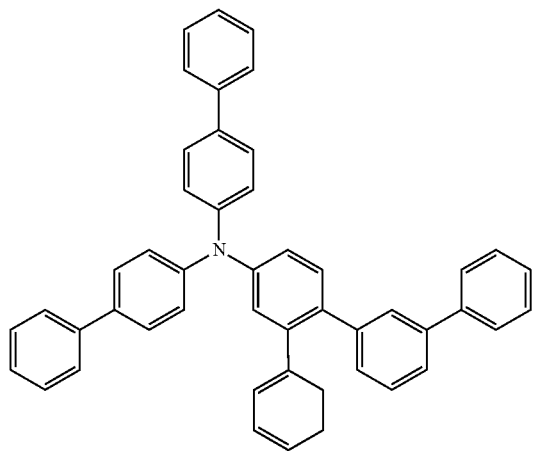
[Chemical Formula 162]
(5-6)
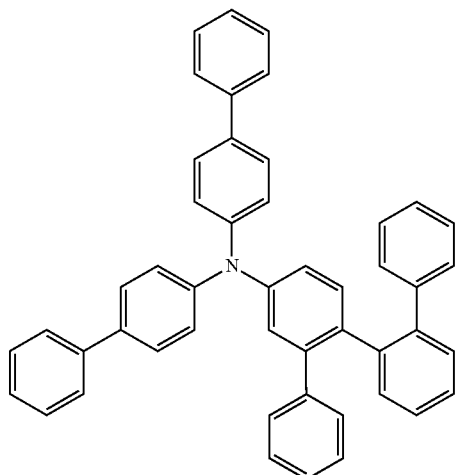

[Chemical Formula 163]
(5-7)
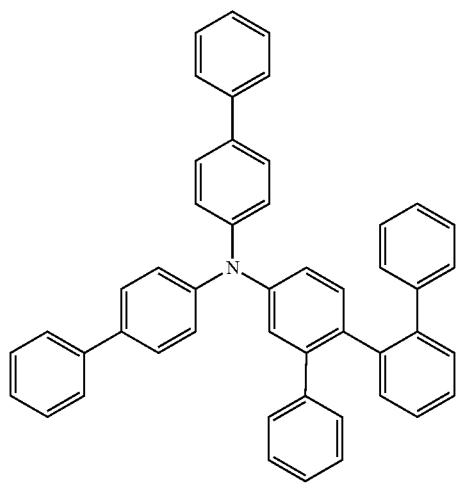
[Chemical Formula 164]
(5-8)
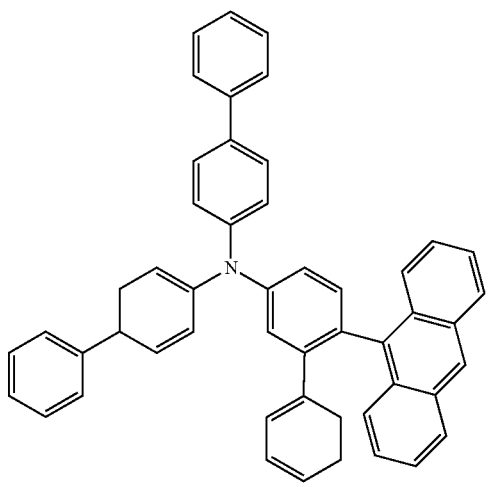
[Chemical Formula 165]
(5-9)
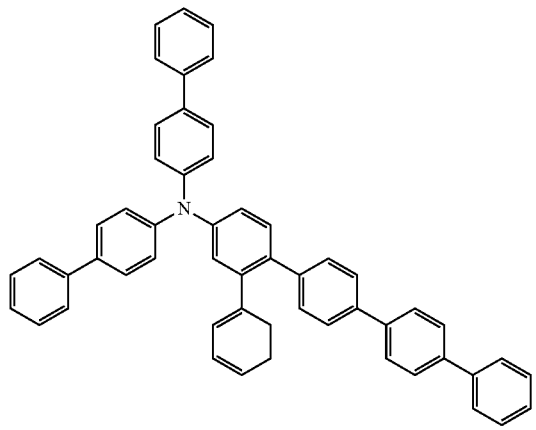
[Chemical Formula 166]
(5-10)
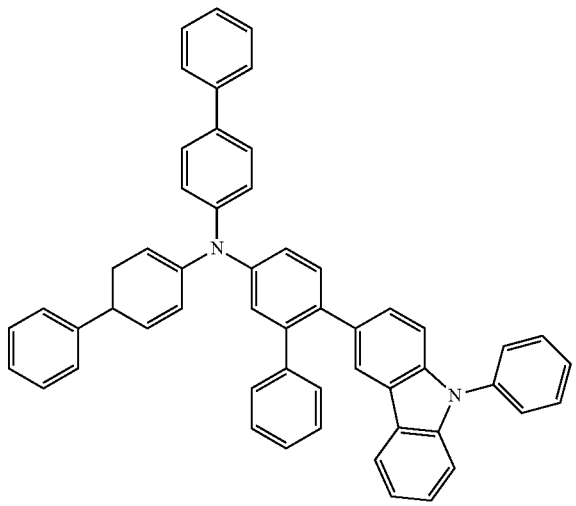
[Chemical Formula 167]
(5-11)
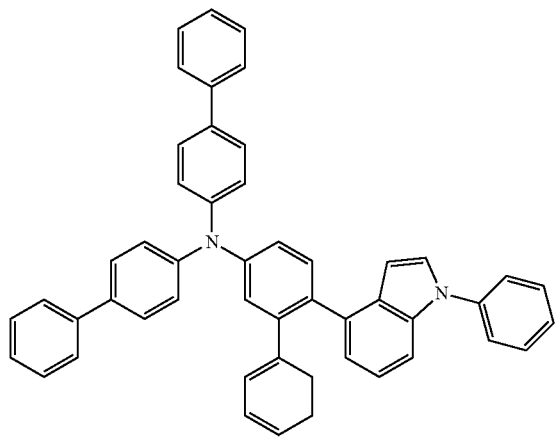
[Chemical Formula 168]
(5-12)
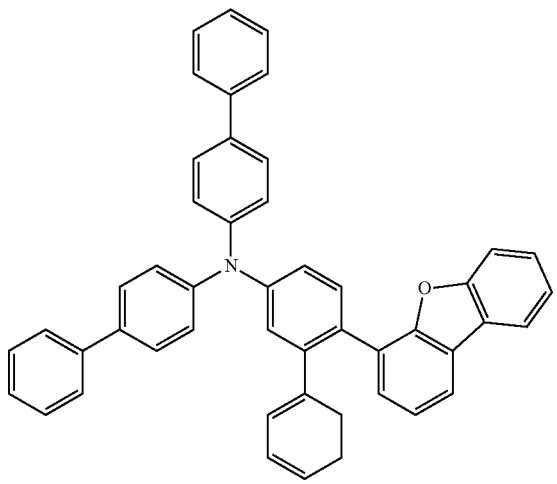

-continued
[Chemical Formula 169]
(5-13)
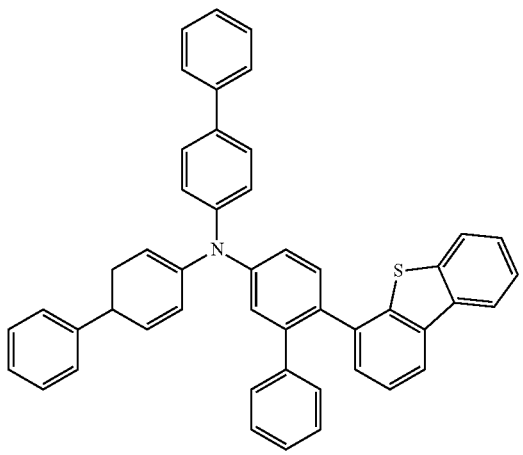
[Chemical Formula 170]
(5-14)
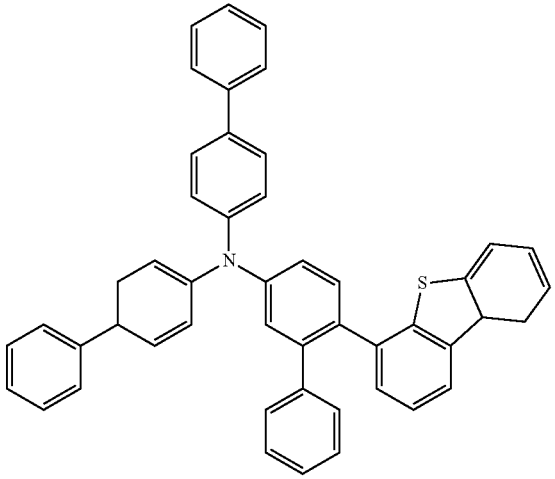
[Chemical Formula 171]
(5-15)
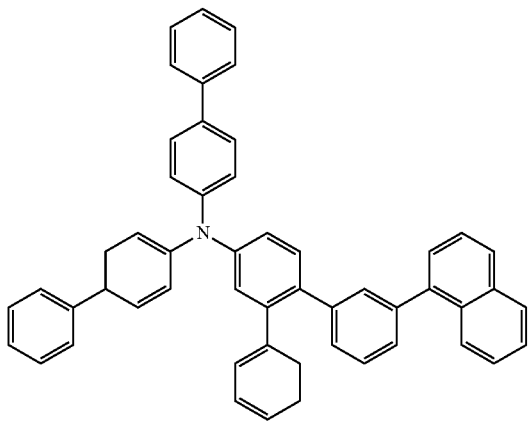
[Chemical Formula 172]
(5-16)
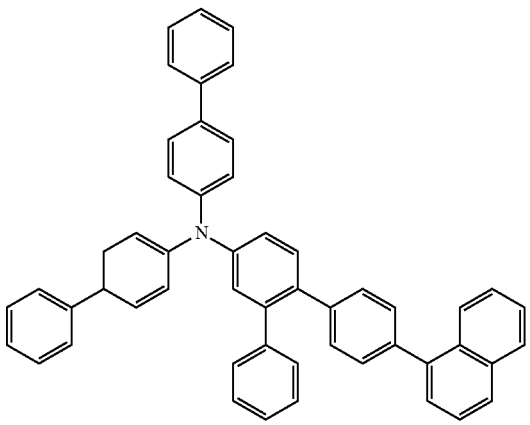
[Chemical Formula 173]
(5-17)
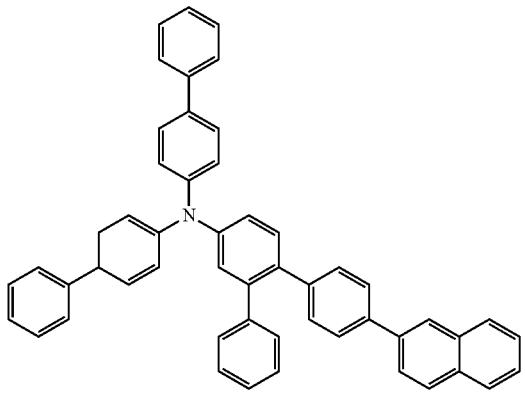
[Chemical Formula 174]
(5-18)
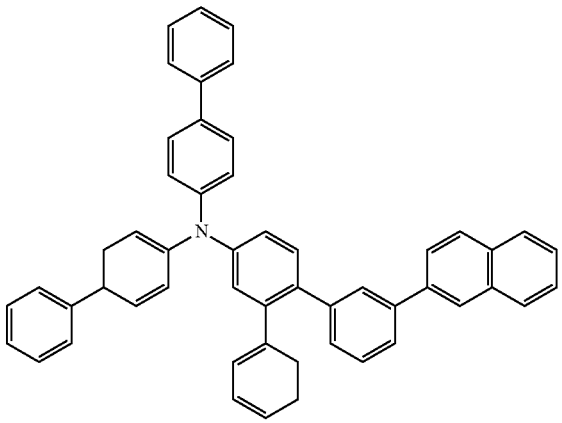

[Chemical Formula 175]
(5-19)
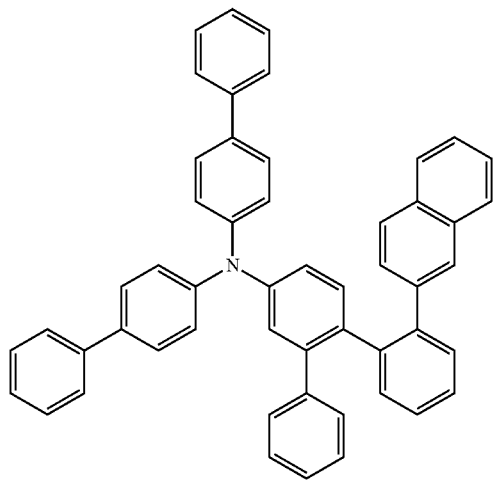
[Chemical Formula 176]
(5-20)
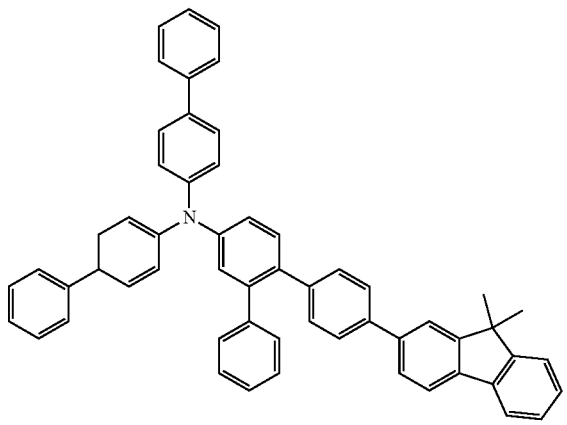
[Chemical Formula 177]
(5-21)
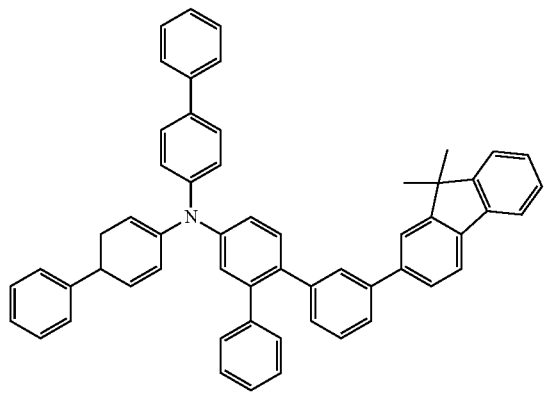
[Chemical Formula 178]
(5-22)
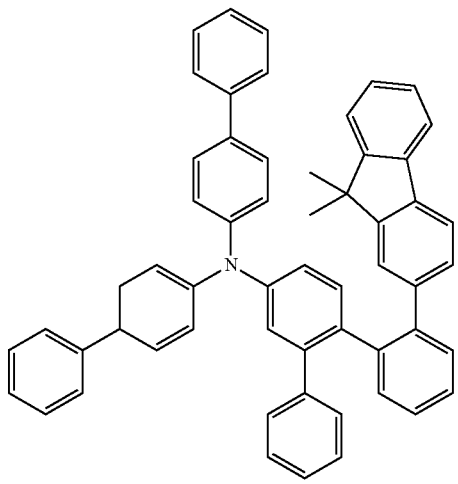
[Chemical Formula 179]
(5-23)
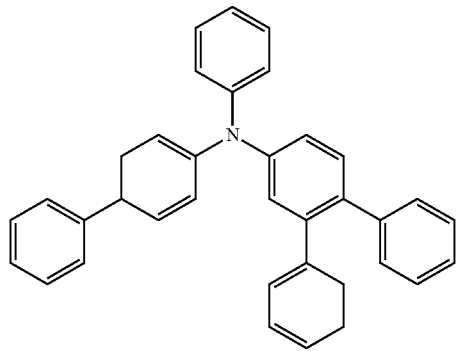
[Chemical Formula 180]
(5-24)
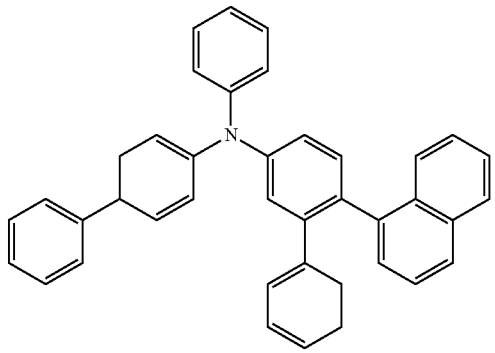

-continued
[Chemical Formula 181]
(5-25)
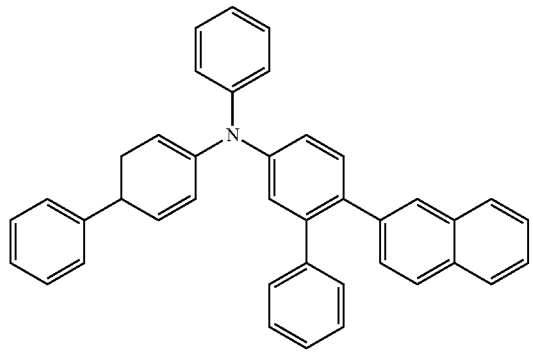
[Chemical Formula 182]
(5-26)
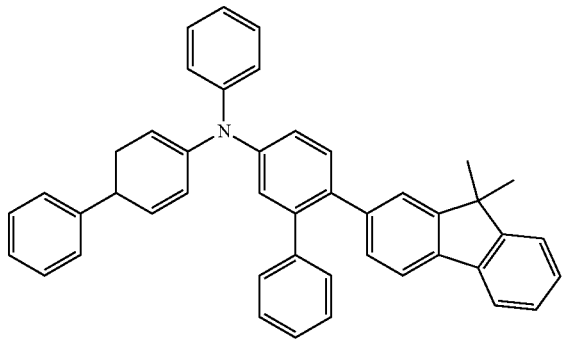
[Chemical Formula 183]
(5-27)
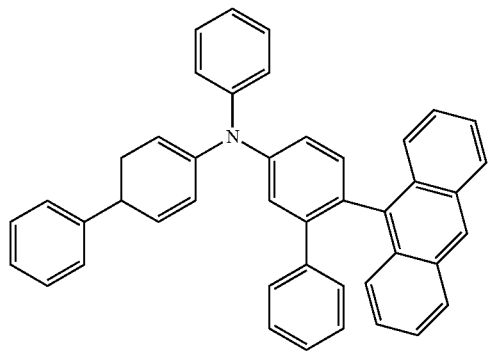
[Chemical Formula 184]
(5-28)
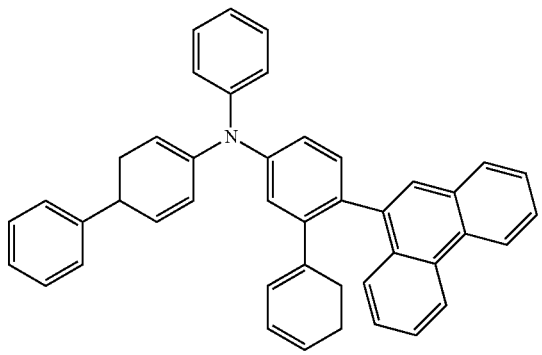
[Chemical Formula 185]
(5-29)
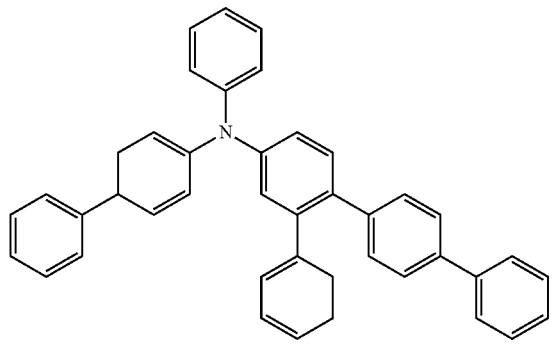
[Chemical Formula 186]
(5-30)
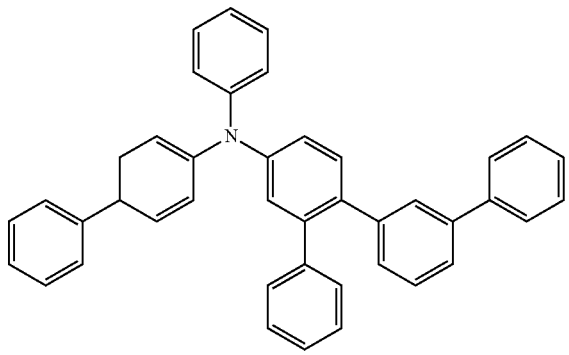

-continued
[Chemical Formula 187]
(5-31)
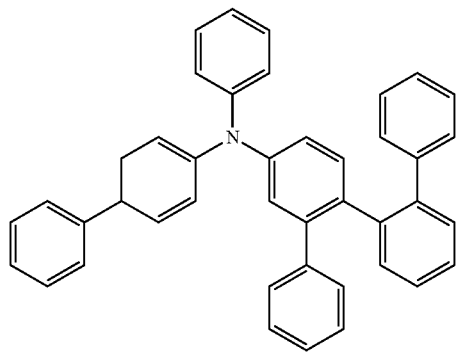
[Chemical Formula 188]
(5-32)
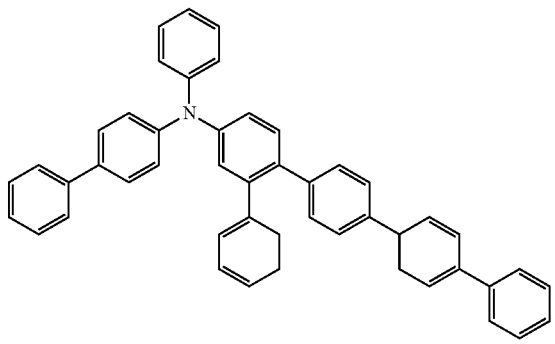
[Chemical Formula 189]
(5-33)
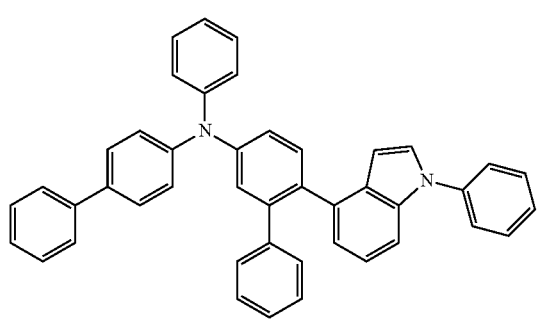
[Chemical Formula 190]
(5-34)
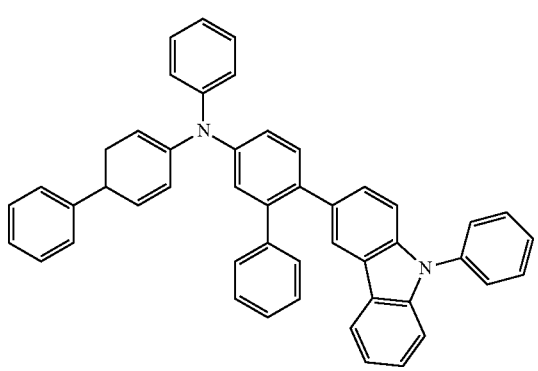
[Chemical Formula 191]
(5-35)
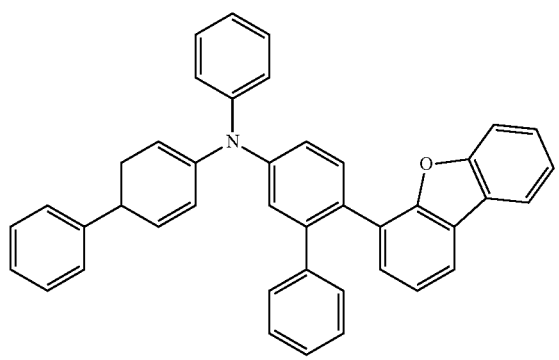
[Chemical Formula 192]
(5-36)
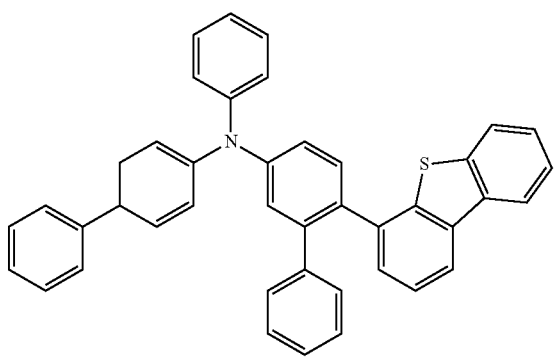
[Chemical Formula 193]
(5-37)
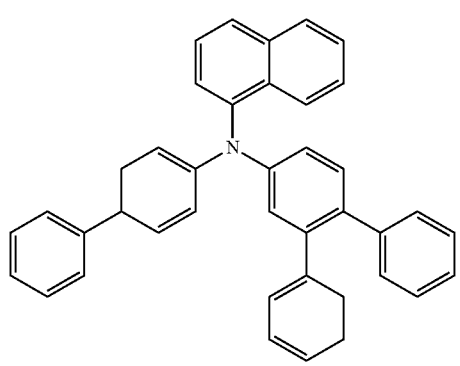
[Chemical Formula 194]
(5-38)
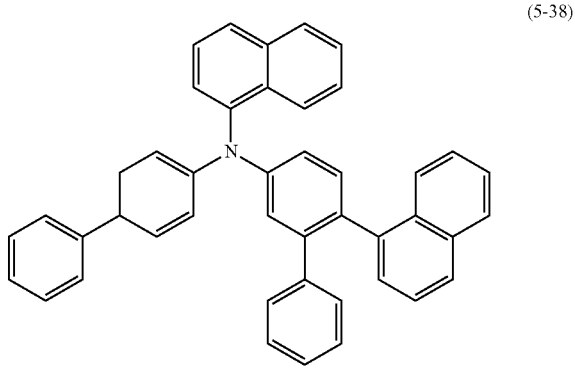

-continued
[Chemical Formula 195]
(5-39)
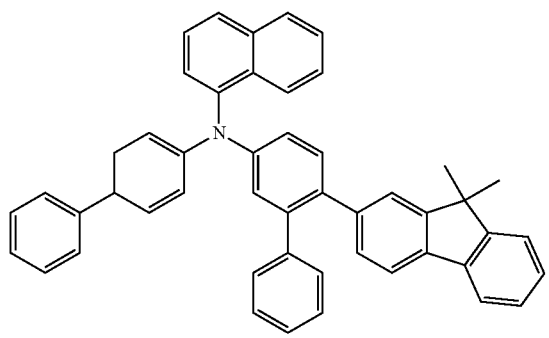
[Chemical Formula 196]
(5-40)
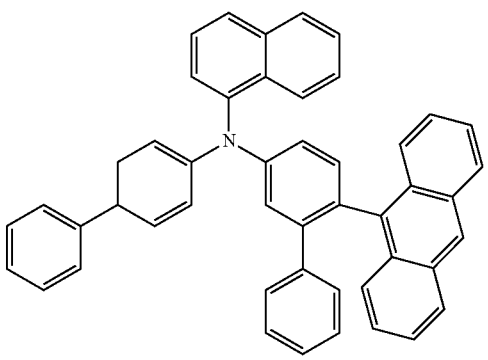
[Chemical Formula 197]
(5-41)
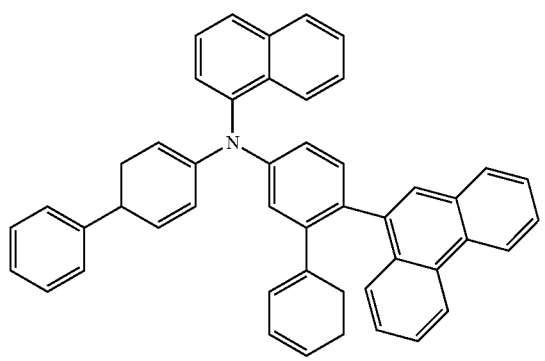
[Chemical Formula 198]
(5-42)
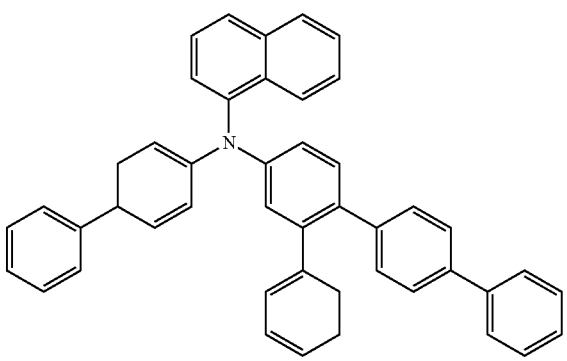
[Chemical Formula 199]
(5-43)
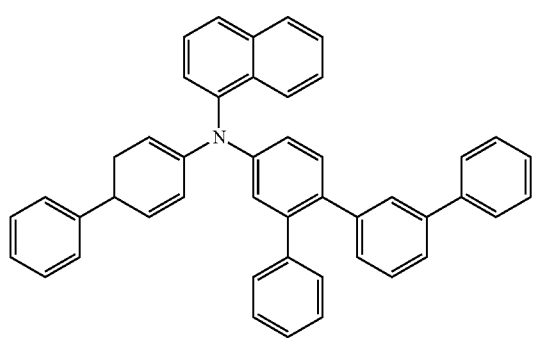
[Chemical Formula 200]
(5-44)
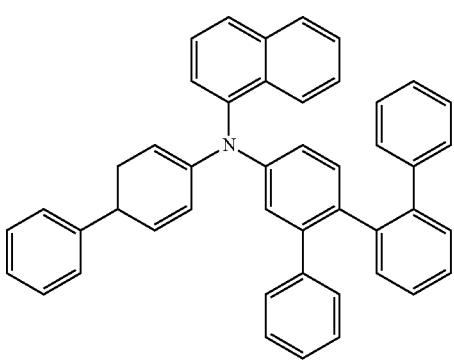
[Chemical Formula 201]
(5-45)
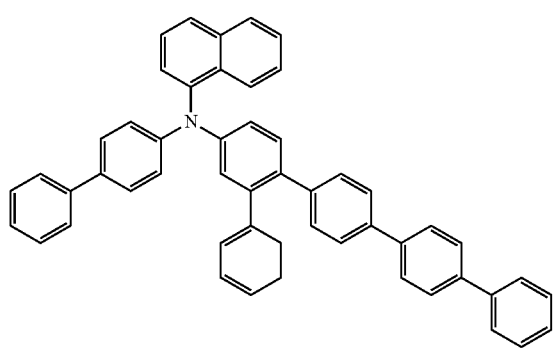
[Chemical Formula 202]
(5-46)
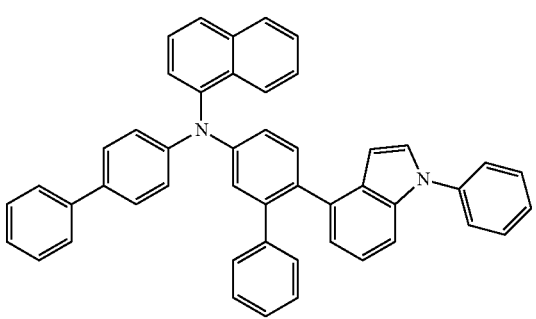

-continued
[Chemical Formula 203]
(5-47)
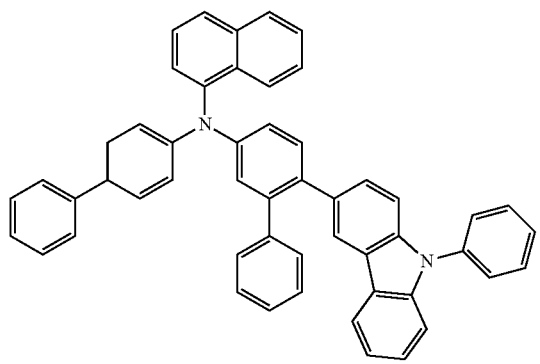
[Chemical Formula 204]
(5-48)
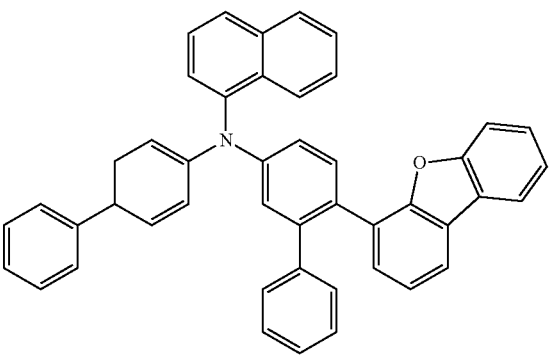
[Chemical Formula 205]
(5-49)
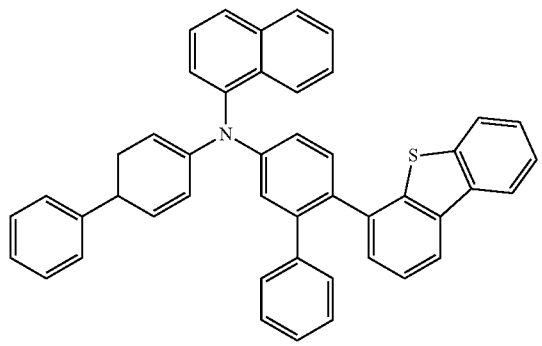
[Chemical Formula 206]
(5-50)
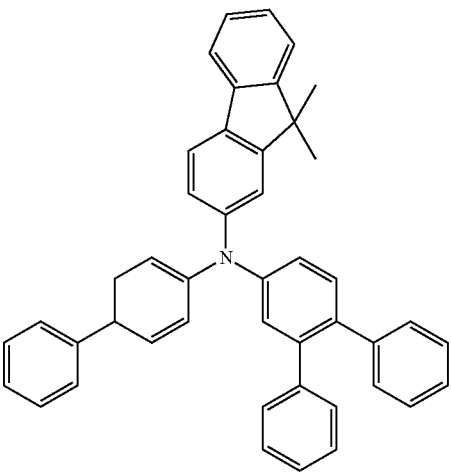
[Chemical Formula 207]
(5-51)
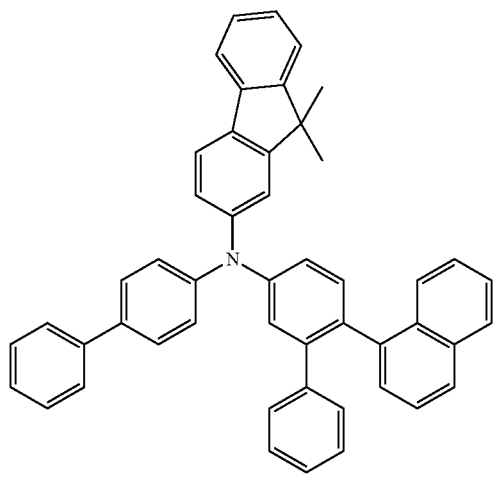
[Chemical Formula 208]
(5-52)
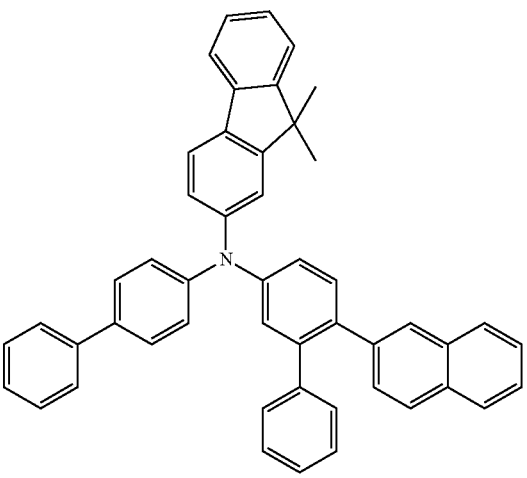

[Chemical Formula 209]
(5-53)
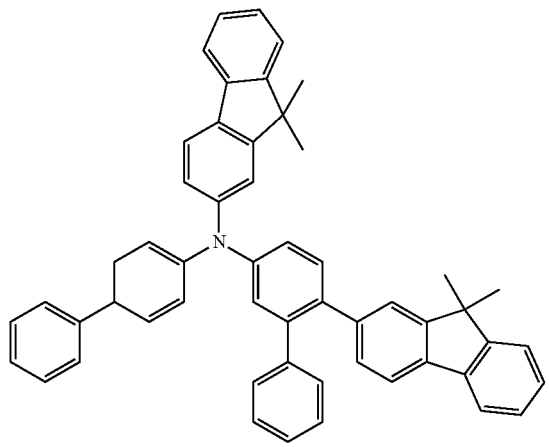
[Chemical Formula 210]
(5-54)
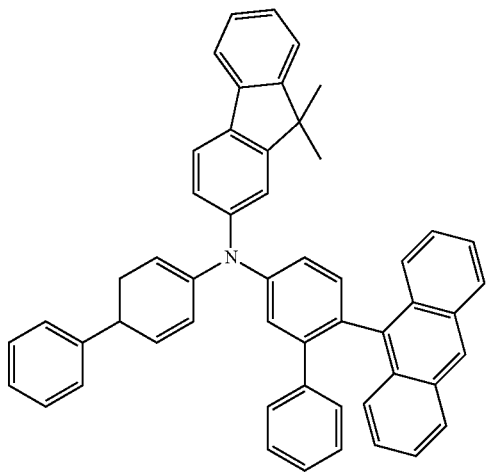
[Chemical Formula 211]
(5-55)
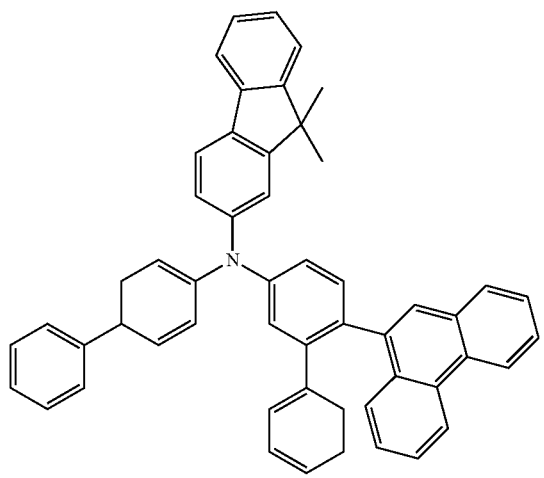
[Chemical Formula 212]
(5-56)
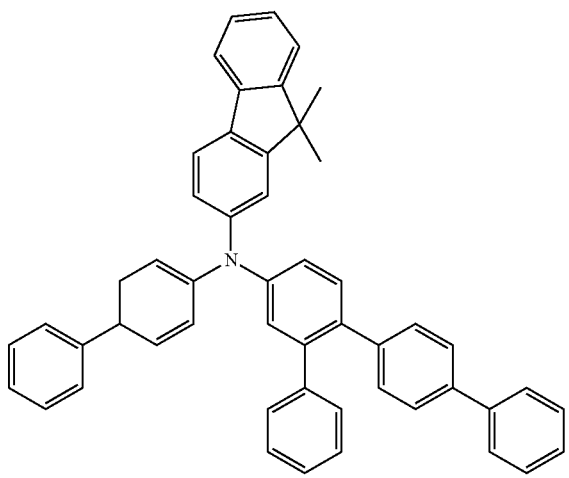
[Chemical Formula 213]
(5-57)
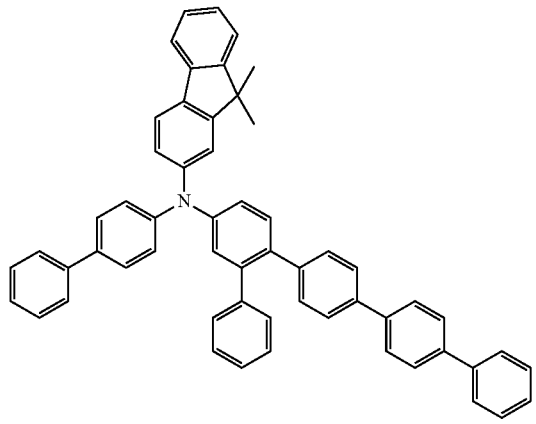
[Chemical Formula 214]
(5-58)
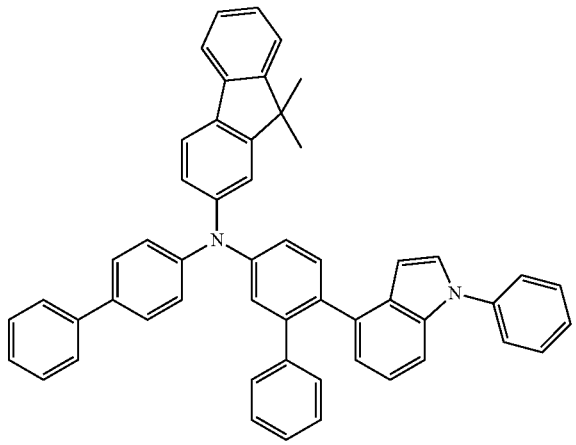

[Chemical Formula 215]
(5-59)
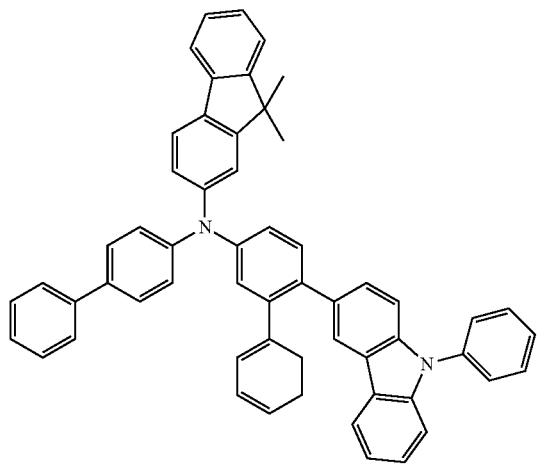
[Chemical Formula 216]
(5-60)
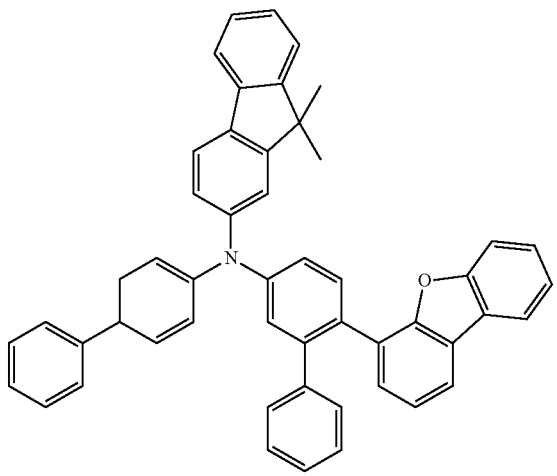
[Chemical Formula 217]
(5-61)
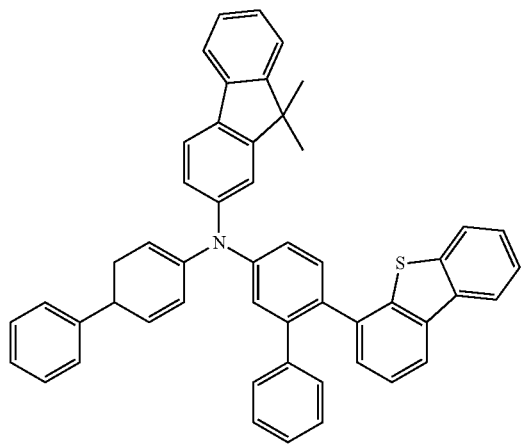
[Chemical Formula 218]
(5-62)
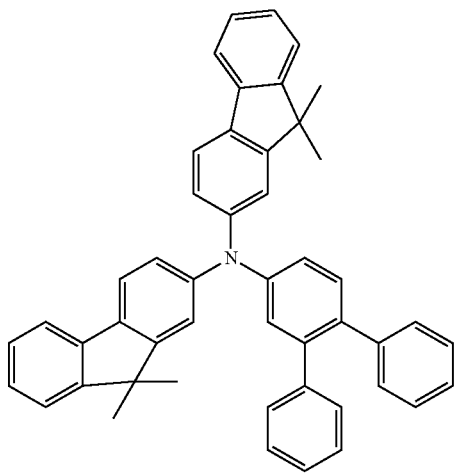
[Chemical Formula 219]
(5-63)
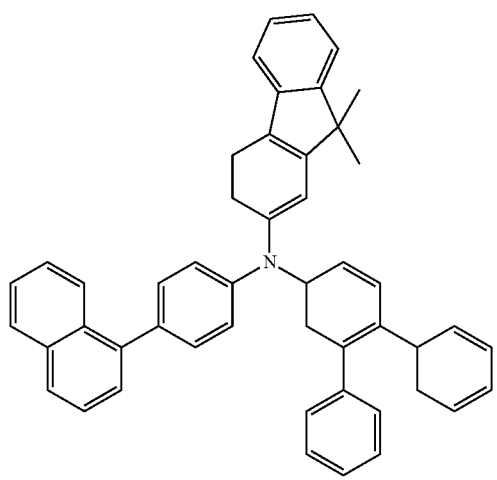
[Chemical Formula 220]
(5-64)
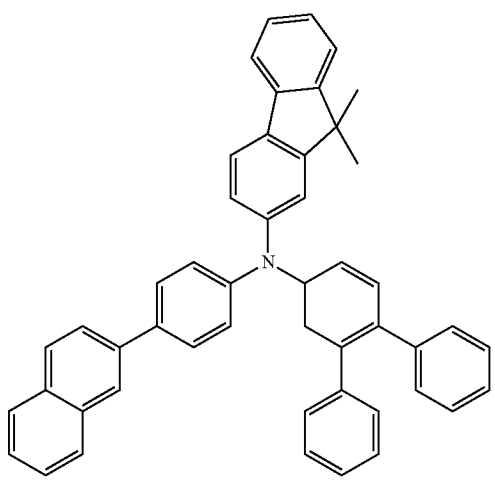

[Chemical Formula 221]
(5-65)
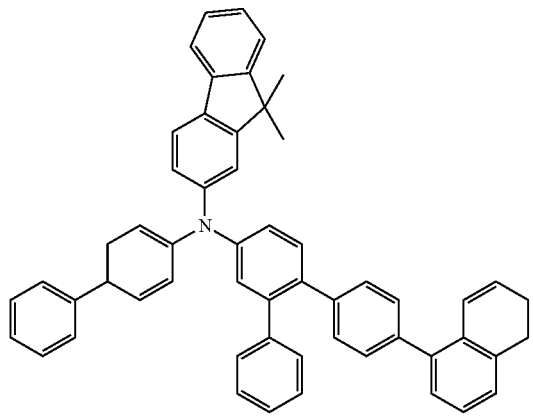
[Chemical Formula 222]
(5-66)
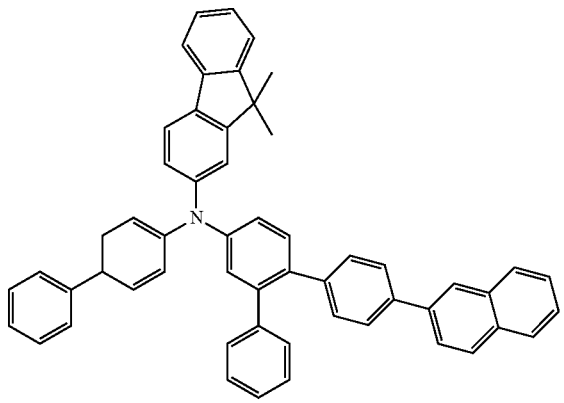
[Chemical Formula 223]
(5-67)
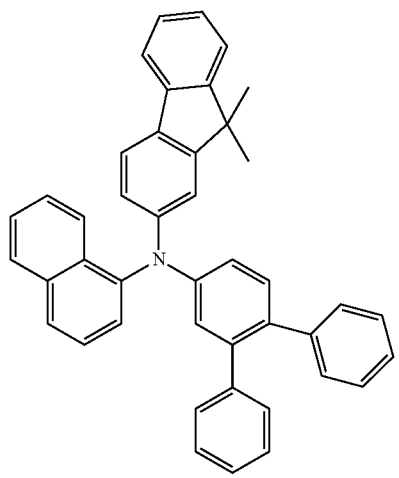
[Chemical Formula 224]
(5-68)
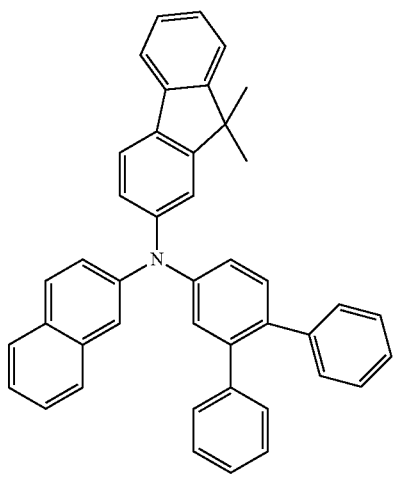
[Chemical Formula 225]
(5-69)
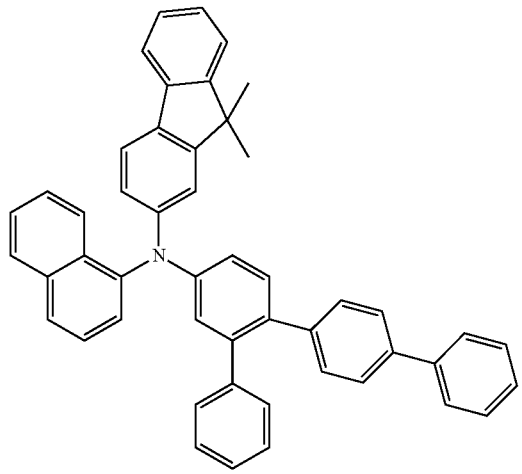
[Chemical Formula 226]
(5-70)
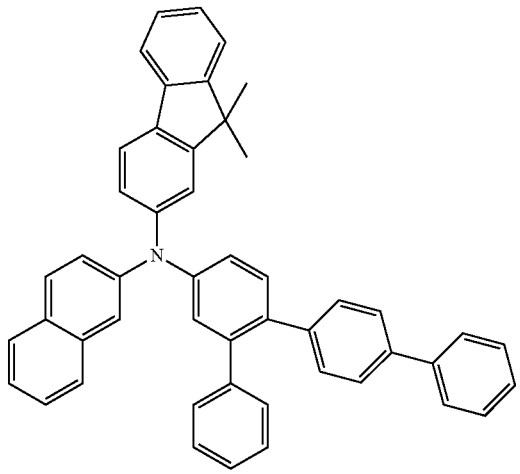

[Chemical Formula 227]
(5-71)
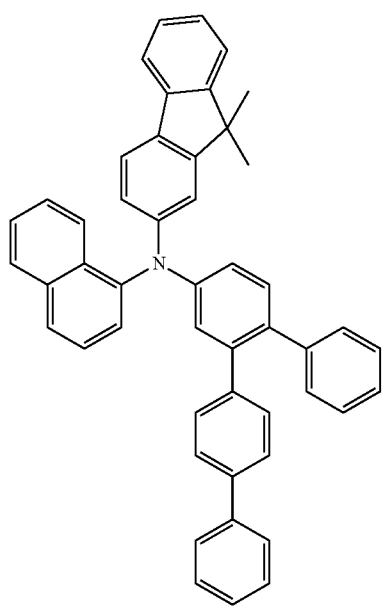
[Chemical Formula 228]
(5-72)
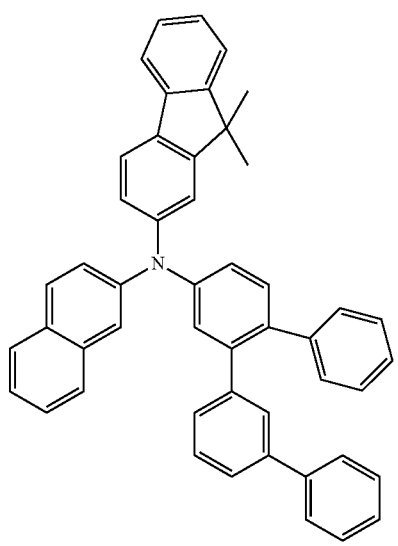
[Chemical Formula 229]
(5-73)
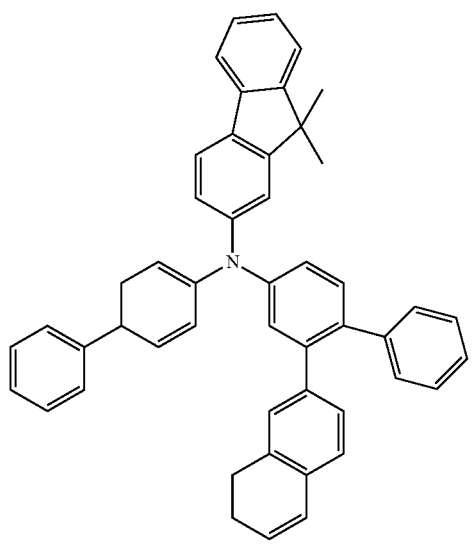
[Chemical Formula 230]
(5-74)
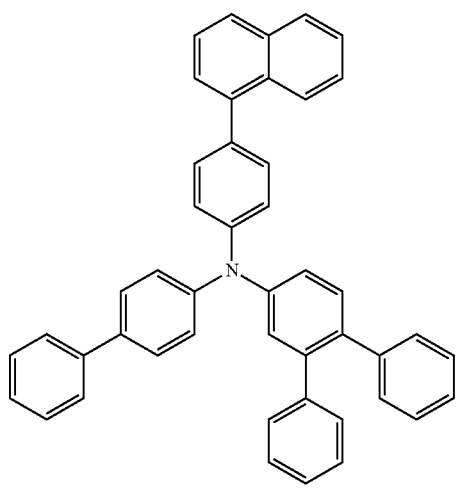

[Chemical Formula 231]
(5-75)
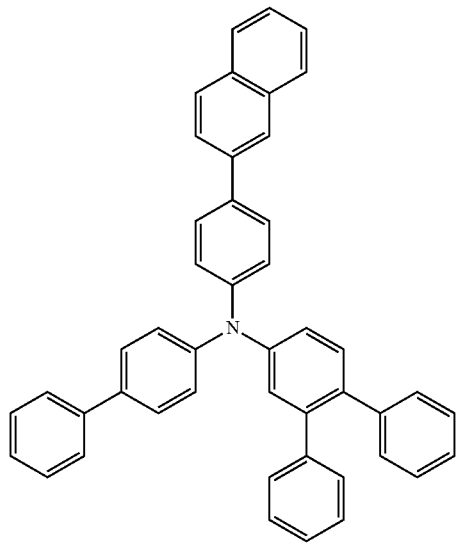
[Chemical Formula 232]
(5-76)
[Chemical Formula 233]
(5-77)
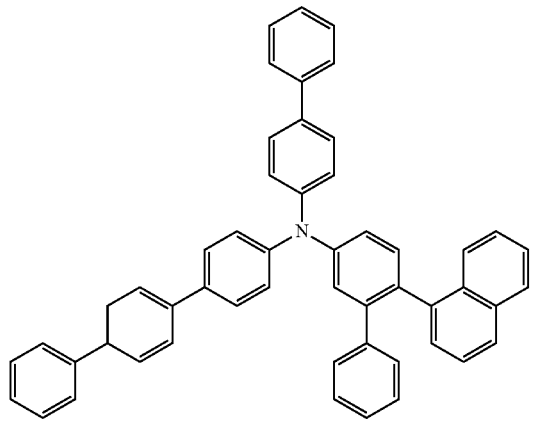
[Chemical Formula 234]
(5-78)
[Chemical Formula 235]
(5-79)
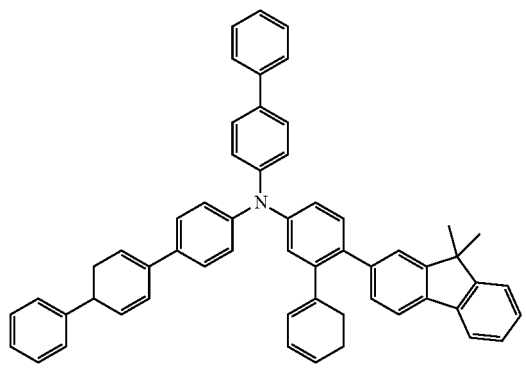
[Chemical Formula 236]
(5-80)
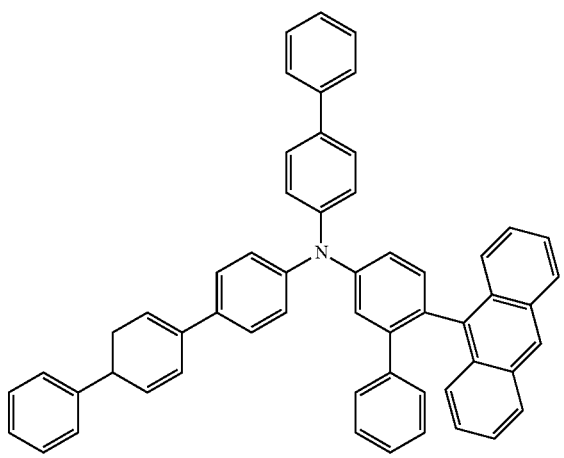

[Chemical Formula 237]
(5-81)
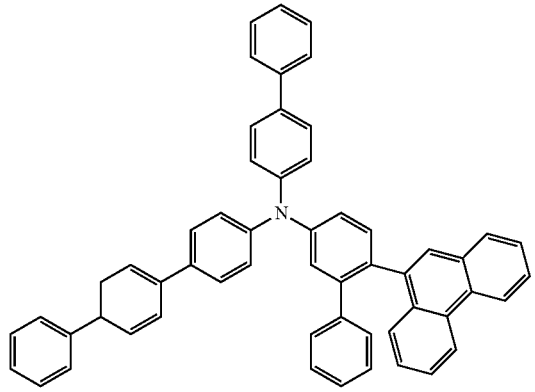
[Chemical Formula 238]
(5-82)
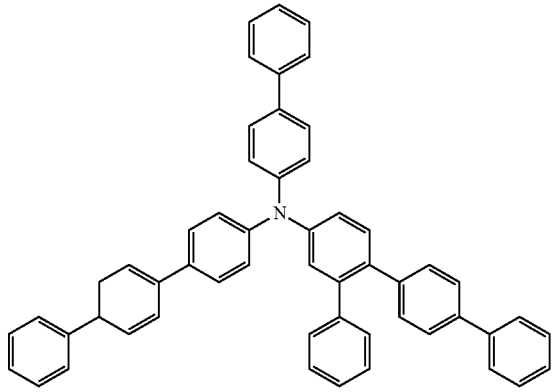
[Chemical Formula 239]
(5-83)
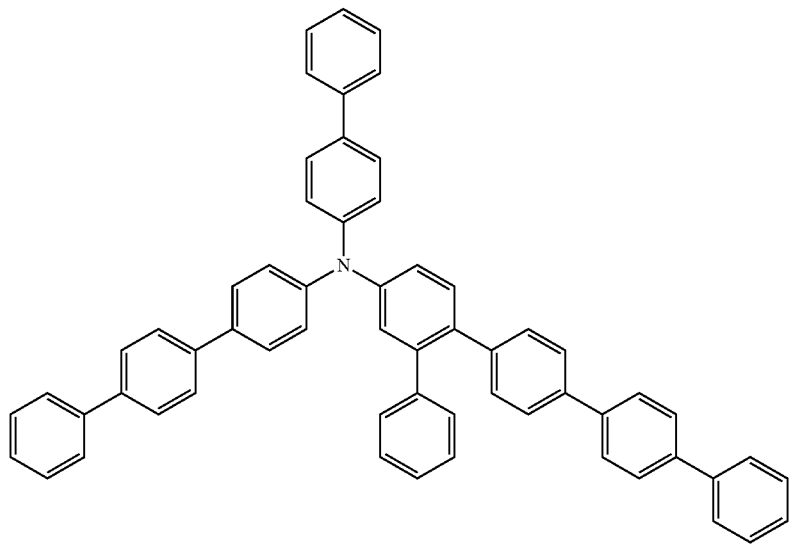
[Chemical Formula 240]
(5-84)
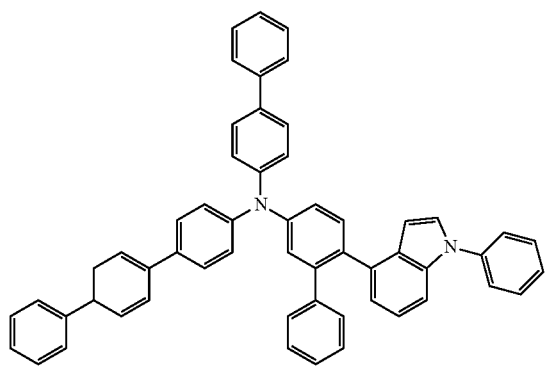
[Chemical Formula 241]
(5-85)
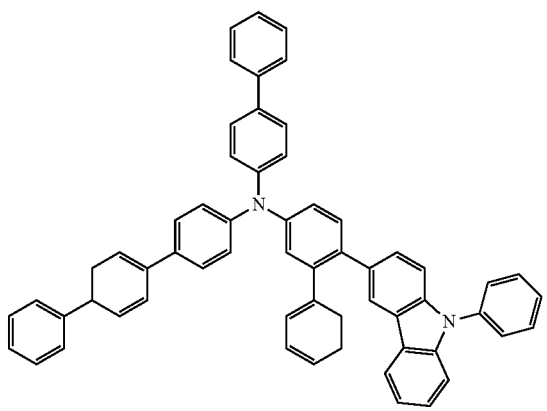

[Chemical Formula 242]
(5-86)
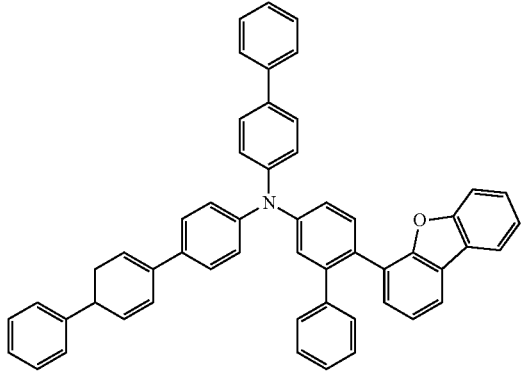
[Chemical Formula 243]
(5-87)
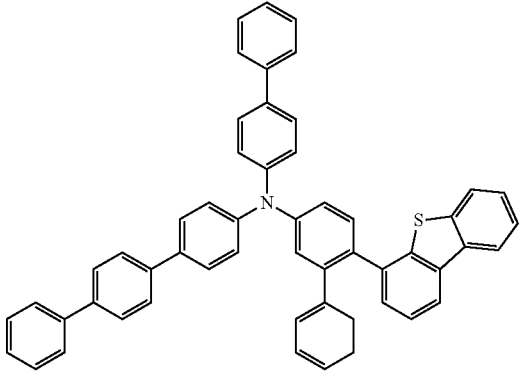
[Chemical Formula 244]
(5-88)
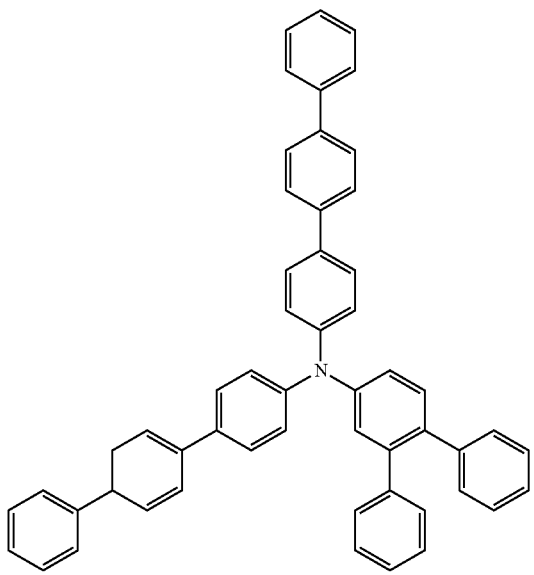
[Chemical Formula 245]
(5-89)
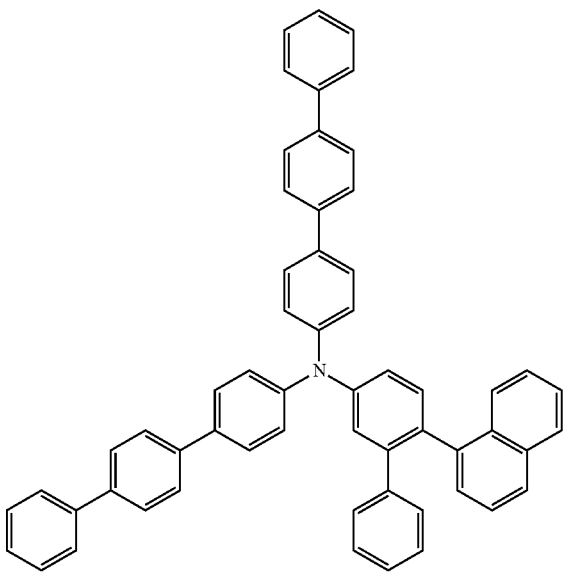
[Chemical Formula 246]
(5-90)
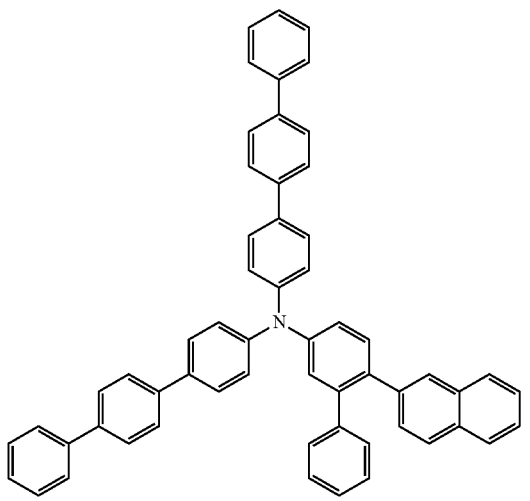
[Chemical Formula 247]
(5-91)
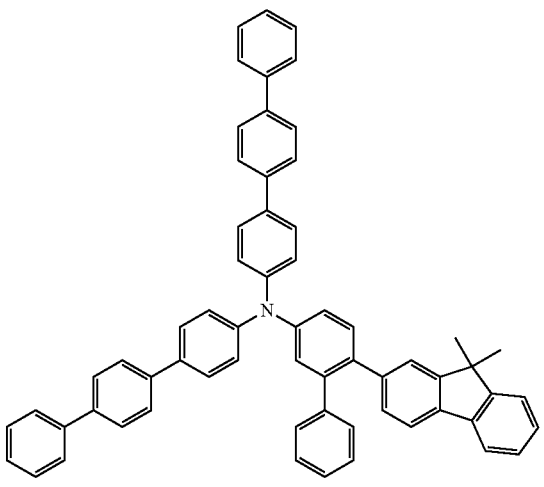

-continued
[Chemical Formula 248]
(5-92)
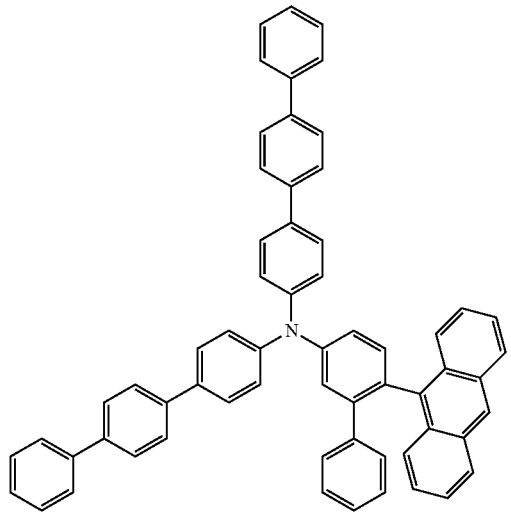
[Chemical Formula 249]
(5-93)
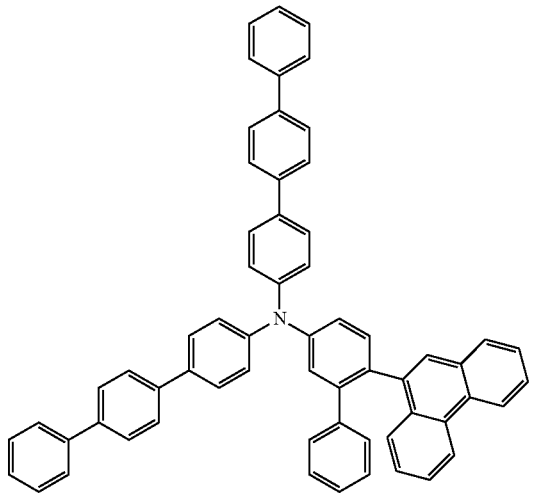
[Chemical Formula 250]
(5-94)
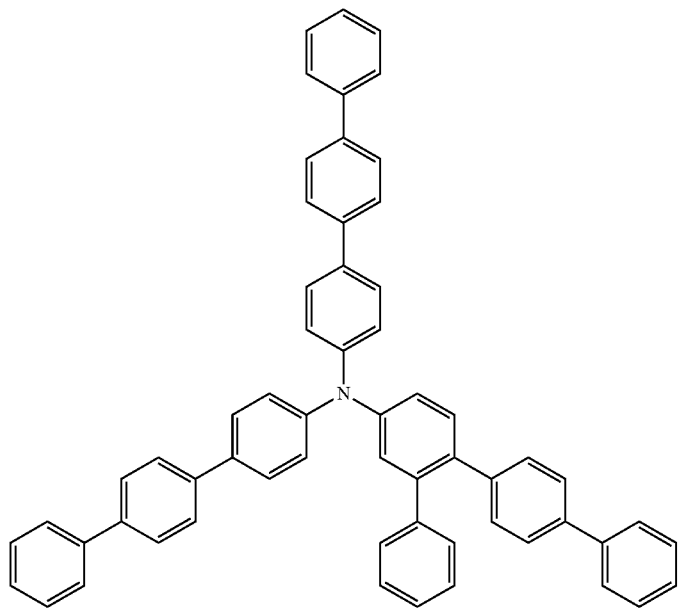

[Chemical Formula 251]
(5-95)
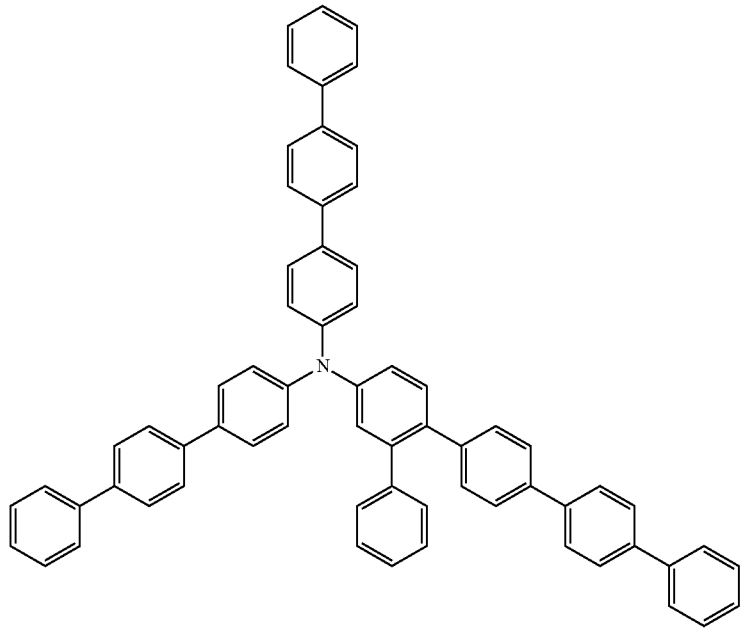
[Chemical Formula 252]
(5-96)
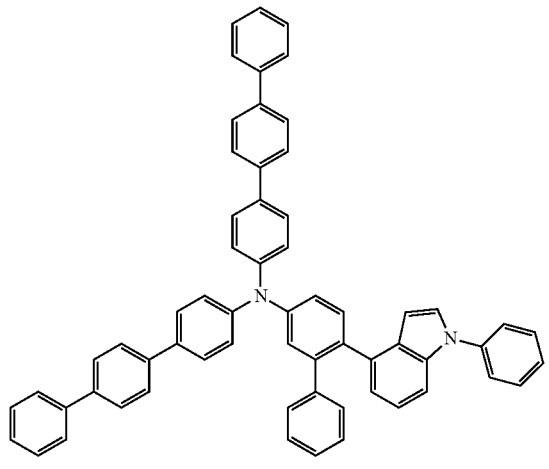
[Chemical Formula 253]
(5-97)
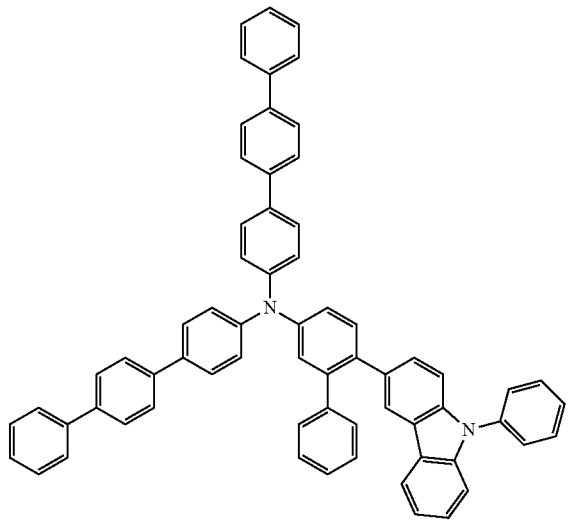

[Chemical Formula 254]
(5-98)
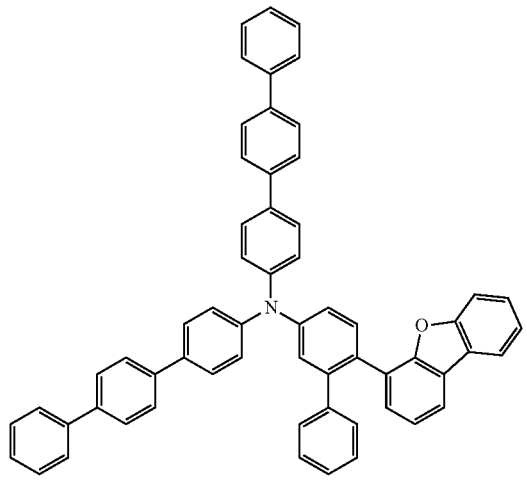
[Chemical Formula 255]
(5-99)
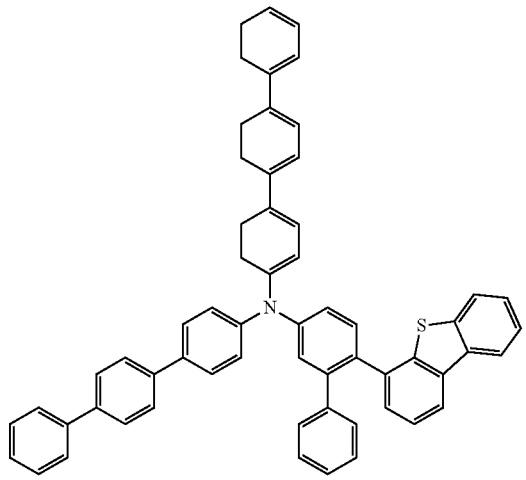
[Chemical Formula 256]
(5-100)
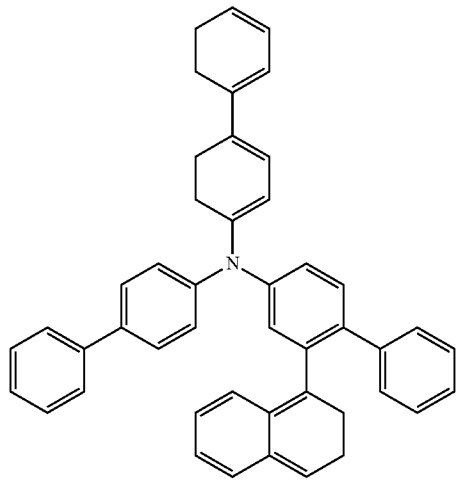
[Chemical Formula 257]
(5-101)
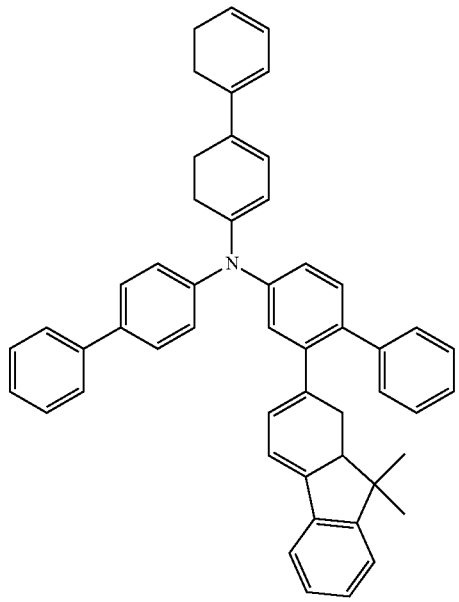

[Chemical Formula 258]
(5-102)
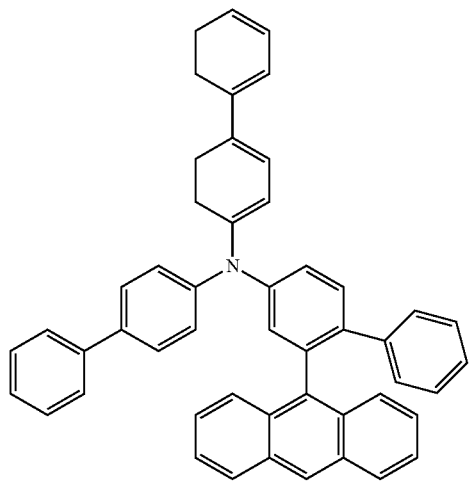
[Chemical Formula 259]
(5-103)
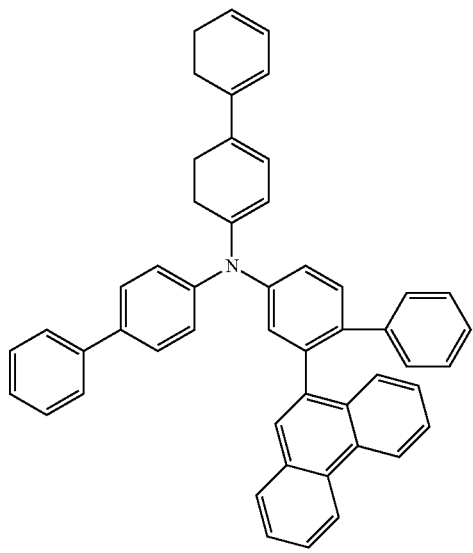
[Chemical Formula 260]
(5-104)
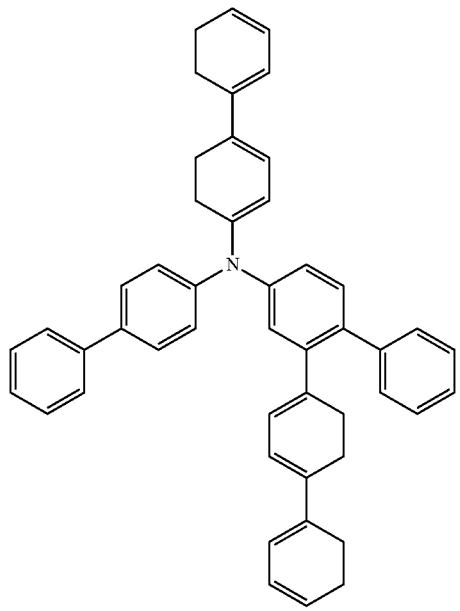
[Chemical Formula 261]
(5-105)
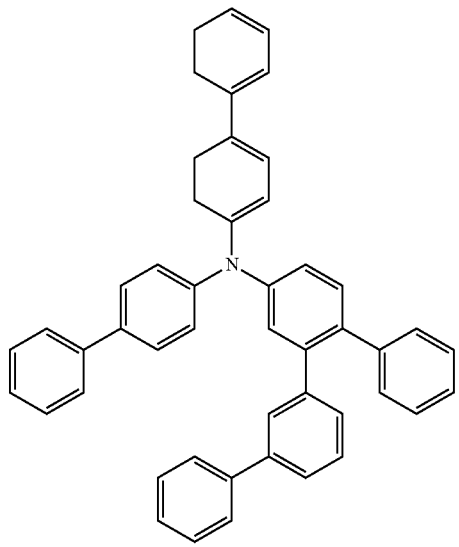

-continued
[Chemical Formula 262]
(5-106)
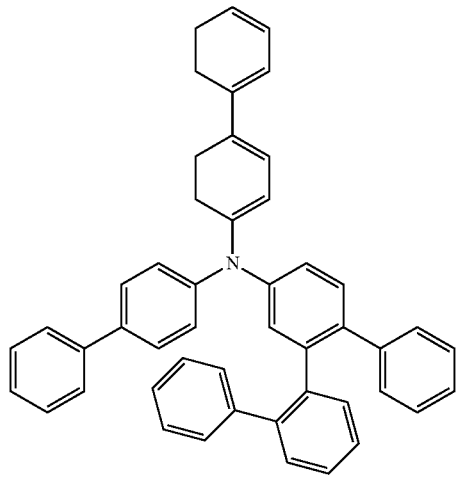
[Chemical Formula 263]
(5-107)
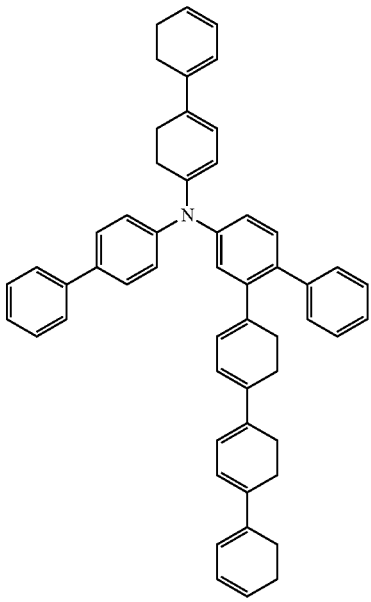
[Chemical Formula 264]
(5-108)
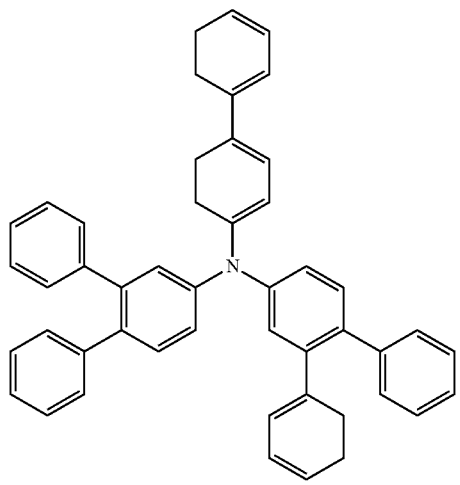
[Chemical Formula 265]
(5-109)
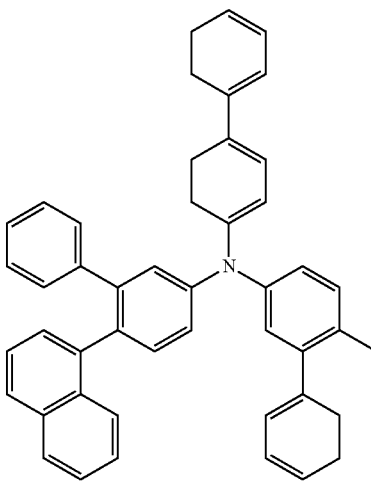
[Chemical Formula 266]
(5-110)
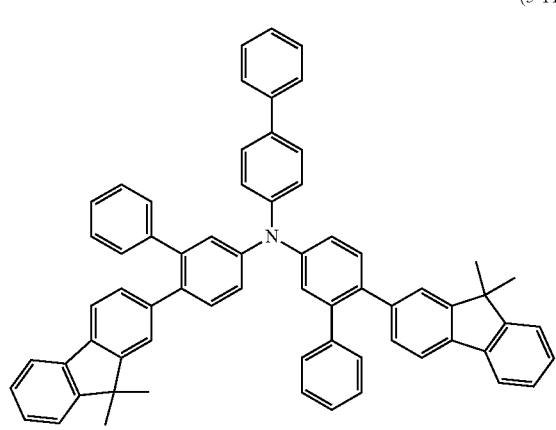
[Chemical Formula 267]
(5-111)
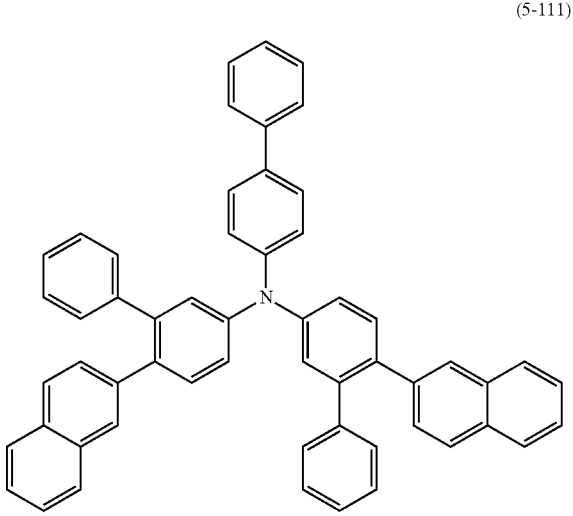

[Chemical Formula 268]
(5-112)
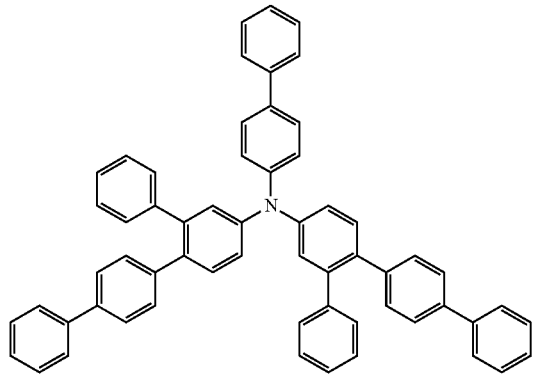
[Chemical Formula 269]
(5-113)
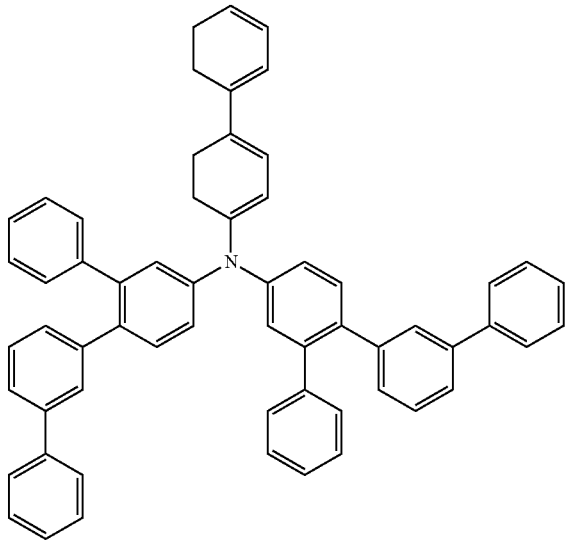
[Chemical Formula 270]
(5-114)
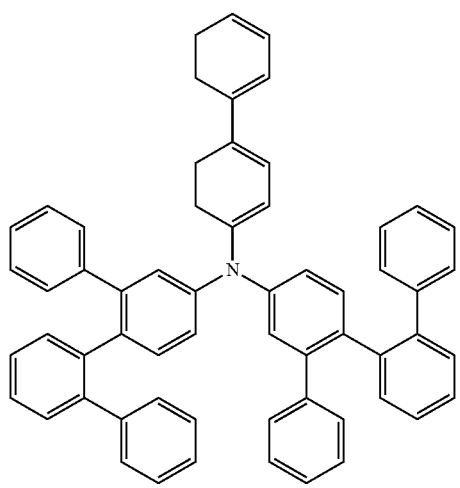
[Chemical Formula 271]
(5-115)
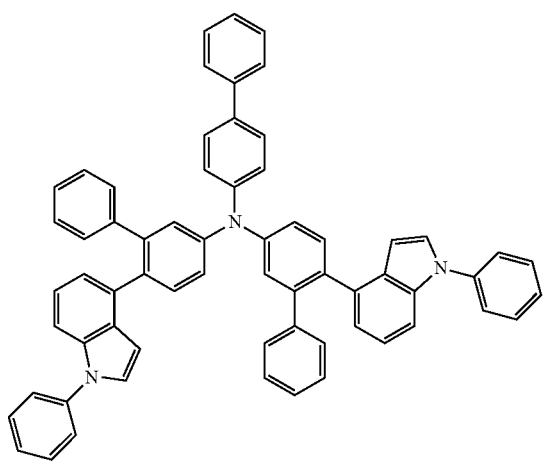

[Chemical Formula 272]
(5-116)
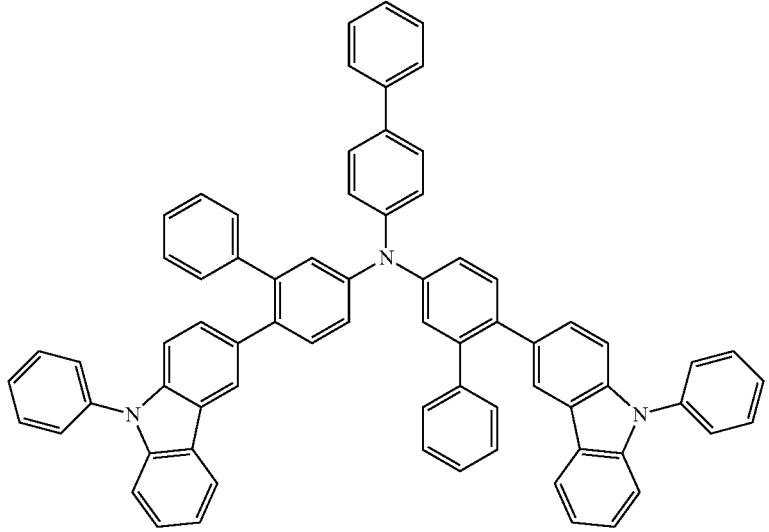
[Chemical Formula 273]
(5-117)
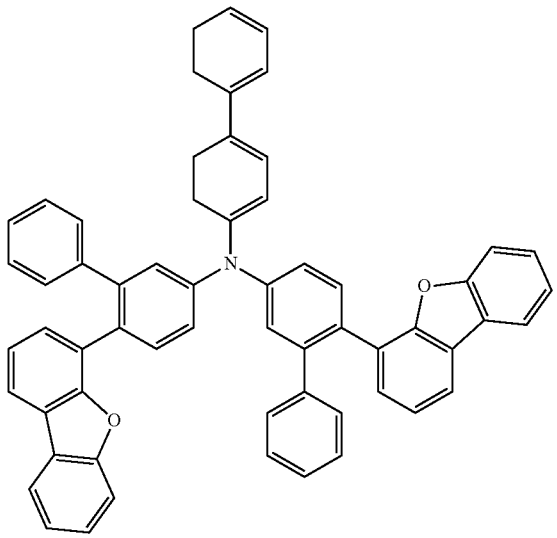
[Chemical Formula 274]
(5-117)
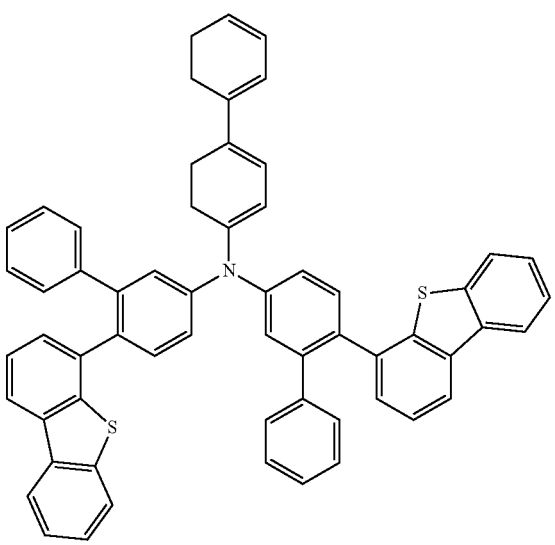
[Chemical Formula 275]
(5-119)
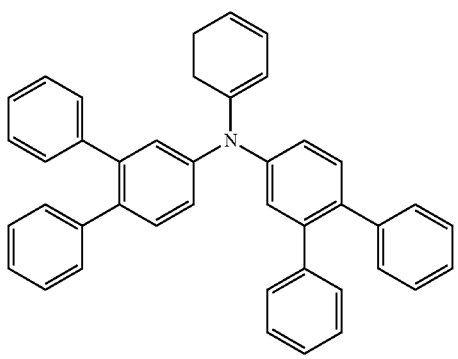
[Chemical Formula 276]
(5-120)
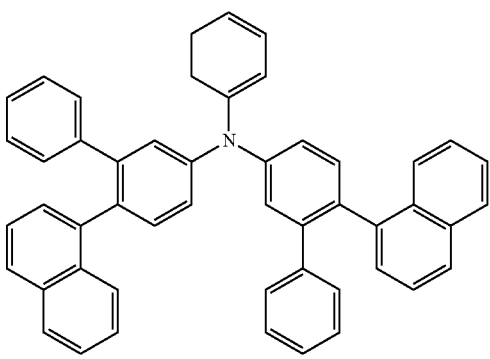

-continued
[Chemical Formula 277]
(5-121)
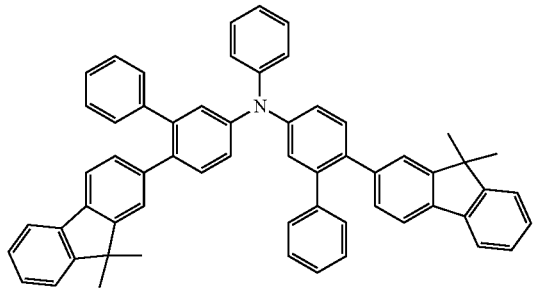
[Chemical Formula 278]
(5-122)
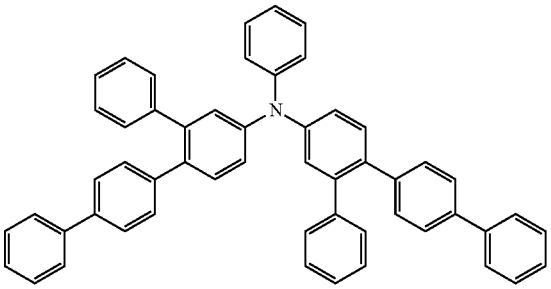
[Chemical Formula 279]
(5-123)
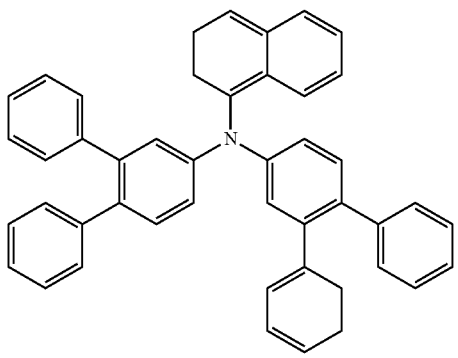
[Chemical Formula 280]
(5-124)
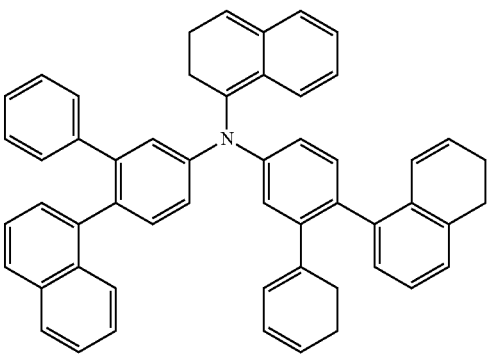
[Chemical Formula 281]
(5-125)
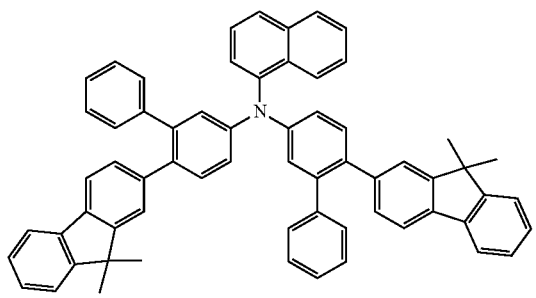
[Chemical Formula 282]
(5-126)
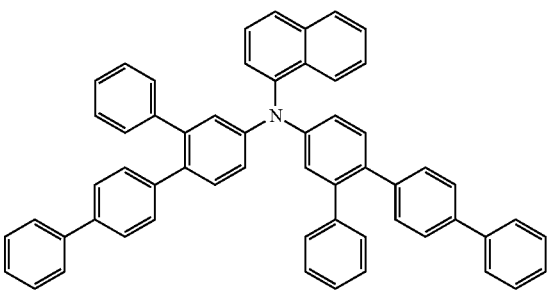
[Chemical Formula 283]
(5-127)
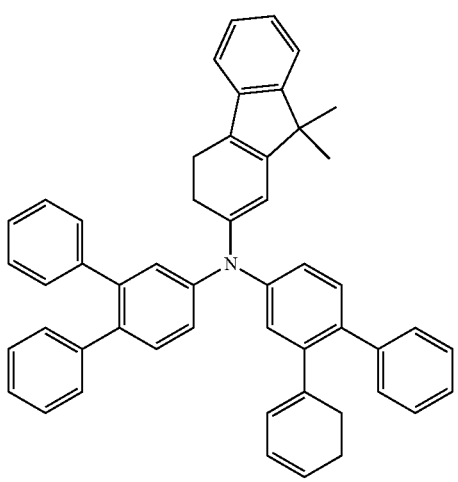
[Chemical Formula 284]
(5-128)
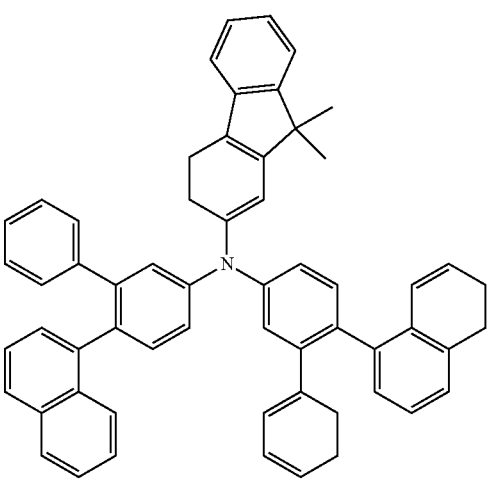

[Chemical Formula 285]
(5-129)
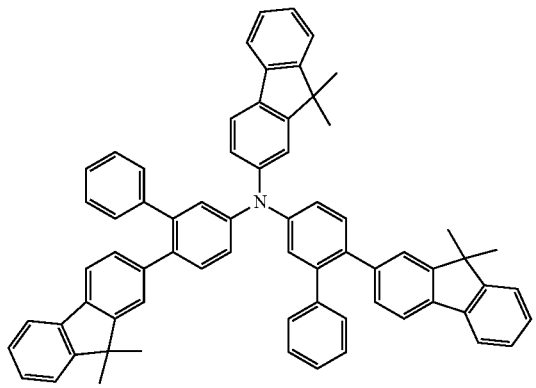
[Chemical Formula 286]
(5-130)
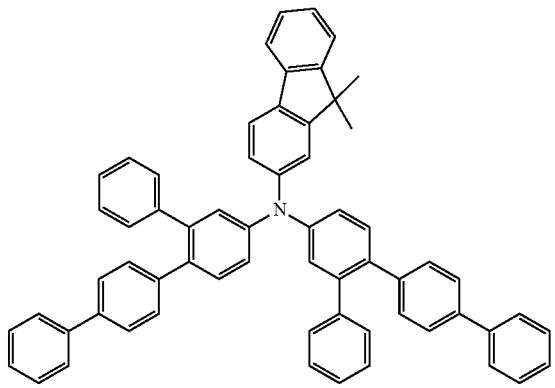
[Chemical Formula 287]
(5-131)
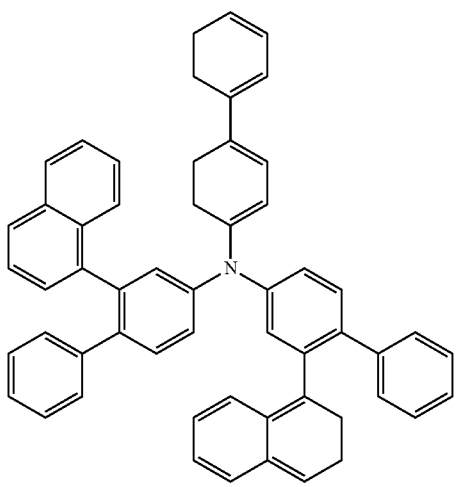
[Chemical Formula 288]
(5-132)
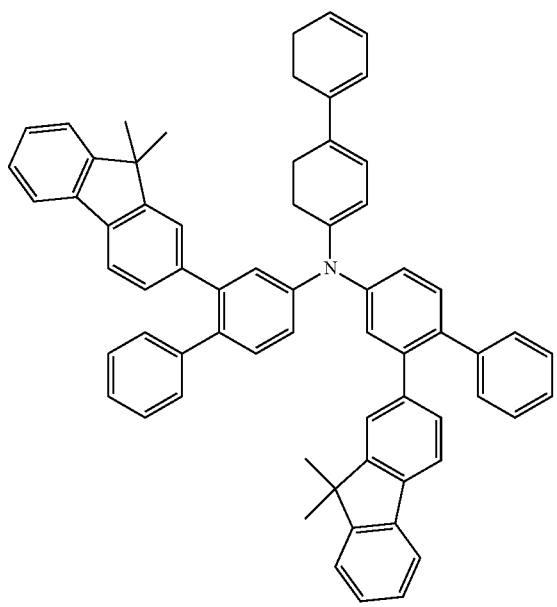
[Chemical Formula 289]
(5-133)
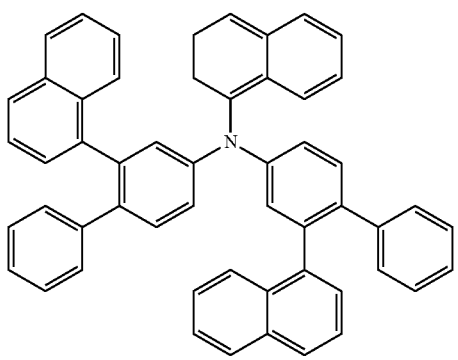
[Chemical Formula 290]
(5-134)
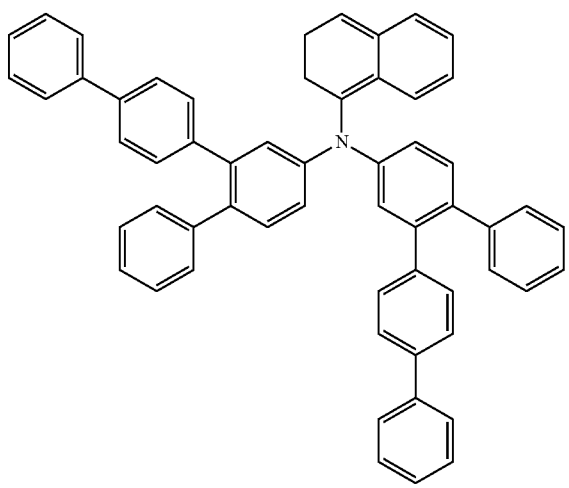

[Chemical Formula 291]
(5-135)
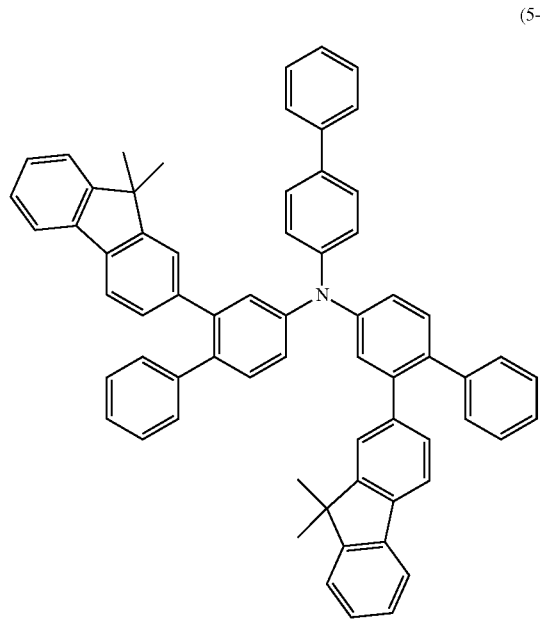
[Chemical Formula 292]
(5-136)
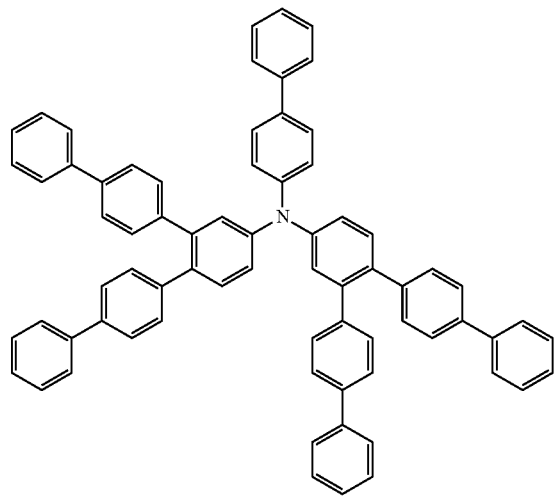
[Chemical Formula 293]
(5-137)
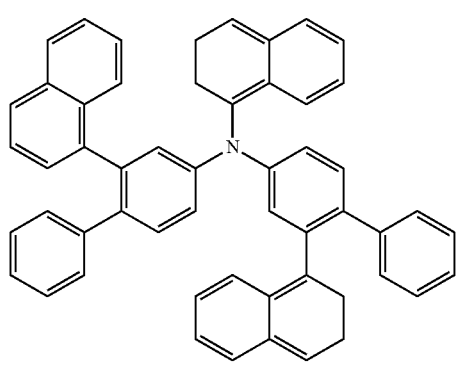
[Chemical Formula 294]
(5-138)
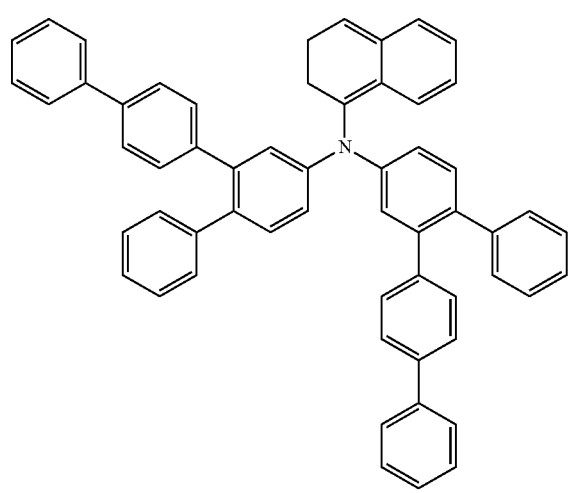

[Chemical Formula 295]
(5-139)
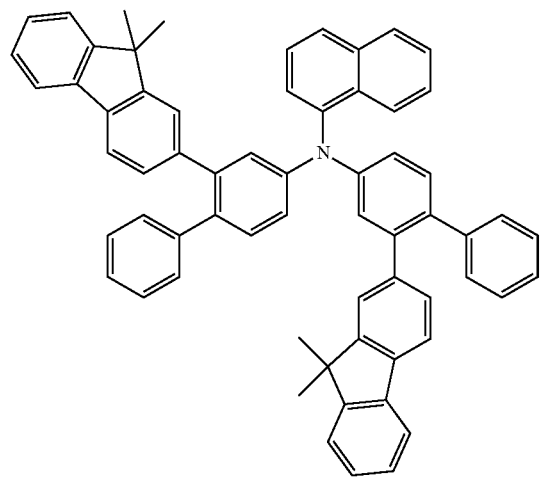
[Chemical Formula 296]
(5-140)
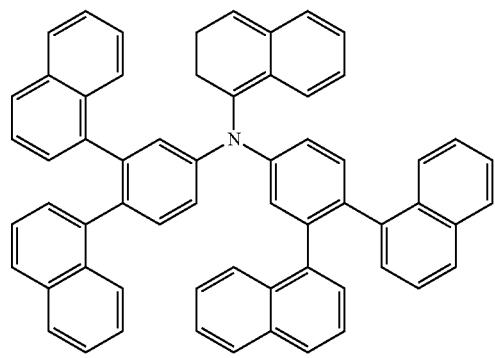
[Chemical Formula 297]
(5-141)
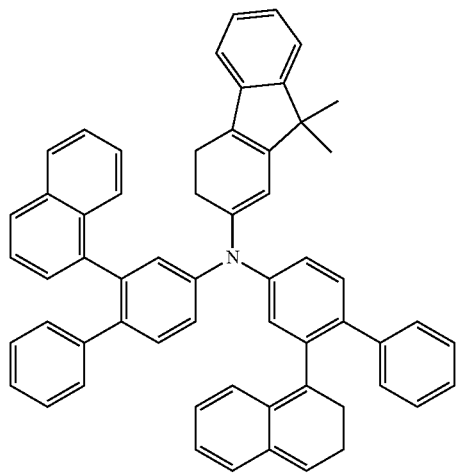
[Chemical Formula 298]
(5-142)
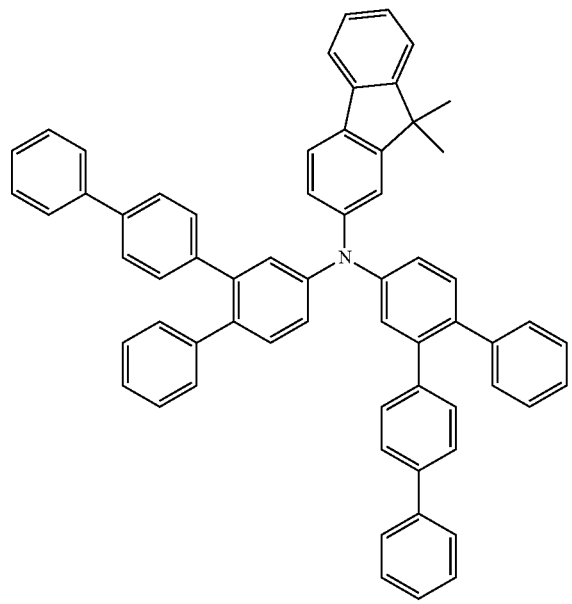

[Chemical Formula 299]
(5-143)
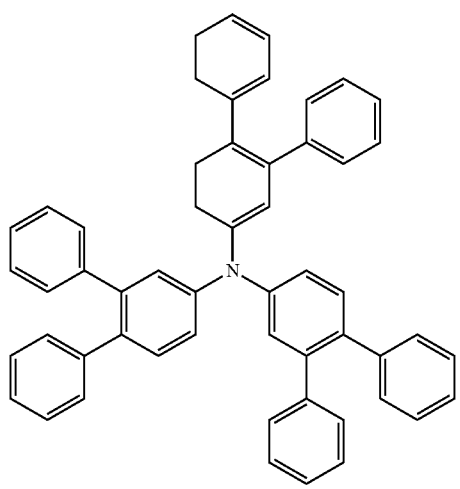
[Chemical Formula 300]
(5-144)
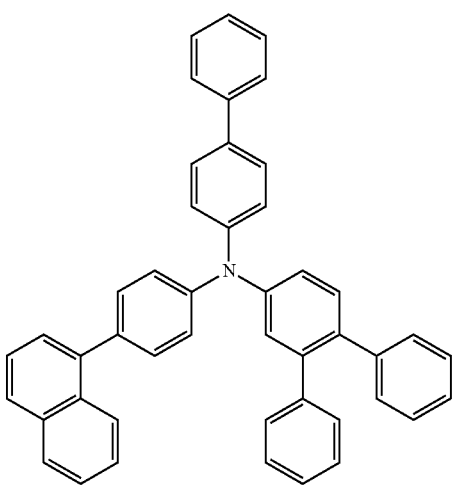
[Chemical Formula 301]
(5-145)
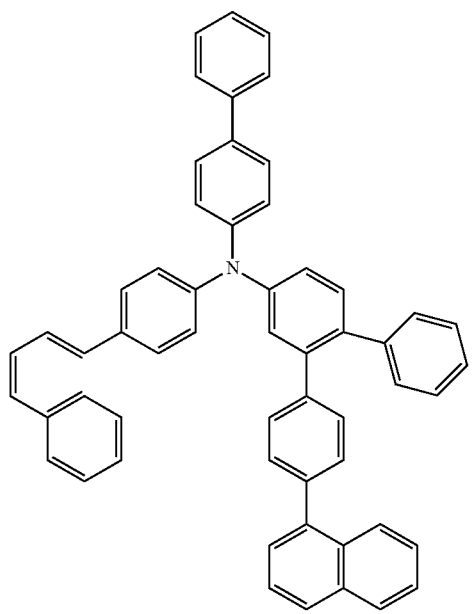
The following presents specific examples of preferred compounds among the compounds of the general formula (6a) having an anthracene ring structure and preferably used in the organic EL device of the present invention. The present invention and, however, is not restricted to these compounds

[Chemical Formula 302]
(6a-1)
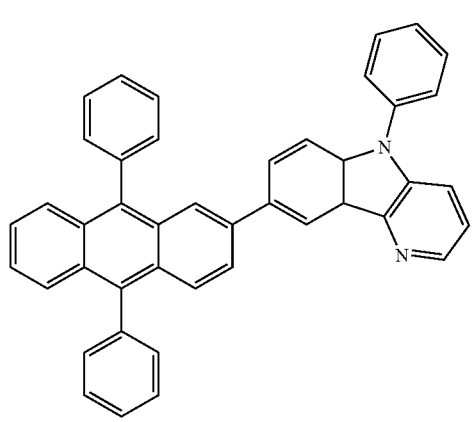
[Chemical Formula 303]
(6a-2)
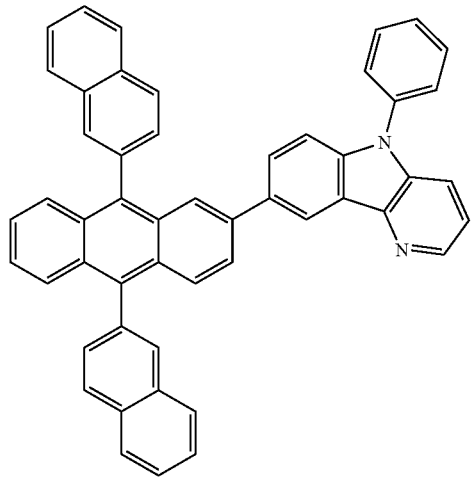
[Chemical Formula 304]
(6a-3)
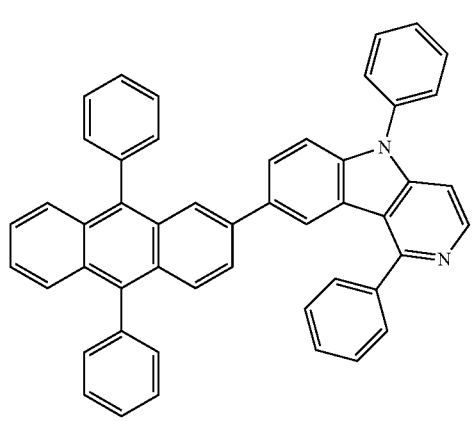
[Chemical Formula 305]
(6a-4)
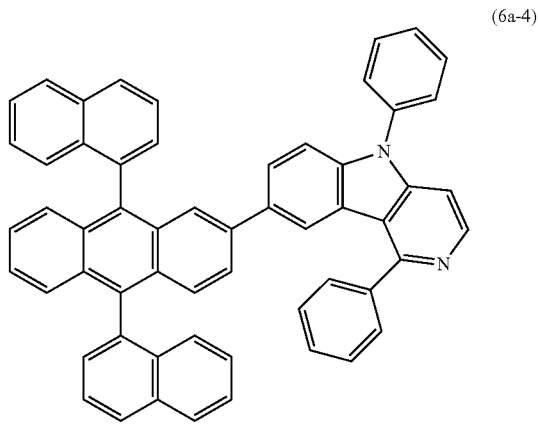
[Chemical Formula 306]
(6a-5)
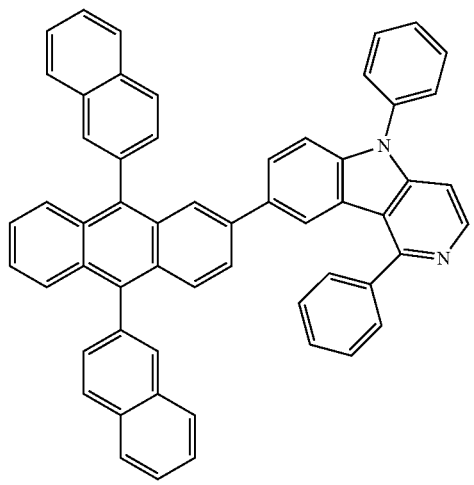
[Chemical Formula 307]
(6a-6)
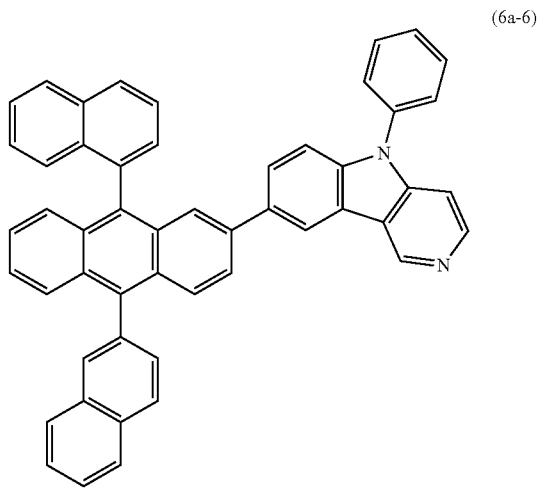

[Chemical Formula 308] (6a-7)
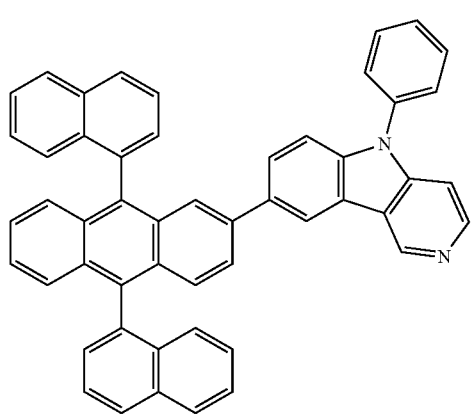
[Chemical Formula 309] (6a-8)
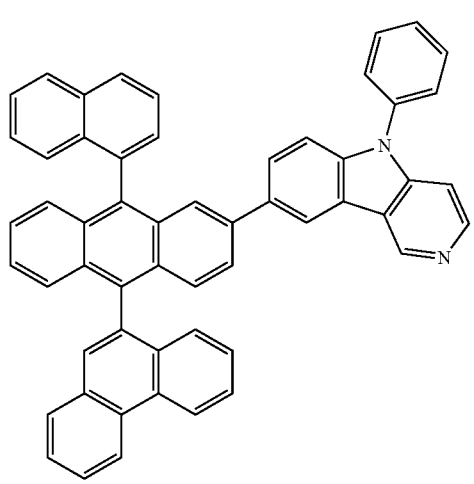
[Chemical Formula 310] (6a-9)
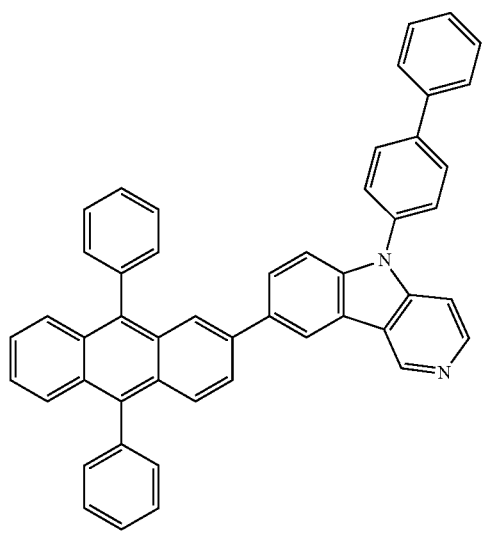
[Chemical Formula 311] (6a-10)
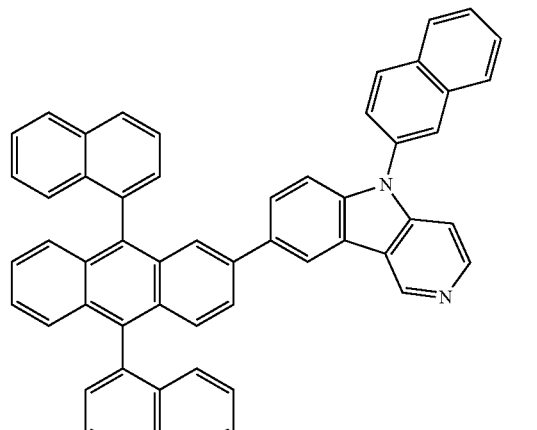
[Chemical Formula 312] (6a-11)
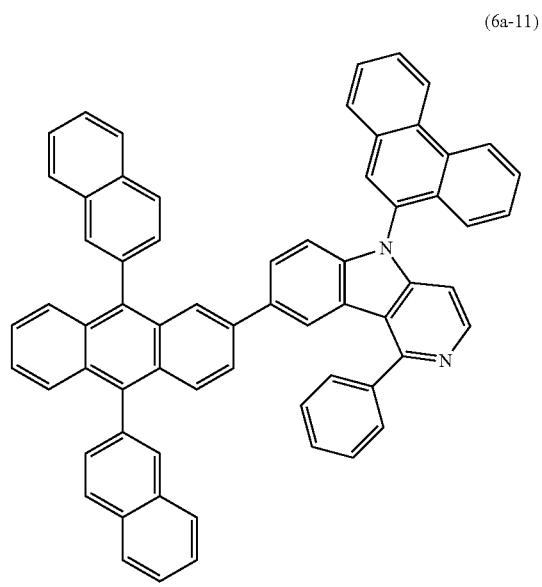
[Chemical Formula 313] (6a-12)
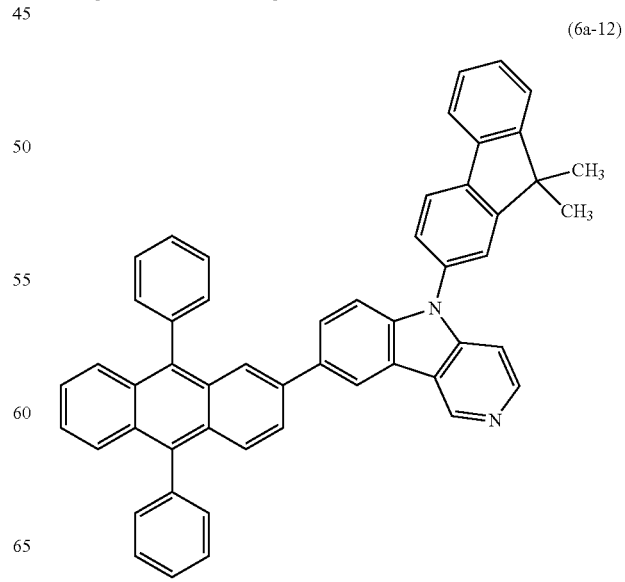

[Chemical Formula 314]
(6a-13)
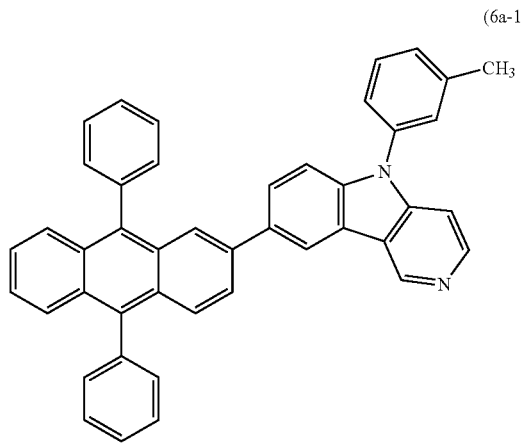
[Chemical Formula 315]
(6a-14)
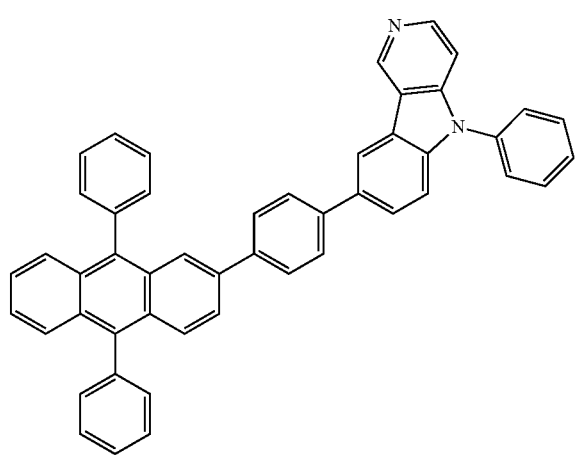
[Chemical Formula 316]
(6a-15)
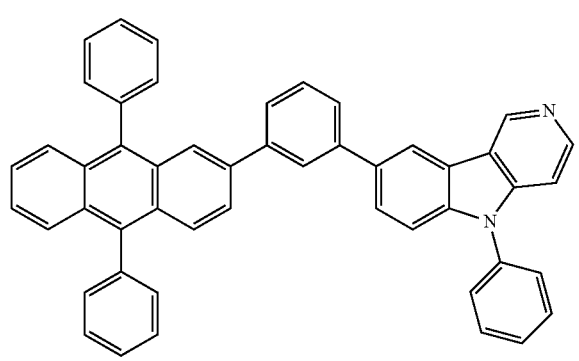
[Chemical Formula 317]
(6a-16)
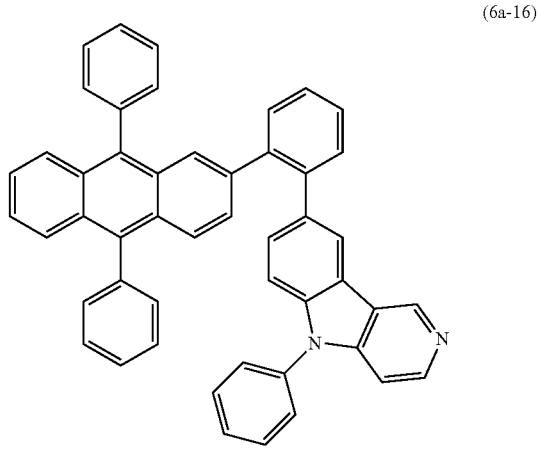
[Chemical Formula 318]
(6a-17)
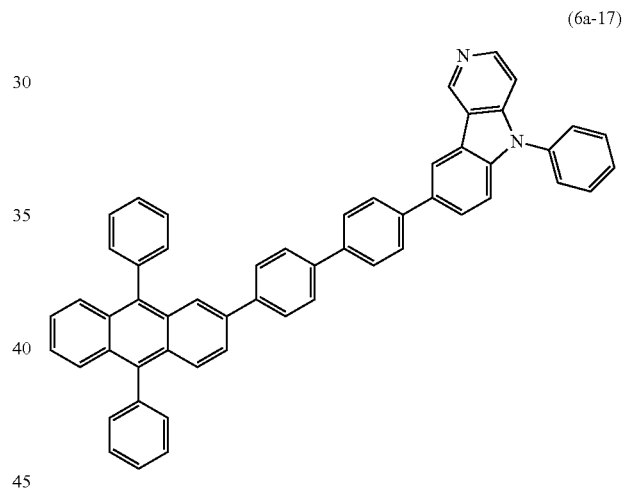
[Chemical Formula 319]
(6a-18)
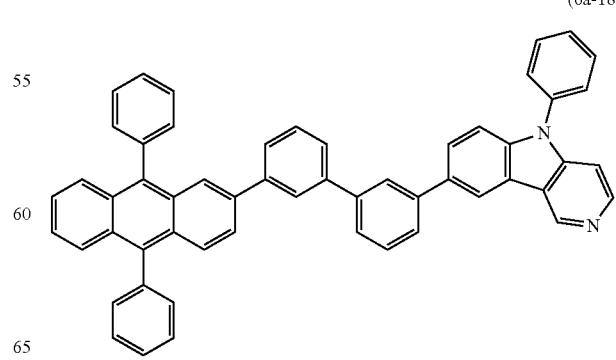

-continued

[Chemical Formula 320] (6a-19)

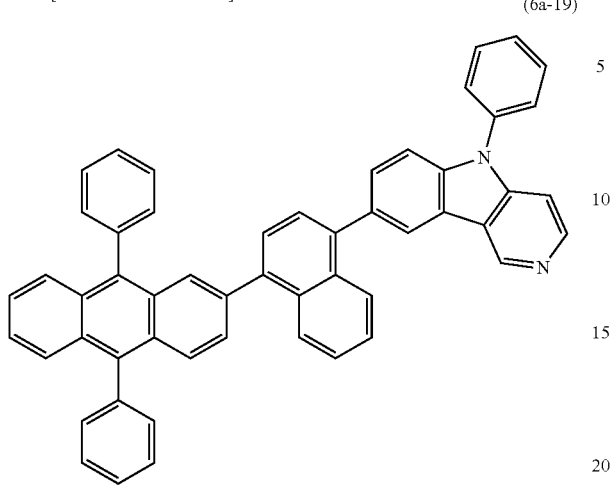

[Chemical Formula 321] (6a-20)

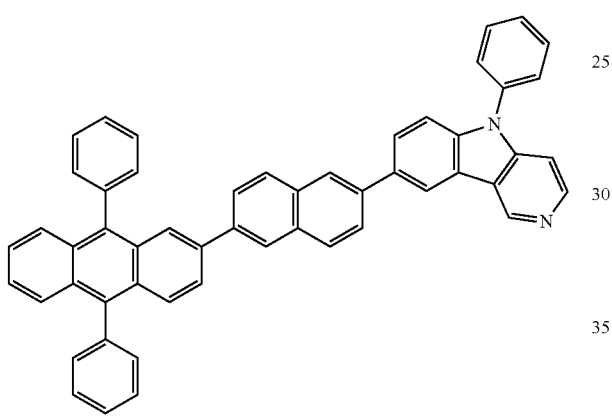

The following presents specific examples of preferred compounds among the compounds of the general formula (6b) having an anthracene ring structure and preferably used in the organic EL device of the present invention. The present invention and, however, is not restricted to these compounds.

[Chemical Formula 322] (6b-1)

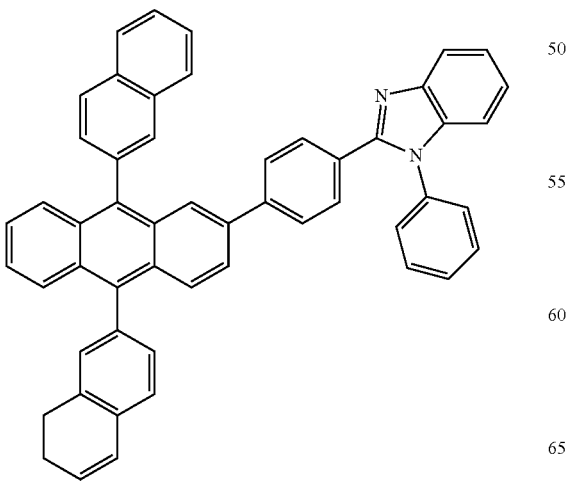

[Chemical Formula 323] (6b-2)

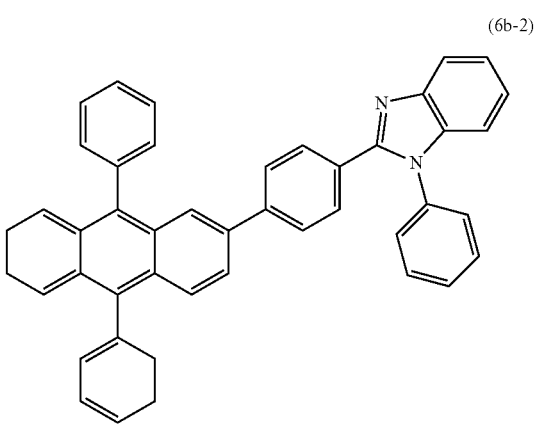

[Chemical Formula 324] (6b-3)

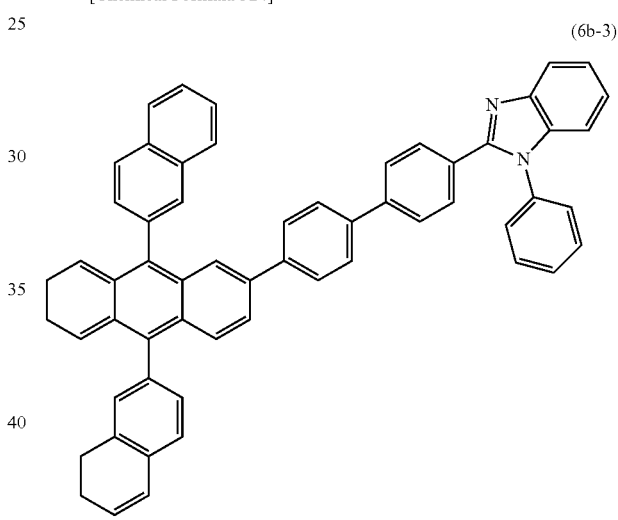

[Chemical Formula 325] (6b-4)

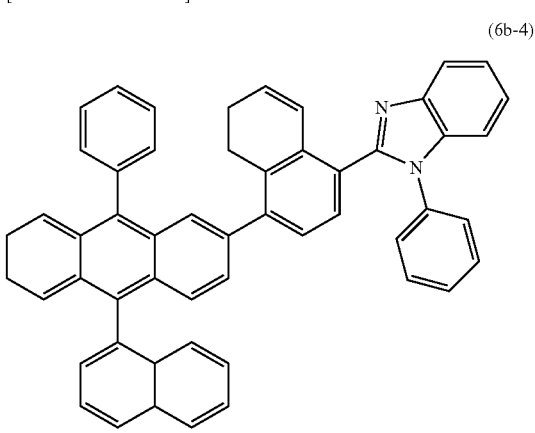

-continued

[Chemical Formula 326]

(6b-5)

[Chemical Formula 327]

(6b-6)

[Chemical Formula 328]

(6b-7)

[Chemical Formula 329]

(6b-8)

[Chemical Formula 330]

(6b-9)

[Chemical Formula 331]

(6b-10)

[Chemical Formula 332]

(6b-11)

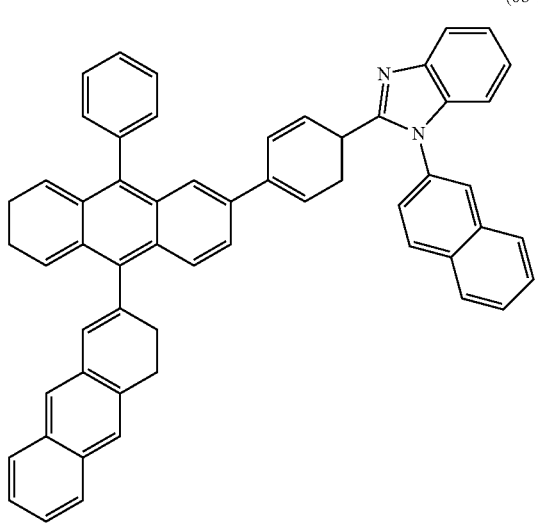

[Chemical Formula 333]

(6b-12)

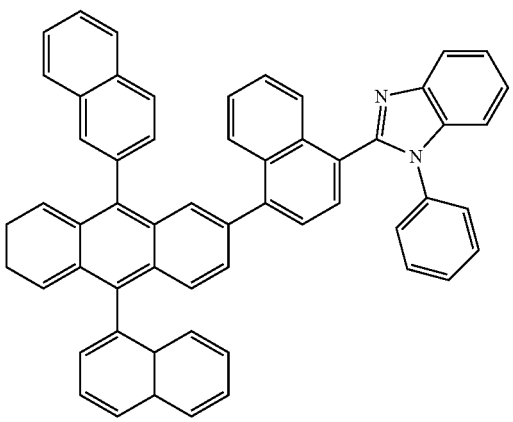

[Chemical Formula 334]

(6b-13)

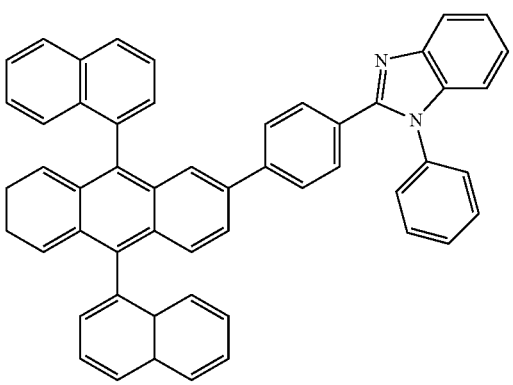

[Chemical Formula 335]

(6b-14)

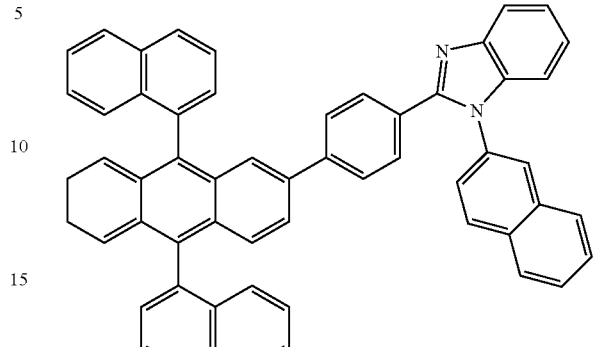

[Chemical Formula 336]

(6b-15)

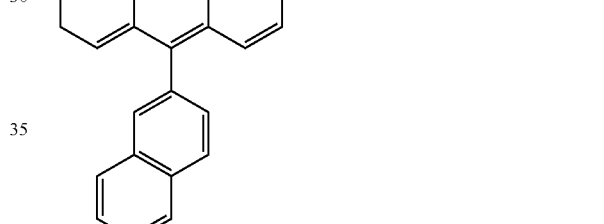

[Chemical Formula 337]

(6b-16)

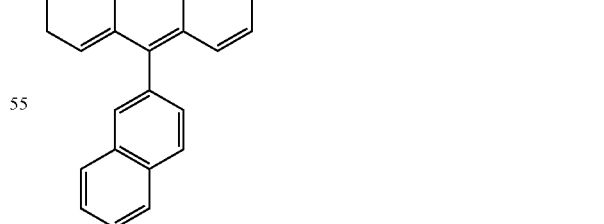

The following presents specific examples of preferred compounds among the compounds of the general formula (6c) having an anthracene ring structure and preferably used in the organic EL device of the present invention. The present invention and, however, is not restricted to these compounds.

[Chemical Formula 338]
(6c-1)
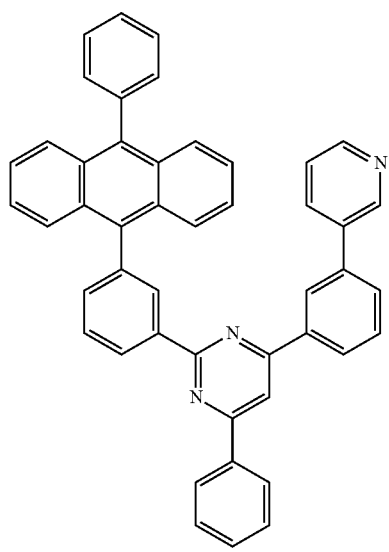
[Chemical Formula 339]
(6c-2)
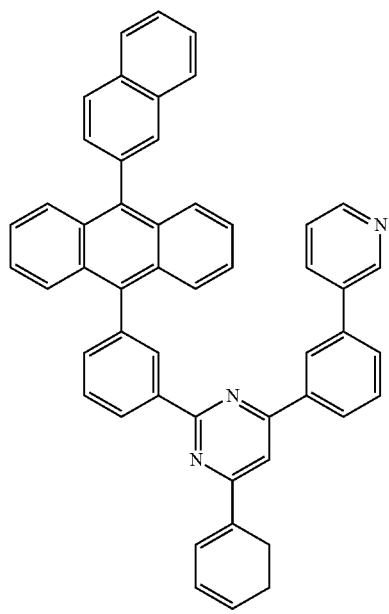
[Chemical Formula 340]
(6c-3)
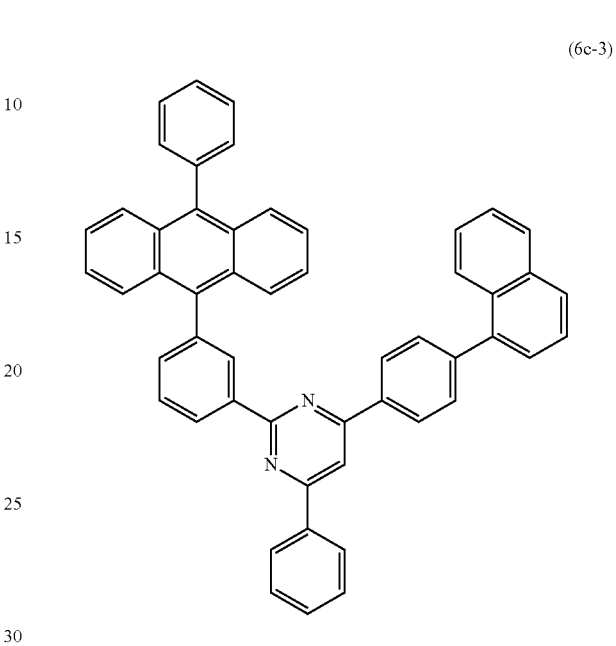
[Chemical Formula 341]
(6c-4)
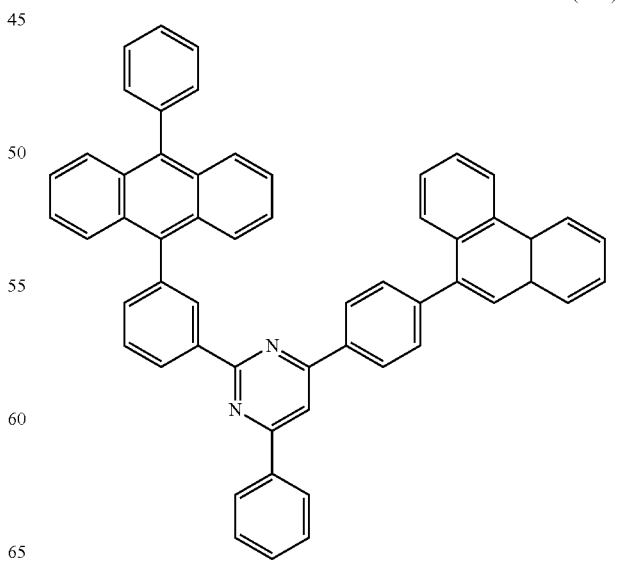

[Chemical Formula 342]
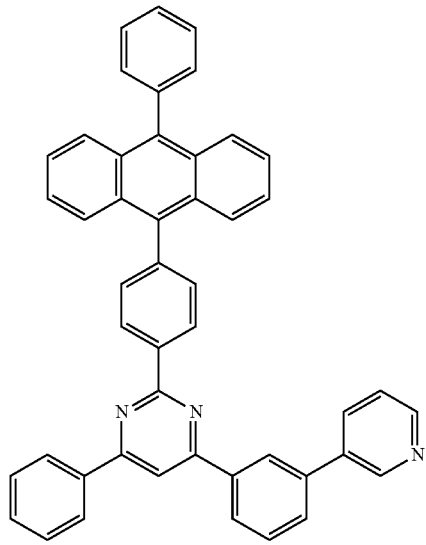
(6c-5)
[Chemical Formula 343]
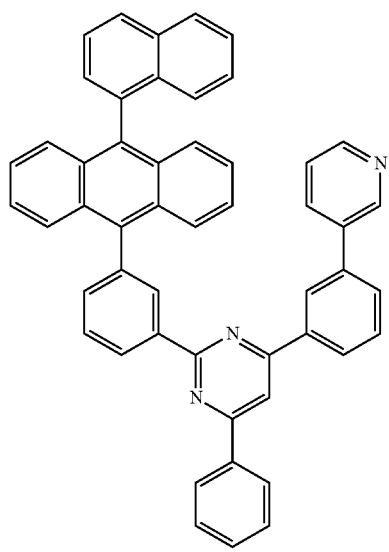
(6c-6)
[Chemical Formula 344]
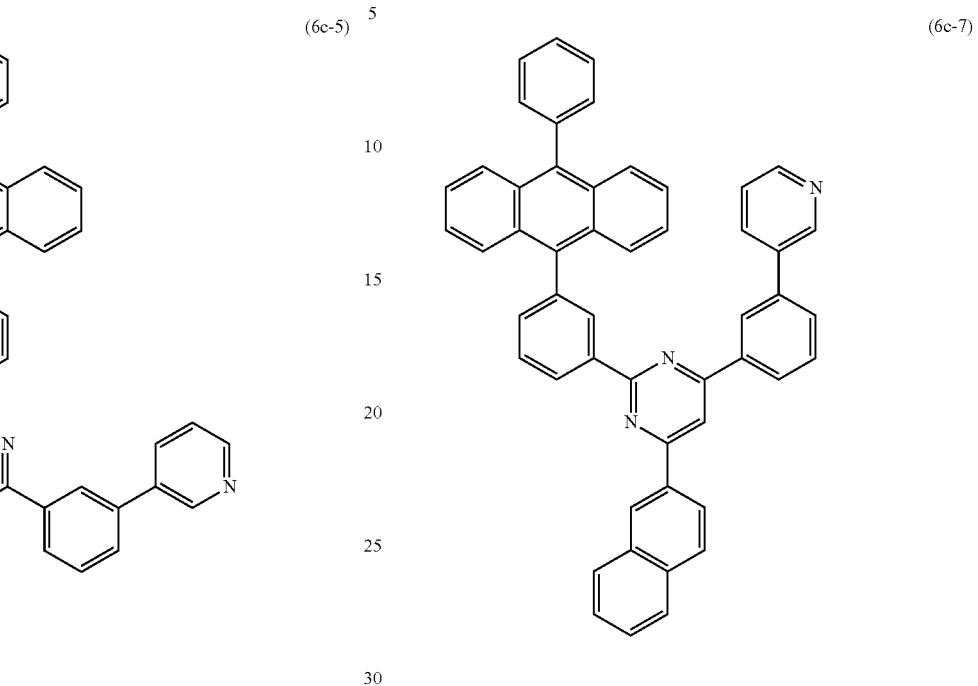
(6c-7)
[Chemical Formula 345]
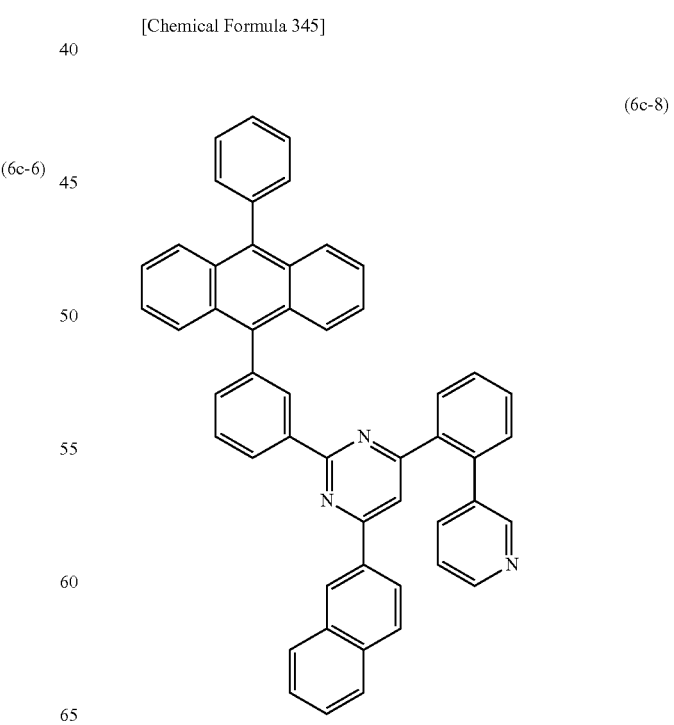
(6c-8)

[Chemical Formula 346]
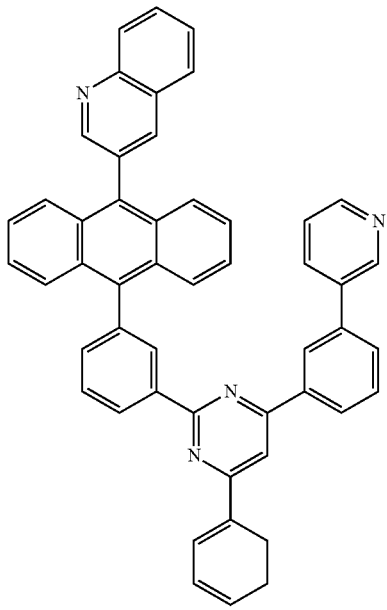
(6c-9)
[Chemical Formula 347]
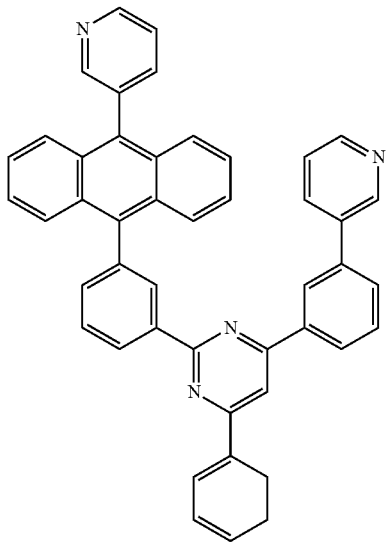
(6c-10)
[Chemical Formula 348]
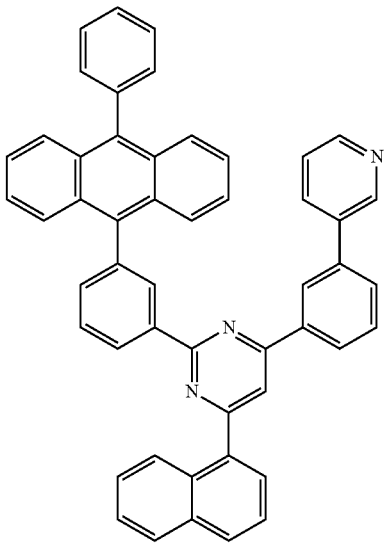
(6c-11)
[Chemical Formula 349]
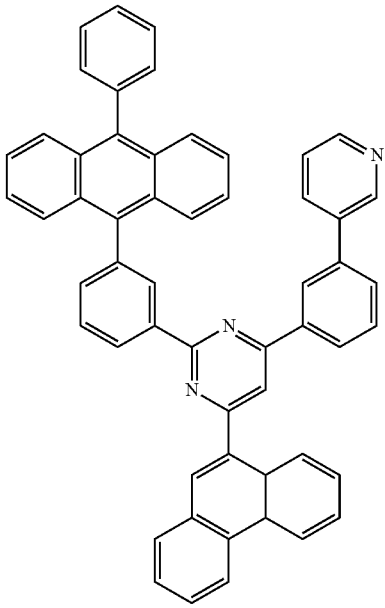
(6c-12)

[Chemical Formula 350]
(6c-13)
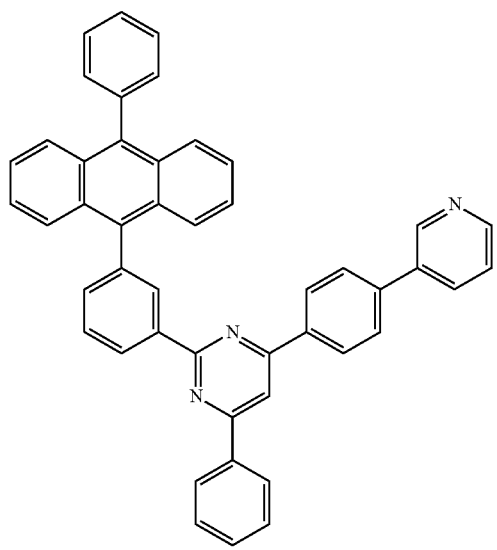
[Chemical Formula 351]
(6c-14)
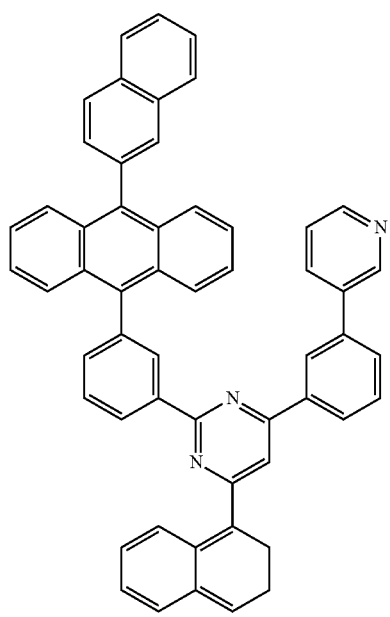
[Chemical Formula 352]
(6c-15)
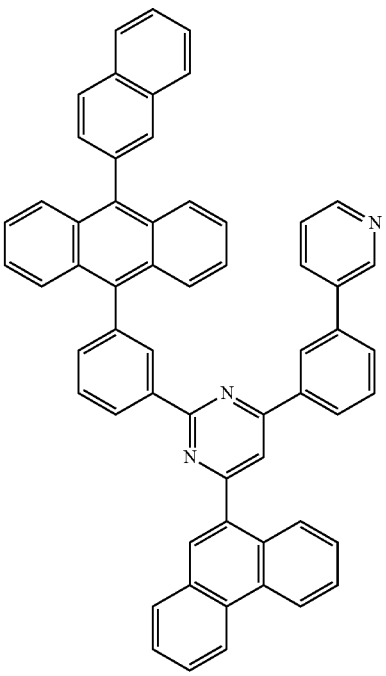
[Chemical Formula 353]
(6c-16)
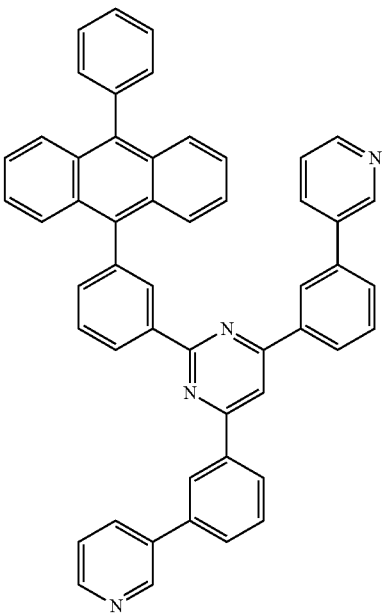

[Chemical Formula 354]
(6c-17)
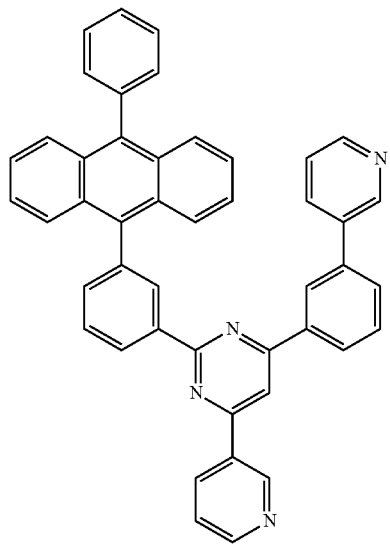
[Chemical Formula 355]
(6c-18)
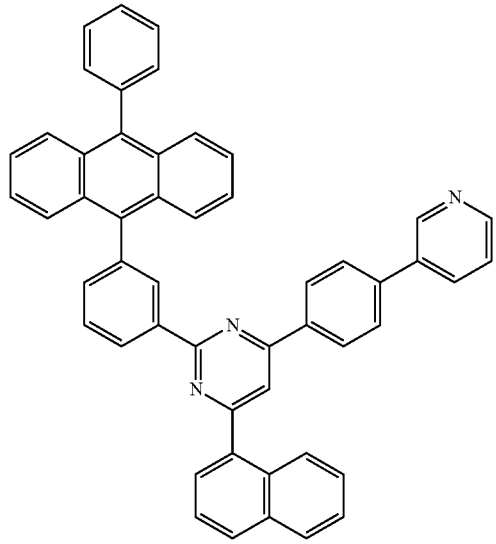
[Chemical Formula 356]
(6c-19)
[Chemical Formula 357]
(6c-20)
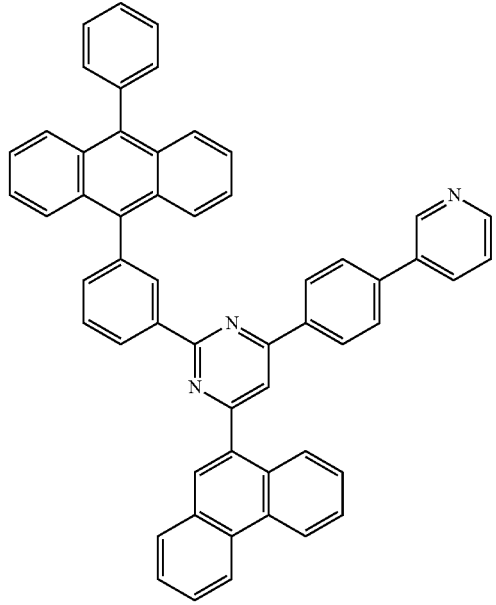

[Chemical Formula 358]
(6c-21)
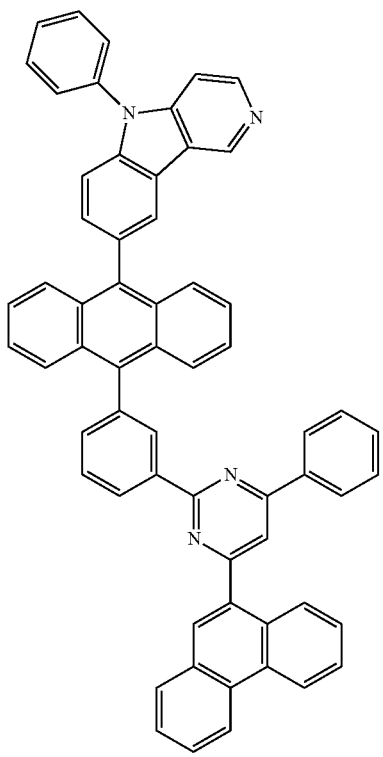
[Chemical Formula 359]
(6c-22)
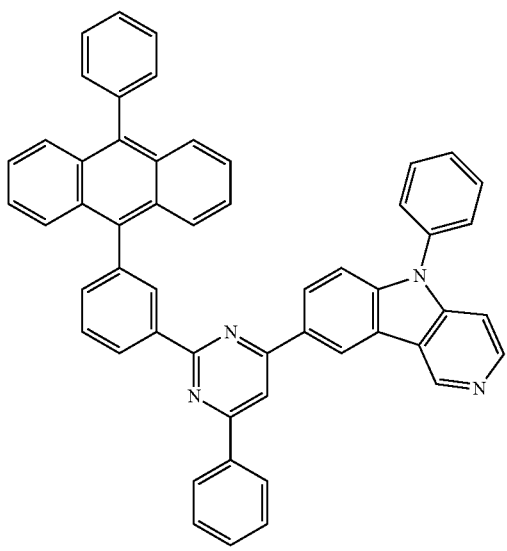
[Chemical Formula 360]
(6c-23)
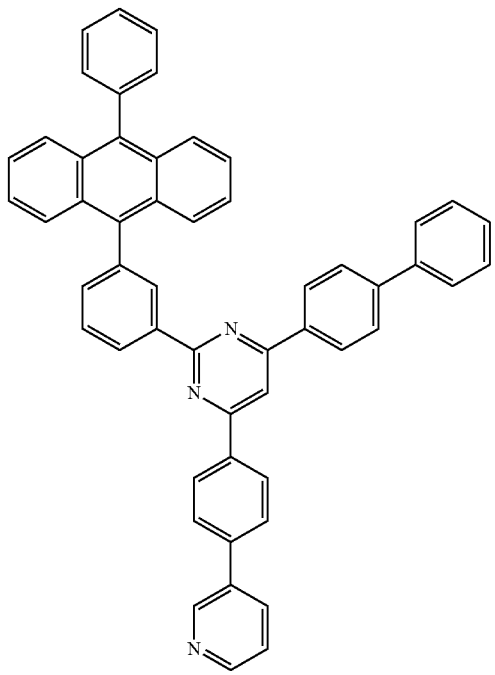
[Chemical Formula 361]
(6c-24)
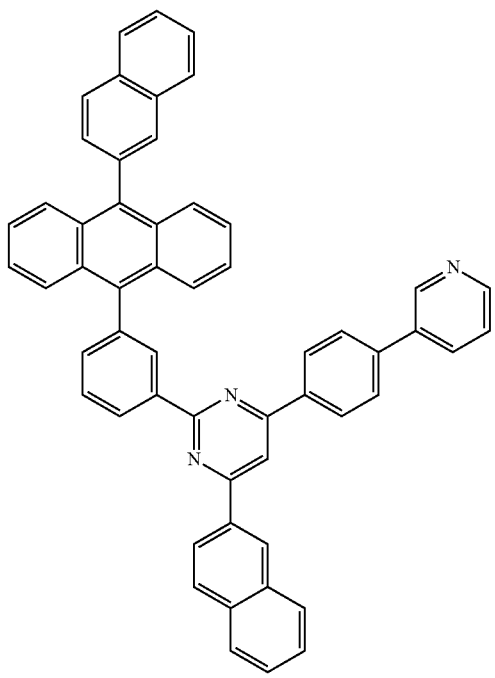

[Chemical Formula 362]
(6c-25)
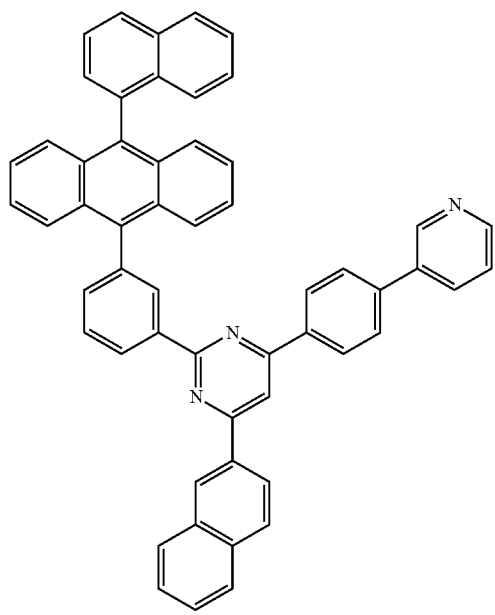
[Chemical Formula 363]
(6c-26)
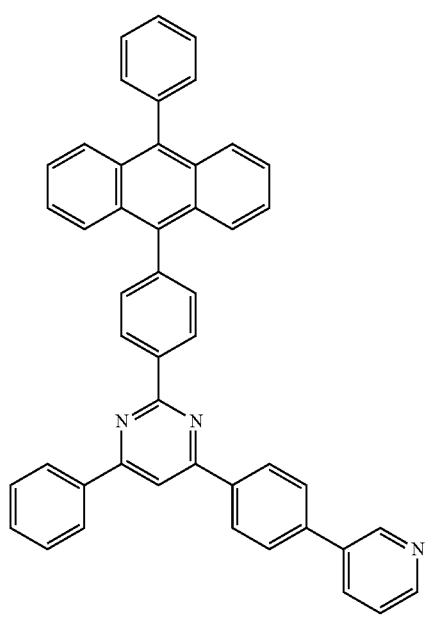
[Chemical Formula 364]
(6c-27)
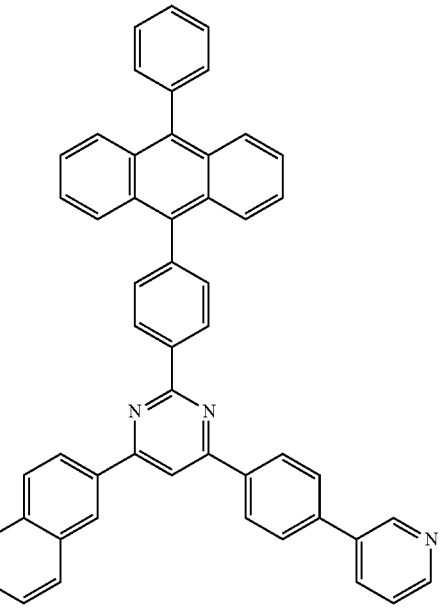
[Chemical Formula 365]
(6c-28)

[Chemical Formula 366]

(6c-29)

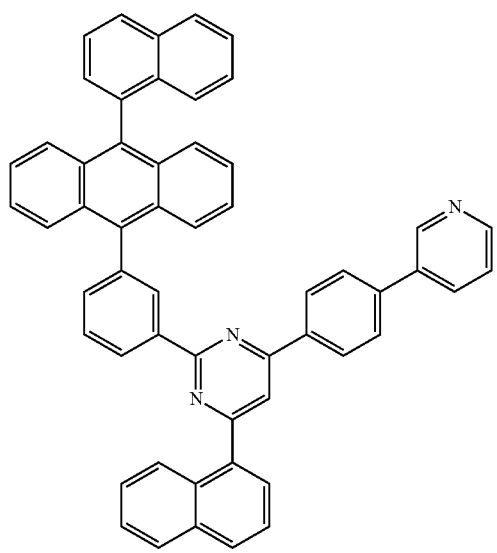

[Chemical Formula 367]

(6c-30)

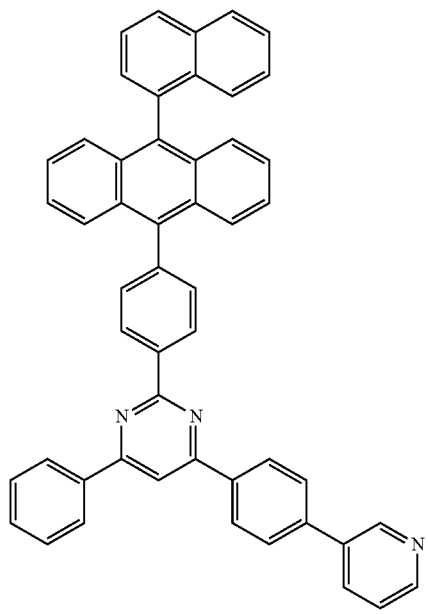

[Chemical Formula 368]

(7-1)

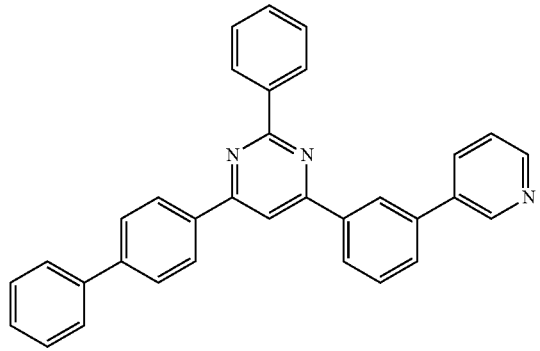

[Chemical Formula 369]

(7-2)

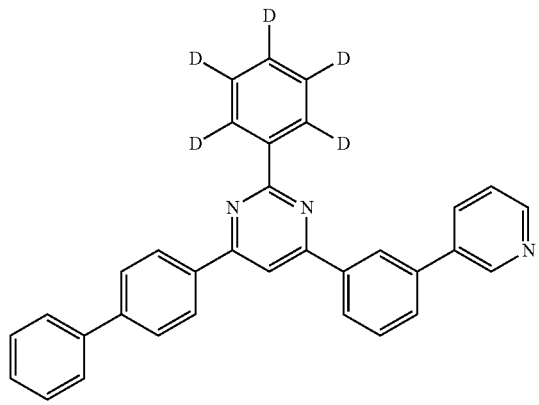

[Chemical Formula 370]

(7-3)

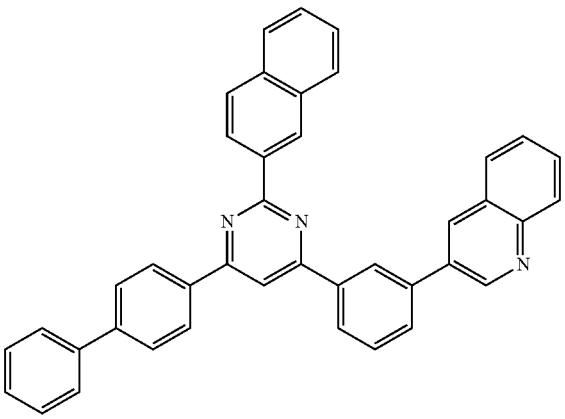

The compounds having an anthracene ring structure described above can be synthesized by a known method (refer to PTLs 10 to 12, for example).

The following presents specific examples of preferred compounds among the compounds of the general formula (7) preferably used in the organic EL device of the present invention and having a pyrimidine ring structure. The present invention, however, is not restricted to these compounds.

[Chemical Formula 371]
(7-4)
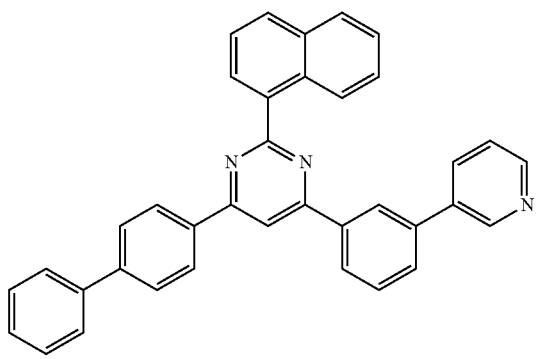
[Chemical Formula 372]
(7-5)
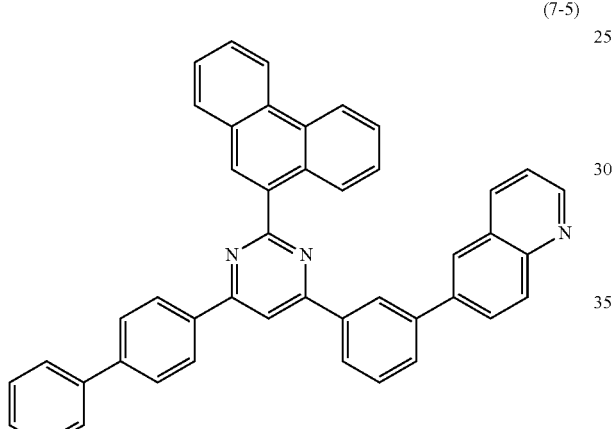
[Chemical Formula 373]
(7-6)
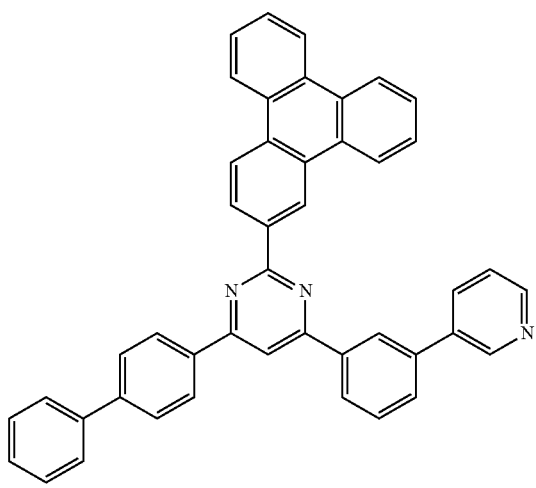
[Chemical Formula 374]
(7-7)
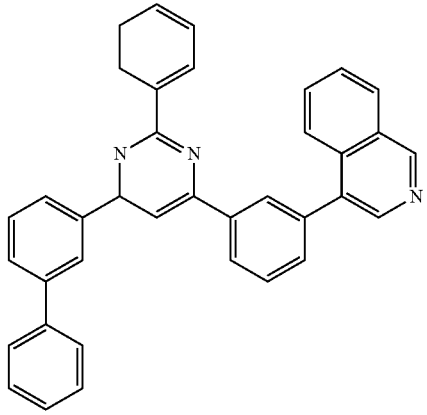
[Chemical Formula 375]
(7-8)
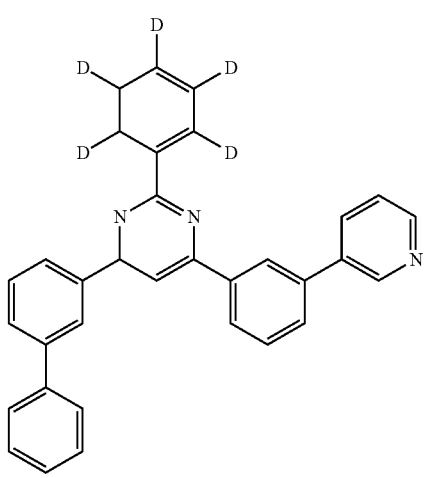
[Chemical Formula 376]
(7-9)
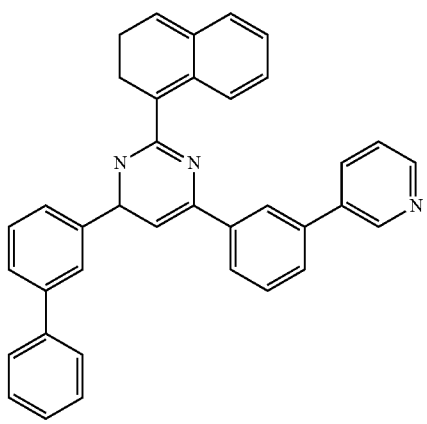

[Chemical Formula 377]
(7-10)
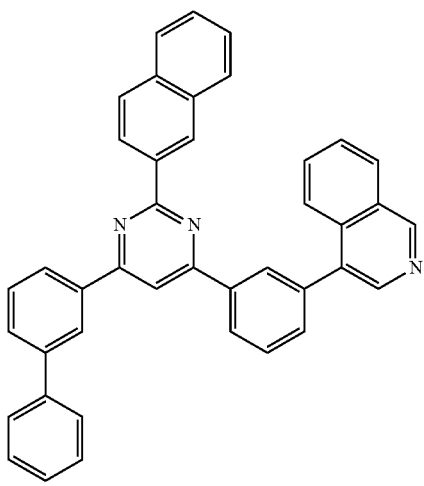
[Chemical Formula 378]
(7-11)
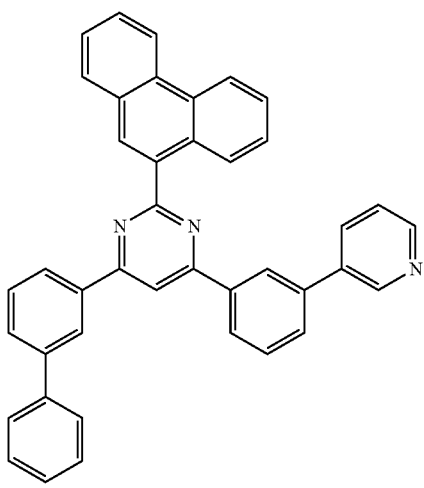
[Chemical Formula 379]
(7-12)
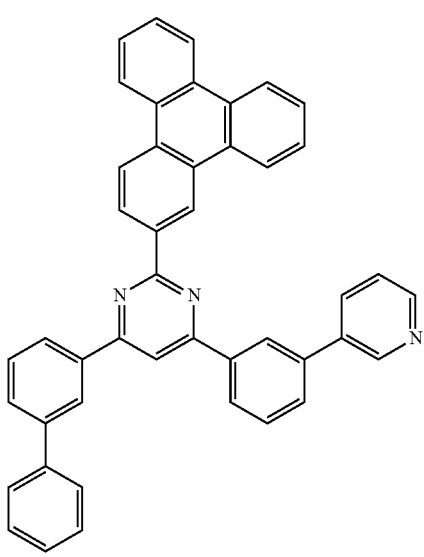
[Chemical Formula 380]
(7-13)
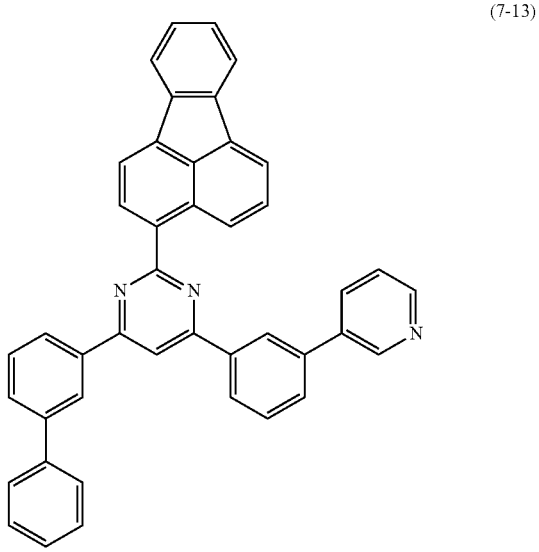
[Chemical Formula 381]
(7-14)
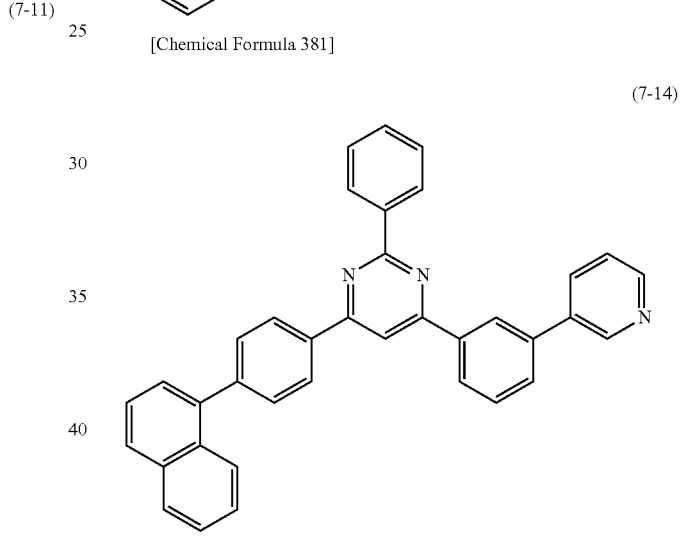
[Chemical Formula 382]
(7-15)
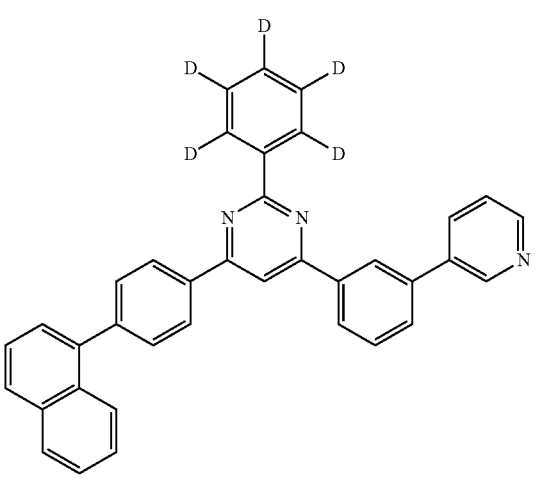

[Chemical Formula 383]
(7-16)
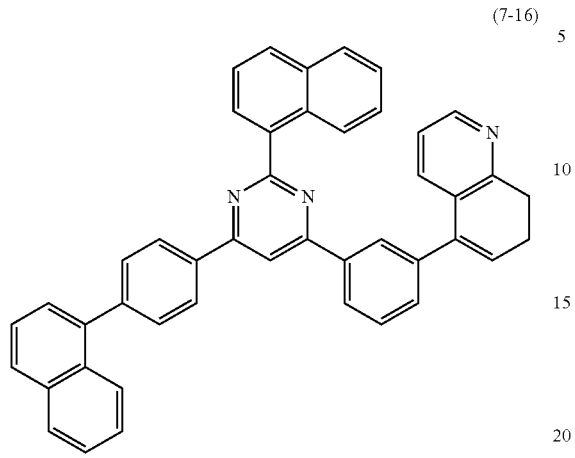
[Chemical Formula 384]
(7-17)
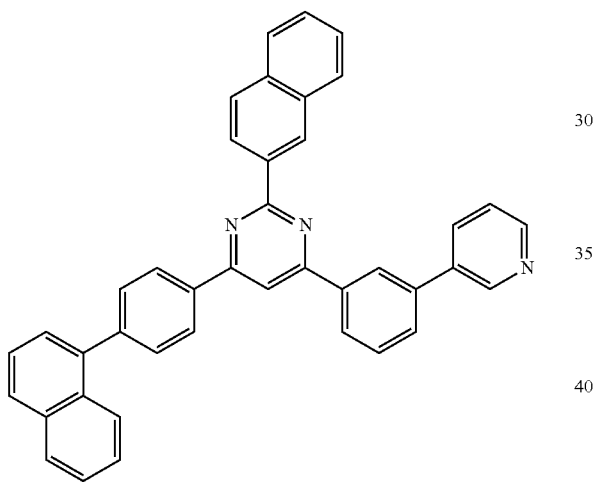
[Chemical Formula 385]
(7-18)
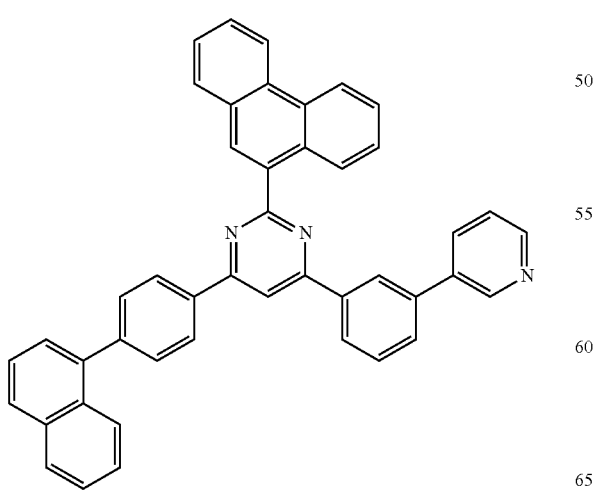
[Chemical Formula 386]
(7-19)
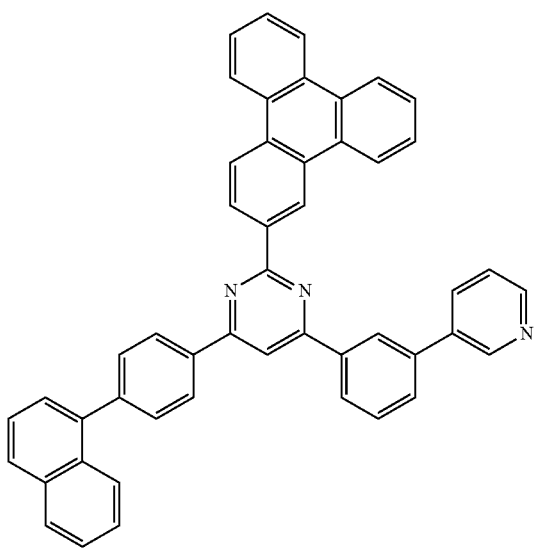
[Chemical Formula 387]
(7-20)
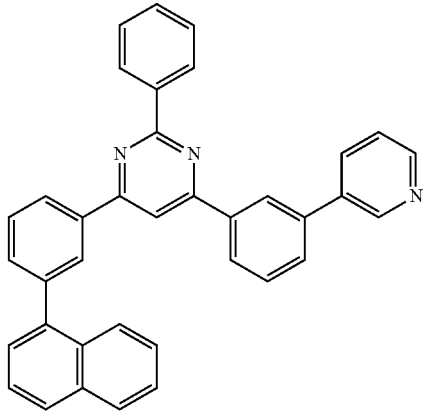
[Chemical Formula 388]
(7-21)
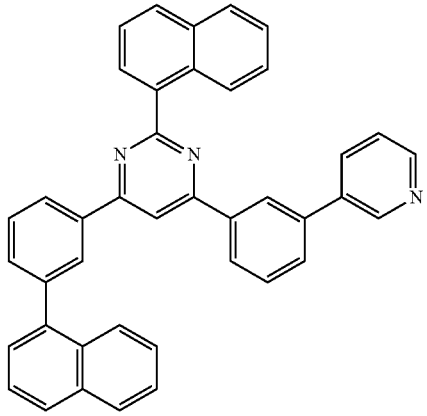

[Chemical Formula 389]
(7-22)
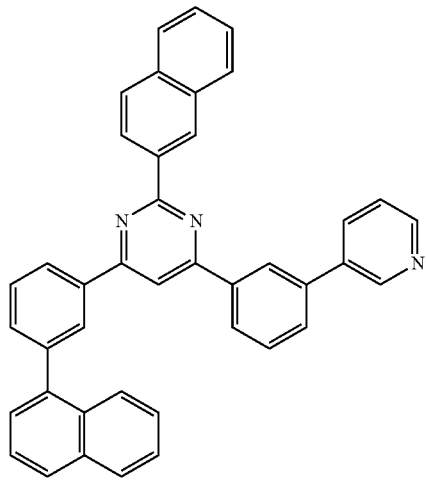
[Chemical Formula 390]
(7-23)
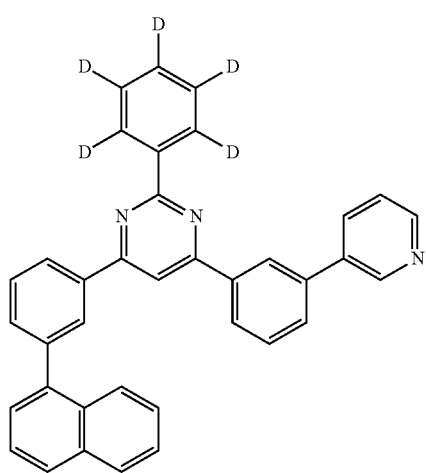
[Chemical Formula 391]
(7-24)
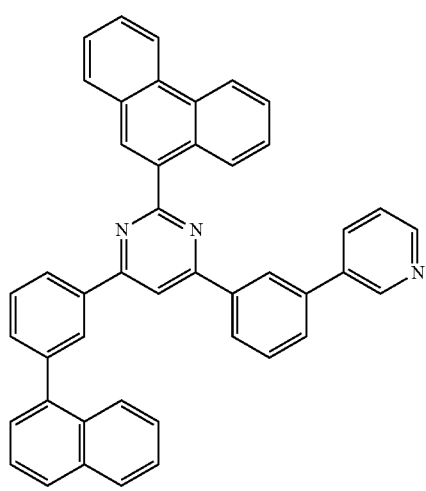
[Chemical Formula 392]
(7-25)
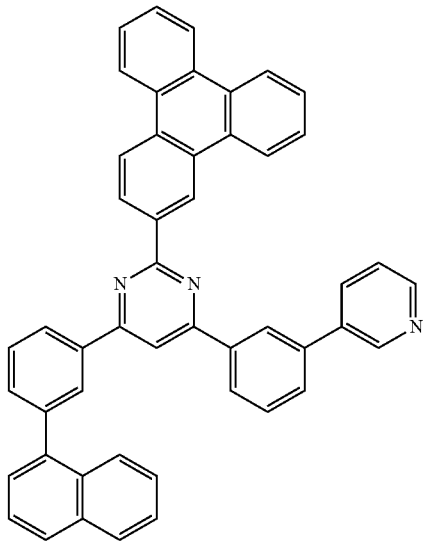
[Chemical Formula 393]
(7-26)
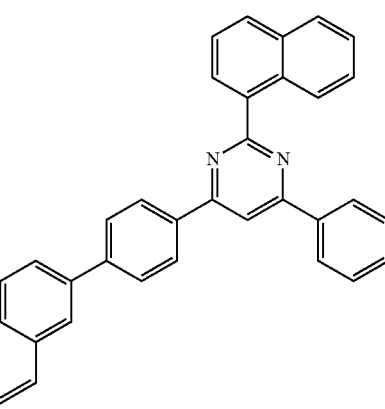
[Chemical Formula 394]
(7-27)

[Chemical Formula 395]
(7-28)
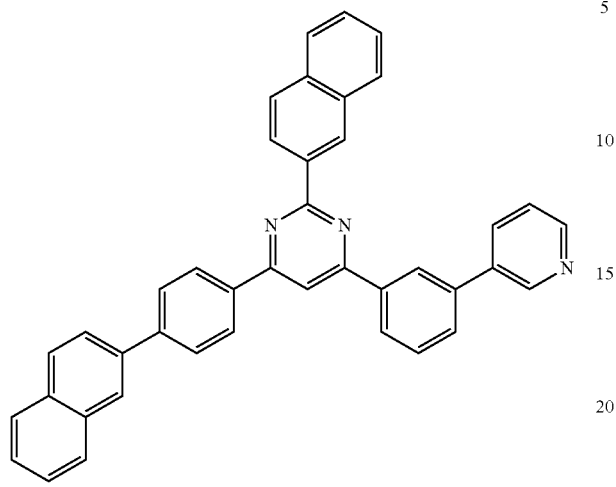
[Chemical Formula 396]
(7-29)
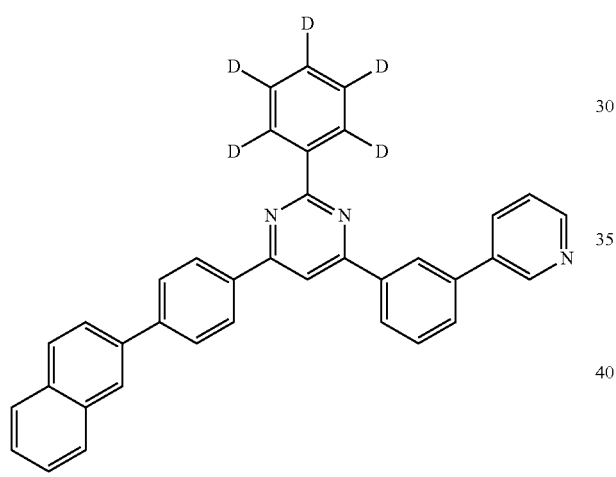
[Chemical Formula 397]
(7-30)
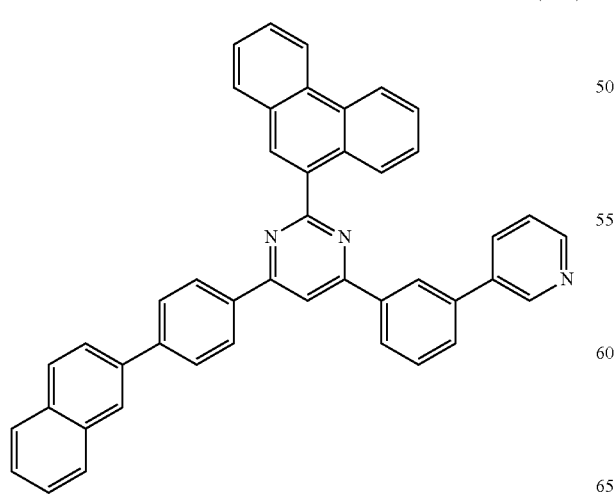
[Chemical Formula 398]
(7-31)
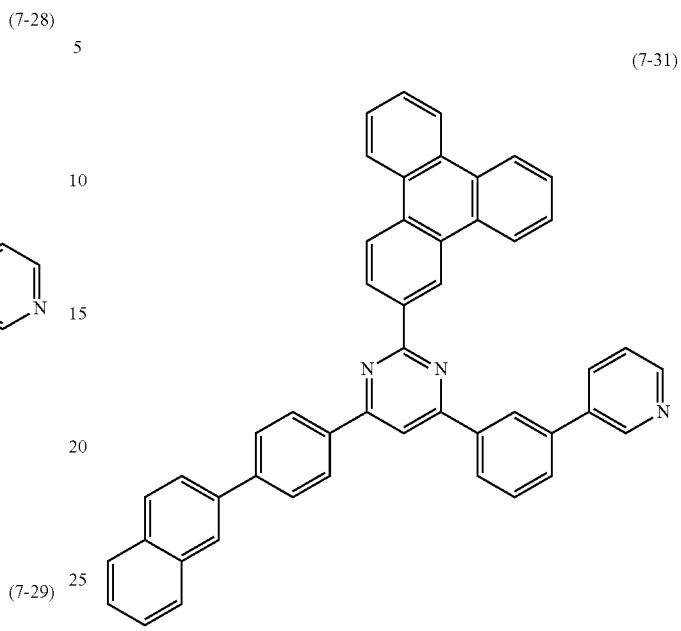
[Chemical Formula 399]
(7-32)
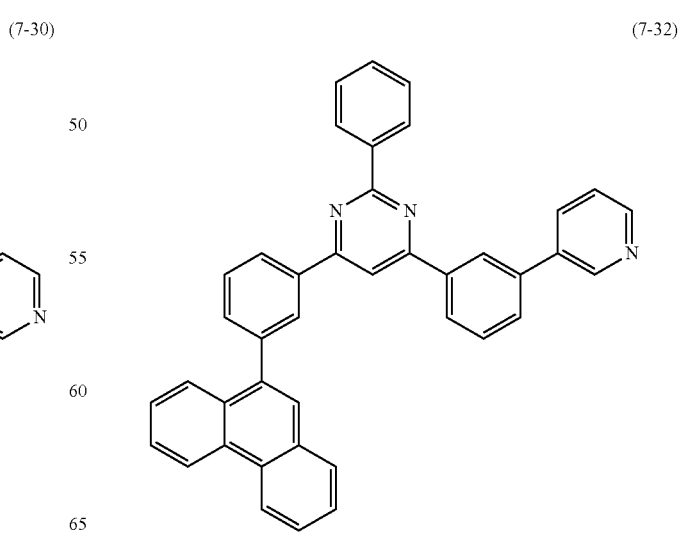

[Chemical Formula 400]
(7-33)
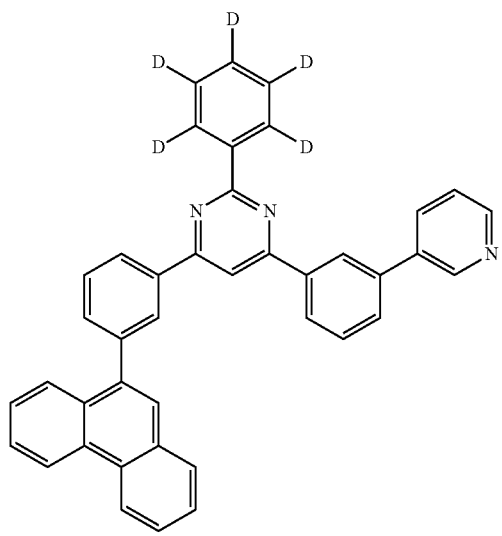
[Chemical Formula 401]
(7-34)
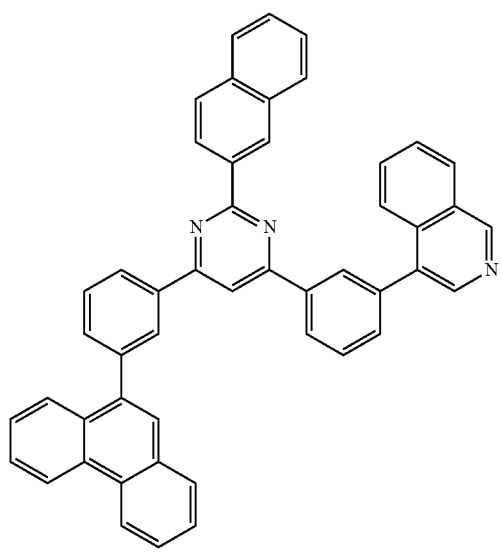
[Chemical Formula 402]
(7-35)
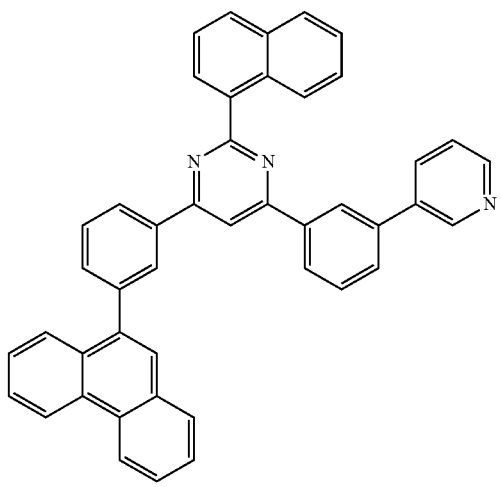
[Chemical Formula 403]
(7-36)
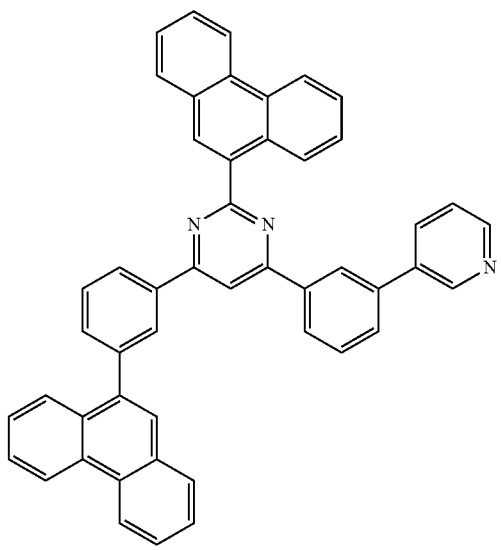

[Chemical Formula 404]
(7-37)
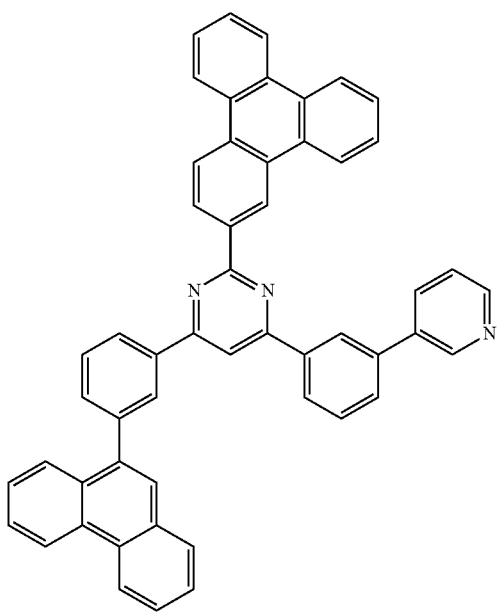
[Chemical Formula 405]
(7-38)
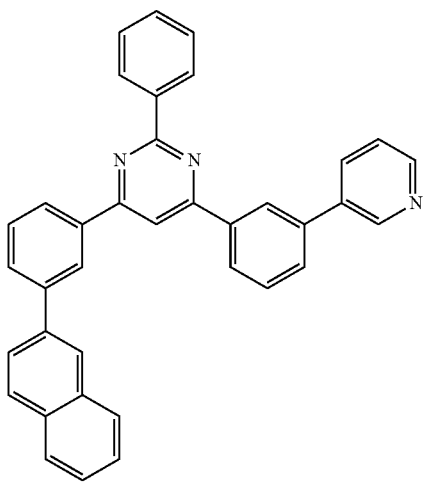
[Chemical Formula 406]
(7-39)
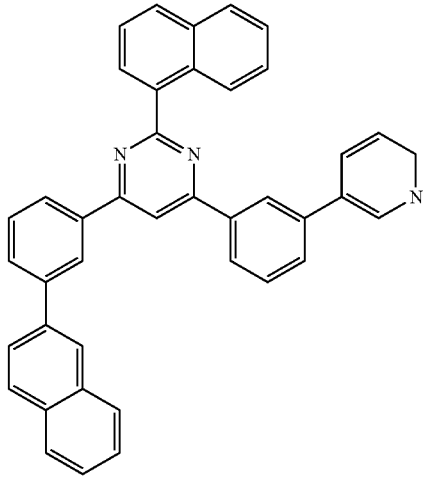
[Chemical Formula 407]
(7-40)
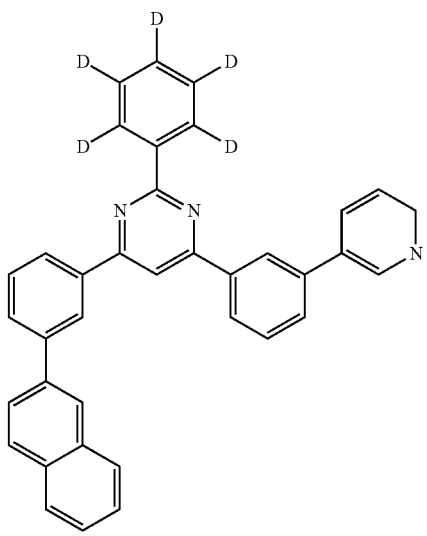
[Chemical Formula 408]
(7-41)

[Chemical Formula 409]
(7-42)
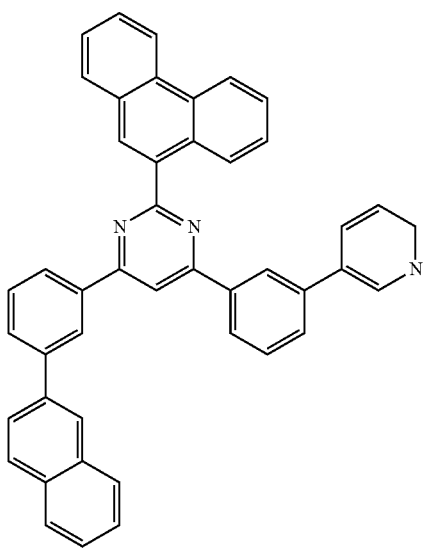
[Chemical Formula 410]
(7-43)
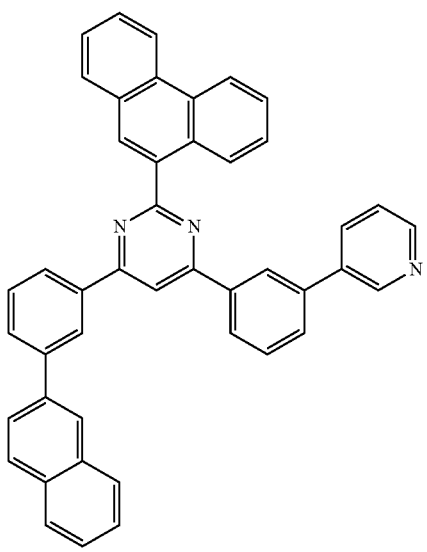
[Chemical Formula 411]
(7-44)
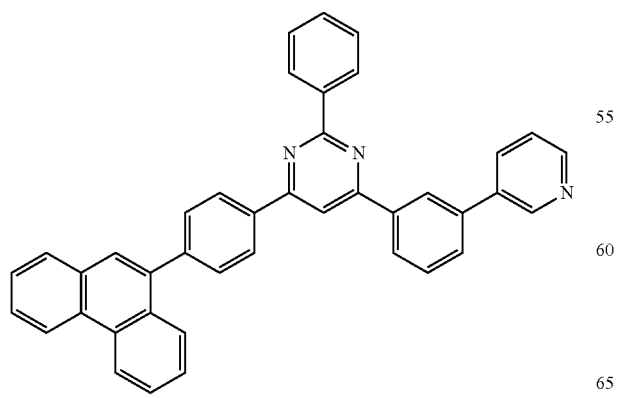
[Chemical Formula 412]
(7-45)
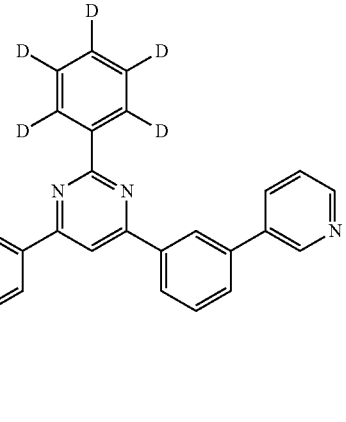
[Chemical Formula 413]
(7-46)
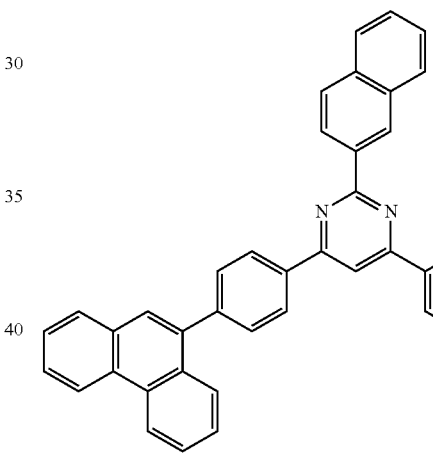
[Chemical Formula 414]
(7-47)
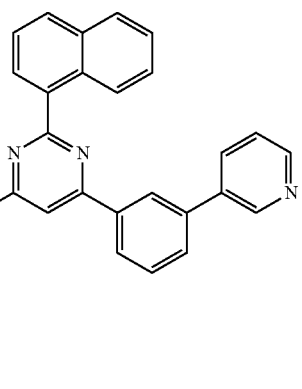

[Chemical Formula 415]
(7-48)
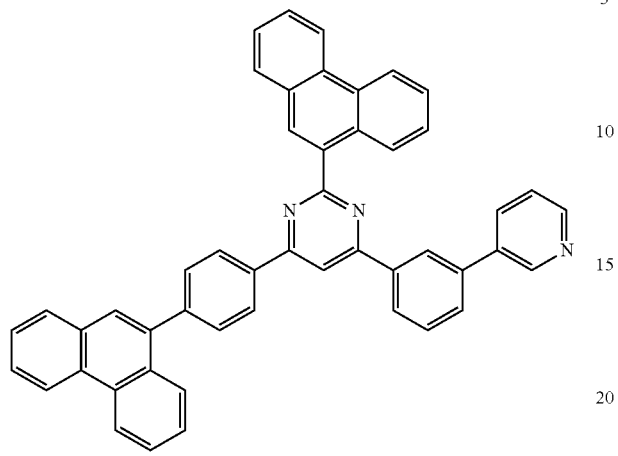
[Chemical Formula 416]
(7-49)
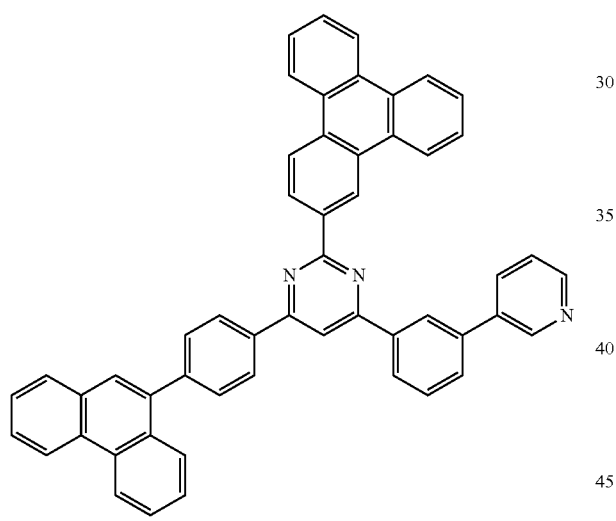
[Chemical Formula 417]
(7-50)
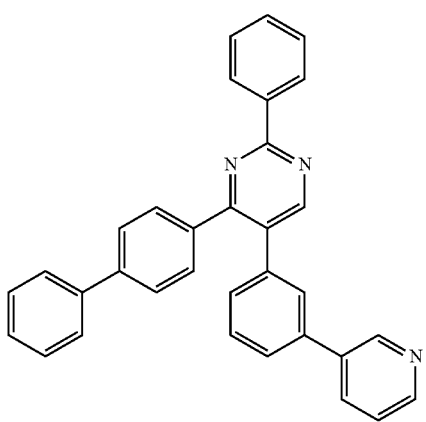
[Chemical Formula 418]
(7-51)
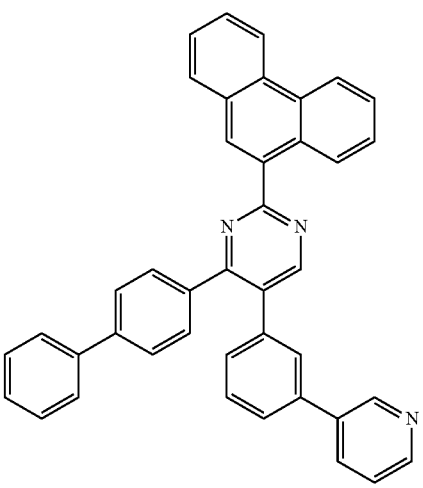
[Chemical Formula 419]
(7-52)
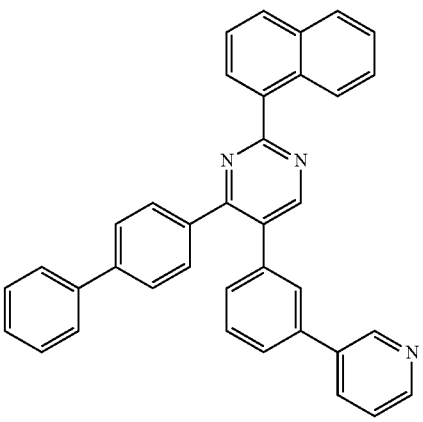
[Chemical Formula 420]
(7-53)
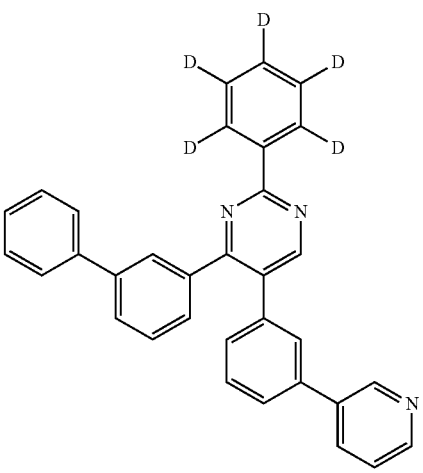

[Chemical Formula 421]
(7-54)
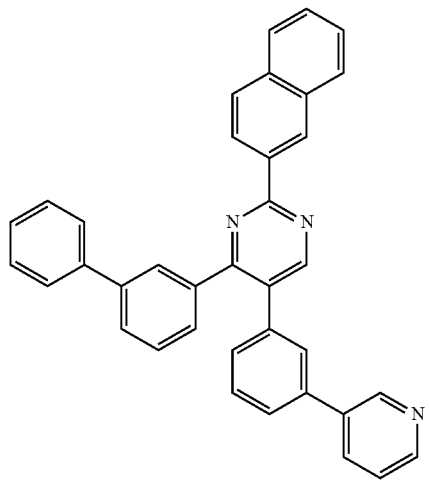
[Chemical Formula 422]
(7-55)
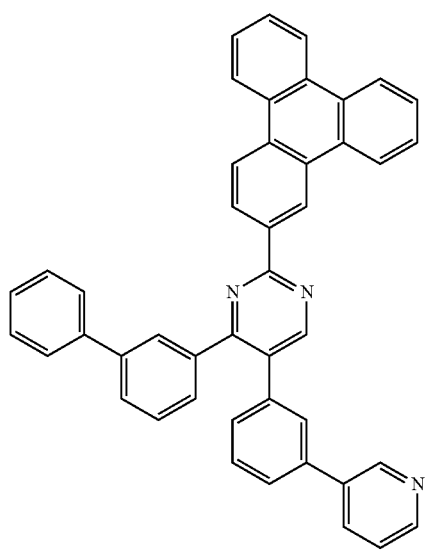
[Chemical Formula 423]
(7-56)
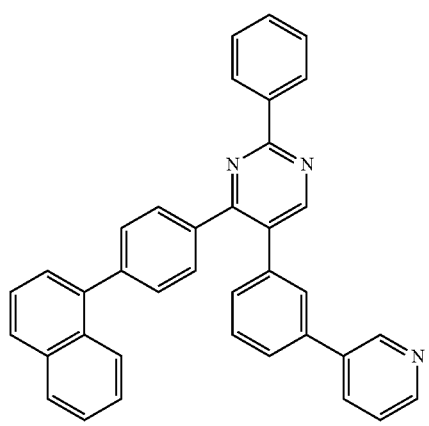
[Chemical Formula 424]
(7-57)
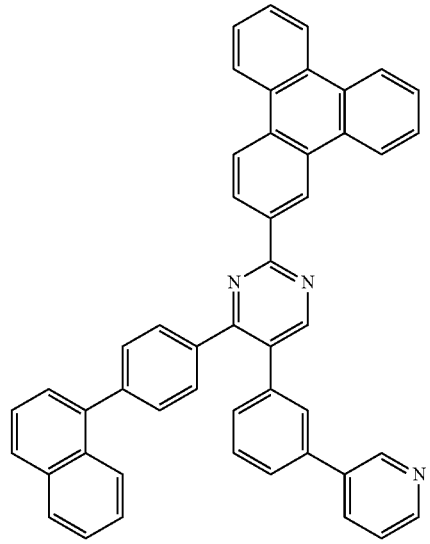
[Chemical Formula 425]
(7-58)
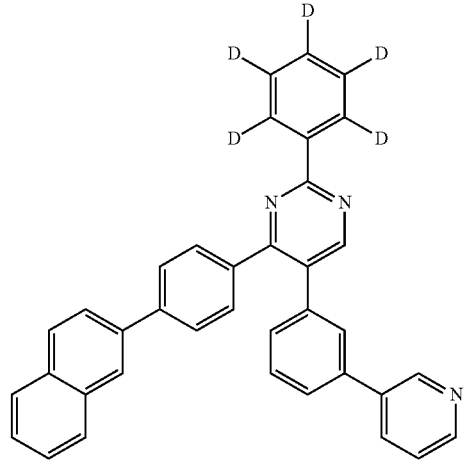
[Chemical Formula 426]
(7-59)
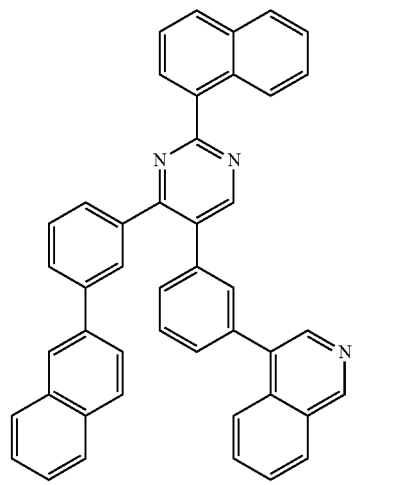

-continued
[Chemical Formula 427]
(7-60)
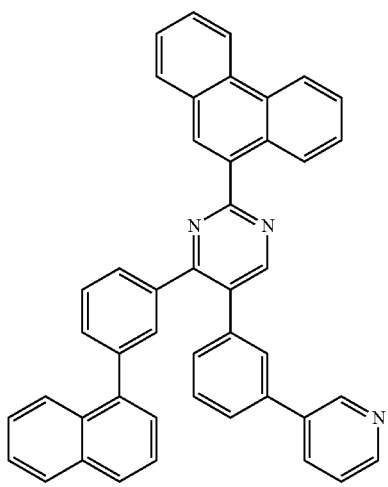
[Chemical Formula 428]
(7-61)
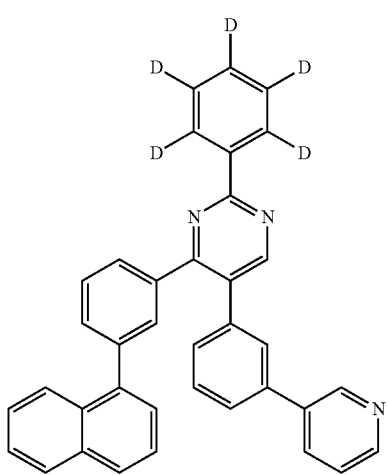
[Chemical Formula 429]
(7-62)
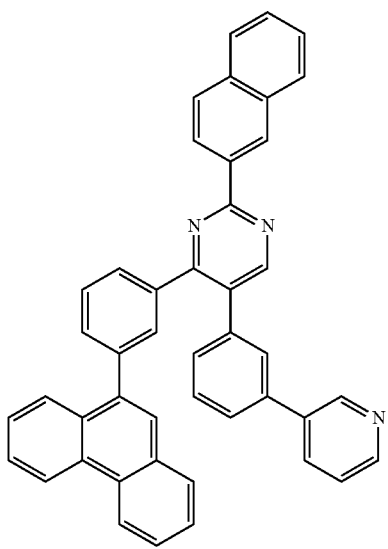
-continued
[Chemical Formula 430]
(7-63)
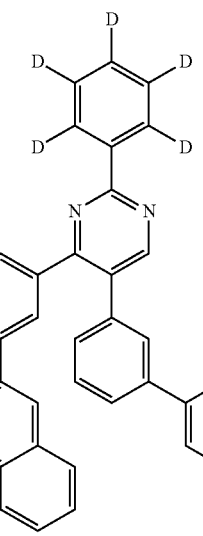
[Chemical Formula 431]
(7-64)
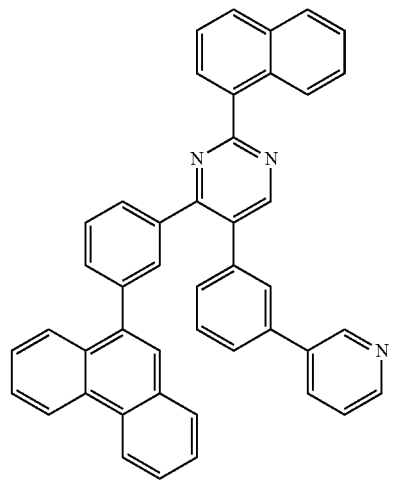
[Chemical Formula 432]
(7-65)
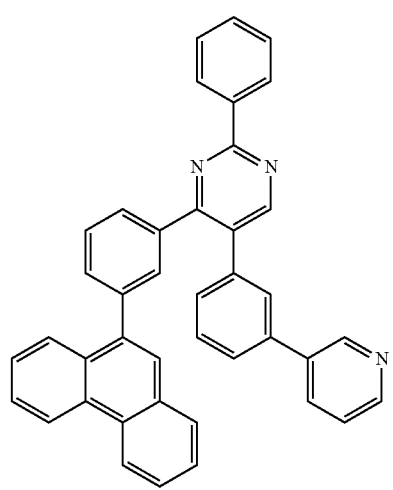

[Chemical Formula 433]
(7-66)
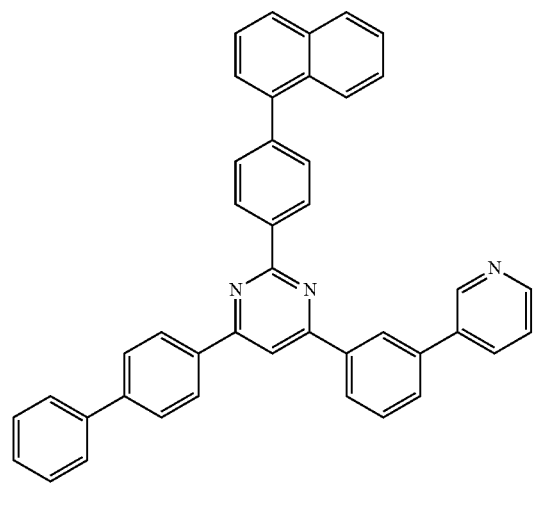
[Chemical Formula 434]
(7-67)
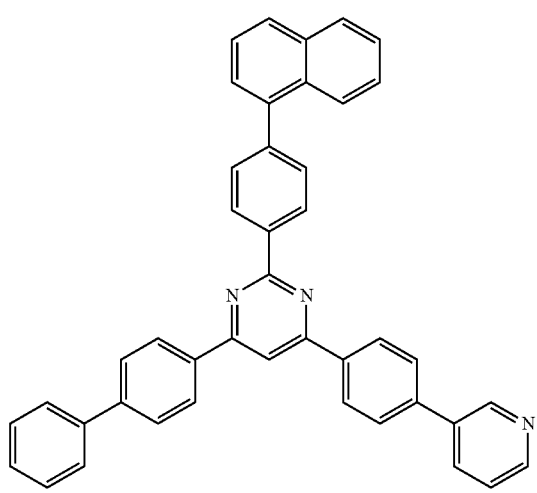
[Chemical Formula 435]
(7-68)
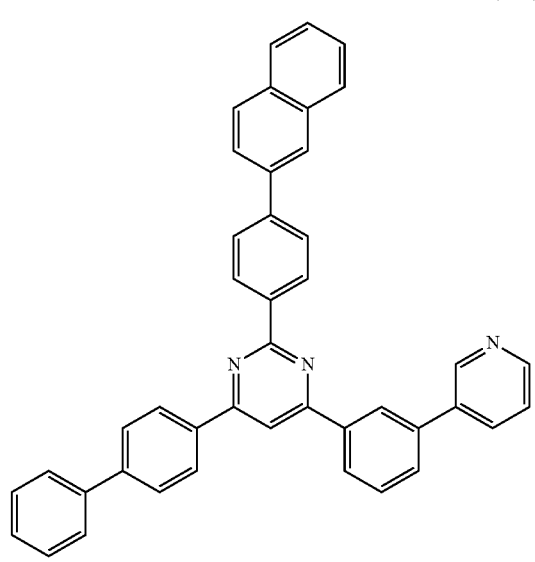
[Chemical Formula 436]
(7-69)
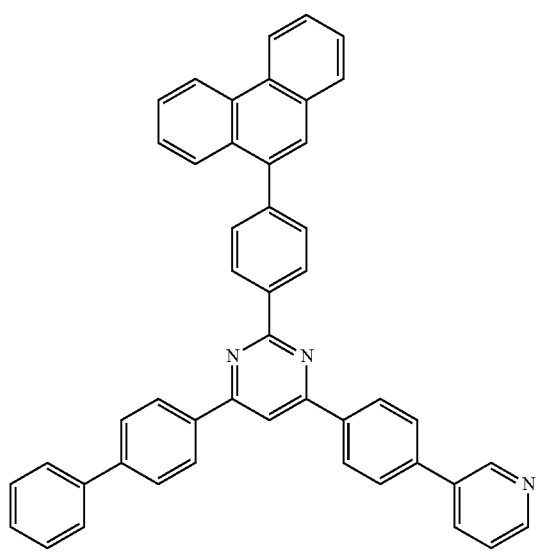

-continued
[Chemical Formula 437]
(7-70)
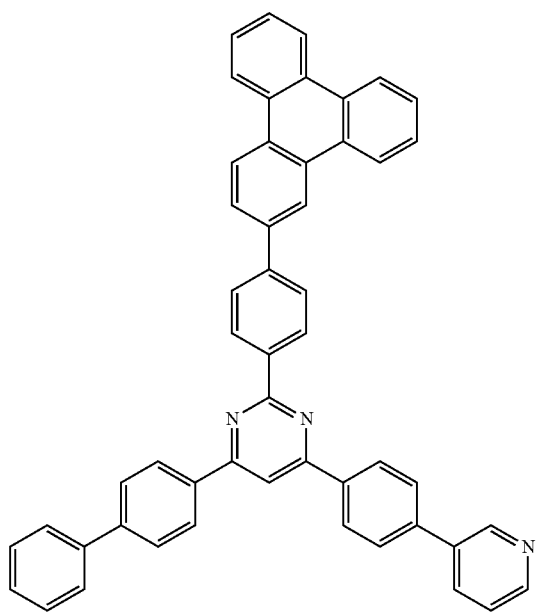
[Chemical Formula 438]
(7-71)
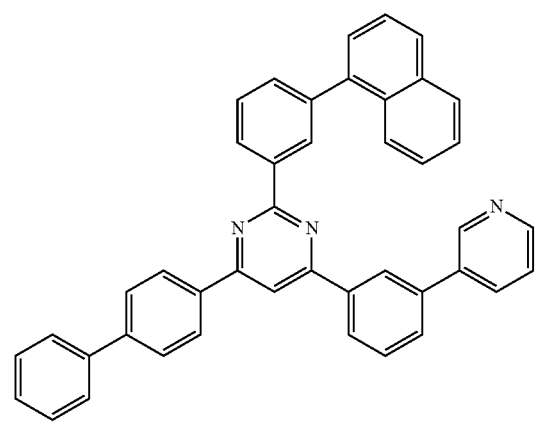
[Chemical Formula 439]
(7-72)
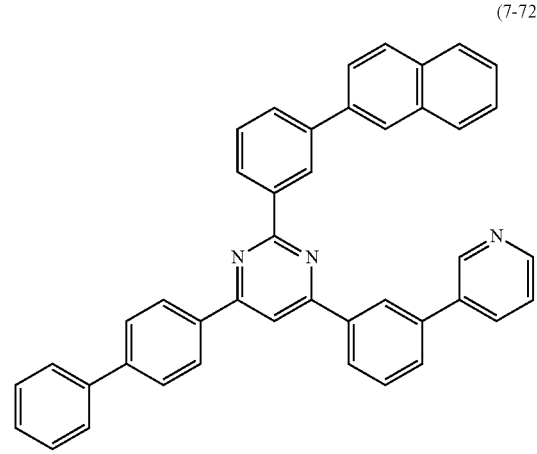
-continued
[Chemical Formula 440]
(7-73)
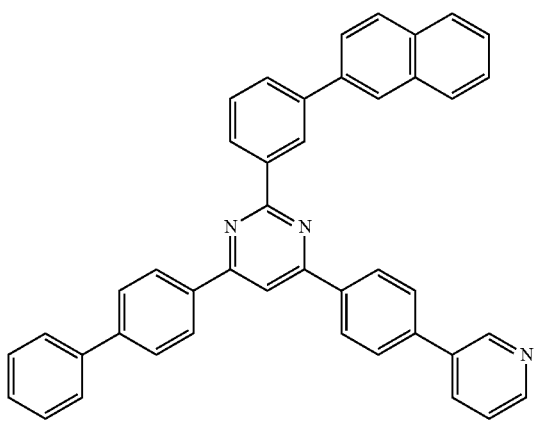
[Chemical Formula 441]
(7-74)
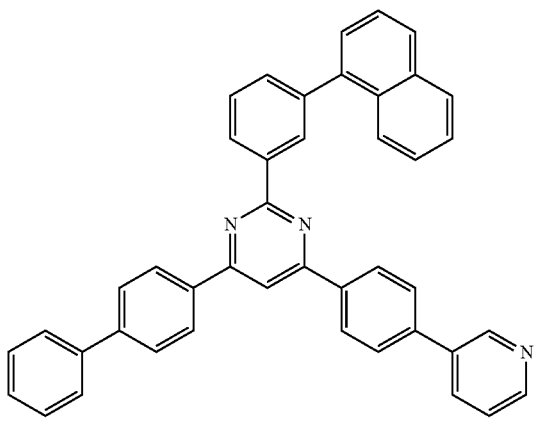
[Chemical Formula 442]
(7-75)
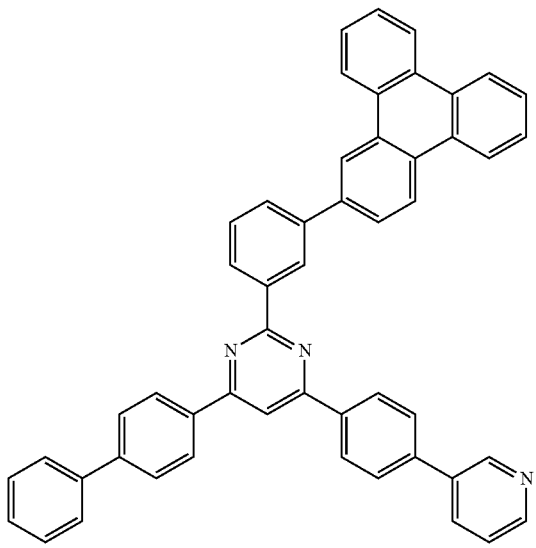

[Chemical Formula 443]
(7-76)
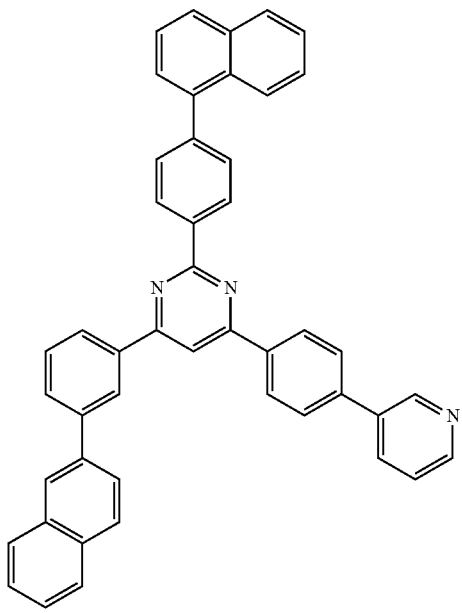
[Chemical Formula 444]
(7-77)
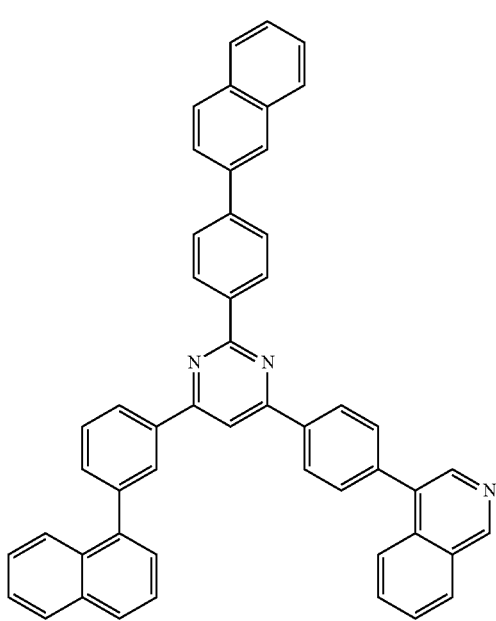
[Chemical Formula 445]
(7-78)
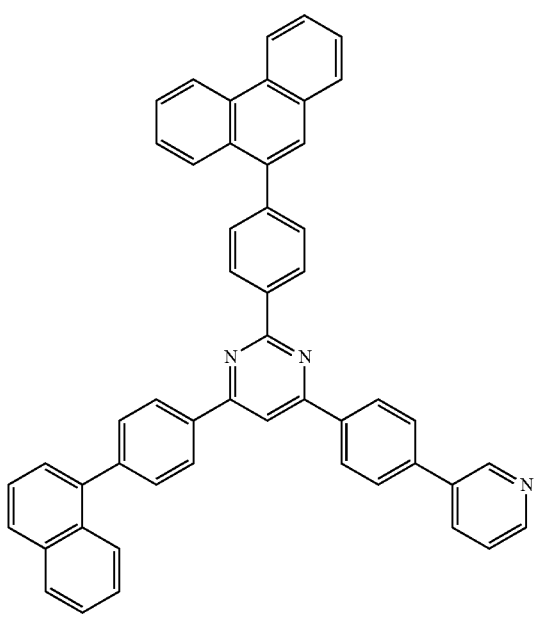
[Chemical Formula 446]
(7-79)
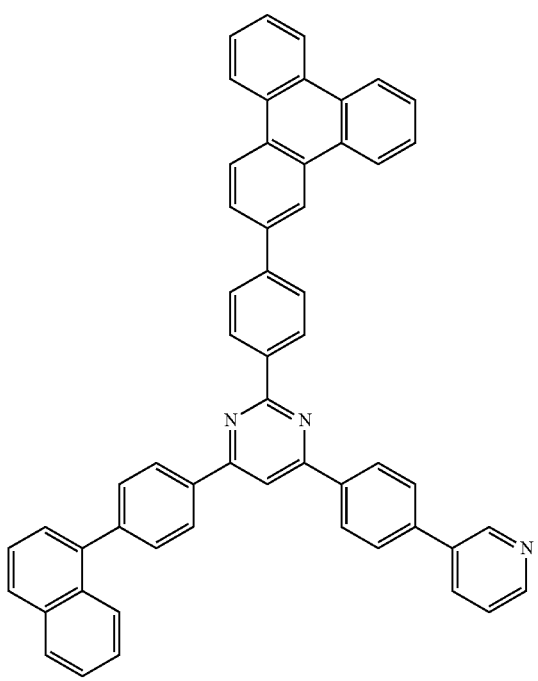

[Chemical Formula 447]
(7-80)
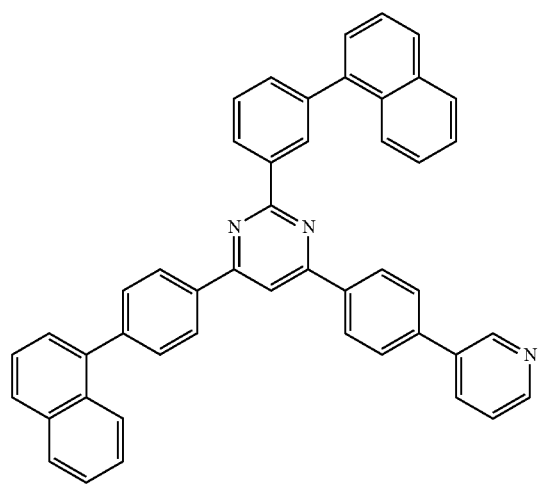
[Chemical Formula 448]
(7-81)
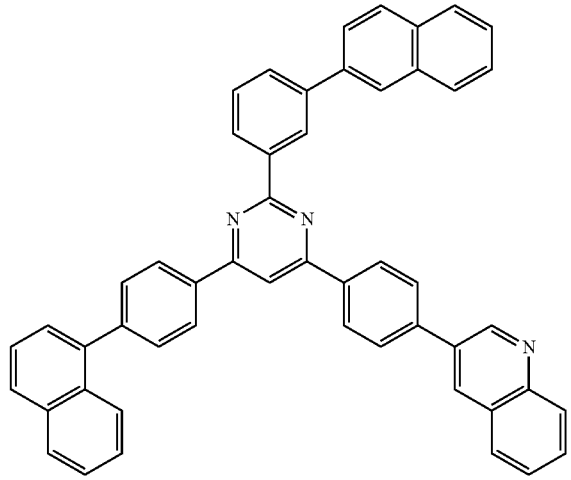
[Chemical Formula 449]
(7-82)
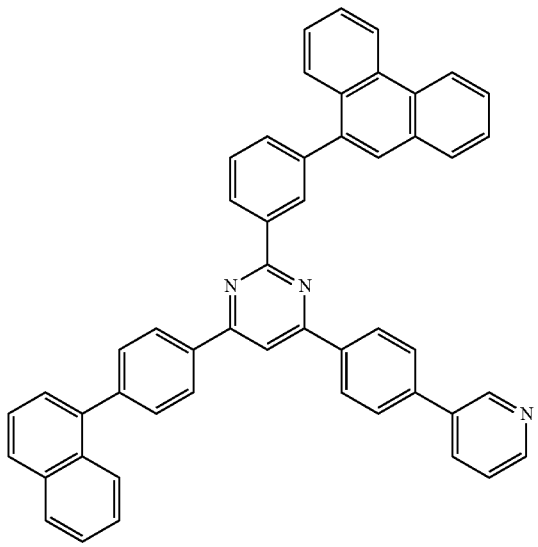
[Chemical Formula 450]
(7-83)
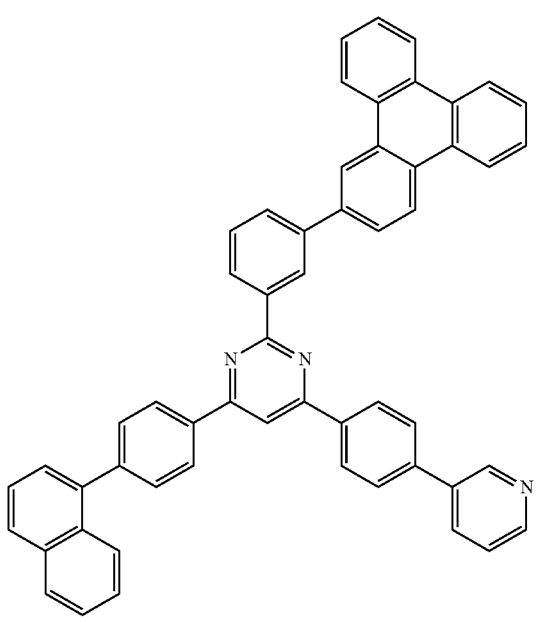

[Chemical Formula 451]
(7-84)
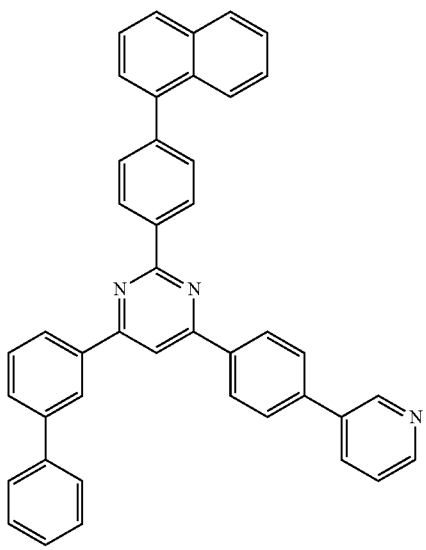
[Chemical Formula 452]
(7-85)
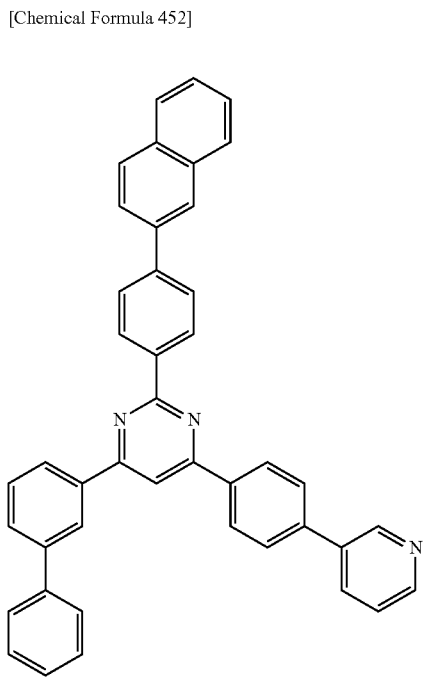
[Chemical Formula 453]
(7-86)
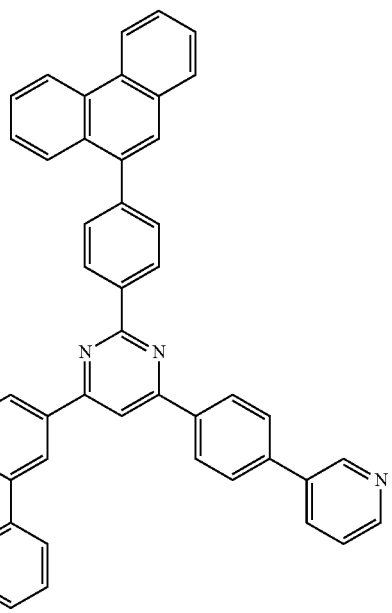
[Chemical Formula 454]
(7-87)
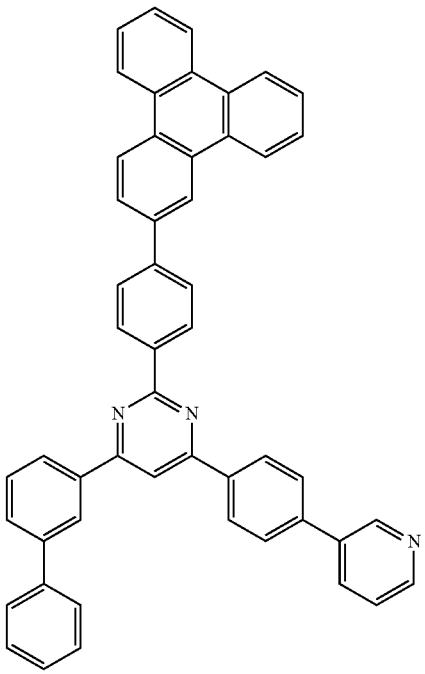

[Chemical Formula 455]
(7-88)
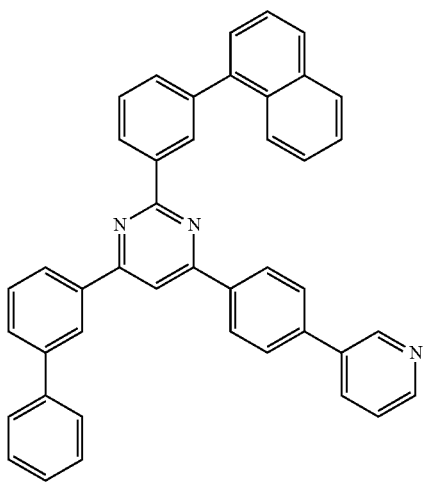
[Chemical Formula 456]
(7-89)
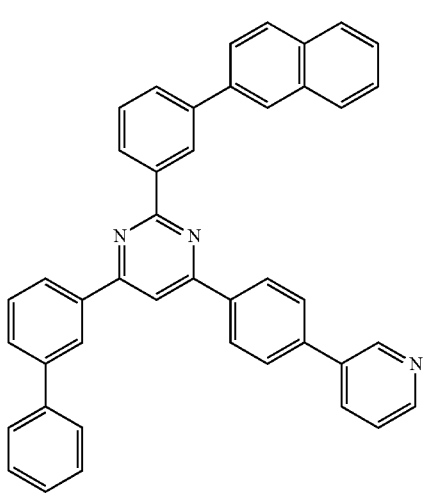
[Chemical Formula 457]
(7-90)
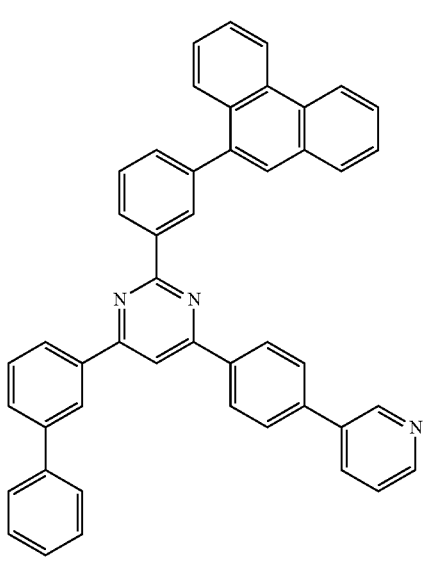
[Chemical Formula 458]
(7-91)
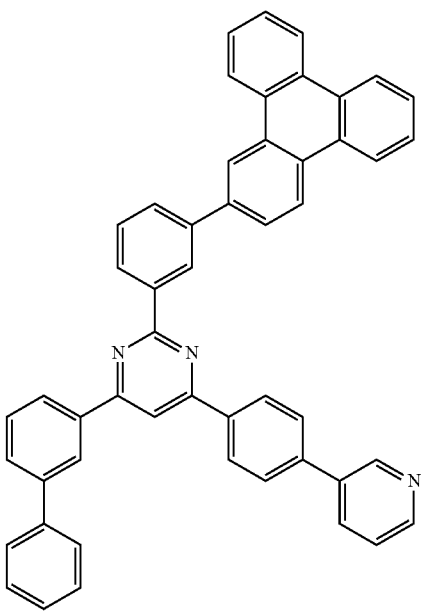
[Chemical Formula 459]
(7-92)
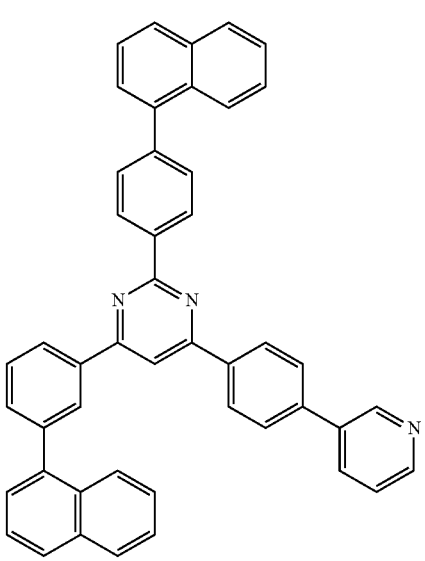

[Chemical Formula 460]
(7-93)
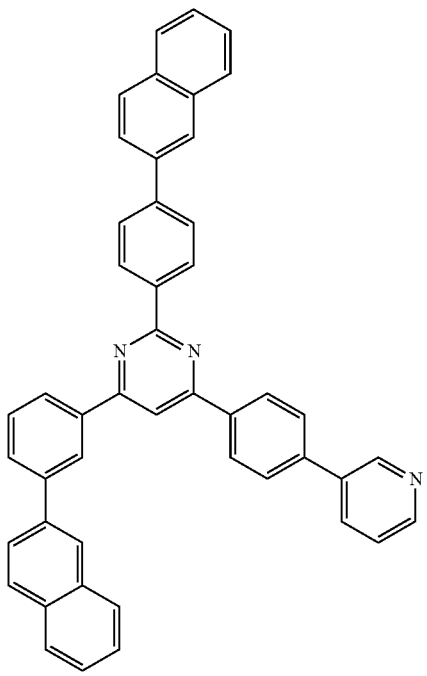
[Chemical Formula 461]
(7-94)
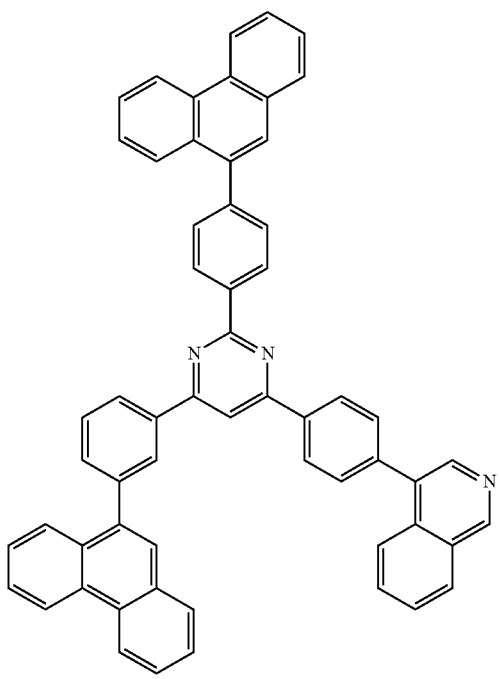
[Chemical Formula 462]
(7-95)
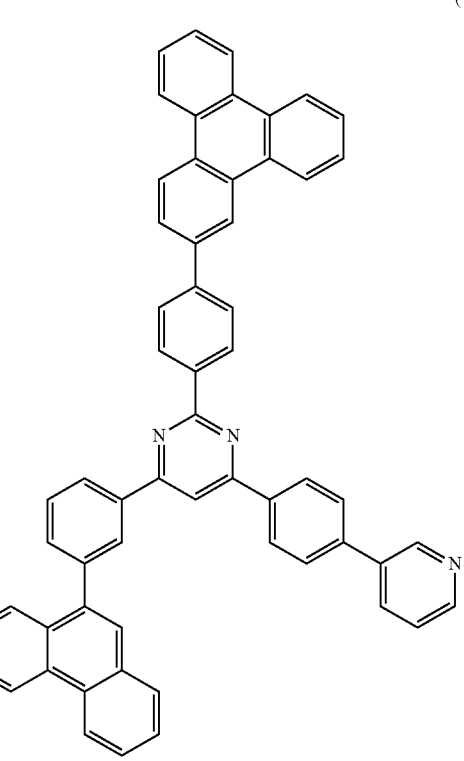
[Chemical Formula 463]
(7-96)
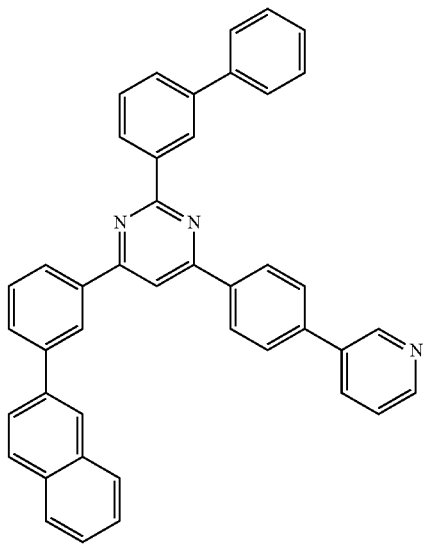

[Chemical Formula 464]
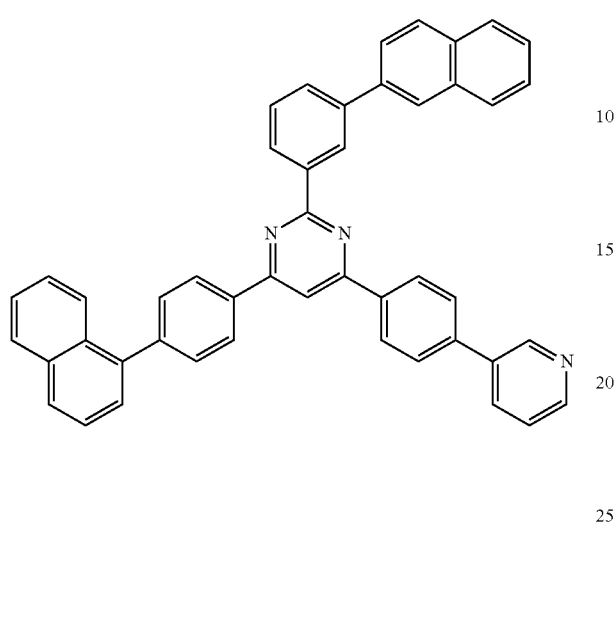
(7-97)
[Chemical Formula 465]
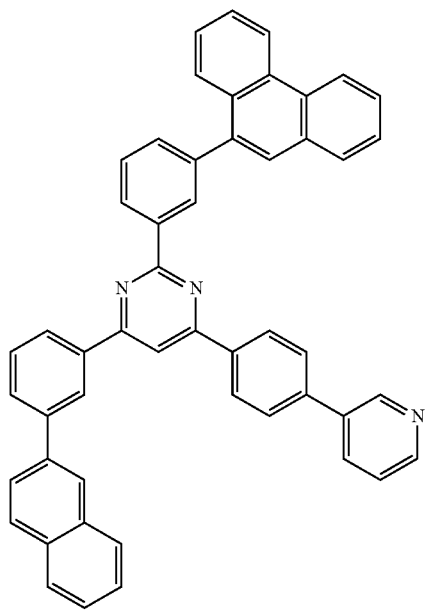
(7-98)
[Chemical Formula 466]
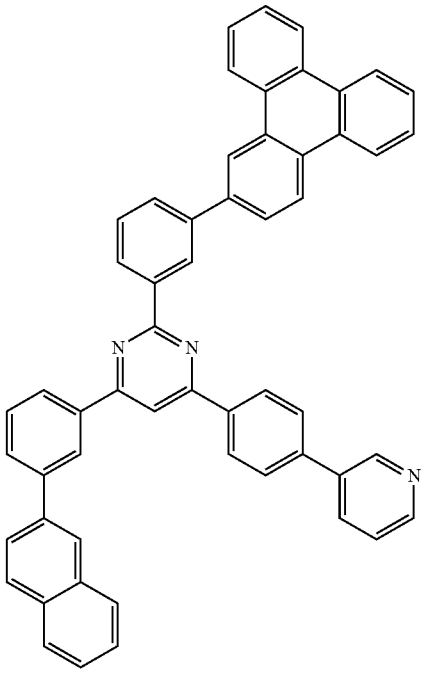
(7-99)
[Chemical Formula 467]
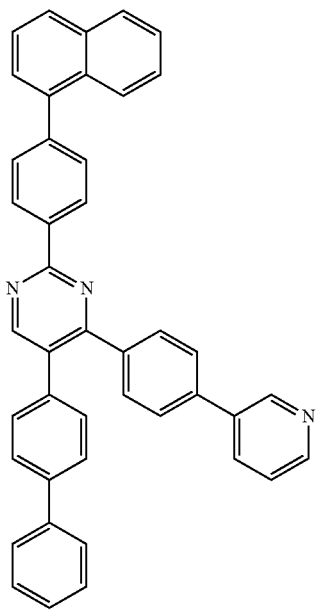
(7-100)

[Chemical Formula 468]
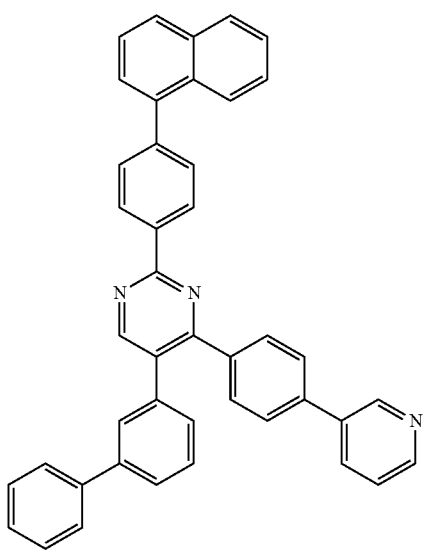
(7-101)
[Chemical Formula 469]
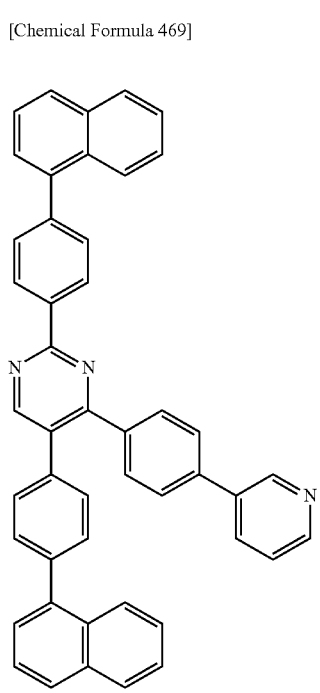
(7-102)
[Chemical Formula 470]
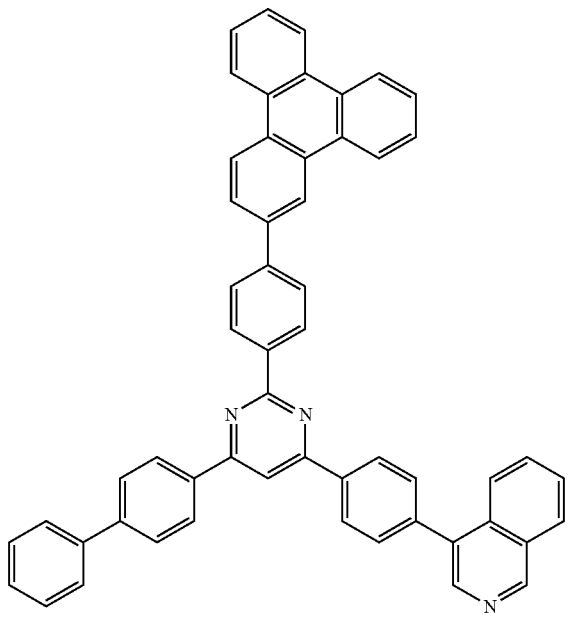
(7-103)
[Chemical Formula 471]
(7-104)

[Chemical Formula 472] (7-105)
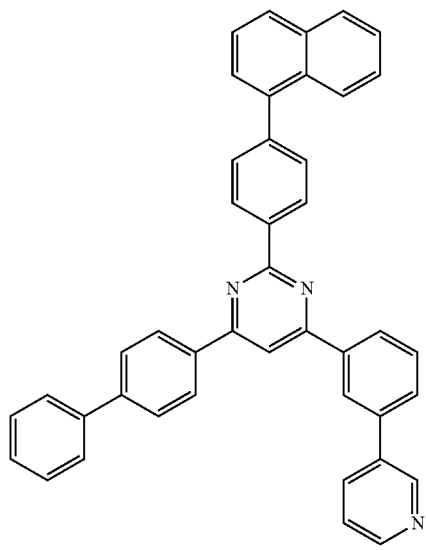
[Chemical Formula 473] (7-106)
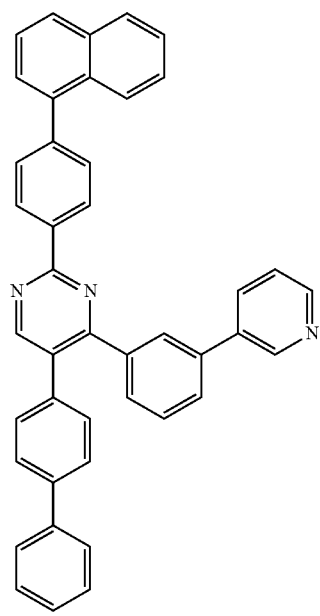
[Chemical Formula 474] (7-107)
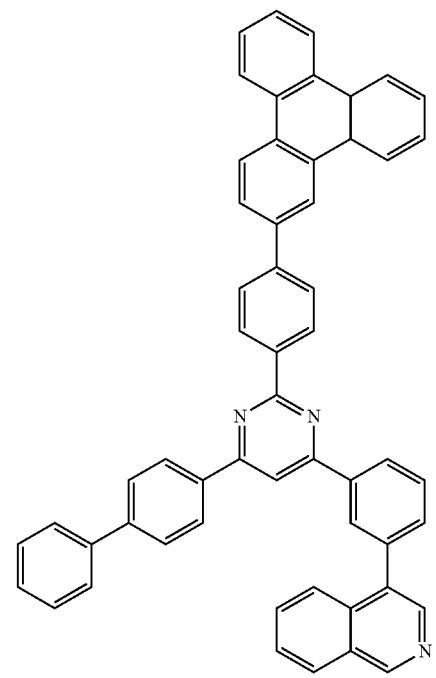
[Chemical Formula 475] (7-108)
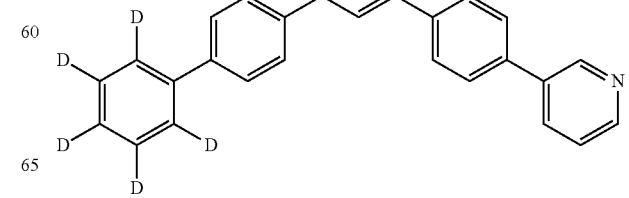

[Chemical Formula 476]
(7-109)
[Chemical Formula 477]
(7-110)
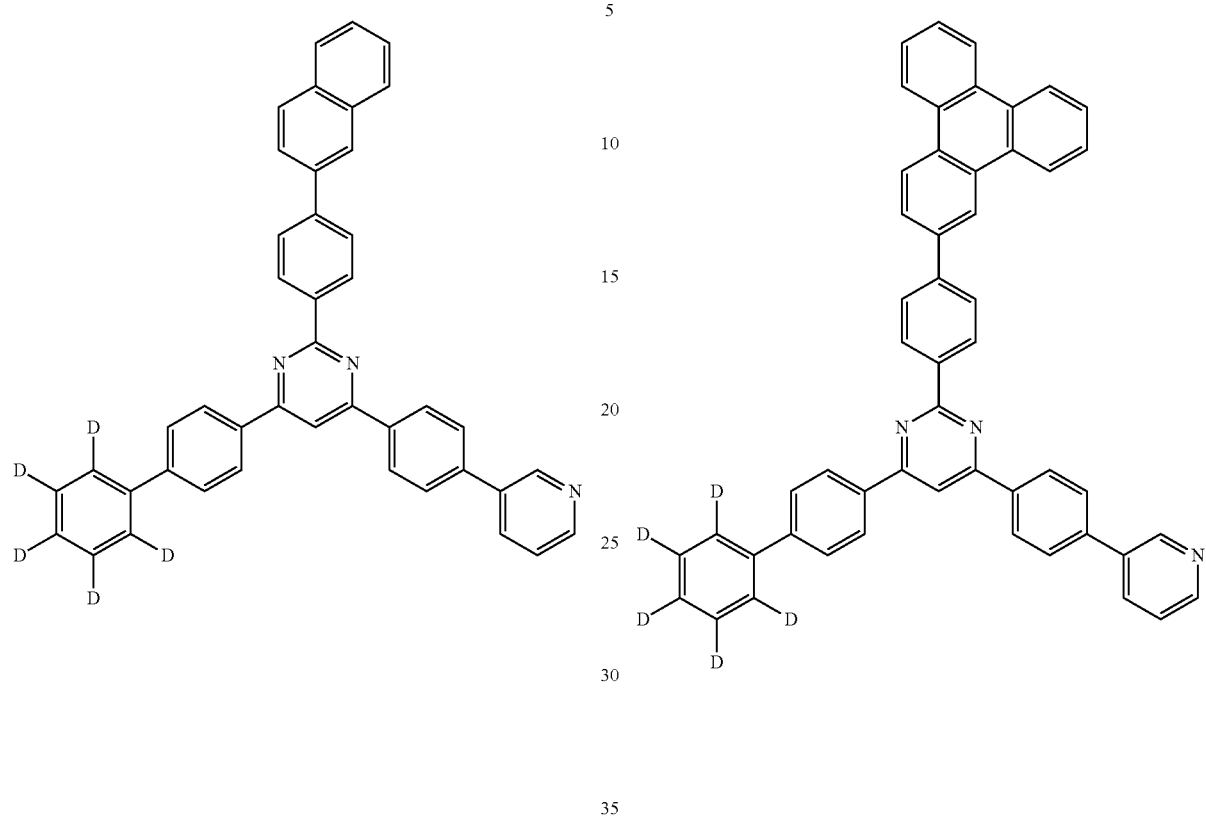
[Chemical Formula 478]
(7-111)
[Chemical Formula 479]
(7-112)
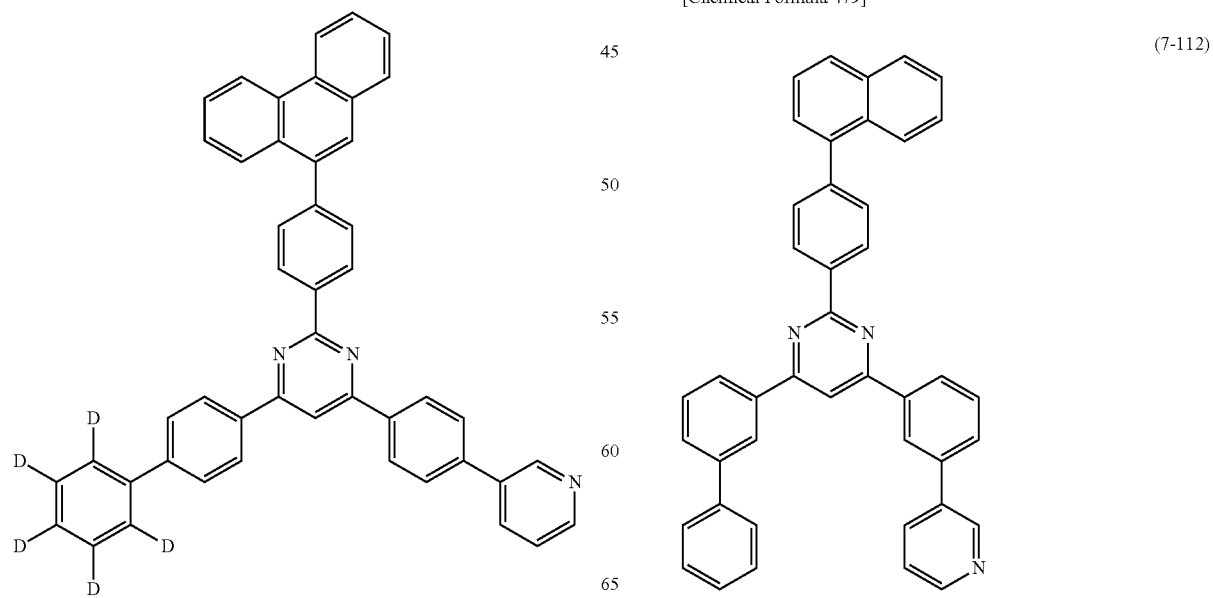

[Chemical Formula 480]
(7-113)
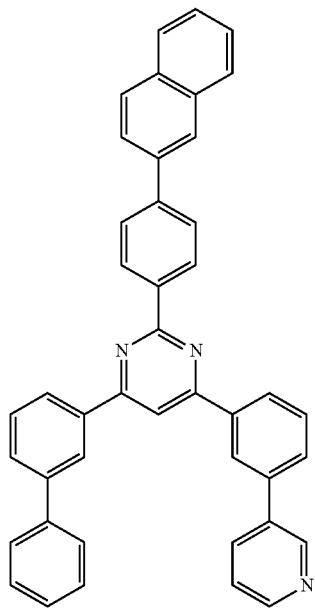
[Chemical Formula 481]
(7-114)
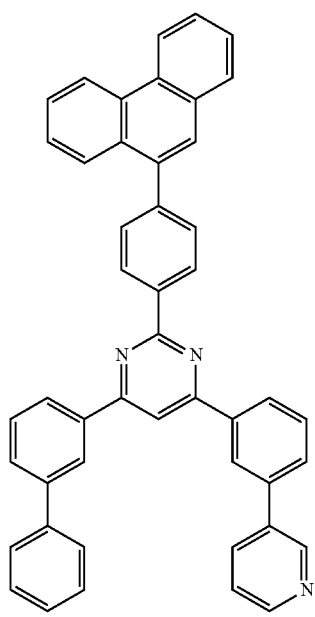
[Chemical Formula 482]
(7-115)
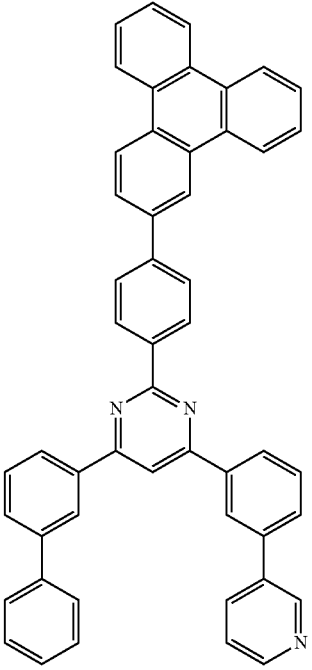
[Chemical Formula 483]
(7-116)
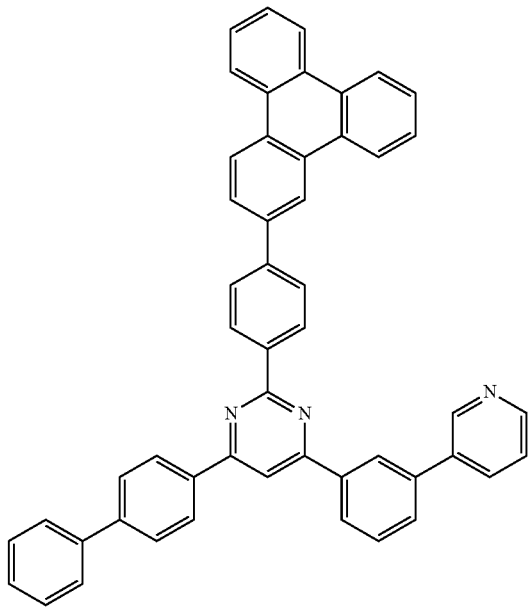

[Chemical Formula 484]
(7-117)
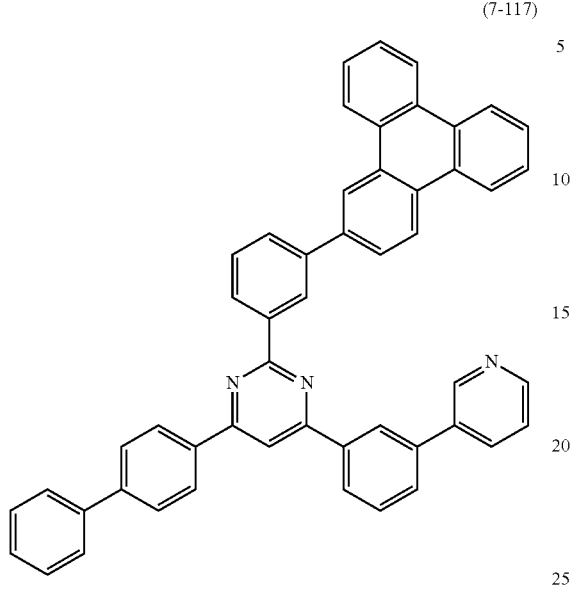
[Chemical Formula 485]
(7-118)
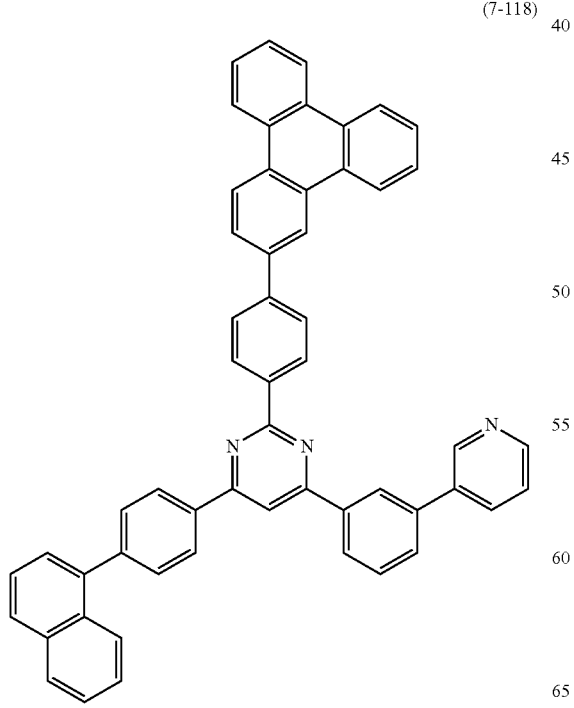
[Chemical Formula 486]
(7-119)
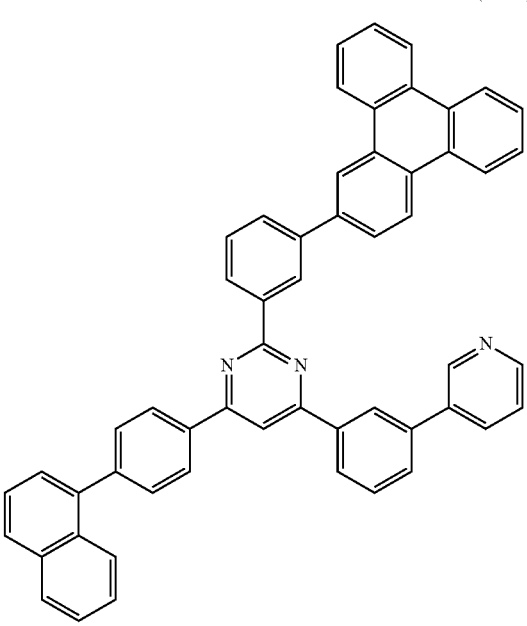
[Chemial Formula 487]
(7-120)
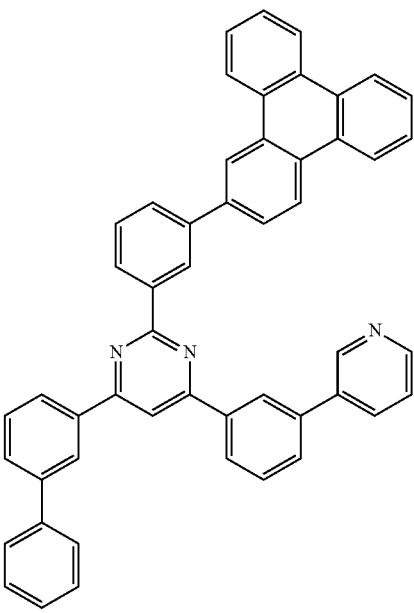

[Chemical Formula 488]
(7-121)
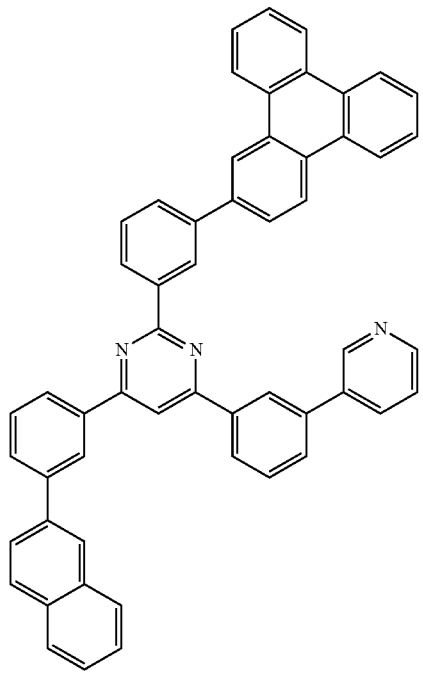
[Chemical Formula 489]
(7-122)
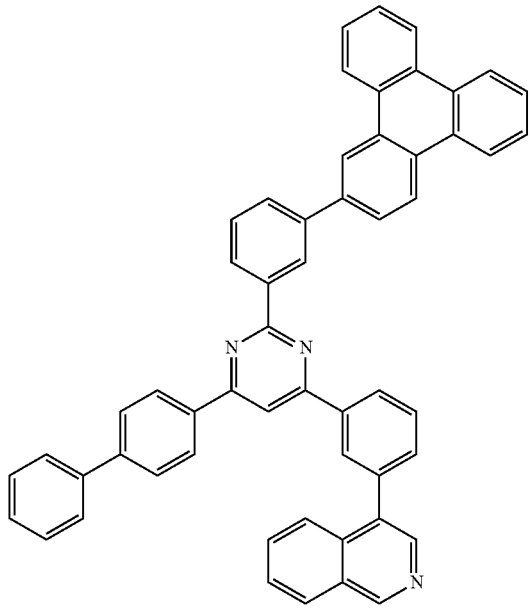
[Chemical Formula 490]
(7-123)
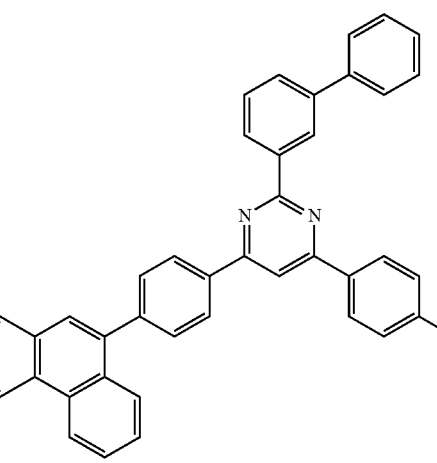
[Chemical Formula 491]
(7-124)
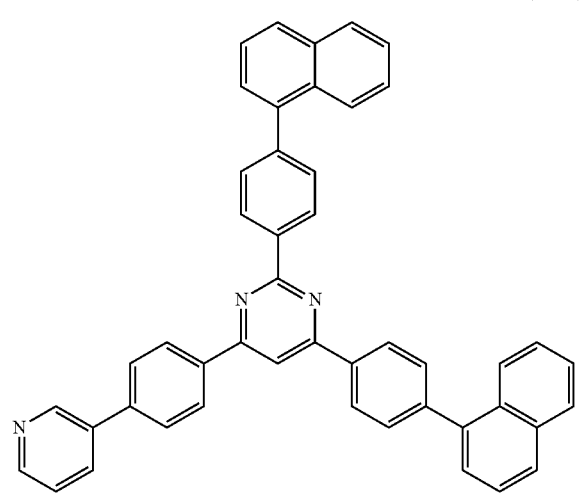
[Chemical Formula 492]
(7-125)

[Chemical Formula 493]

(7-126)

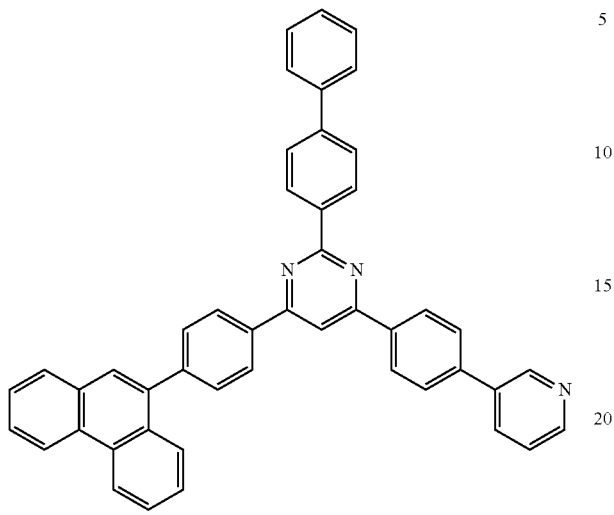

The compounds having a pyrimidine ring structure described above can be synthesized by a known method (refer to PTLs 10 and 11, for example).

The following presents specific examples of preferred compounds among the compounds of the general formula (9) preferably used in the organic EL device of the present invention and having a benzotriazole ring structure. The present invention, however, is not restricted to these compounds.

[Chemical Formula 494]

(9-1)

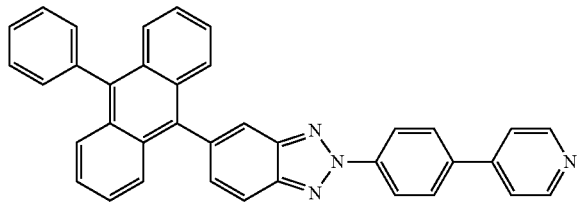

[Chemical Formula 495]

(9-2)

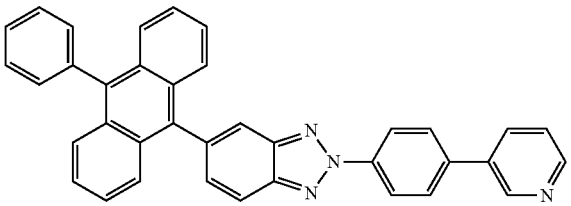

[Chemical Formula 496]

(9-3)

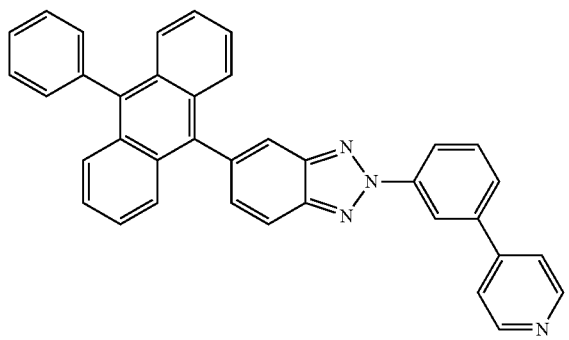

[Chemical Formula 497]

(9-4)

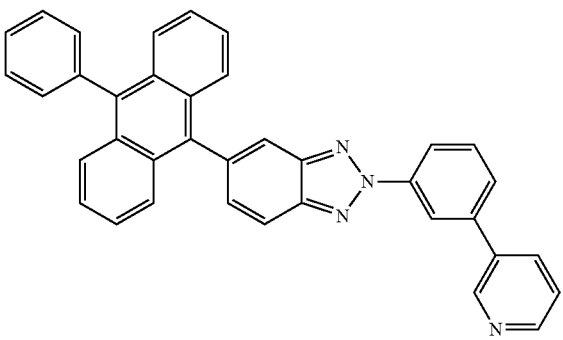

[Chemical Formula 498]

(9-5)

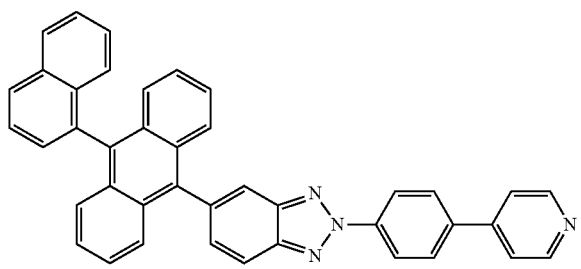

[Chemical Formula 499]

(9-6)

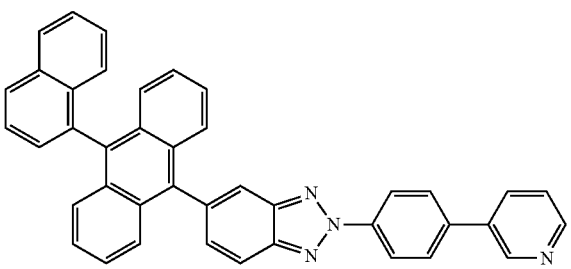

[Chemical Formula 500]
(9-7)
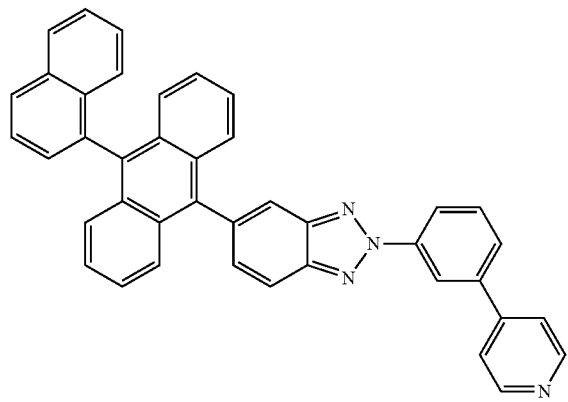
[Chemical Formula 501]
(9-8)
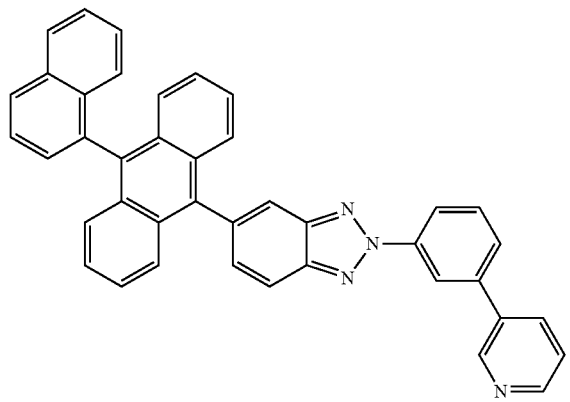
[Chemical Formula 502]
(9-9)
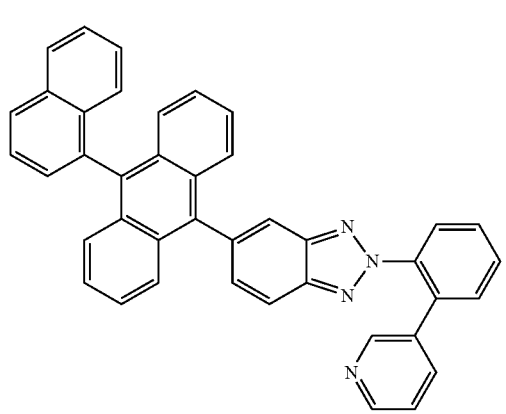
[Chemical Formula 503]
(9-10)
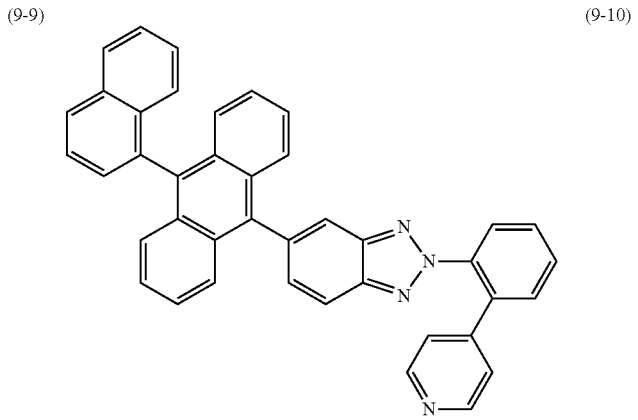
[Chemical Formula 504]
(9-11)
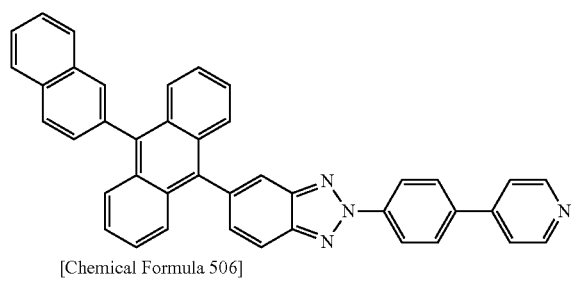
[Chemical Formula 505]
(9-12)
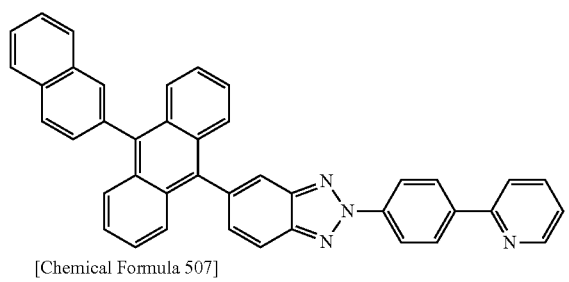
[Chemical Formula 506]
(9-13)
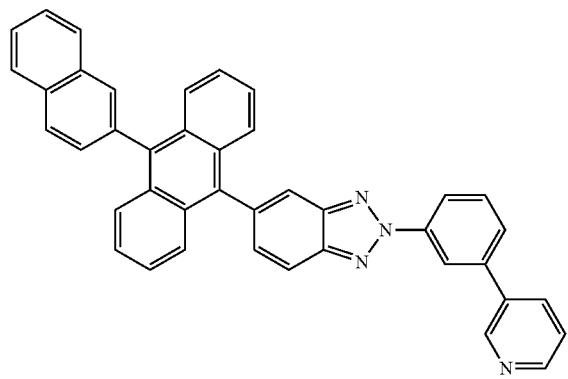
[Chemical Formula 507]
(9-14)
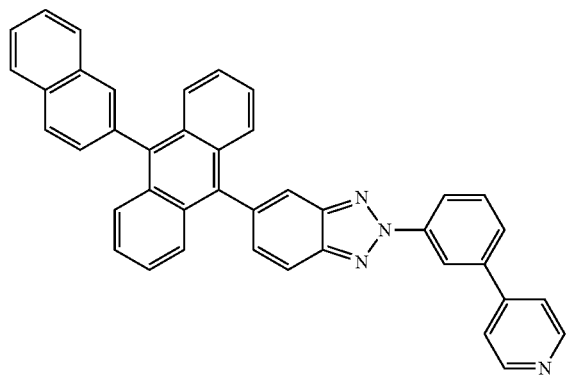

[Chemical Formula 508]
(9-15)
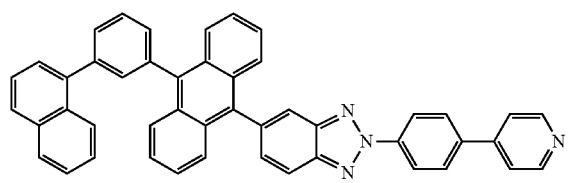
[Chemical Formula 509]
(9-16)
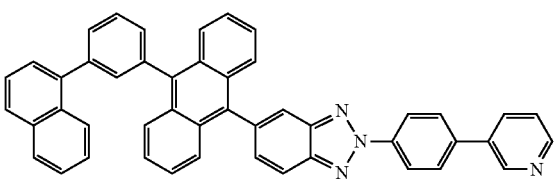
[Chemical Formula 510]
(9-17)
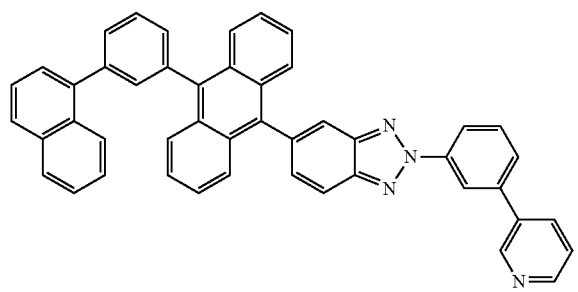
[Chemical Formula 511]
(9-18)
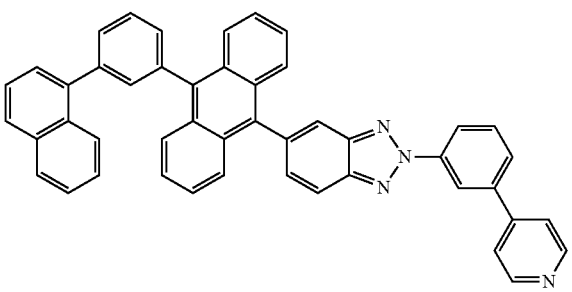
[Chemical Formula 512]
(9-19)
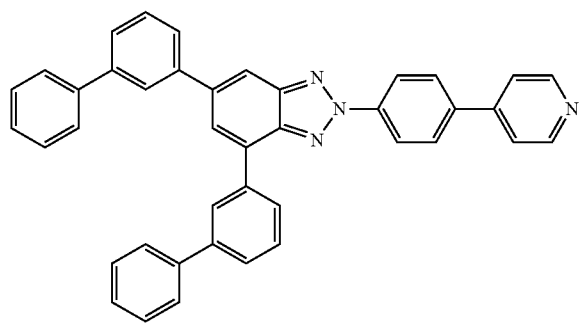
[Chemical Formula 513]
(9-20)
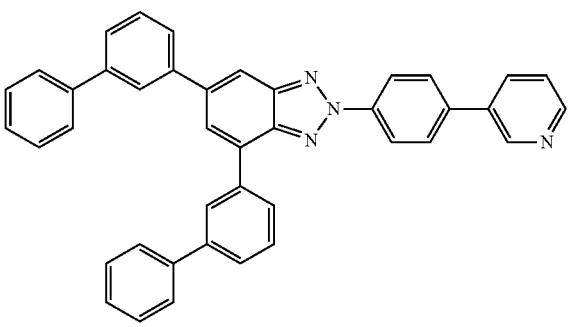
[Chemical Formula 514]
(9-21)
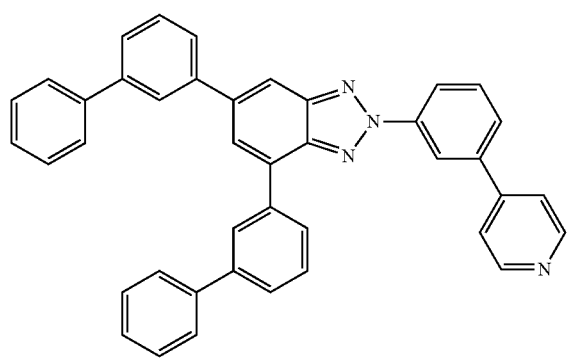
[Chemical Formula 515]
(9-22)
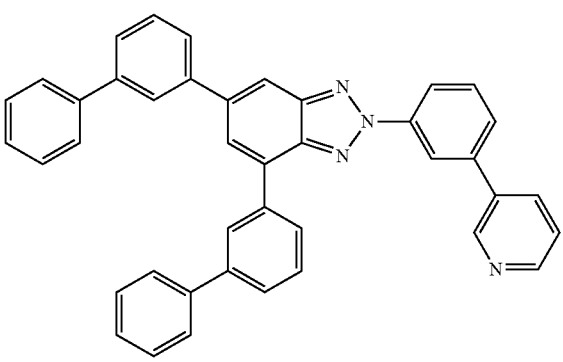

-continued
[Chemical Formula 516]
(9-23)
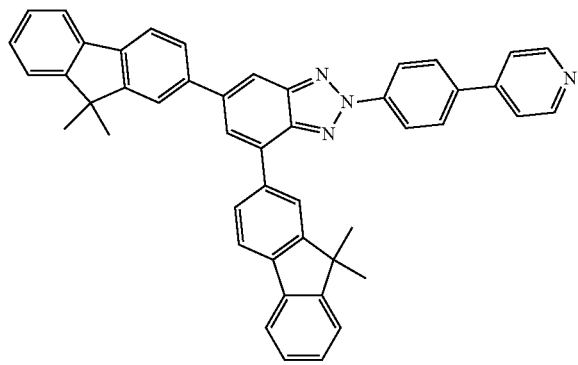
[Chemical Formula 517]
(9-24)
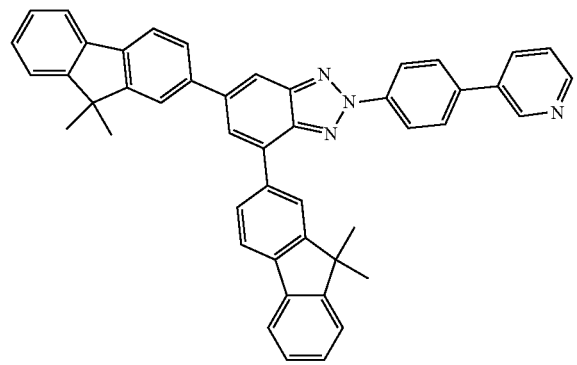
[Chemical Formula 518]
(9-25)
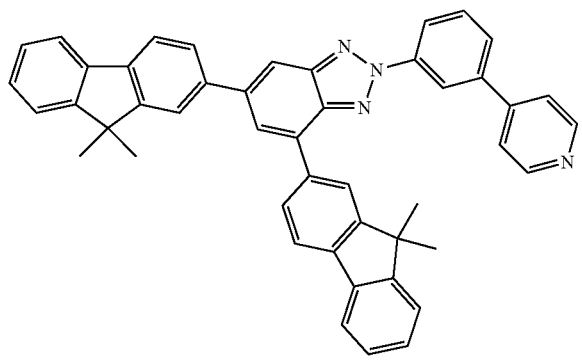
[Chemical Formula 519]
(9-26)
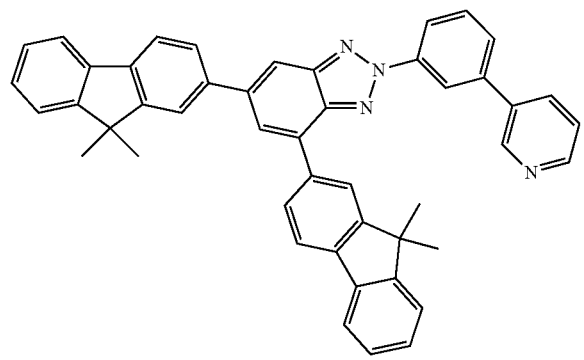
[Chemical Formula 520]
(9-27)
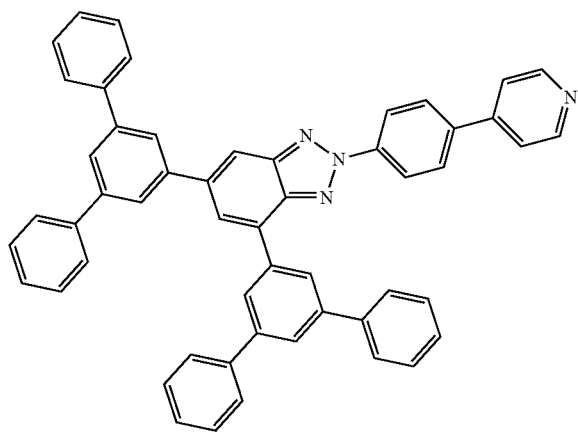
[Chemical Formula 521]
(9-28)
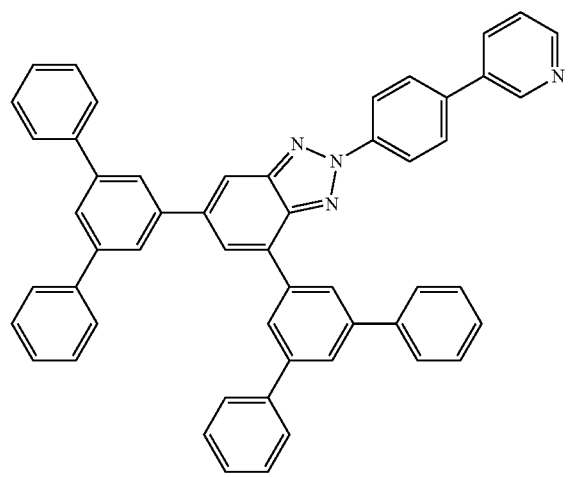

[Chemical Formula 522]
(9-29)
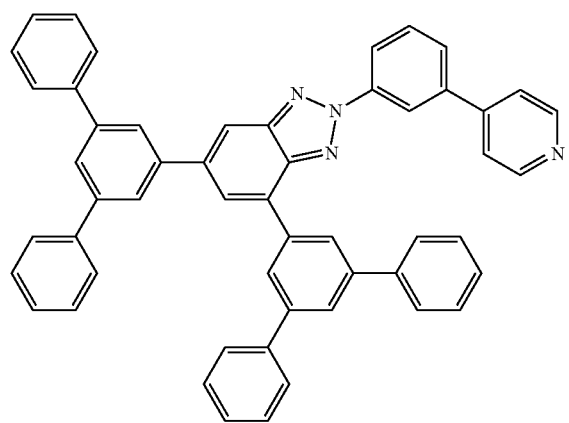
[Chemical Formula 523]
(9-30)
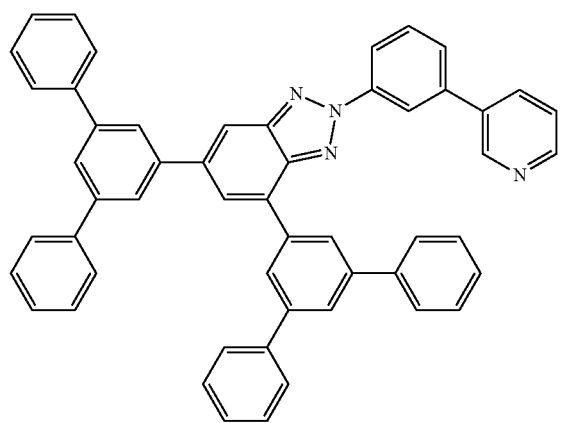
[Chemical Formula 524]
(9-31)
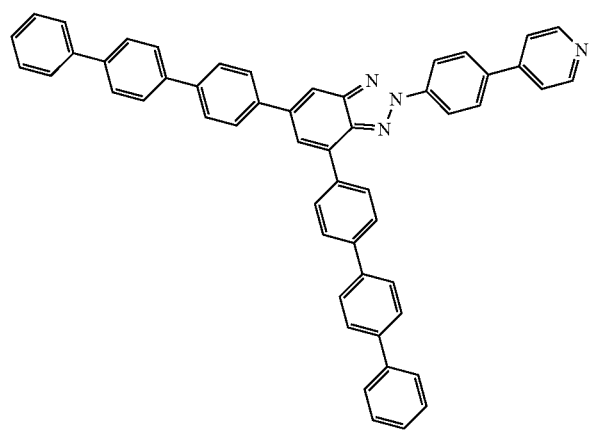
[Chemical Formula 525]
(9-32)
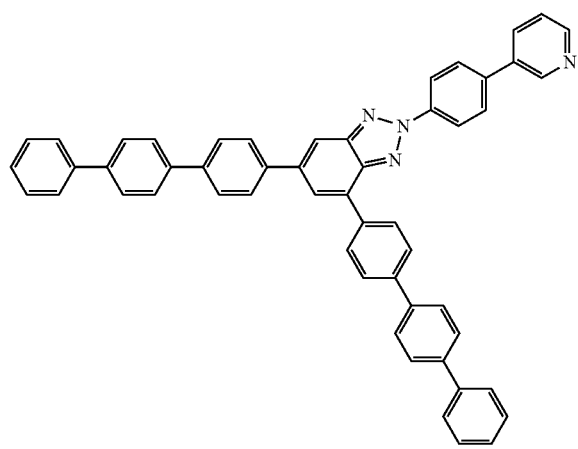
[Chemical Formula 526]
(9-33)
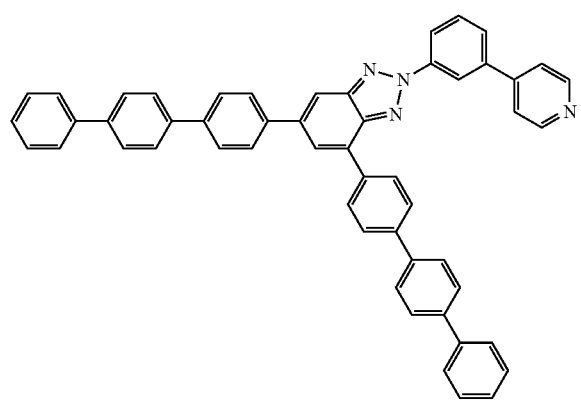
[Chemical Formula 527]
(9-34)
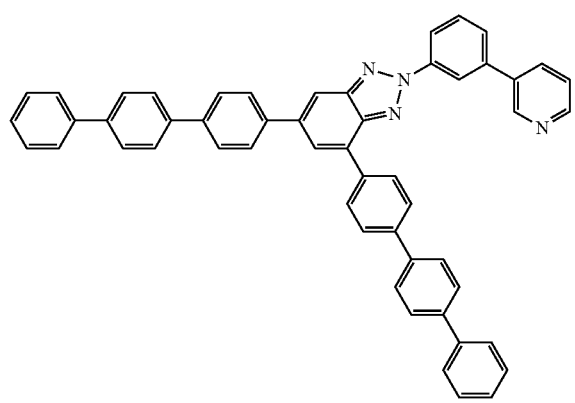

-continued
[Chemical Formula 528]
(9-35)
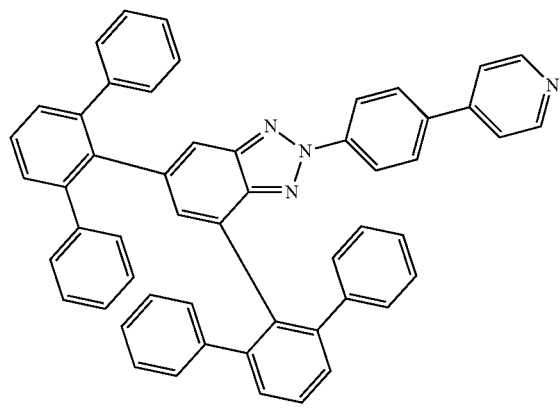
[Chemical Formula 529]
(9-36)
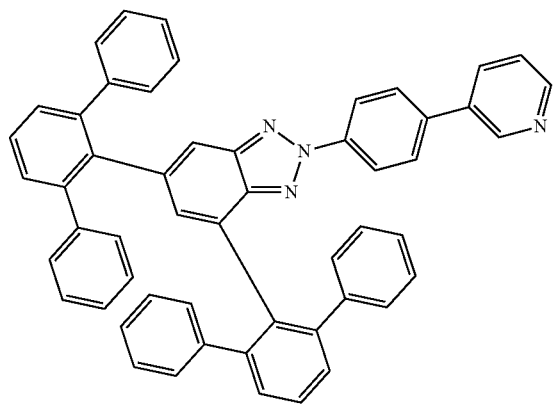
[Chemical Formula 530]
(9-37)
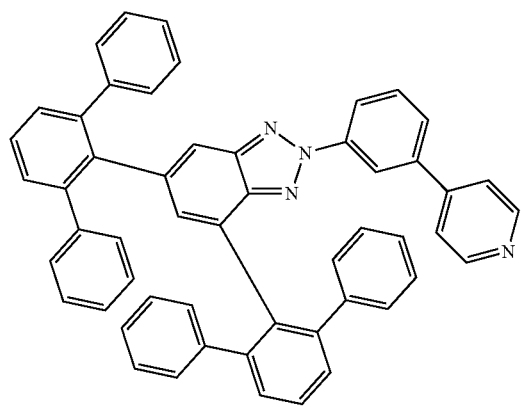
[Chemical Formula 531]
(9-38)
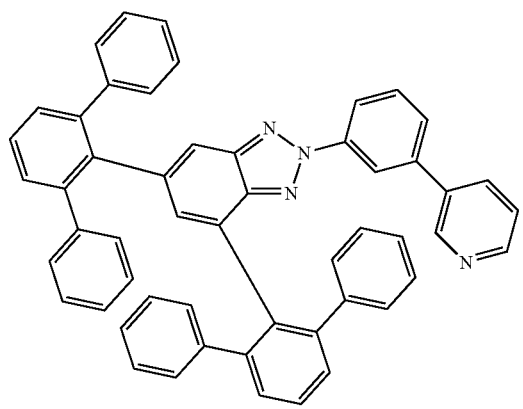
[Chemical Formula 532]
(9-39)
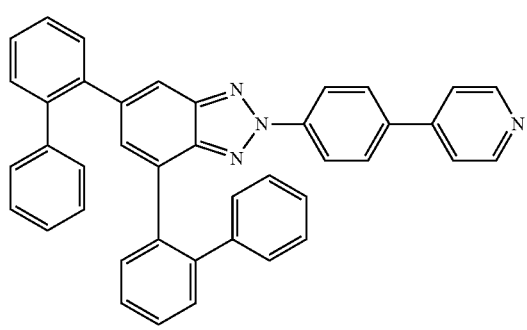
[Chemical Formula 533]
(9-40)
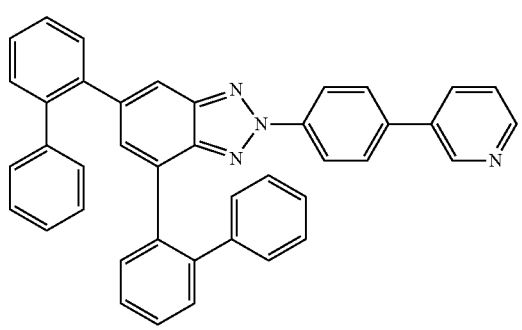

[Chemical Formula 534]
(9-41)
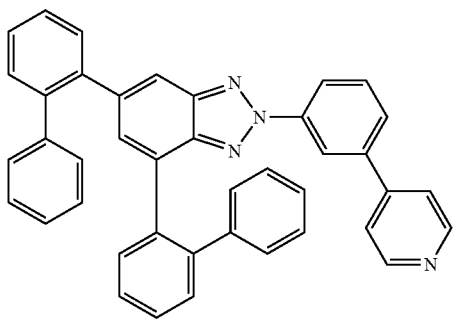
[Chemical Formula 535]
(9-42)
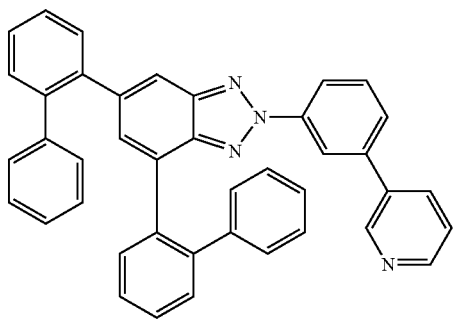
[Chemical Formula 536]
(9-43)
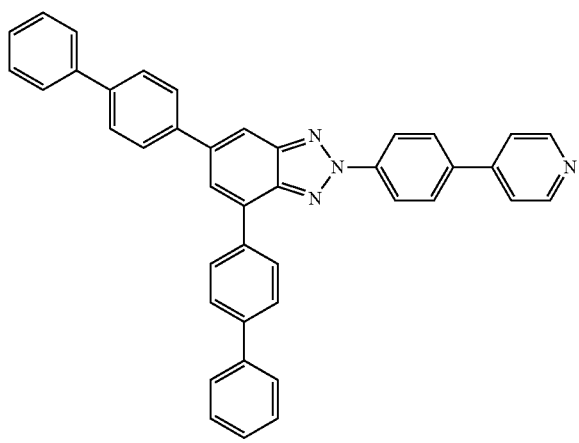
[Chemical Formula 537]
(9-44)
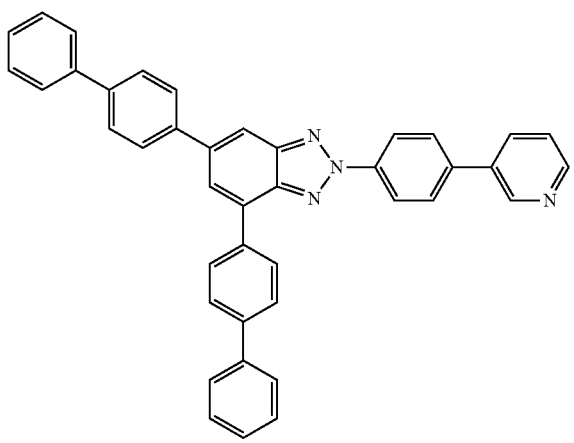
[Chemical Formula 538]
(9-45)
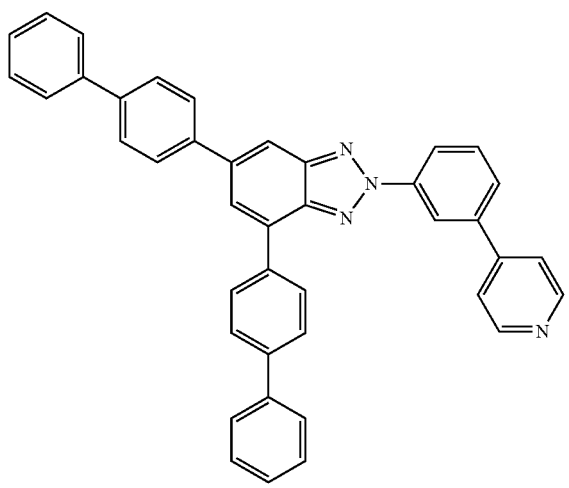
[Chemical Formula 539]
(9-46)
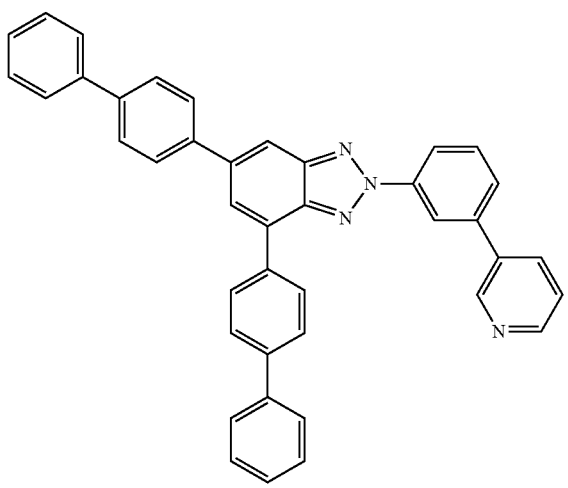

[Chemical Formula 540]
(9-47)
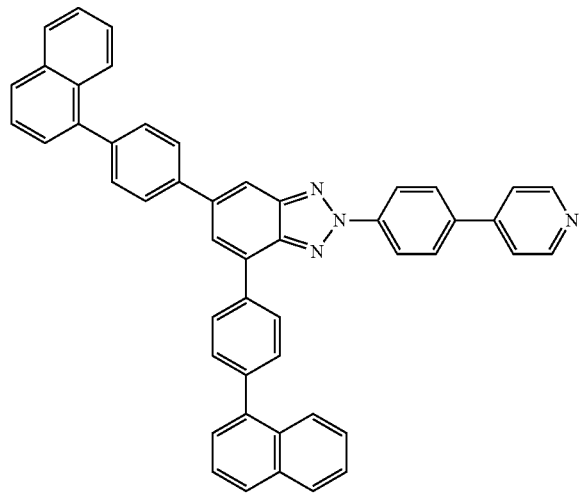
[Chemical Formula 541]
(9-48)
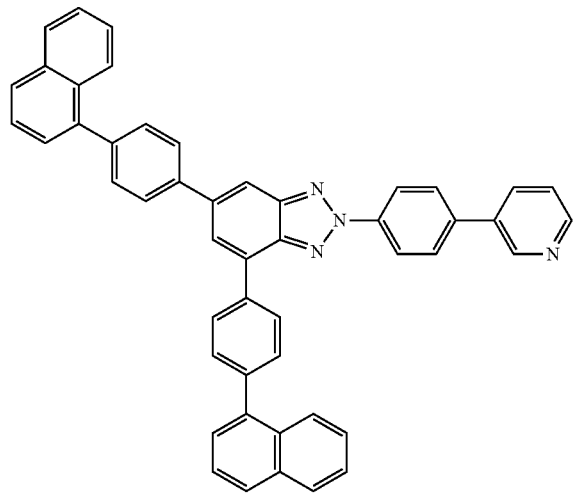
[Chemical Formula 542]
(9-49)
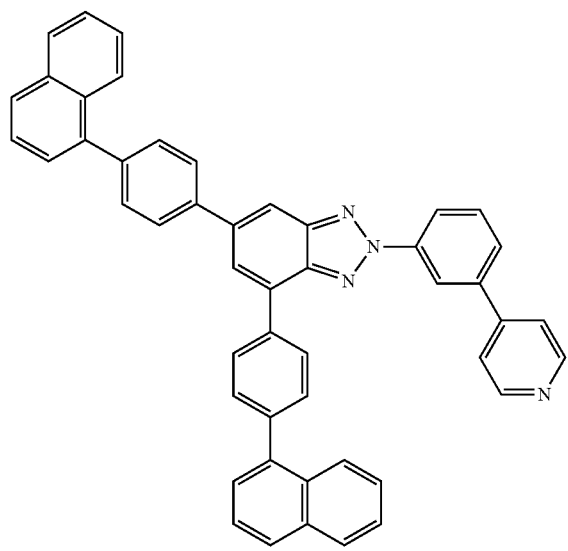
[Chemical Formula 543]
(9-50)
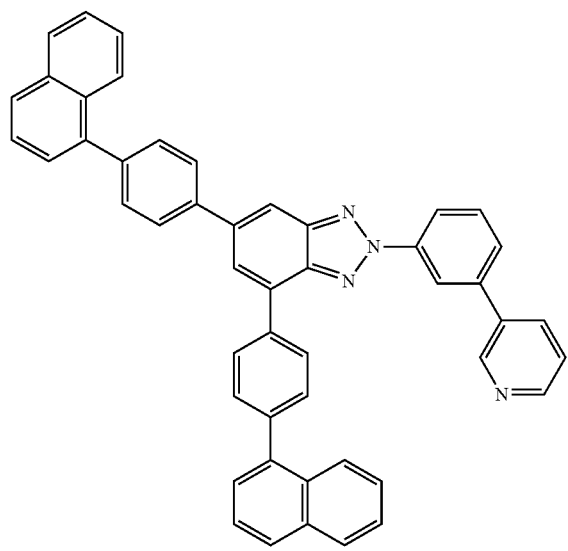
[Chemical Formula 544]
(9-51)
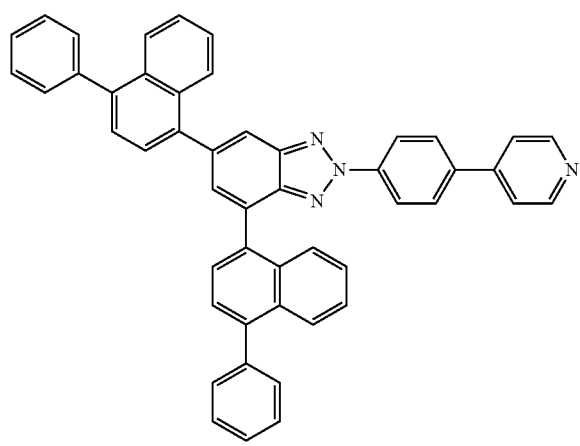
[Chemical Formula 545]
(9-52)
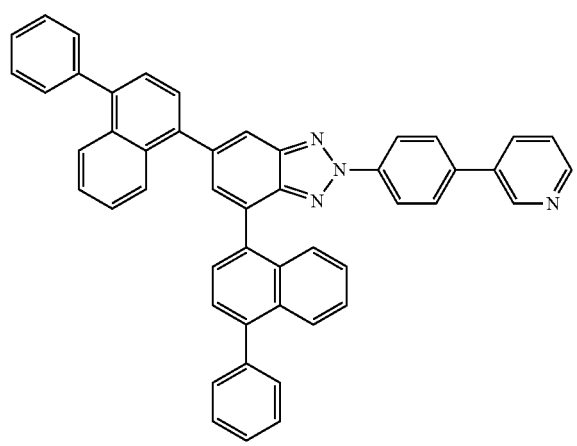

[Chemical Formula 546]
(9-53)
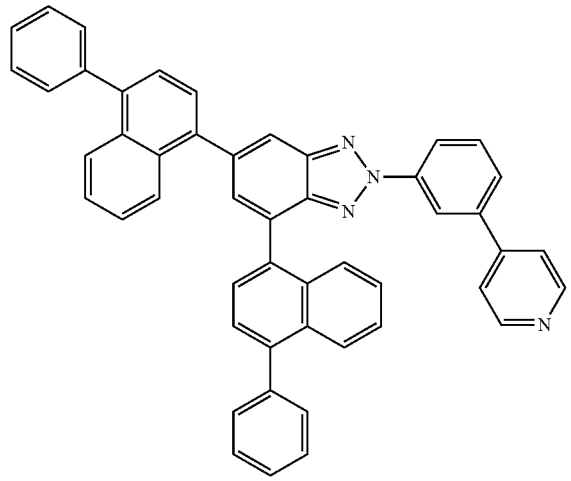
[Chemical Formula 547]
(9-54)
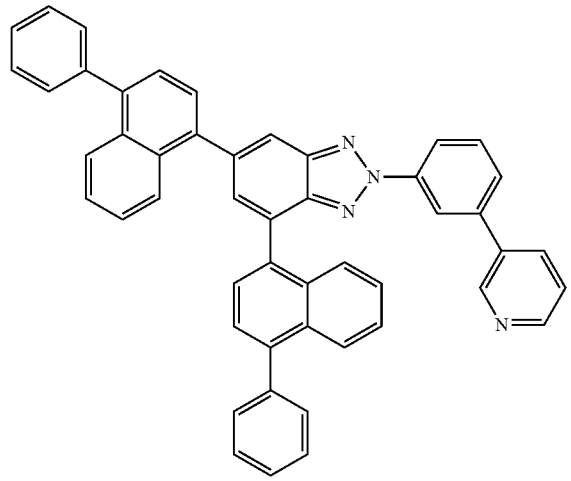
[Chemical Formula 548]
(9-55)
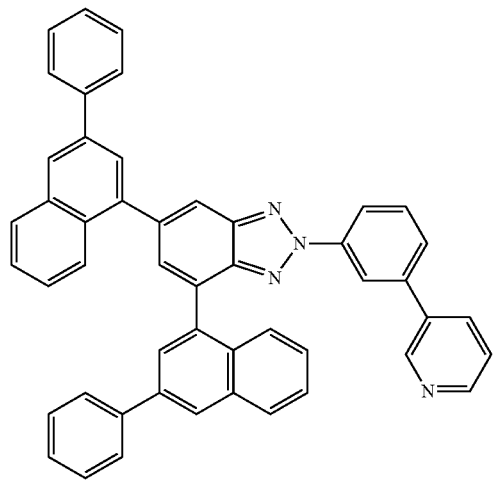
[Chemical Formula 549]
(9-56)
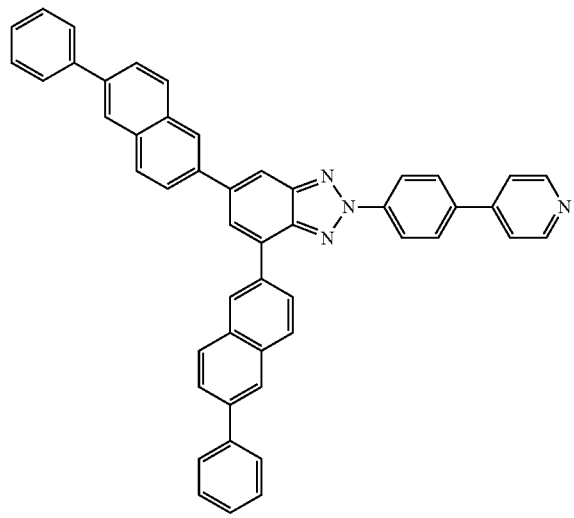

[Chemical Formula 550]
(9-57)
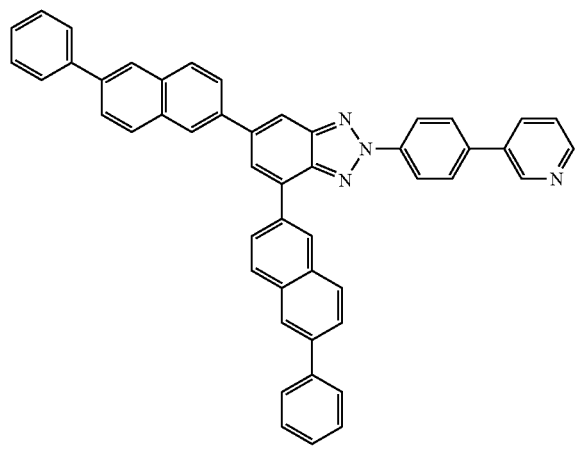
[Chemical Formula 551]
(9-58)
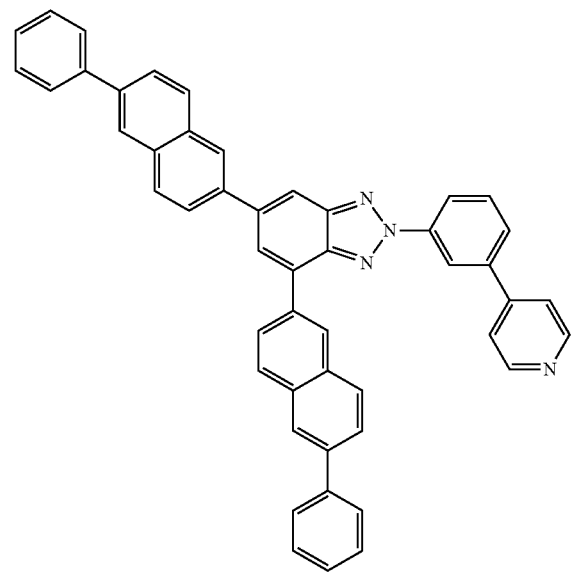
[Chemical Formula 552]
(9-59)
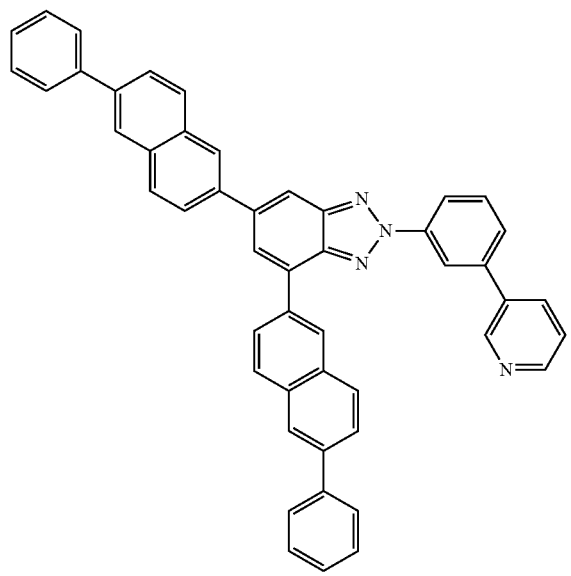
[Chemical Formula 553]
(9-60)
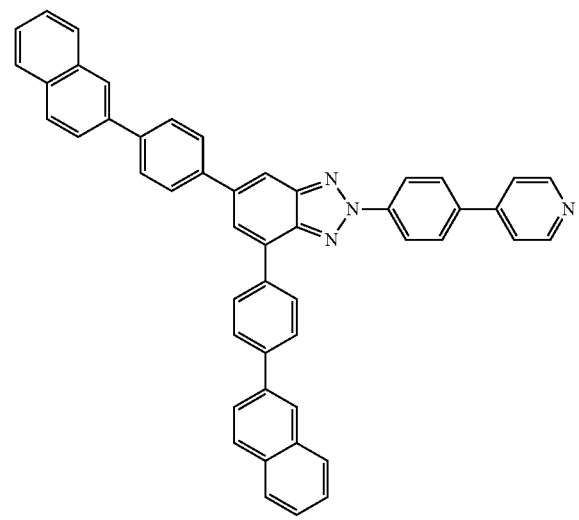

[Chemical Formula 554]
(9-61)
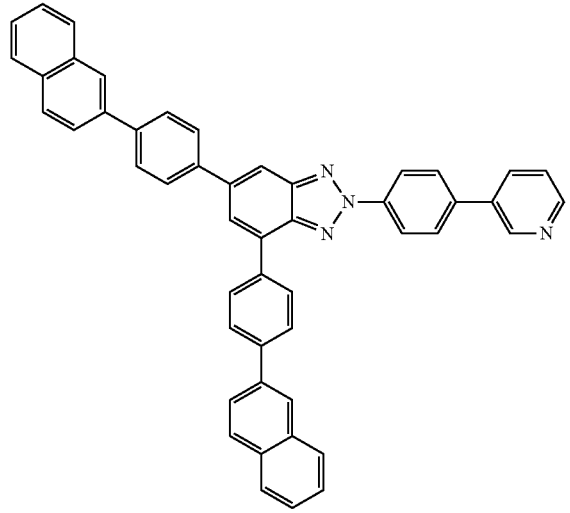
[Chemical Formula 555]
(9-62)
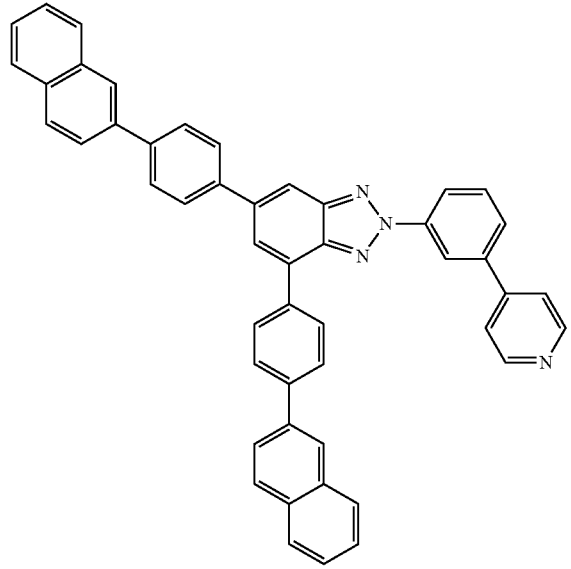
[Chemical Formula 556]
(9-63)
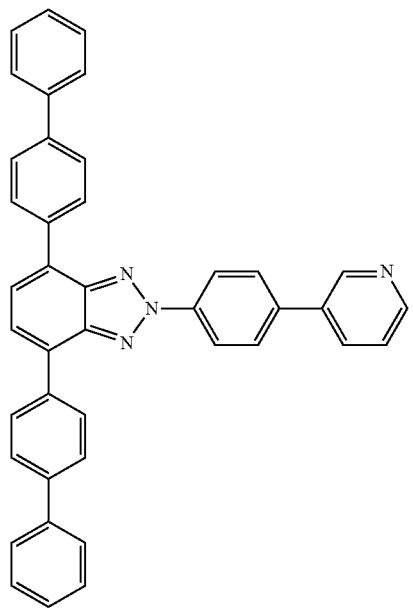
[Chemical Formula 557]
(9-64)
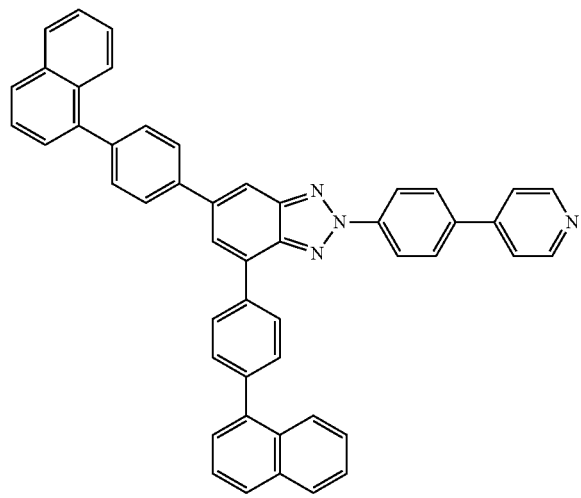

[Chemical Formula 558]
(9-65)
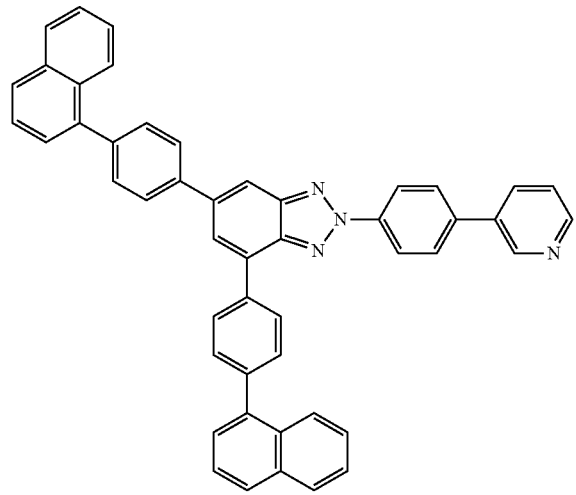
[Chemical Formula 559]
(9-66)
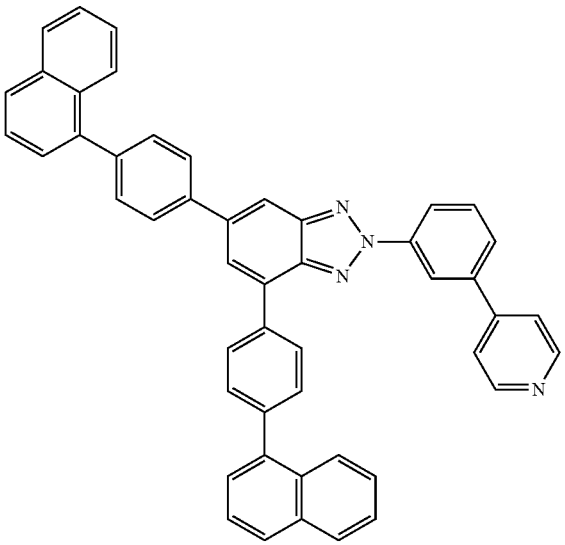
[Chemical Formula 560]
(9-67)
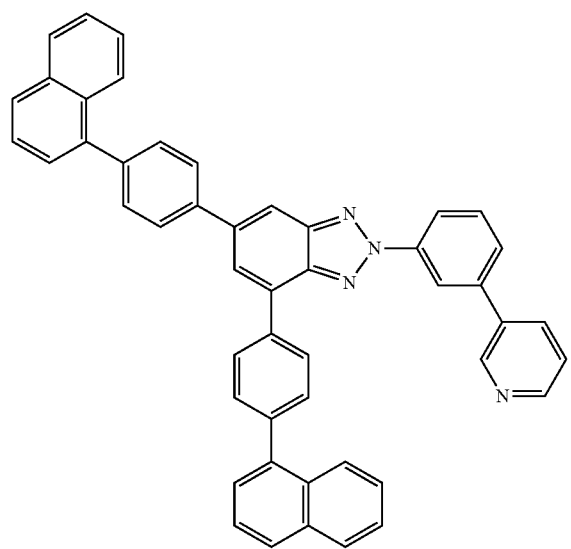
[Chemical Formula 561]
(9-68)
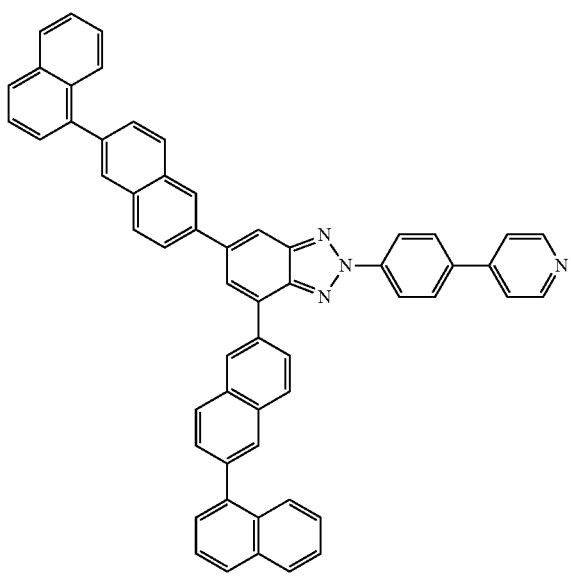

-continued
[Chemical Formula 562]
(9-69)
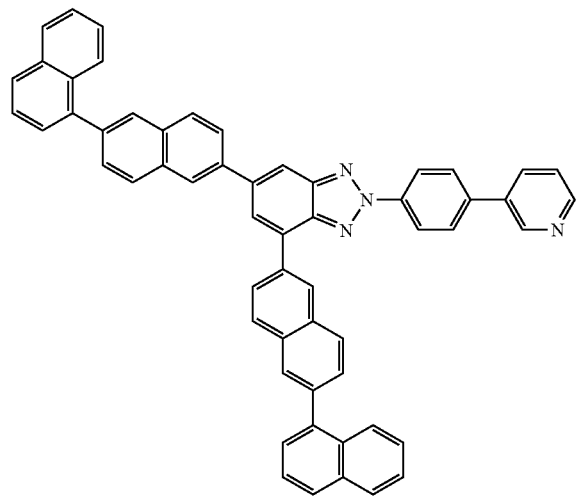
[Chemical Formula 563]
(9-70)
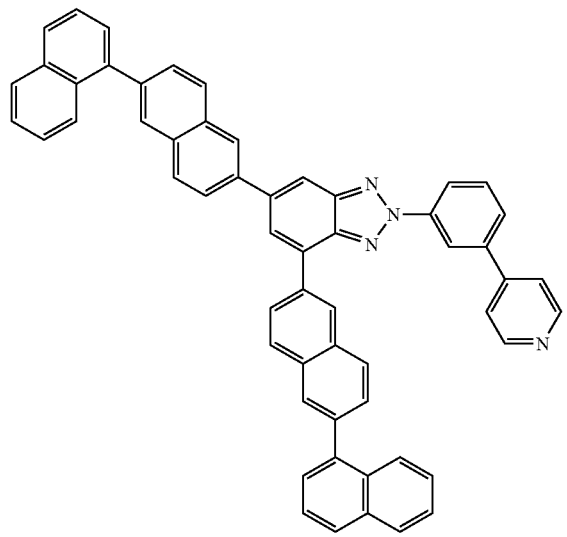
[Chemical Formula 564]
(9-71)
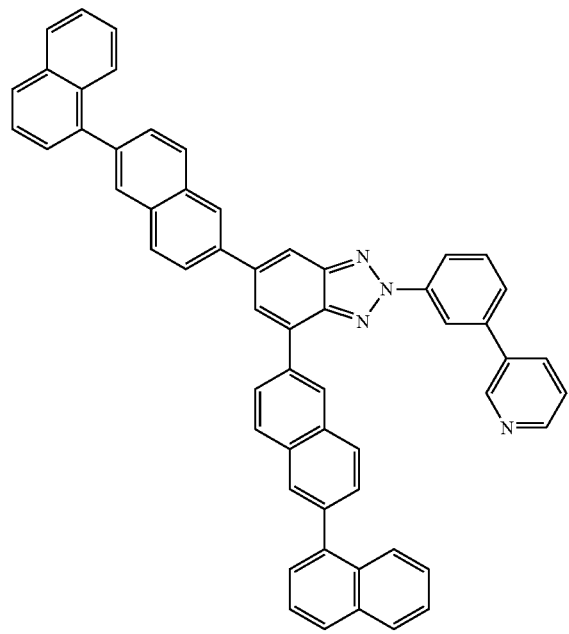
[Chemical Formula 565]
(9-72)
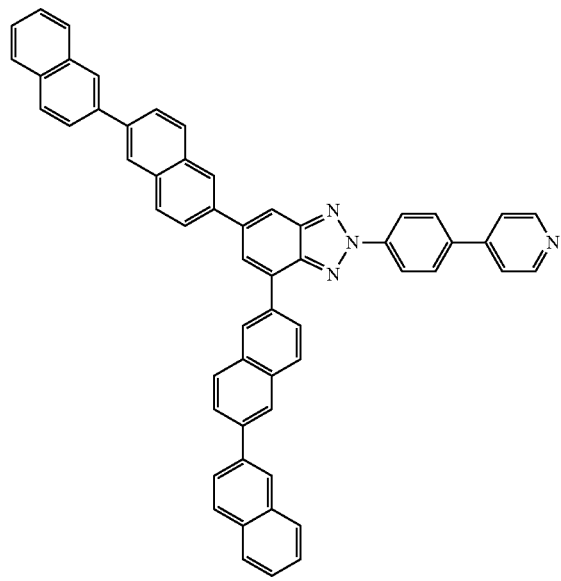

[Chemical Formula 566]
(9-73)
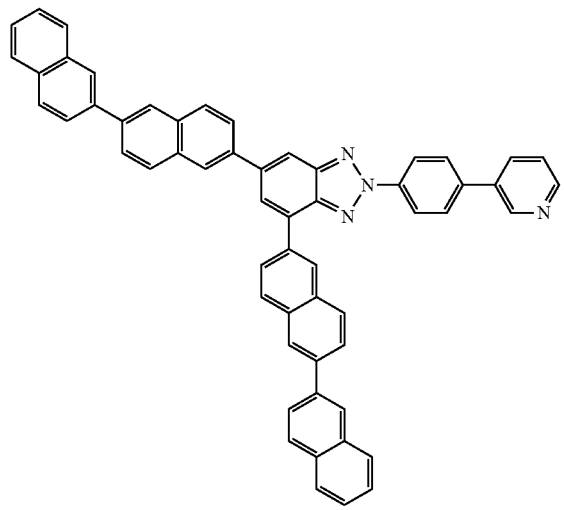
[Chemical Formula 567]
(9-74)
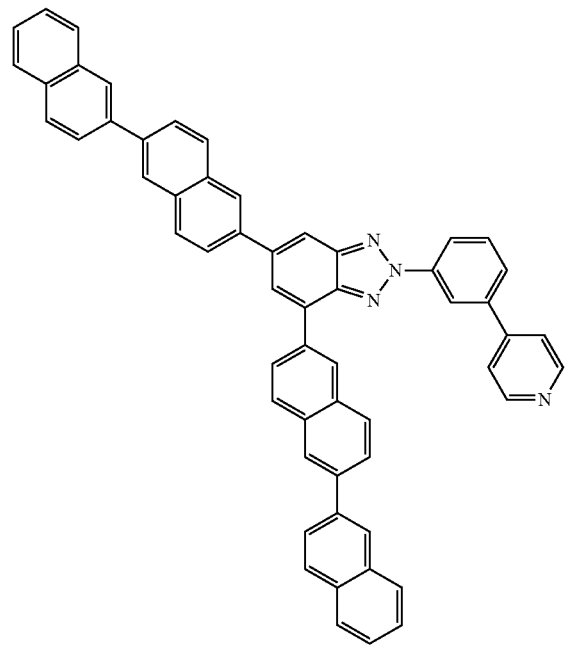
[Chemical Formula 568]
(9-75)
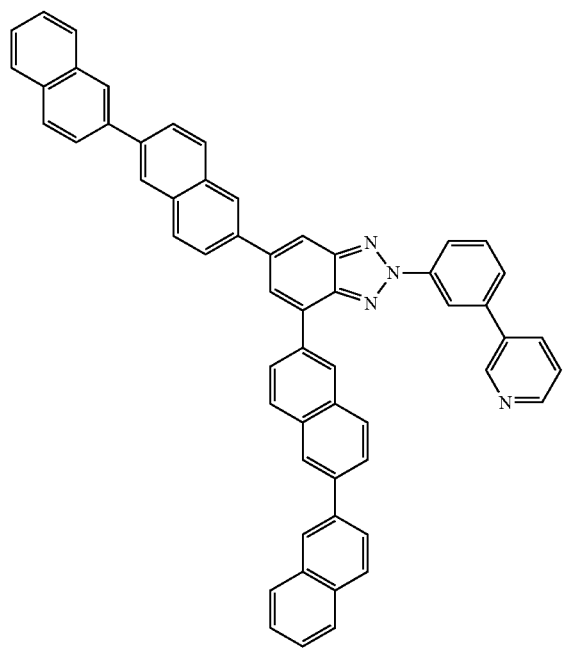
[Chemical Formula 569]
(9-76)
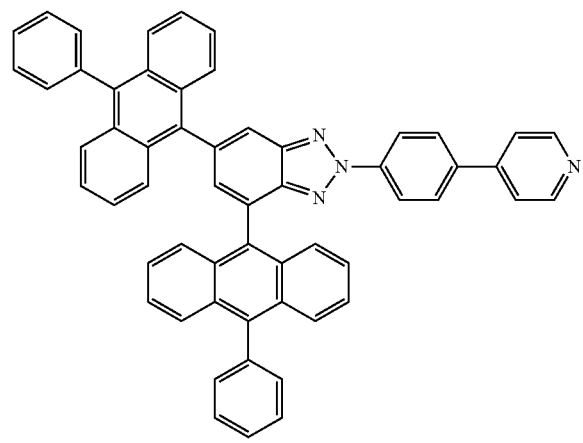

[Chemical Formula 570]
(9-77)
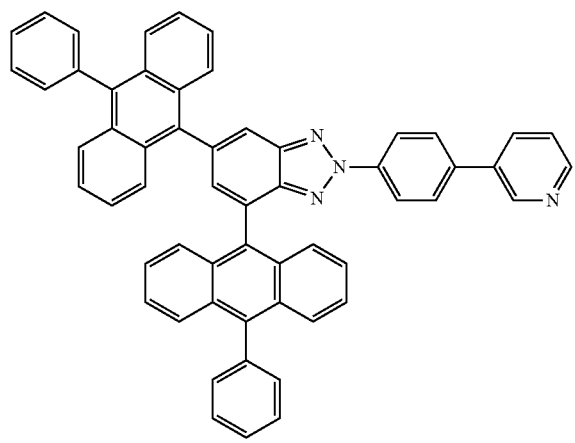
[Chemical Formula 571]
(9-78)
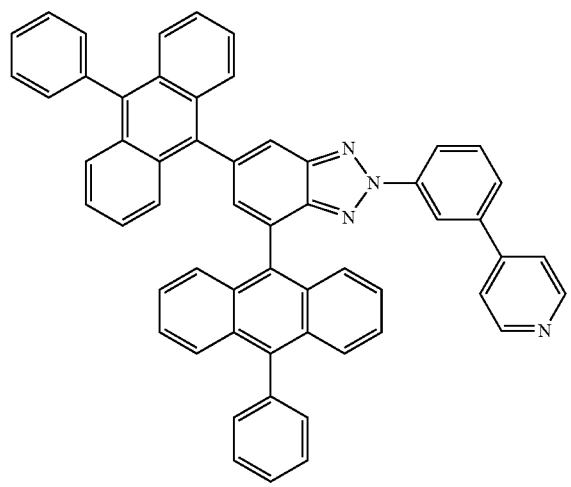
[Chemical Formula 572]
(9-79)
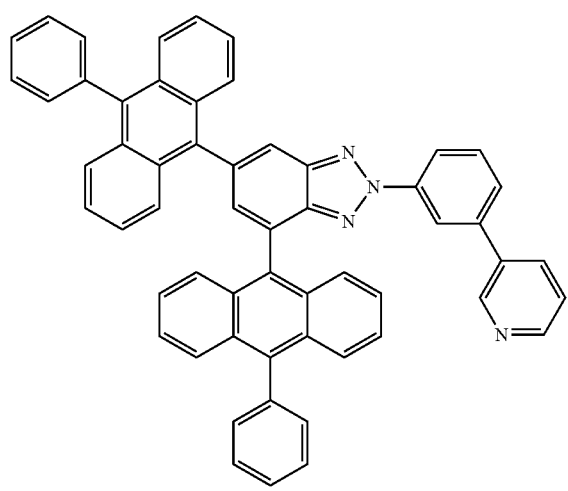
[Chemical Formula 573]
(9-80)
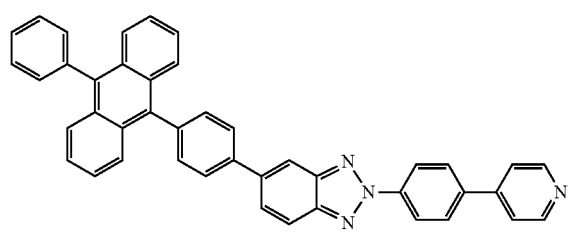
[Chemical Formula 574]
(9-81)
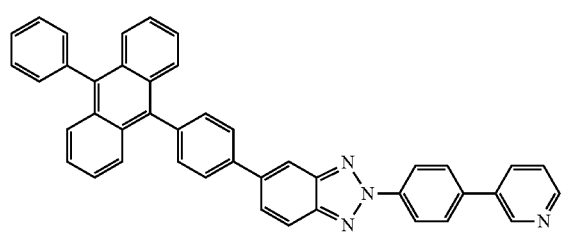
[Chemical Formula 575]
(9-82)
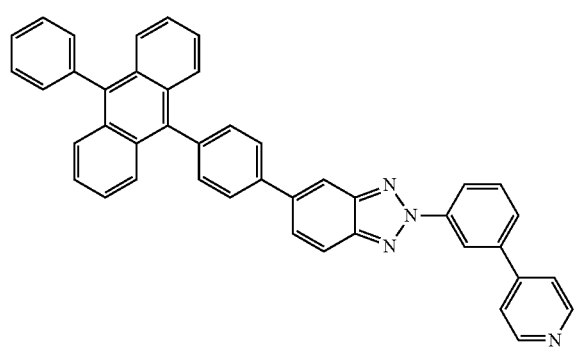

[Chemical Formula 576]
(9-83)
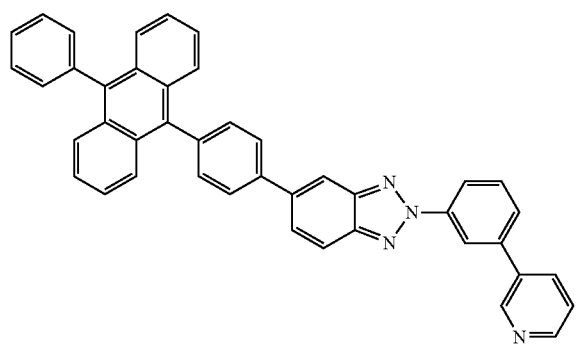
[Chemical Formula 577]
(9-84)
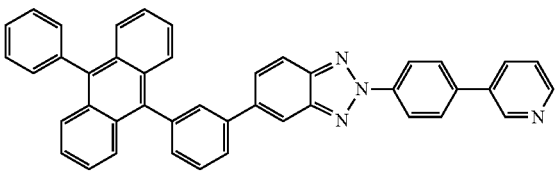
[Chemical Formula 578]
(9-85)
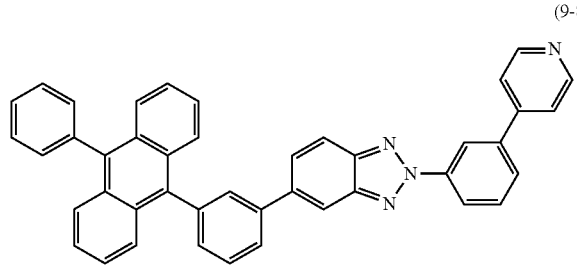
[Chemical Formula 579]
(9-86)
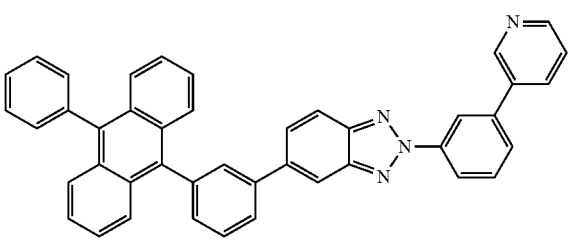
[Chemical Formula 580]
(9-87)
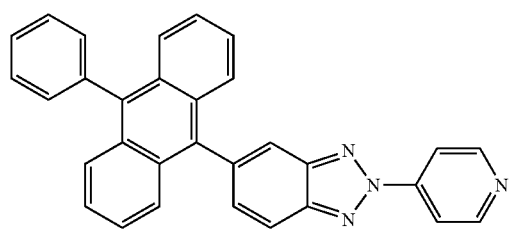
[Chemical Formula 581]
(9-88)
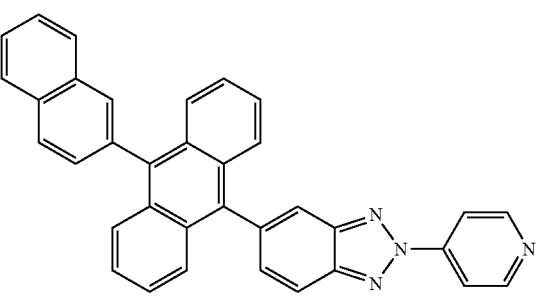
[Chemical Formula 582]
(9-89)
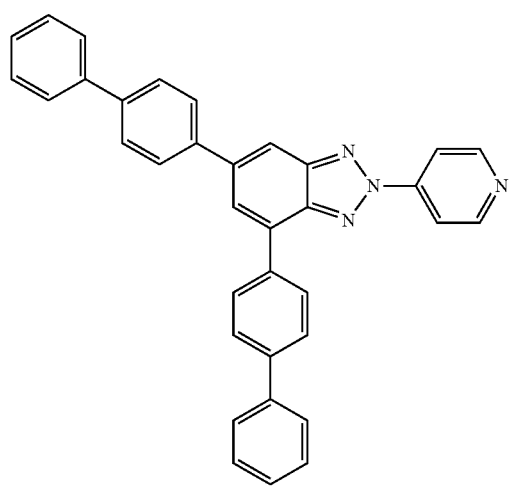
[Chemical Formula 583]
(9-90)
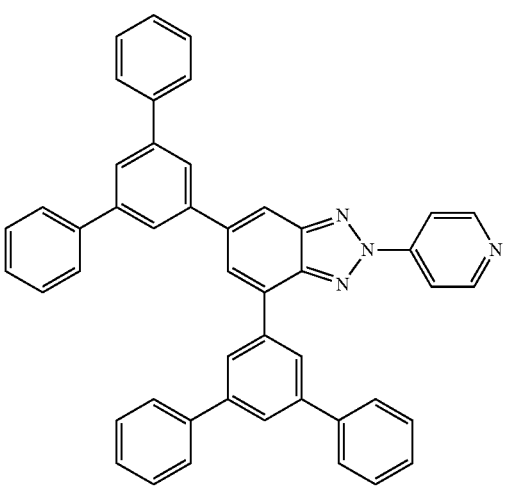

-continued
[Chemical Formula 584]
(9-91)
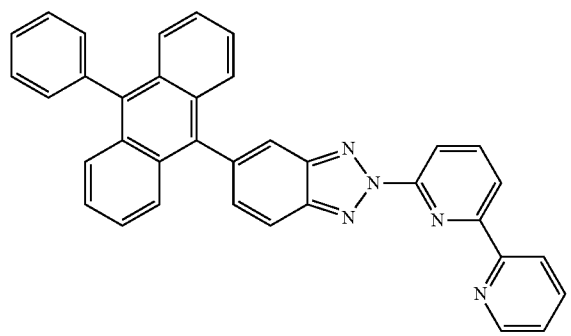
[Chemical Formula 585]
(9-92)
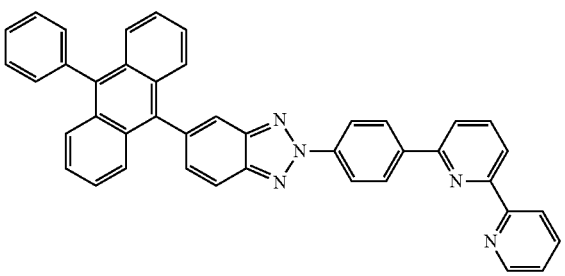
[Chemical Formula 586]
(9-93)
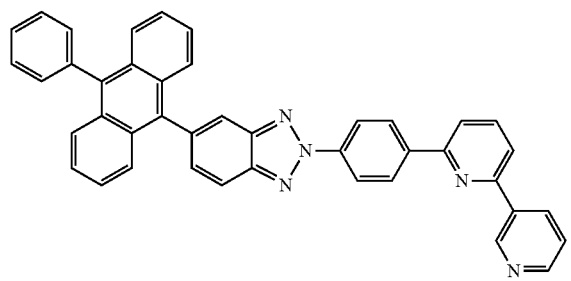
[Chemical Formula 587]
(9-94)
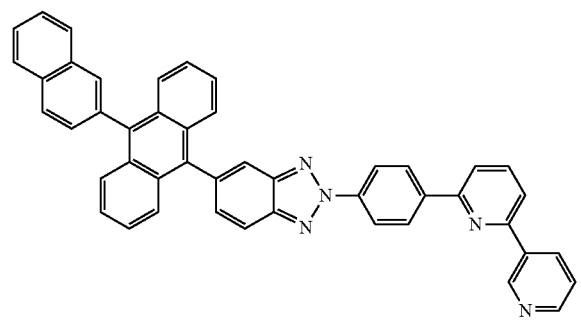
[Chemical Formula 588]
(9-95)
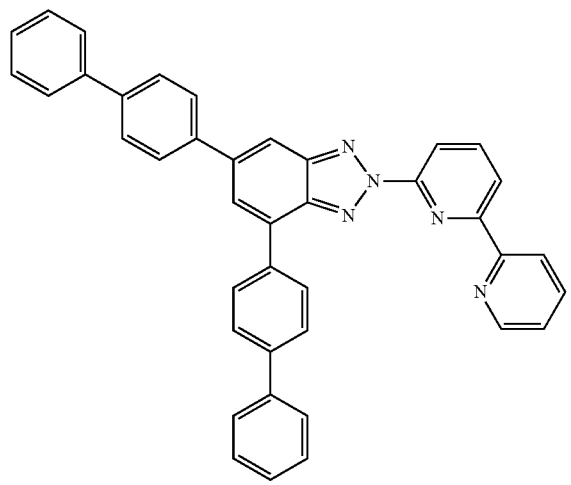
[Chemical Formula 589]
(9-96)
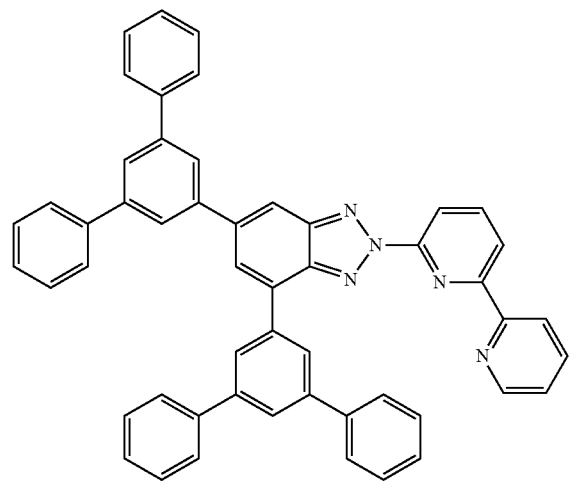

-continued
[Chemical Formula 590]
(9-97)
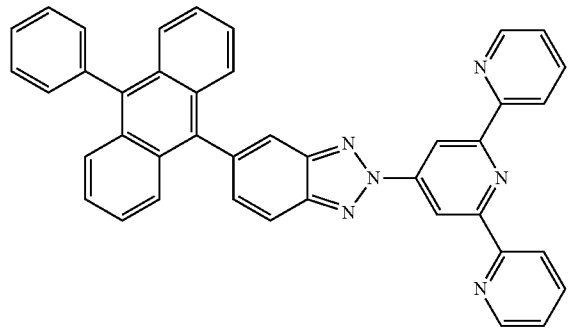
[Chemical Formula 591]
(9-98)
[Chemical Formula 592]
(9-99)
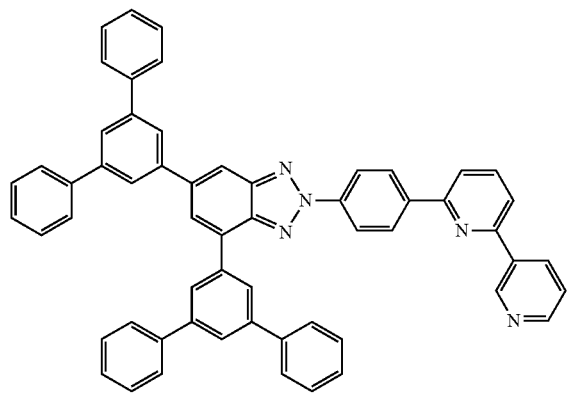
[Chemical Formula 593]
(9-100)
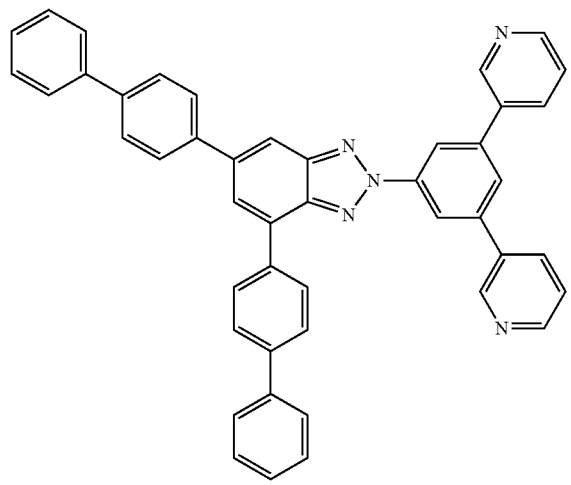
[Chemical Formula 594]
(9-101)
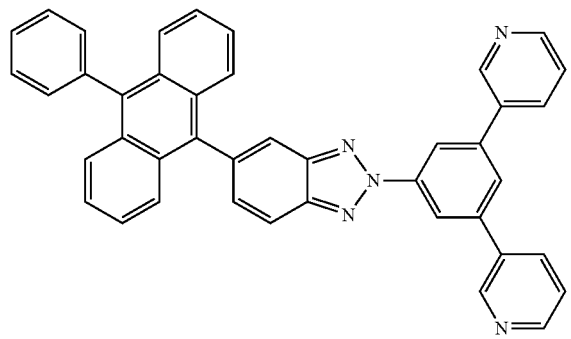
[Chemical Formula 595]
(9-102)
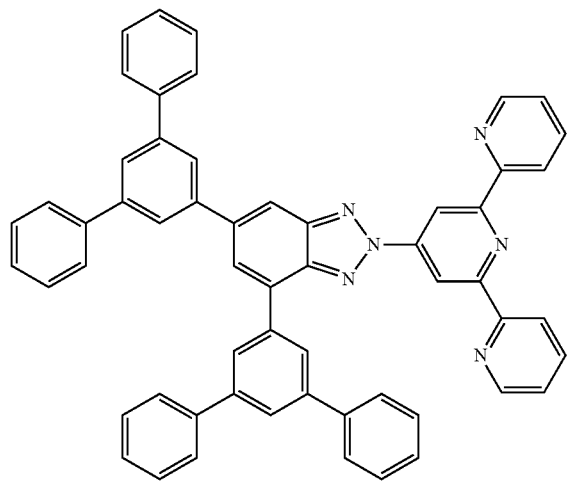

-continued
[Chemical Formula 596]
(9-103)
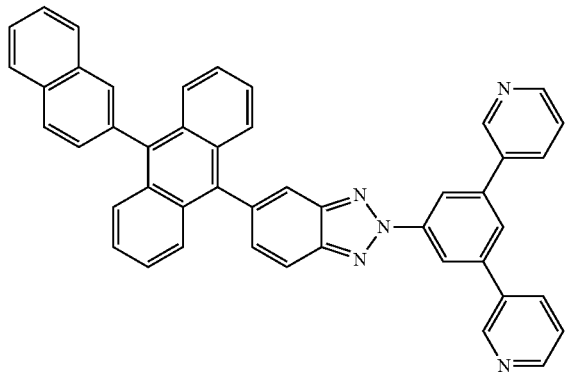
[Chemical Formula 597]
(9-104)
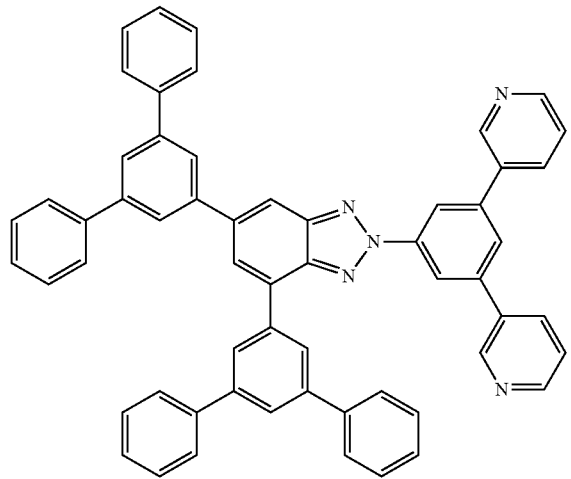
[Chemical Formula 598]
(9-105)
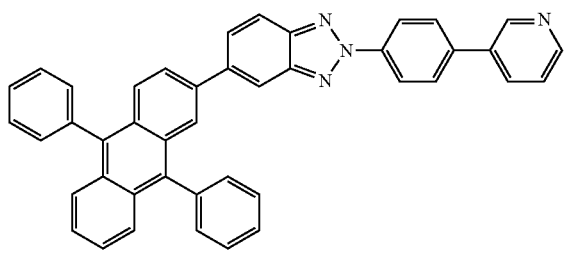
[Chemical Formula 599]
(9-106)
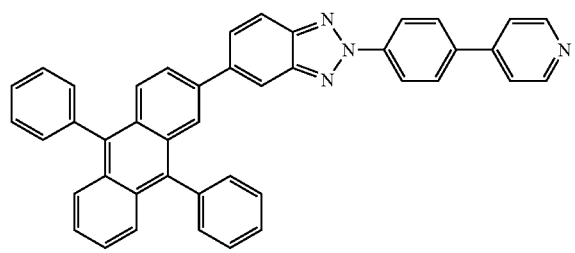
[Chemical Formula 600]
(9-107)
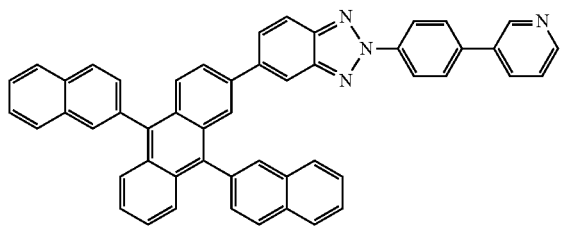
[Chemical Formula 601]
(9-108)
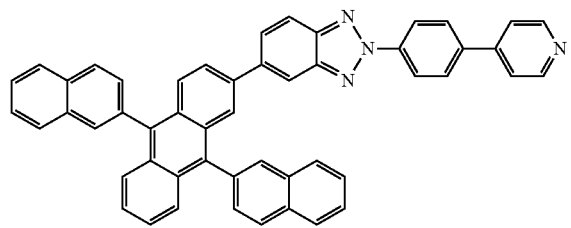
[Chemical Formula 602]
(9-109)
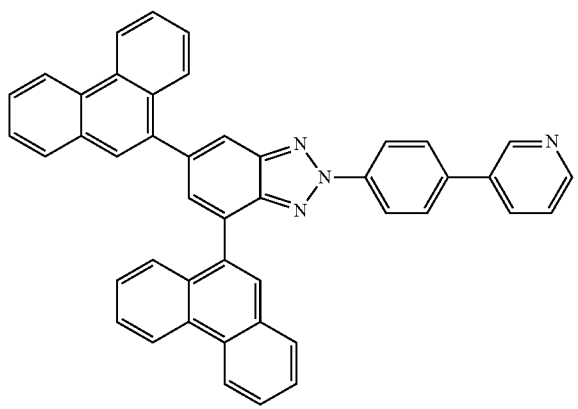
[Chemical Formula 603]
(9-110)
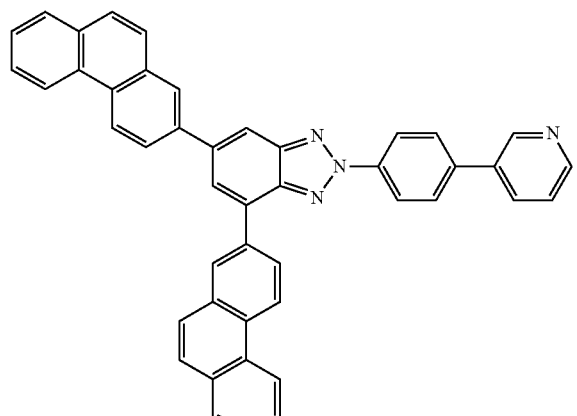

-continued
[Chemical Formula 604]
(9-111)
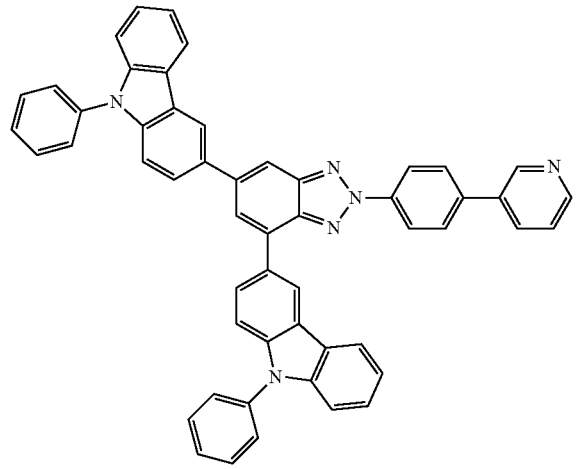
[Chemical Formula 605]
(9-112)
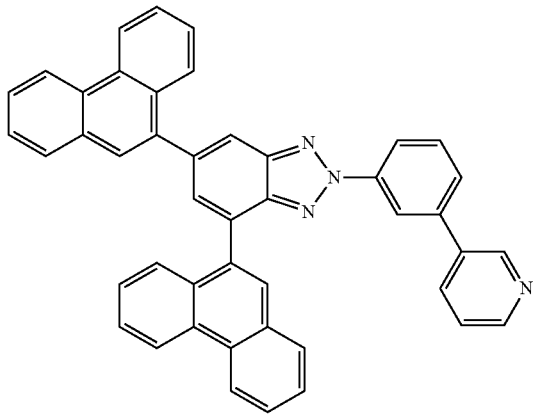
[Chemical Formula 606]
(9-113)
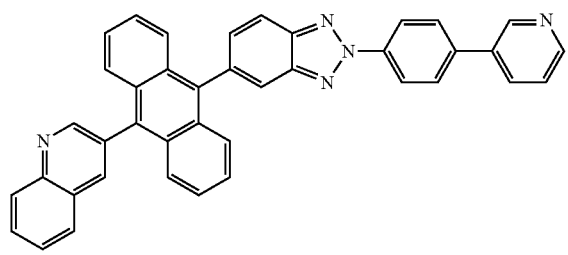
[Chemical Formula 607]
(9-114)
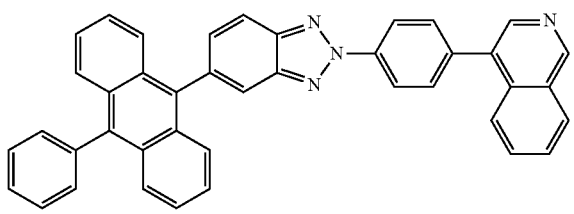
[Chemical Formula 608]
(9-115)
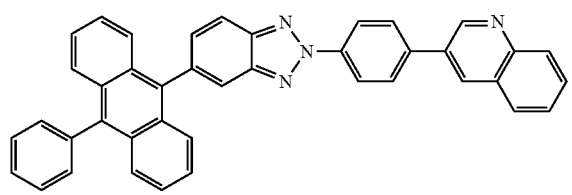
[Chemical Formula 609]
(9-116)
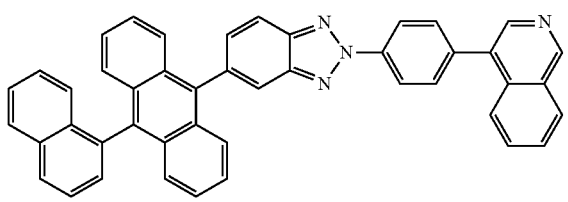
[Chemical Formula 610]
(9-117)
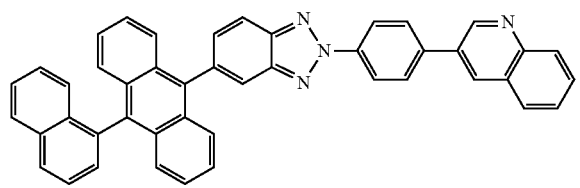
[Chemical Formula 611]
(9-118)
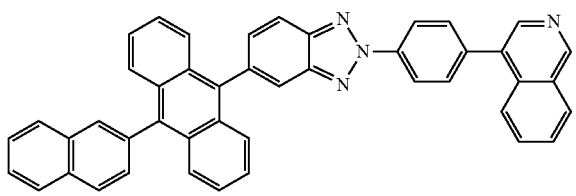
[Chemical Formula 612]
(9-119)
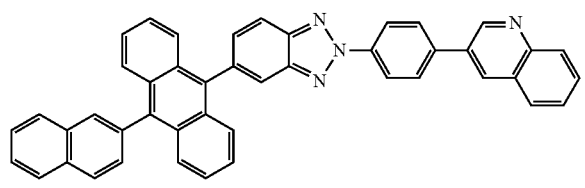
[Chemical Formula 613]
(9-120)
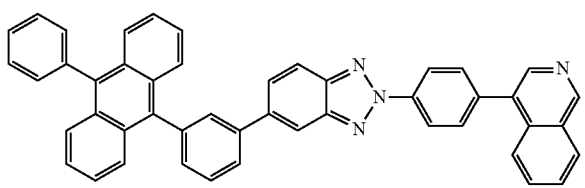

[Chemical Formula 614]
(9-121)
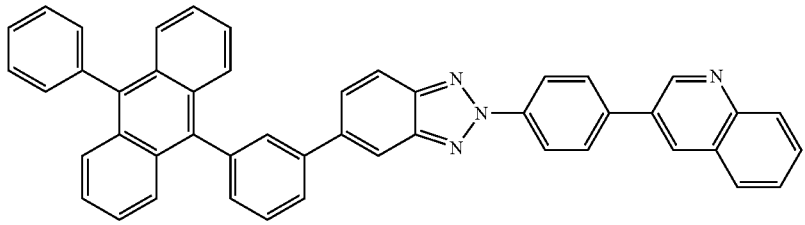
[Chemical Formula 615]
(9-122)
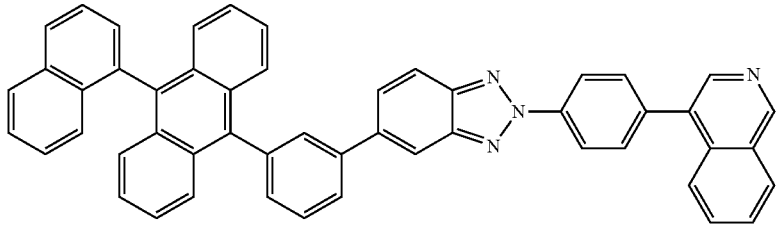
[Chemical Formula 616]
(9-123)
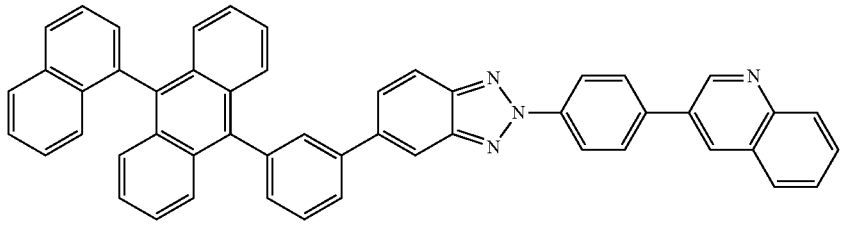
[Chemical Formula 617]
(9-124)
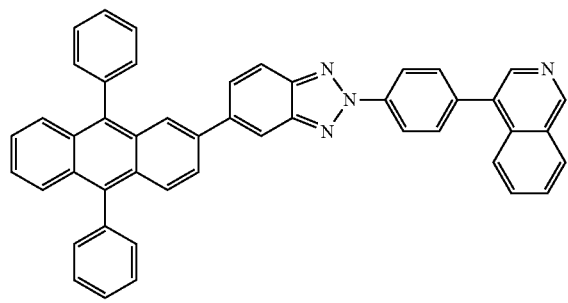
[Chemical Formula 618]
(9-125)
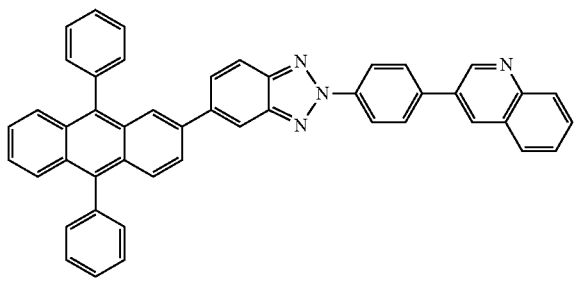

[Chemical Formula 619]
(9-126)
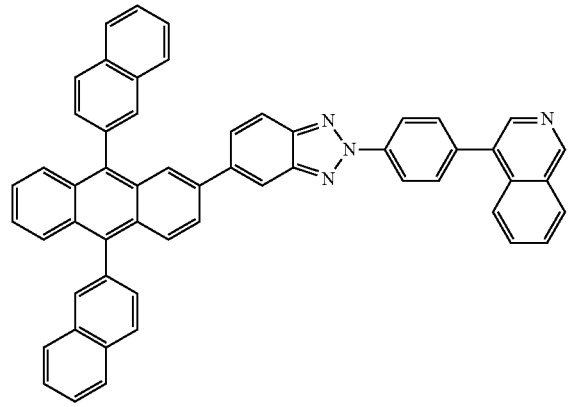
[Chemical Formula 620]
(9-127)
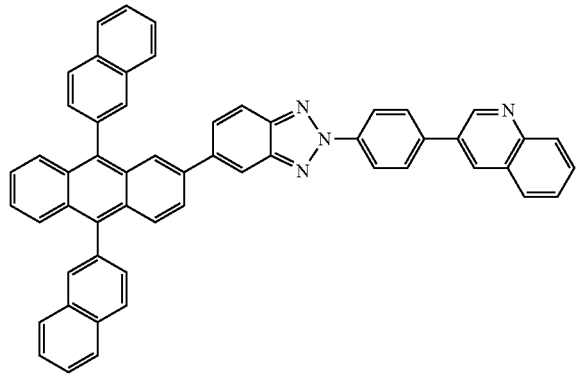
[Chemical Formula 621]
(9-128)
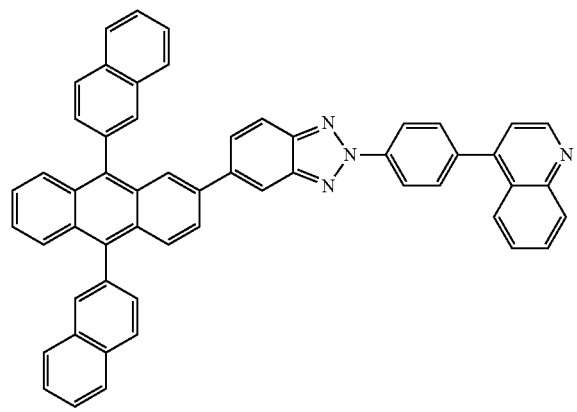
[Chemical Formula 622]
(9-129)
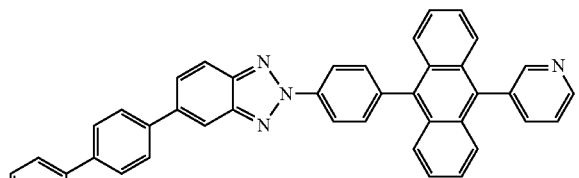
[Chemical Formula 623]
(9-130)
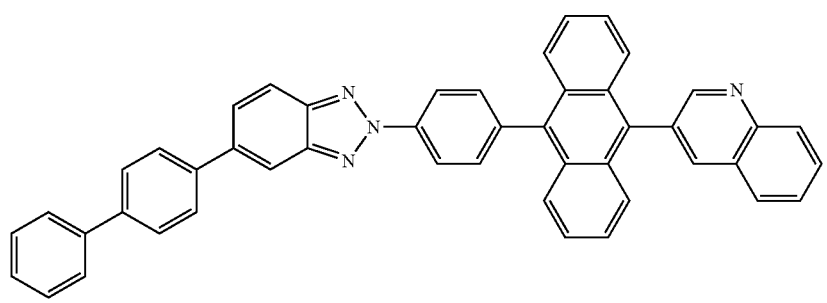

[Chemical Formula 624]
(9-131)
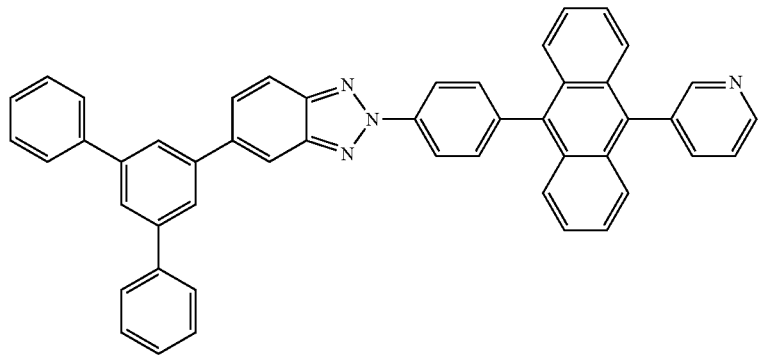
[Chemical Formula 625]
(9-132)
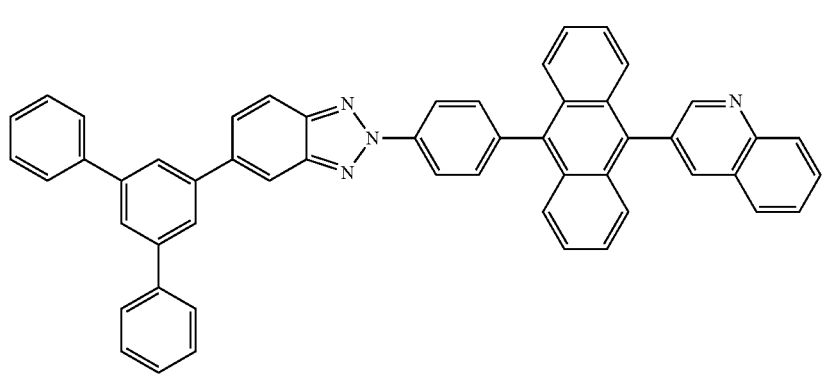
[Chemical Formula 626]
(9-133)
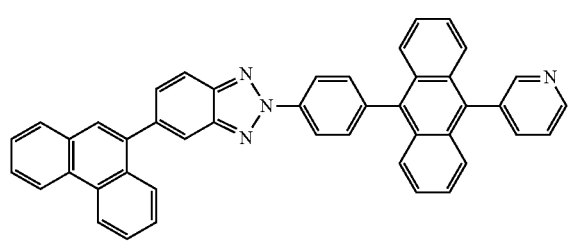
[Chemical Formula 627]
(9-134)
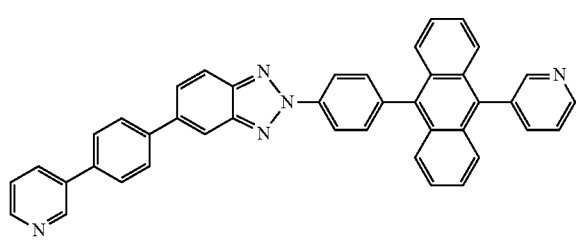
[Chemical Formula 628]
(9-135)
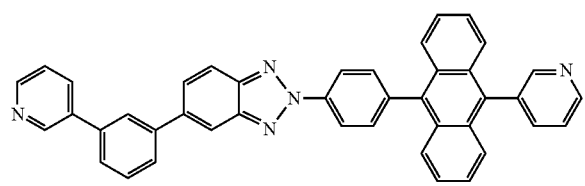
[Chemical Formula 629]
(9-136)
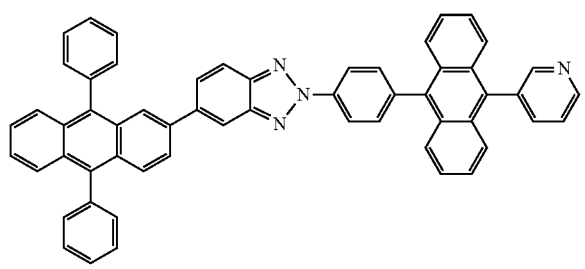

[Chemical Formula 630]
(9-137)
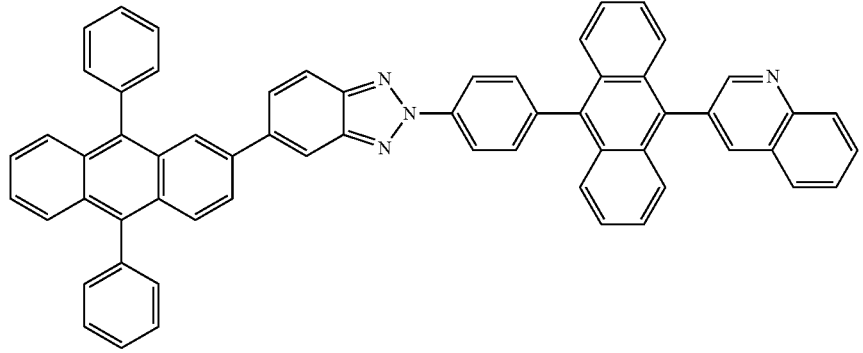
[Chemical Formula 631]
(9-138)
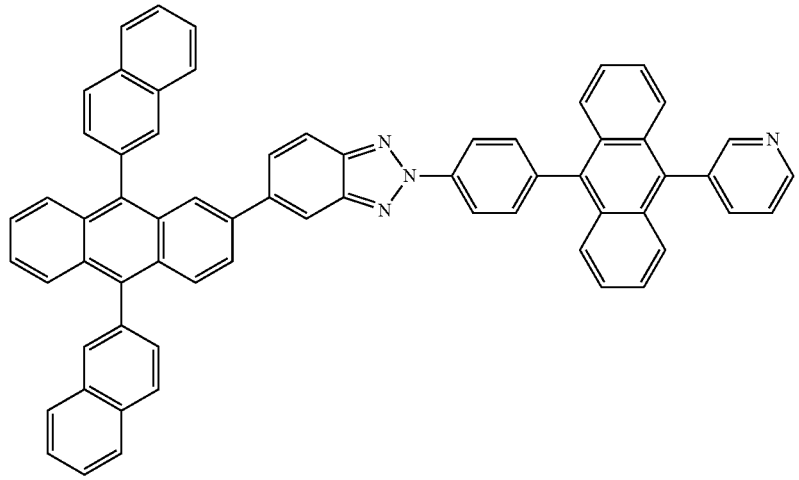
[Chemical Formula 632]      [Chemical Formula 633]
(9-139)      (9-140)
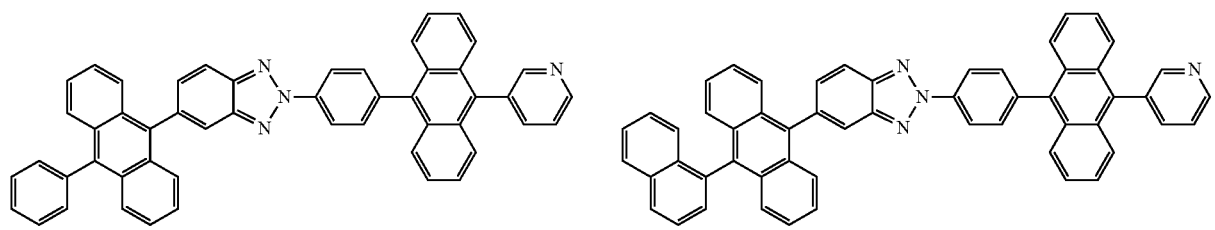
[Chemical Formula 634]
(6-141)
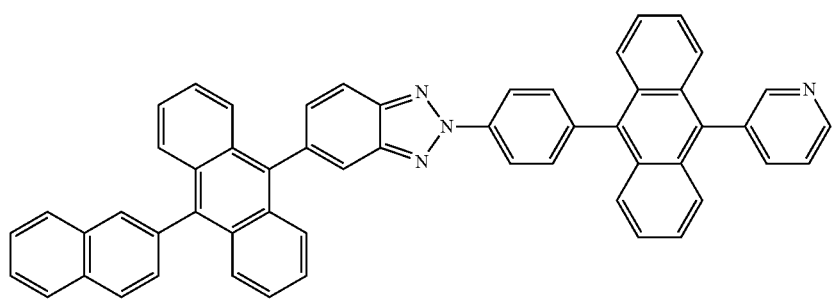

-continued
[Chemical Formula 635]
(9-142)
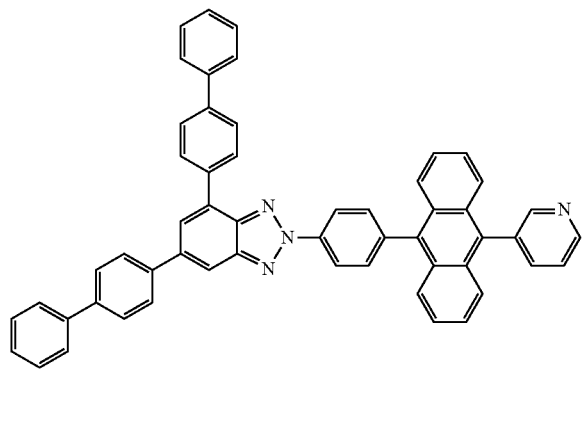
[Chemical Formula 636]
(9-143)
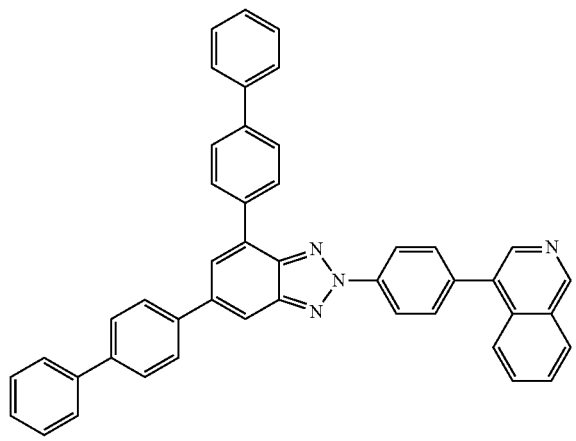
[Chemical Formula 637]
(9-144)
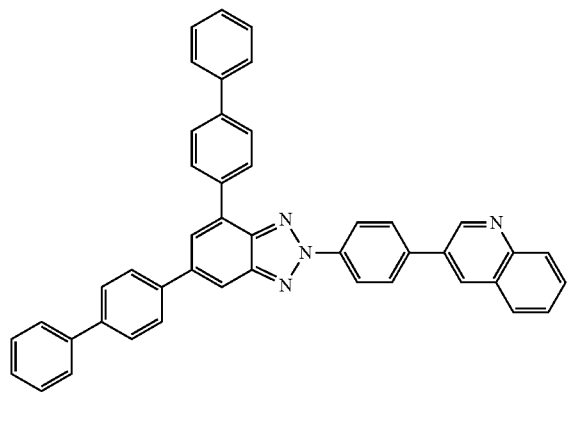
[Chemical Formula 638]
(9-145)
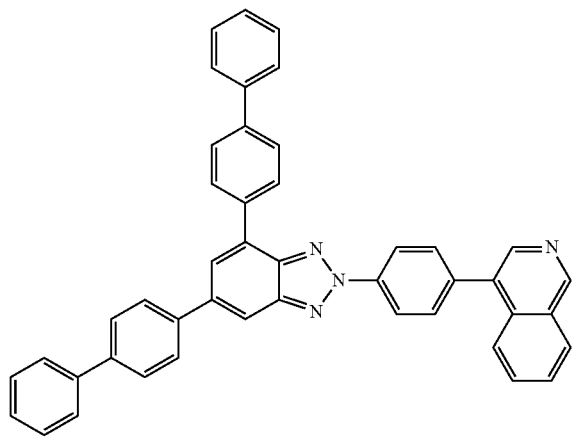
[Chemical Formula 639]
(9-146)
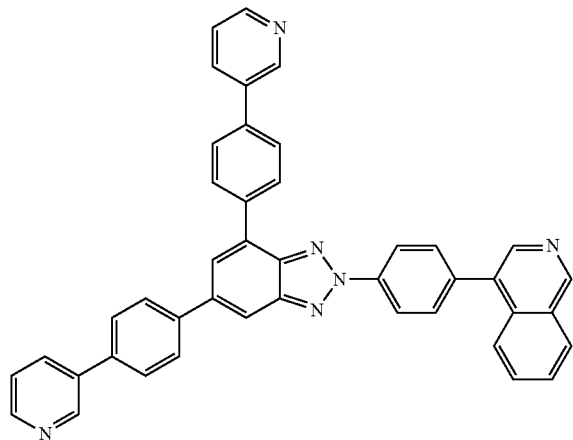
[Chemical Formula 640]
(9-147)
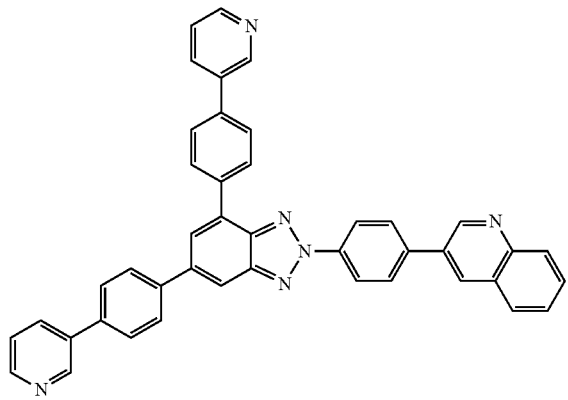

[Chemical Formula 641]
(9-148)
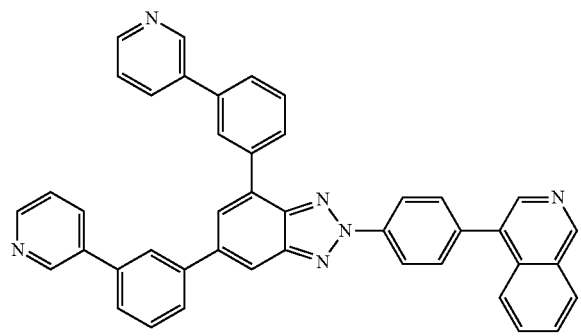
[Chemical Formula 642]
(9-149)
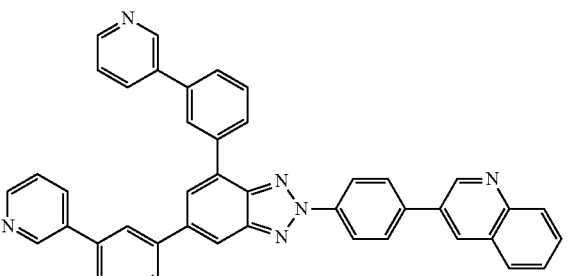
[Chemical Formula 643]
(9-150)
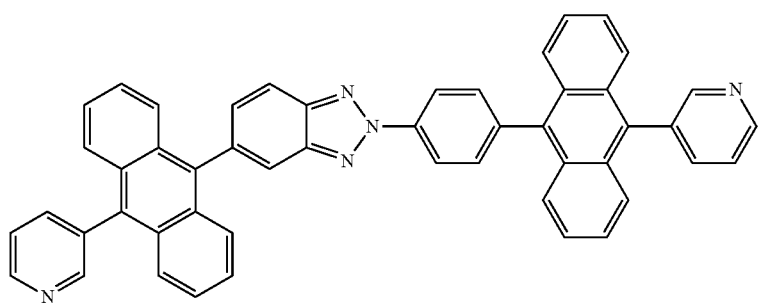
[Chemical Formula 644]
(9-151)
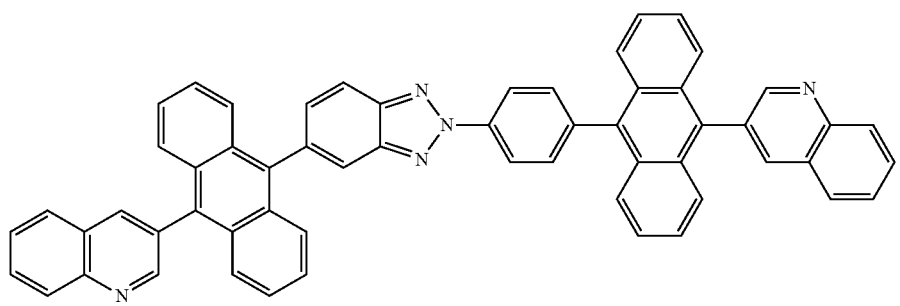
[Chemical Formula 645]
(9-152)
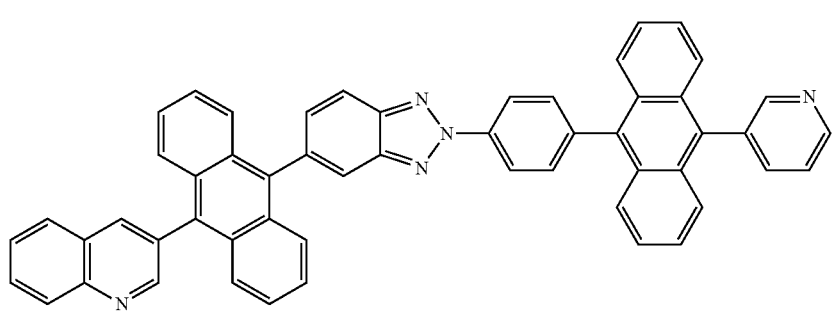

[Chemical Formula 646]
(9-153)
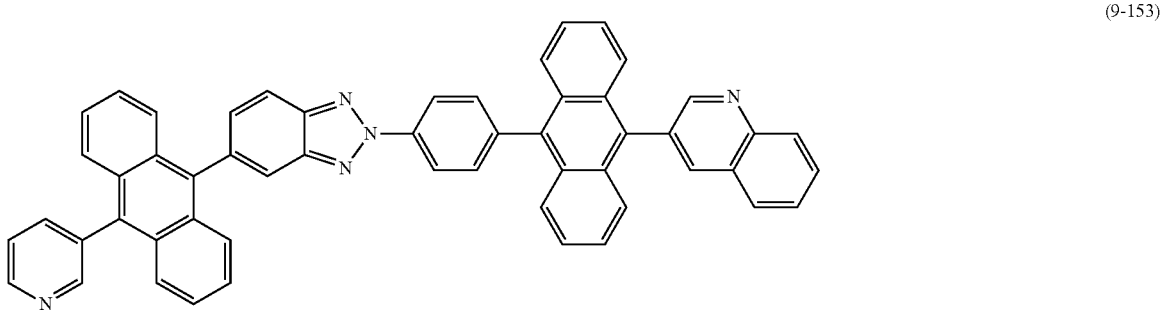
[Chemical Formula 647]
(9-154)
[Chemical Formula 648]
(9-155)
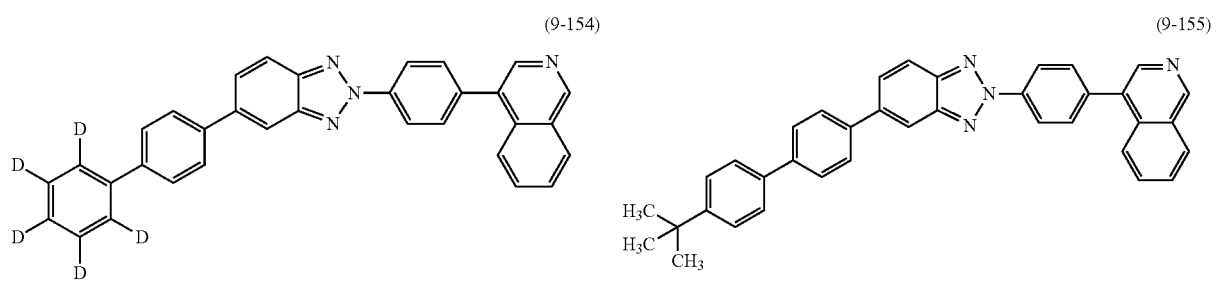
[Chemical Formula 649]
(9-156)
[Chemical Formula 650]
(9-157)
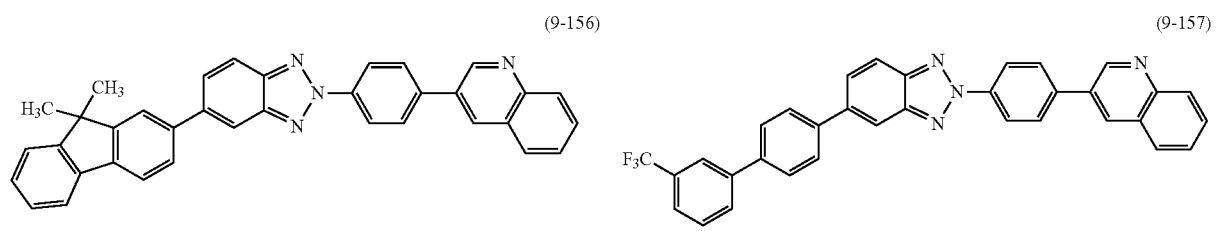
[Chemical Formula 651]
(9-158)
[Chemical Formula 652]
(9-159)
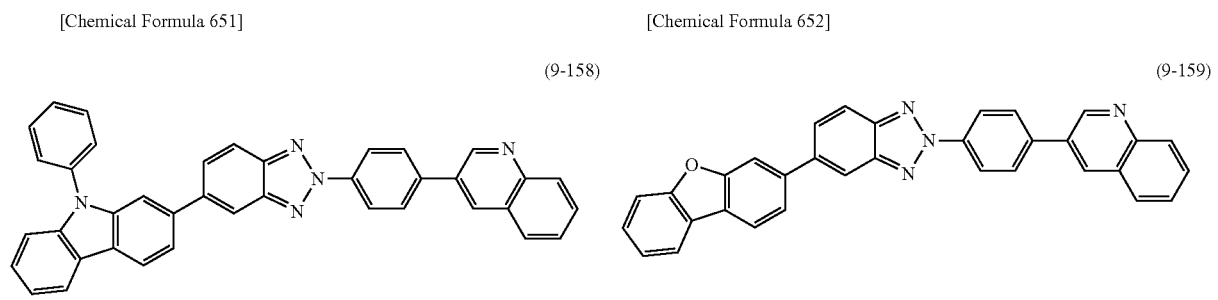
[Chemical Formula 653]
(9-160)
[Chemical Formula 654]
(9-161)
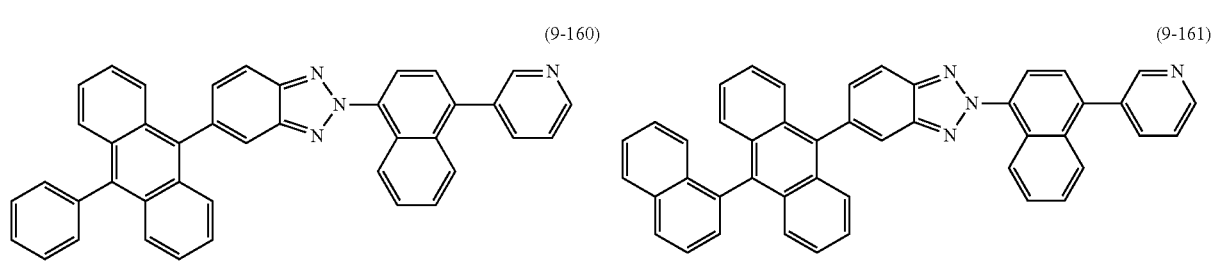

[Chemical Formula 655]
(9-162)
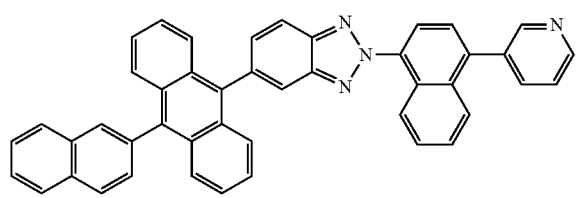
[Chemical Formula 656]
(9-163)
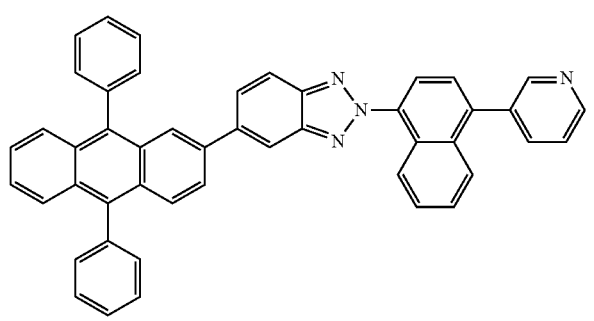
[Chemical Formula 657]
(9-164)
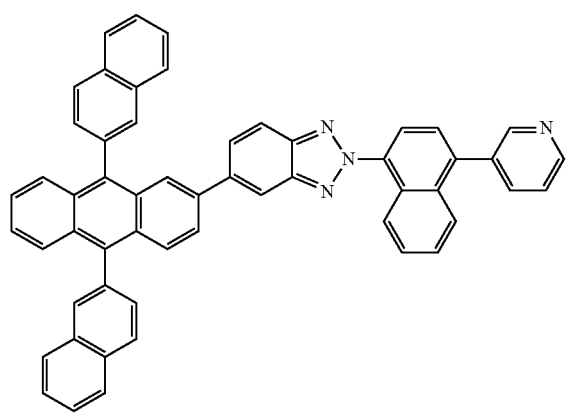
[Chemical Formula 658]
(9-165)
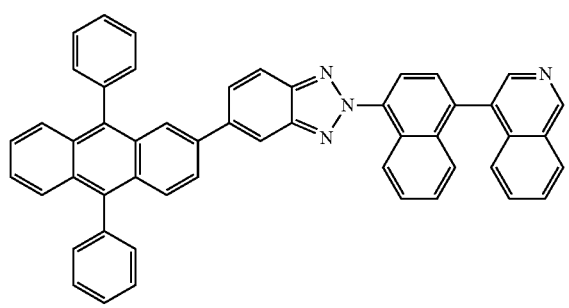
[Chemical Formula 659]
(9-166)
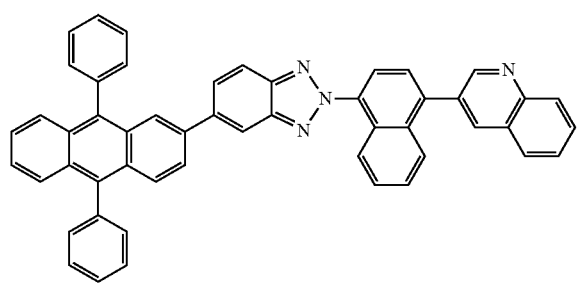
[Chemical Formula 660]
(9-167)
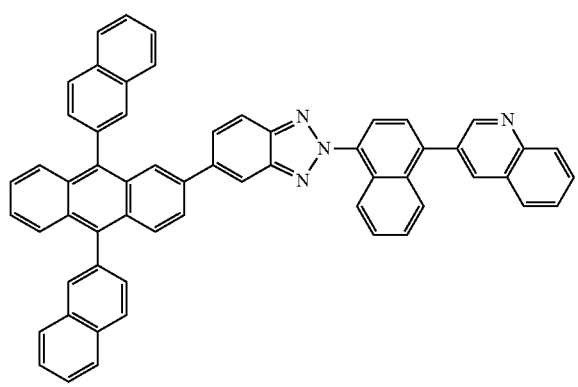

[Chemical Formula 661]
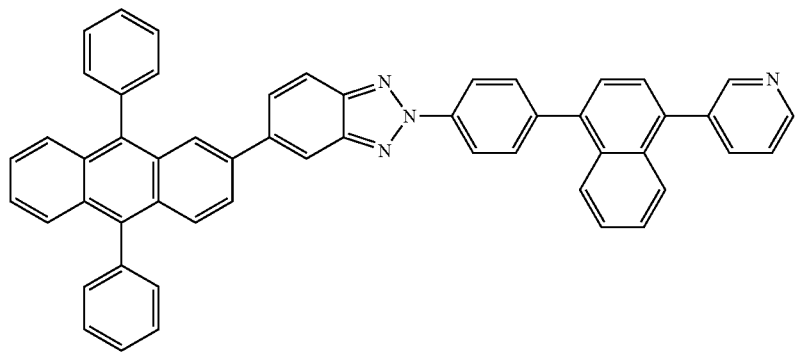
(9-168)
[Chemical Formula 662]
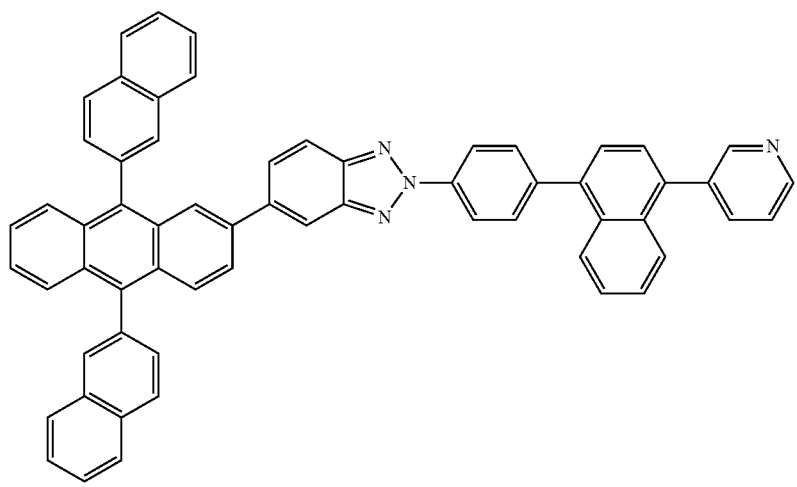
(9-169)
[Chemical Formula 663]
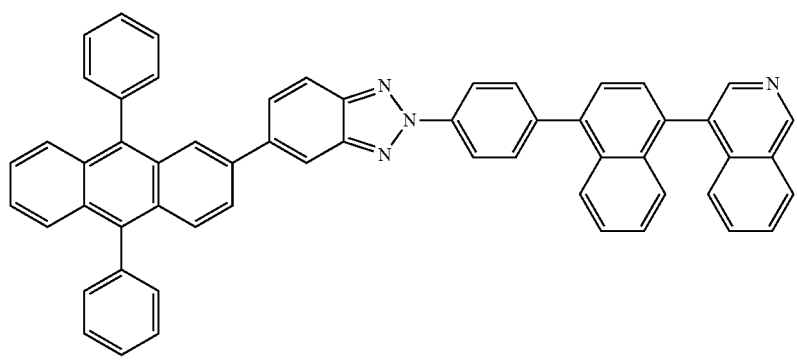
(9-170)

[Chemical Formula 664]
(9-171)
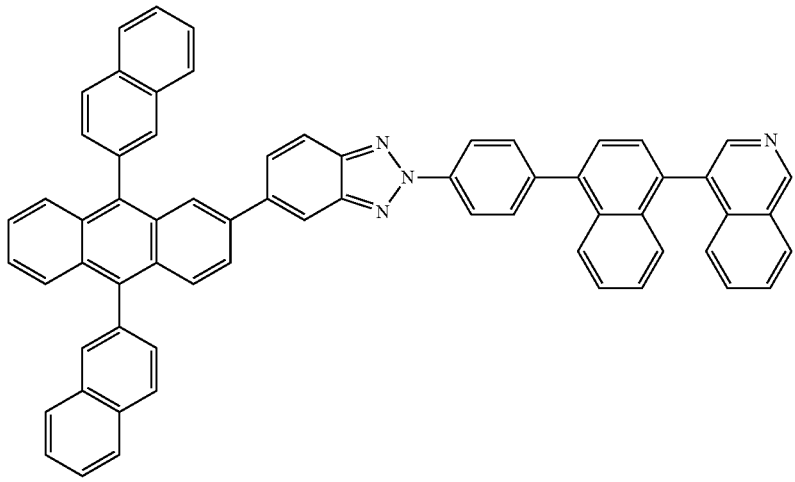
[Chemical Formula 665]
(9-172)
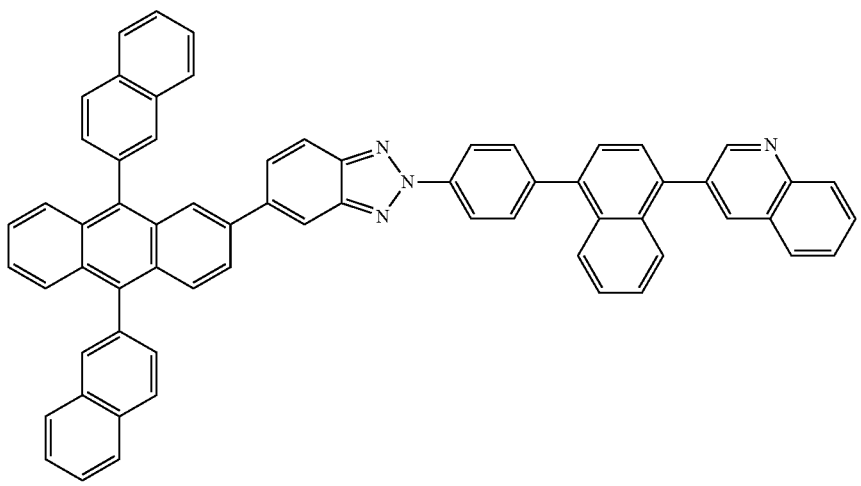
[Chemical Formula 666]
(9-173)
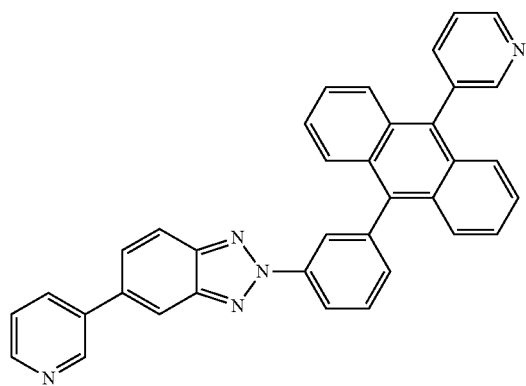
[Chemical Formula 667]
(9-174)
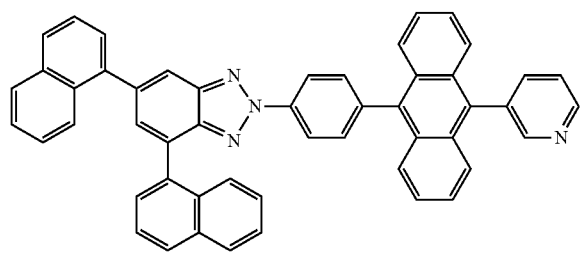

[Chemical Formula 668]
(9-175)
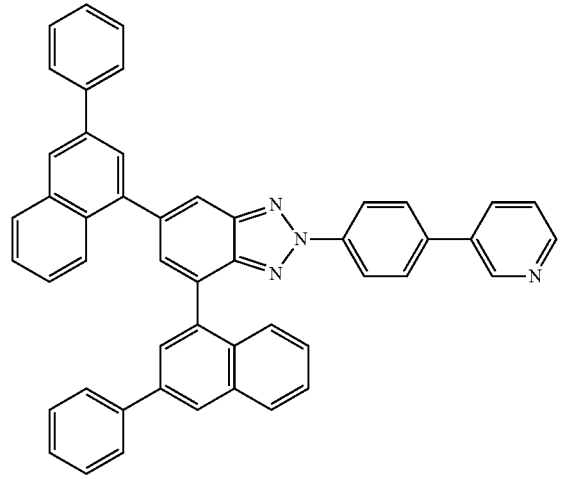
[Chemical Formula 669]
(9-176)
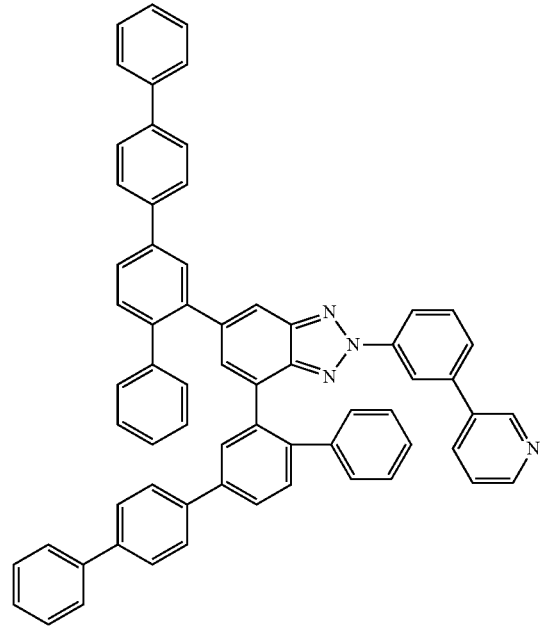
[Chemical Formula 670]
(9-177)
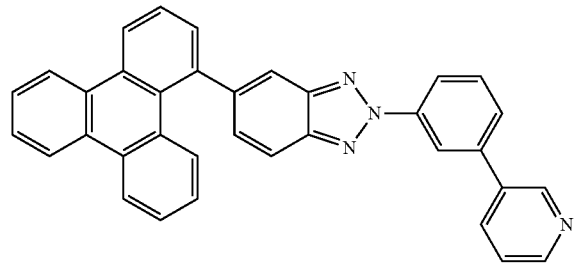
[Chemical Formula 671]
(9-178)
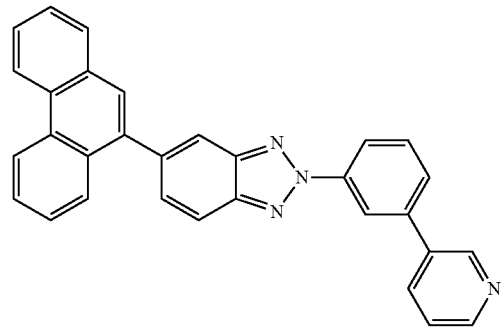
[Chemical Formula 672]
(9-179)
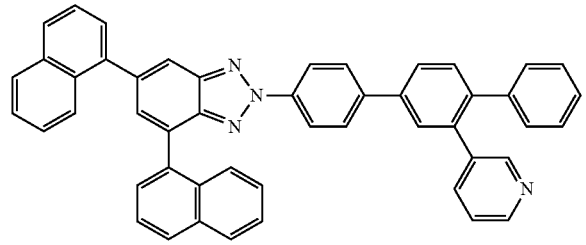
[Chemical Formula 673]
(9-180)
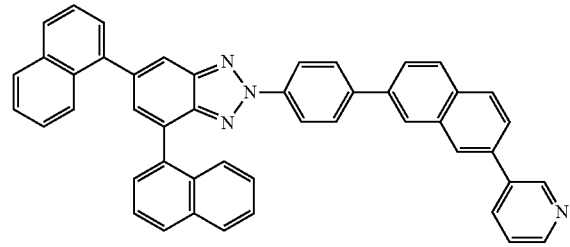

[Chemical Formula 674]

(9-181)

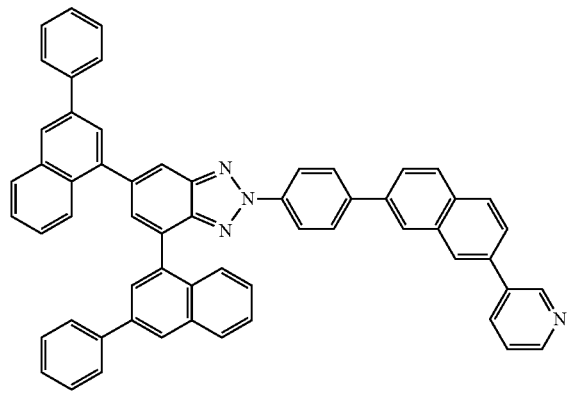

[Chemical Formula 675]

(9-182)

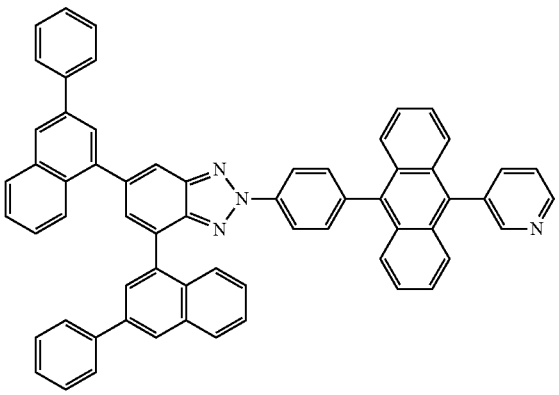

[Chemical Formula 676]

(9-183)

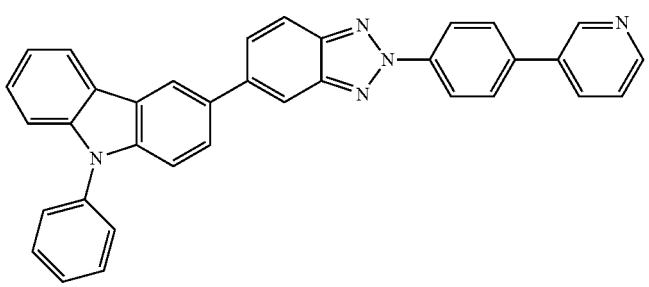

The compounds having a benzotriazole ring structure described above can be synthesized by a known method (refer to PTL 13, for example).

The arylamine compounds of the general formula (5) were purified by methods such as column chromatography, adsorption using, for example, a silica gel, activated carbon, or activated clay, recrystallization or crystallization using a solvent, and a sublimation purification method. The compounds were identified by an NMR analysis. A melting point, a glass transition point (Tg), and a work function were measured as material property values. The melting point can be used as an index of vapor deposition, the glass transition point (Tg) as an index of stability in a thin-film state, and the work function as an index of hole transportability and hole blocking performance.

Other compounds used for the organic EL device of the present invention were purified by methods such as column chromatography, adsorption using, for example, a silica gel, activated carbon, or activated clay, and recrystallization or crystallization using a solvent, and finally purified by sublimation.

The melting point and the glass transition point (Tg) were measured by a high-sensitive differential scanning calorimeter (DSC3100SA produced by Bruker AXS) using powder.

For the measurement of the work function, a 100 nm-thick thin film was fabricated on an ITO substrate, and an ionization potential measuring device (PYS-202 produced by Sumitomo Heavy Industries, Ltd.) was used.

The organic EL device of the present invention may have a structure including an anode, a hole injection layer, a first hole transport layer, a second hole transport layer, a light emitting layer, an electron transport layer, an electron injection layer, and a cathode successively formed on a substrate, optionally with an electron blocking layer between the second hole transport layer and the light emitting layer, and a hole blocking layer between the light emitting layer and the electron transport layer. Some of the organic layers in the multilayer structure may be omitted, or may serve more than one function. For example, a single organic layer may serve as the electron injection layer and the electron transport layer. Further, the organic layers having a same function may have a laminate structure of two or more layers, for example, the light emitting layers may have a laminate structure of two or more layers, or the electron transport layers may have a laminate structure of two or more layers.

Electrode materials with high work functions such as ITO and gold are used as the anode of the organic EL device of the present invention.

As the hole injection layer of the organic EL device of the present invention, a material obtained by p-doping an arylamine compound represented by the above general formula (1) with an electron acceptor is preferably used.

As hole-injecting and transporting materials which can be mixed with or used simultaneously with the arylamine compound represented by the above general formula (1), materials such as starburst-type triphenylamine derivatives and various triphenylamine tetramers; porphyrin compounds as represented by copper phthalocyanine; accepting heterocyclic compounds such as hexacyano azatriphenylene and coating-type polymer materials; and the like can be used. These materials may be formed into a thin film by a vapor deposition method or other known methods such as a spin coating method and an inkjet method.

As the first hole transport layer of the organic EL device of the present invention, a hole transport arylamine compound may be used, in addition to the arylamine compound of the general formula (3) and the arylamine compound of the general formula (4). Further, a coating type polymer material, such as poly(3,4-ethylenedioxythiophene) (PEDOT)/poly(styrenesulfonate) (PSS), a polymer compound having a structure of a benzidine derivative such as TPD as a partial structure thereof, and the like may be used.

As the first hole transport layer of the organic EL device of the present invention, a hole transport arylamine compound is preferably used, and the arylamine compound of the general formula (3) or the arylamine compound of the general formula (4) is more preferably used. The compounds that are not subjected to p-type doping are particularly preferably used.

These may be individually deposited for film forming, but may be used as a single layer deposited mixed with other materials, or may be formed as a laminate of individually deposited layers, a laminate of mixedly deposited layers, or a laminate of an individually deposited layer and a mixedly deposited layer. These materials may be formed into a thin film by a vapor deposition method or other known methods such as a spin coating method and an inkjet method.

As the second hole transport layer of the organic EL device of the present invention, a hole transport arylamine compound may be used, in addition to the arylamine compound of the general formula (5). Further, a coating type polymer material, such as poly(3,4-ethylenedioxythiophene) (PEDOT)/poly(styrenesulfonate) (PSS), a polymer compound having a structure of a benzidine derivative such as TPD as a partial structure thereof, and the like may be used.

As the second hole transport layer of the organic EL device of the present invention, a hole transport arylamine compound is preferably used, and the arylamine compound of the general formula (5) is more preferably used. The compounds that are not subjected to p-type doping are particularly preferably used.

These may be individually deposited for film forming, but may be used as a single layer deposited mixed with other materials, or may be formed as a laminate of individually deposited layers, a laminate of mixedly deposited layers, or a laminate of an individually deposited layer and a mixedly deposited layer. These materials may be formed into a thin film by a vapor deposition method or other known methods such as a spin coating method and an inkjet method.

As the electron blocking layer of the organic EL device of the present invention, the arylamine compound of the general formula (5) is preferably used, and in addition, compounds having an electron blocking effect can be used, for example, a hole transport arylamine compound, such as the arylamine compound of the general formula (3) and the arylamine compound of the general formula (4); carbazole derivatives such as 4,4',4"-tri(N-carbazolyl)triphenylamine (TCTA), 9,9-bis[4-(carbazol-9-yl)phenyl]fluorene, 1,3-bis(carbazol-9-yl)benzene (mCP), and 2,2-bis(4-carbazol-9-yl-phenyl)adamantane (Ad-Cz); and compounds having a triphenylsilyl group and a triarylamine structure, as represented by 9-[4-(carbazol-9-yl)phenyl]-9-[4-(triphenylsilyl)phenyl]-9H-fluorene. These may be individually deposited for film forming, but may be used as a single layer deposited mixed with other materials, or may be formed as a laminate of individually deposited layers, a laminate of mixedly deposited layers, or a laminate of an individually deposited layer and a mixedly deposited layer. These materials may be formed into a thin film by a vapor deposition method or other known methods such as a spin coating method and an inkjet method.

In the organic EL device of the present invention, it is preferable that the electron acceptor in the layer on the side of the light emitting layer with respect to the hole injection layer, particularly the layer adjacent to the light emitting layer (for example, the second hole transport layer and the electron blocking layer) is not subjected to p-type doping.

In the layer adjacent to the light emitting layer, an arylamine compound having a high electron blocking performance is preferably used, and the arylamine compound of the general formula (5) and the like are preferably used.

The thicknesses of these layers are not particularly limited, as far as the thicknesses are ordinarily used, and may be, for example, 20 to 100 nm for the first hole transport layer, 5 to 100 nm for the second hole transport layer, and 5 to 30 nm for the electron blocking layer, and in the case of the device containing a red light emitting dopant as a material of the light emitting layer, the thickness is preferably 30 to 100 nm for the first hole transport layer, 30 to 100 nm for the second hole transport layer, and 5 to 30 nm for the electron blocking layer.

As the material used for the light emitting layer of the organic EL device of the present invention, various metal complexes, anthracene derivatives, bis(styryl)benzene derivatives, pyrene derivatives, oxazole derivatives, and polyparaphenylene vinylene derivatives, may be used in addition to quinolinol derivative metal complexes such as $Alq_3$. Further, the light emitting layer may be made of a host material and a dopant material. Examples of the host material can be preferably anthracene derivatives. Other examples of the host material include quinoxaline derivatives, isoquinoline derivatives, triazine derivatives, benzimidazole derivatives, polydialkyl fluorene derivatives, and aluminum complexes, in addition to the above light-emitting materials. Examples of the dopant material include quinacridone, coumarin, rubrene, and derivatives of these compounds, and also include benzopyran derivatives, indenophenanthrene derivatives, rhodamine derivatives, and aminostyryl derivatives. These may be individually deposited for film forming, but may be used as a single layer deposited mixed with other materials, or may be formed as a laminate of individually deposited layers, a laminate of mixedly deposited layers, or a laminate of an individually deposited layer and a mixedly deposited layer.

Further, the light-emitting material may preferably be a phosphorescent material. As the phosphorescent material, an iridium complex can be preferably used, and in addition, metal complexes of metals such as platinum may be used. Examples of the phosphorescent materials preferably include red phosphorescent materials, such as bis(3-methyl-2-phenylquinoline) iridium(III) acetylacetonate (Ir(3'-Mepq)$_2$(acac)), Ir(piq)$_3$, and Btp$_2$Ir(acac), and also include green phosphorescent materials, such as Ir(ppy)$_3$, and blue phosphorescent materials, such as FIrpic and FIr6. As the host material in this case, quinazoline derivatives may be preferably used, and in addition, a heterocyclic compound having an indole ring as a partial structure of the condensed ring, a heterocyclic compound having a carbazole ring as a partial structure of the condensed ring, and the like may be used. As the hole injecting and transporting host material, carbazole derivatives, such as 4,4'-di(N-carbazolyl)biphenyl (CBP), TCTA, and mCP may be used. As the electron transporting host material, p-bis(triphenylsilyl)benzene (UGH2) and 2,2',2"-(1,3,5-phenylene)-tris(1-phenyl-1H-benzimidazole) (TPBI), and the like may be used. In this way, a high-performance organic EL device can be produced.

In order to avoid concentration quenching, the doping of the host material with the phosphorescent light-emitting material should preferably be made by co-evaporation in a range of 1 to 30 weight percent with respect to the whole light emitting layer.

Further, examples of the light-emitting material should preferably be delayed fluorescent-emitting material such as a CDCB derivative of PIC-TRZ, CC2TA, PXZ-TRZ, 4CzIPN or the like (refer to NPL 3, for example).

These materials may be formed into a thin film by a vapor deposition method or other known methods such as a spin coating method and an inkjet method.

The hole blocking layer of the organic EL device of the present invention may be formed by using hole blocking compounds such as various rare earth complexes, triazole derivatives, triazine derivatives, and oxadiazole derivatives, in addition to phenanthroline derivatives such as bathocuproin (BCP), and the metal complexes of quinolinol derivatives such as aluminum(III) bis(2-methyl-8-quinolinate)-4-phenylphenolate (BAlq). These materials may also serve as the material of the electron transport layer. These may be individually deposited for film forming, may be used as a single layer deposited mixed with other materials, or may be formed as a laminate of individually deposited layers, a laminate of mixedly deposited layers, or a laminate of the individually deposited layer and the mixedly deposited layer. These materials may be formed into a thin-film by using a vapor deposition method or other known methods such as a spin coating method and an inkjet method.

The material used for the electron transport layer of the organic EL device of the present invention can be preferably the compounds of the general formula (6) having an anthracene ring structure, the compounds of the general formula (7) having a pyrimidine ring structure, and the compounds of the general formula (9) having a benzotriazole ring structure. Other examples of the material can be metal complexes of quinolinol derivatives such as Alq$_3$ and BAlq, various metal complexes, triazole derivatives, triazine derivatives, oxadiazole derivatives, pyridine derivatives, pyrimidine derivatives, benzimidazole derivatives, thiadiazole derivatives, anthracene derivatives, carbodiimide derivatives, quinoxaline derivatives, pyridoindole derivatives, phenanthroline derivatives, and silole derivatives. These may be individually deposited for film forming, may be used as a single layer deposited mixed with other materials, or may be formed as a laminate of individually deposited layers, a laminate of mixedly deposited layers, or a laminate of the individually deposited layer and the mixedly deposited layer. These materials may be formed into a thin film by a vapor deposition method or other known methods such as a spin coating method and an inkjet method.

Examples of material used for the electron injection layer of the organic EL device of the present invention can be alkali metal salts such as lithium fluoride and cesium fluoride; alkaline earth metal salts such as magnesium fluoride; and metal oxides such as aluminum oxide. However, the electron injection layer may be omitted in the preferred selection of the electron transport layer and the cathode.

The cathode of the organic EL device of the present invention may be made of an electrode material with a low work function such as aluminum, or an alloy of an electrode material with an even lower work function such as a magnesium-silver alloy, a magnesium-indium alloy, or an aluminum-magnesium alloy.

The following describes an embodiment of the present invention in more detail based on Examples. The present invention, however, is not restricted to the following Examples.

Example 1

Synthesis of bis(biphenyl-4-yl)-(6-phenylbiphenyl-3-yl)amine (Compound 5-2)

Bis(biphenyl-4-yl)-(6-bromobiphenyl-3-yl)amine (11.8 g), toluene (94 mL), phenylboronic acid (2.7 g), and an aqueous solution obtained by previously dissolving potassium carbonate (5.9 g) in water (36 mL) were added into a nitrogen-substituted reaction vessel and aerated with nitrogen gas under ultrasonic irradiation for 30 minutes. Tetrakistriphenylphosphine palladium (0.74 g) was added thereto, and the resulting mixture was heated and stirred at 72° C. for 18 hours. After the mixture was cooled to a room temperature, an organic layer was collected by liquid separation. The organic layer was washed with water, and washed with a saturated salt solution sequentially, and then dried over anhydrous magnesium sulfate and concentrated to obtain a crude product. Subsequently, the crude product was purified using column chromatography, whereby a white powder of bis(biphenyl-4-yl)-(6-phenylbiphenyl-3-yl)amine (Compound 5-2, 8.4 g, yield: 72%) was obtained.

[Chemical Formula 677]

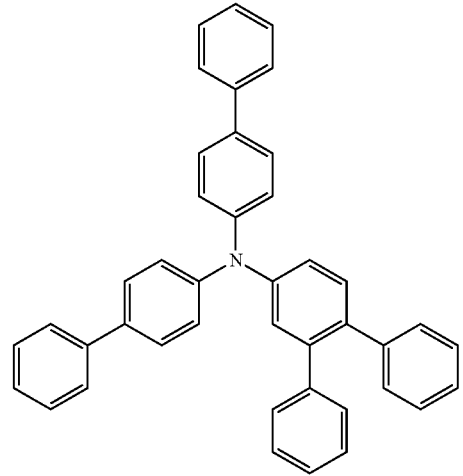

(5-2)

The structure of the obtained white powder was identified by NMR.

$^1$H-NMR (CDCl$_3$) detected 31 hydrogen signals, as follows.

δ (ppm)=7.56-7.68 (7H), 7.45-7.52 (4H) 7.14-7.41 (20H)

Example 2

Synthesis of bis(biphenyl-4-yl)-{6-(naphthyl-1-yl)biphenyl-3-yl}amine (Compound 5-3)

The reaction was carried out under the same conditions as those of Example 1, except that phenylboronic acid was replaced with 1-naphthylboronic acid, whereby a white powder of bis(biphenyl-4-yl)-{6-(naphthyl-1-yl)biphenyl-3-yl}amine (Compound 5-3, 9.2 g, yield: 61%) was obtained.

[Chemical Formula 678]

(5-3)

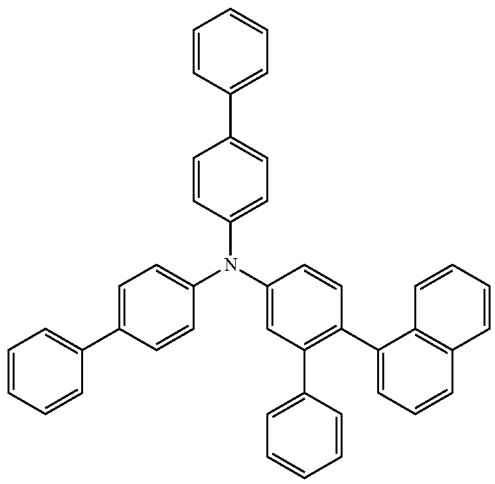

The structure of the obtained white powder was identified by NMR.

¹H-NMR (CDCl₃) detected 33 hydrogen signals, as follows.

δ (ppm)=7.84-7.87 (3H), 7.67-83 (6H), 7.26-7.64 (18H) 7.02-7.04 (6H)

Example 3

Synthesis of bis(biphenyl-4-yl)-{6-(9,9-dimethyl-fluoren-2-yl)biphenyl-3-yl}amine (Compound 5-1)

The reaction was carried out under the same conditions as those of Example 1, except that phenylboronic acid was replaced with (9,9-dimethylfluoren-2-yl)boronic acid, whereby a white powder of bis(biphenyl-4-yl)-{6-(9,9-dimethylfluoren-2-yl)biphenyl-3-yl}amine (Compound 5-1, 9.0 g, yield: 57%) was obtained.

[Chemical Formula 679]

(5-1)

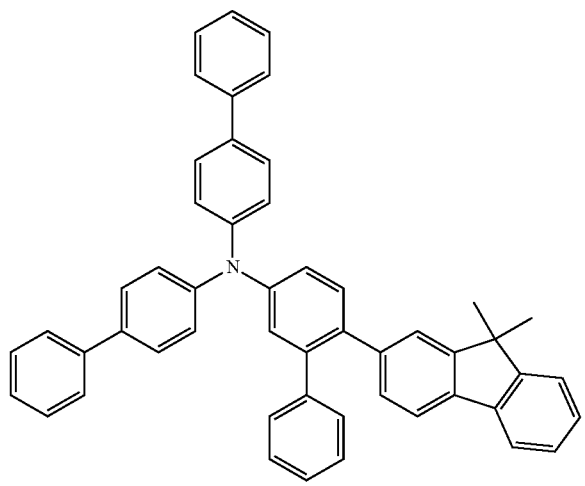

The structure of the obtained white powder was identified by NMR.

¹H-NMR (CDCl₃) detected 39 hydrogen signals, as follows.

δ (ppm)=7.56-7.64 (10H), 7.26-50 (18H), 7.02-7.16 (5H), 1.26 (6H)

Example 4

Synthesis of bis(biphenyl-4-yl)-{6-(biphenyl-4-yl)biphenyl-3-yl}amine (Compound 5-4)

The reaction was carried out under the same conditions as those of Example 1, except that phenylboronic acid was replaced with 4-biphenylboronic acid, whereby a white powder of bis(biphenyl-4-yl)-{6-(biphenyl-4-yl)biphenyl-3-yl}amine (Compound 5-4, 8.6 g, yield: 64%) was obtained.

[Chemical Formula 680]

(5-4)

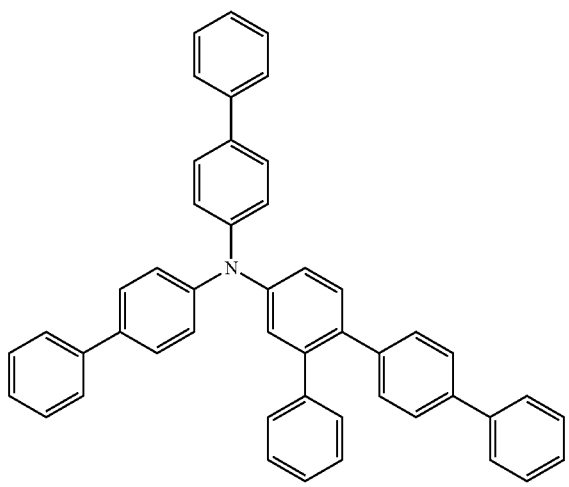

The structure of the obtained white powder was identified by NMR.

¹H-NMR (CDCl₃) detected 35 hydrogen signals, as follows.

δ (ppm)=7.66-7.53 (8H), 7.51-7.15 (27H)

Example 5

Synthesis of bis(biphenyl-4-yl)-{6-(1,1'; 4',1''-terphenyl-4-yl)biphenyl-3-yl}amine (Compound 5-9)

The reaction was carried out under the same conditions as those of Example 1, except that phenylboronic acid was replaced with 4-bromo-1,1'; 4',1''-terphenyl, and bis(biphenyl-4-yl)-(6-bromobiphenyl-3-yl)amine was replaced with bis(biphenyl-4-yl)-{3-phenyl-4-(4,4,5,5-tetramethyl-1,3,2-dioxaborolan-2-yl)phenyl}amine, whereby a white powder of bis(biphenyl-4-yl)-{6-(1,1'; 4',1''-terphenyl-4-yl)biphenyl-3-yl}amine (Compound 5-9, 4.5 g, yield: 40%) was obtained.

[Chemical Formula 681]

(5-9)

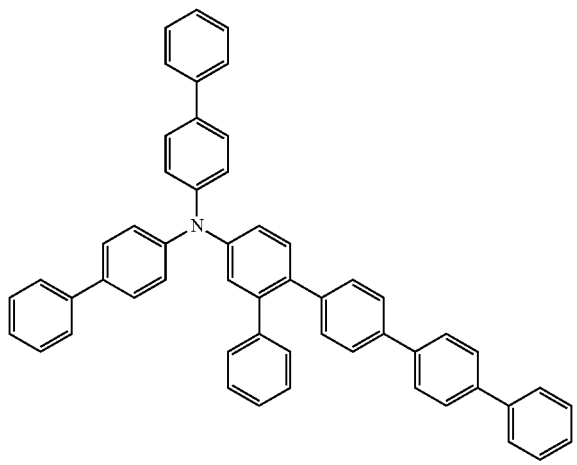

The structure of the obtained white powder was identified by NMR.

¹H-NMR (THF-d$_8$) detected 39 hydrogen signals, as follows.

δ (ppm)=7.73-7.58 (15H), 7.46-7.12 (24H)

Example 6

Synthesis of bis(biphenyl-4-yl)-[6-{4-(naphthalen-1-yl)phenyl)}biphenyl-3-yl]amine (Compound 5-16)

The reaction was carried out under the same conditions as those of Example 1, except that phenylboronic acid was replaced with 4-(naphthalen-1-yl)phenylboronic acid, whereby a white powder of bis(biphenyl-4-yl)-[6-{4-(naphthalen-1-yl)phenyl)}biphenyl-3-yl]amine (Compound 5-16, 11.6 g, yield: 77%) was obtained.

[Chemical Formula 682]

(5-16)

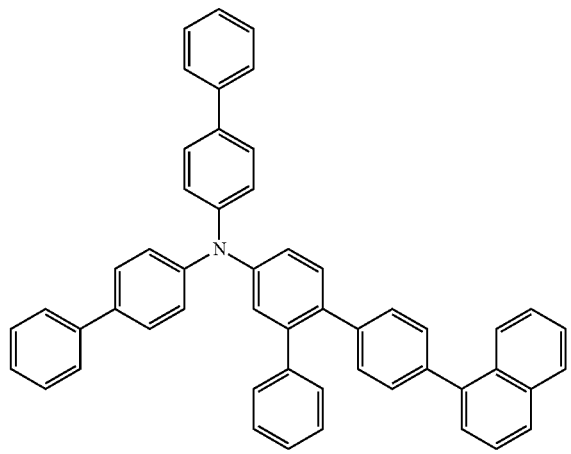

The structure of the obtained white powder was identified by NMR.

¹H-NMR (CDCl$_3$) detected 37 hydrogen signals, as follows.

δ (ppm)=7.95-7.84 (3H), 7.67-7.18 (34H)

Example 7

Synthesis of bis(biphenyl-4-yl)-[6-(9,9-dimethylfluoren-2-yl)phenyl)}biphenyl-3-yl]amine (Compound 5-20)

The reaction was carried out under the same conditions as those of Example 1, except that phenylboronic acid was replaced with 4-(9,9-dimethylfluoren-2-yl)phenylboronic acid, whereby a white powder of bis(biphenyl-4-yl)-[6-(9,9-dimethylfluoren-2-yl)phenyl)}biphenyl-3-yl]amine (Compound 5-20, 13.1 g, yield: 81%) was obtained.

[Chemical Formula 683]

(5-20)

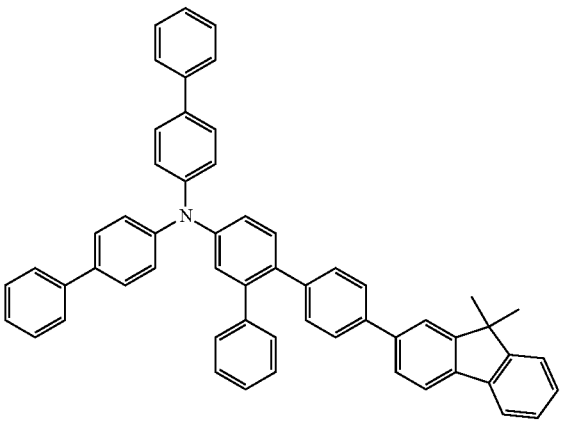

The structure of the obtained white powder was identified by NMR.

¹H-NMR (CDCl$_3$) detected 43 hydrogen signals, as follows.

δ (ppm)=7.78 (2H), 7.68-7.15 (35H), 1.55 (6H)

Example 8

Synthesis of (biphenyl-4-yl)-{6-(biphenyl-4-yl)biphenyl-3-yl}-(9,9-dimethylfluoren-2-yl)amine (Compound 5-56)

The reaction was carried out under the same conditions as those of Example 1, except that phenylboronic acid was replaced with 4-biphenylboronic acid, and bis(biphenyl-4-yl)-(6-bromobiphenyl-3-yl)amine was replaced with (biphenyl-4-yl)-(9,9-dimethylfluoren-2-yl)-(6-bromobiphenyl-3-yl)amine, whereby a white powder of (biphenyl-4-yl)-{6-(biphenyl-4-yl)biphenyl-3-yl}-(9,9-dimethylfluoren-2-yl)amine (Compound 5-56, 17.8 g, yield: 89%) was obtained.

[Chemical Formula 684]

(5-56)

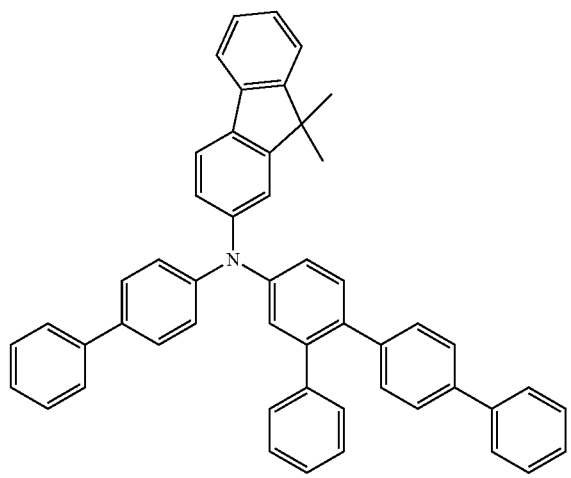

The structure of the obtained white powder was identified by NMR.
¹H-NMR (CDCl₃) detected 39 hydrogen signals, as follows.
δ (ppm)=7.72-7.57 (7H), 7.52-7.33 (9H), 7.32-7.19 (17H), 1.45 (6H)

Example 9

Synthesis of bis(9,9-dimethylfluoren-2-yl)-(6-phenylbiphenyl-3-yl)amine (Compound 5-62)

The reaction was carried out under the same conditions as those of Example 1, except that bis(biphenyl-4-yl)-(6-bromobiphenyl-3-yl)amine was replaced with bis(9,9-dimethylfluoren-2-yl)-(6-bromobiphenyl-3-yl)amine, whereby a white powder of bis(9,9-dimethylfluoren-2-yl)-(6-phenylbiphenyl-3-yl)amine (Compound 5-62, 11.5 g, yield: 57%) was obtained.

[Chemical Formula 685]

(5-62)

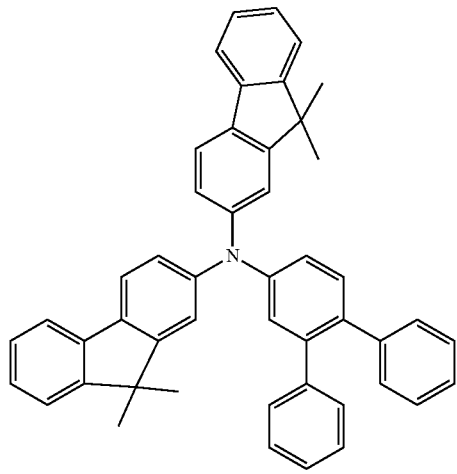

The structure of the obtained white powder was identified by NMR.
¹H-NMR (THF-d₈) detected 39 hydrogen signals, as follows.
δ (ppm)=7.70-7.63 (3H), 7.44-7.02 (24H), 1.46 (12H)

Example 10

Synthesis of bis(6-phenylbiphenyl-3-yl)-(biphenyl-4-yl)amine (Compound 5-108)

The reaction was carried out under the same conditions as those of Example 1, except that bis(biphenyl-4-yl)-(6-bromobiphenyl-3-yl)amine was replaced with bis(6-bromobiphenyl-3-yl)-(biphenyl-4-yl)amine, whereby a white powder of bis(6-phenylbiphenyl-3-yl)-(biphenyl-4-yl)amine (Compound 5-108, 10.2 g, yield: 73%) was obtained.

[Chemical Formula 686]

(5-108)

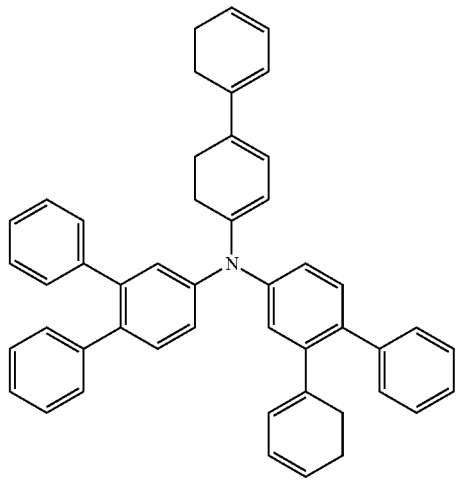

The structure of the obtained white powder was identified by NMR.
¹H-NMR (CDCl₃) detected 35 hydrogen signals, as follows.
δ (ppm)=7.57-7.66 (4H), 7.10-7.49 (31H)

Example 11

Synthesis of tris(6-phenylbiphenyl-3-yl)amine (Compound 5-143)

The reaction was carried out under the same conditions as those of Example 1, except that bis(biphenyl-4-yl)-(6-bromobiphenyl-3-yl)amine was replaced with tris(6-bromobiphenyl-3-yl)amine, whereby a white powder of tris(6-phenylbiphenyl-3-yl)amine (Compound 5-143, 11.1 g, yield: 75%) was obtained.

[Chemical Formula 687]

(5-143)

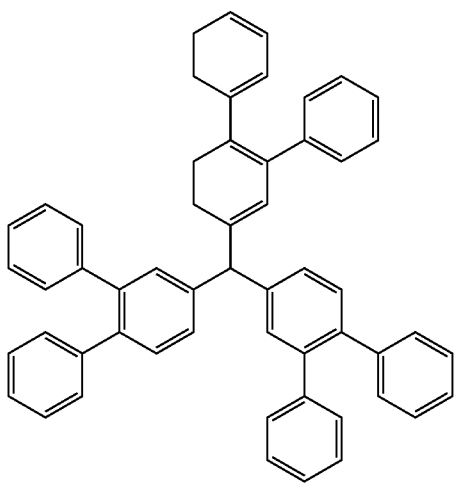

The structure of the obtained white powder was identified by NMR.

¹H-NMR (CDCl₃) detected 39 hydrogen signals, as follows.

δ (ppm)=7.35-7.42 (6H), 7.15-7.35 (33H)

Example 12

The melting points and the glass transition points of the arylamine compounds of the general formula (5) were measured using a high-sensitive differential scanning calorimeter (DSC3100SA produced by Bruker AXS).

|  | Melting point | Glass transition point |
|---|---|---|
| Compound of Example 2 | 242° C. | 103° C. |
| Compound of Example 3 | No melting point observed | 115° C. |
| Compound of Example 4 | No melting point observed | 104° C. |
| Compound of Example 5 | No melting point observed | 117° C. |
| Compound of Example 6 | No melting point observed | 107° C. |
| Compound of Example 7 | 240° C. | 127° C. |
| Compound of Example 8 | No melting point observed | 116° C. |
| Compound of Example 9 | No melting point observed | 119° C. |
| Compound of Example 10 | No melting point observed | 101° C. |
| Compound of Example 11 | No melting point observed | 112° C. |

The arylamine compounds of the general formula (1) have glass transition points of 100° C. or higher, demonstrating that the compounds have a stable thin-film state.

Example 13

A 100 nm-thick vapor-deposited film was fabricated on an ITO substrate using the arylamine compounds of the general formula (5), and a work function was measured using an ionization potential measuring device (PYS-202 produced by Sumitomo Heavy Industries, Ltd.).

|  | Work function |
|---|---|
| Compound of Example 1 | 5.68 eV |
| Compound of Example 2 | 5.72 eV |
| Compound of Example 3 | 5.66 eV |
| Compound of Example 4 | 5.67 eV |
| Compound of Example 5 | 5.70 eV |
| Compound of Example 6 | 5.71 eV |
| Compound of Example 7 | 5.66 eV |
| Compound of Example 8 | 5.62 eV |
| Compound of Example 9 | 5.55 eV |
| Compound of Example 10 | 5.72 eV |
| Compound of Example 11 | 5.75 eV |

As the results show, the arylamine compounds of the general formula (5) have desirable energy levels compared to the work function 5.4 eV of common hole transport materials such as NPD and TPD, and thus possess desirable hole transportability.

Example 14

The LUMO levels of the compound of the general formula (6) having an anthracene ring structure, the compound of the general formula (7) having a pyrimidine ring structure, and the compound of the general formula (9) having a benzotriazole ring structure were calculated. The LUMO level was calculated by obtaining the difference in bandgap estimated from the work function of the thin film measured with an ionization potential measuring device and the absorption spectrum of the thin film measured with an ultraviolet-visible absorption spectrum measuring device.

|  | LUMO level |
|---|---|
| Compound (6b-1) | 3.26 eV |
| Compound (6c-28) | 3.10 eV |
| Compound (7-126) | 3.26 eV |
| Compound (9-112) | 3.15 eV |

It is understood that the compound of the general formula (6) having an anthracene ring structure, the compound of the general formula (7) having a pyrimidine ring structure, and the compound of the general formula (9) having a benzotriazole ring structure have favorable energy levels, as compared to a LUMO level of 2.70 eV of the known electron transport materials, such as TPBi, and thus have a favorable electron injection performance and a favorable electron transport performance.

Example 15

The organic EL device, as shown in FIG. 1, was fabricated by vapor-depositing a hole injection layer 3, a first hole transport layer 4, a second hole transport layer 5, a light emitting layer 6, an electron transport layer 7, an electron injection layer 8, and a cathode (aluminum electrode) 9 in this order on a glass substrate 1 on which an ITO electrode was formed as a transparent anode 2 beforehand.

Specifically, the glass substrate 1 having ITO having a film thickness of 150 nm formed thereon was subjected to ultrasonic washing in isopropyl alcohol for 20 minutes and then dried for 10 minutes on a hot plate heated to 200° C. Thereafter, after performing a UV ozone treatment for 15 minutes, the glass substrate with ITO was installed in a vacuum vapor deposition apparatus, and the pressure was reduced to 0.001 Pa or lower. Subsequently, as the hole injection layer 3 covering the transparent anode 2, an electron acceptor (Acceptor-1) of the structural formula below and Compound (1-1) of the structural formula below were formed in a film thickness of 5 nm by dual vapor deposition at a vapor deposition rate that satisfies a vapor deposition rate ratio of Acceptor-1/Compound (1-1)=3/97. As the first hole transport layer 4 on the hole injection layer 3, Compound (1-1) of the structural formula below was formed in a film thickness of 60 nm. As the second hole transport layer 5 on the first hole transport layer 4, Compound (5-62) of Example 9 was formed in a film thickness of 60 nm. As the light emitting layer 6 on the second hole transport layer 5, Compound EMD-1 of the structural formula below and Compound EMH-1 of the structural formula below (refer to KR-A-2015-042385 and JP-A-2014-513064, for example) were formed in a film thickness of 20 nm by dual vapor deposition at a vapor deposition rate that satisfies a vapor deposition rate ratio of EMD-1/EMH-1=3/97. As the electron transport layer 7 on the light emitting layer 6, Compound (6b-1) having an anthracene ring structure of the structural formula below and Compound ETM-1 of the structural formula below were formed in a film thickness of 30 nm by dual vapor deposition at a vapor deposition rate that satisfies a vapor deposition rate ratio of Compound (6b-1)/ETM-1=50/50. As the electron injection layer 8 on the electron transport layer 7, lithium fluoride was formed in a film thickness of 1 nm. Finally, aluminum was vapor-deposited in a thickness of 100 nm to form the cathode 9. The characteristics of the organic EL device were measured in the atmosphere at ordinary temperature. Table 1 summarizes the results of measurement of emission characteristics when applying a DC voltage to the fabricated organic EL device.

[Chemical Formula 688]

(Acceptor-1)

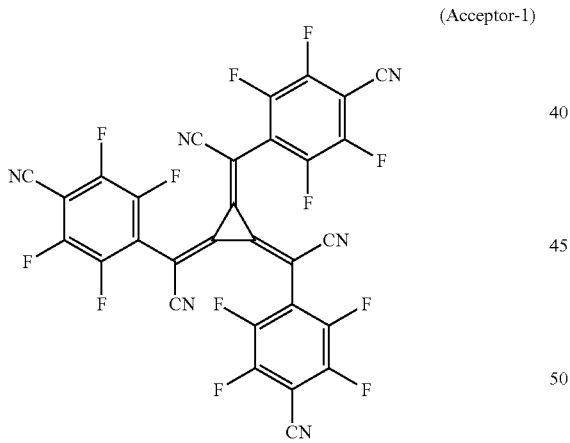

[Chemical Formula 689]

(1-1)

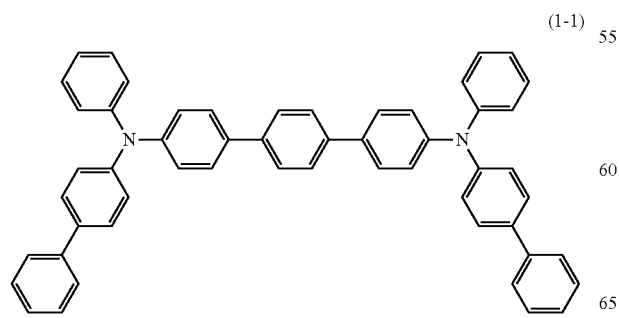

[Chemical Formula 690]

(5-62)

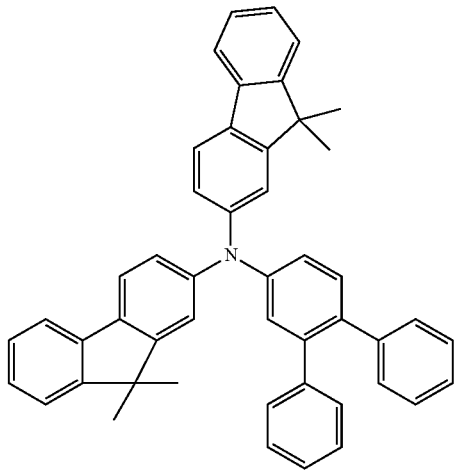

[Chemical Formula 691]

(EMD-1)

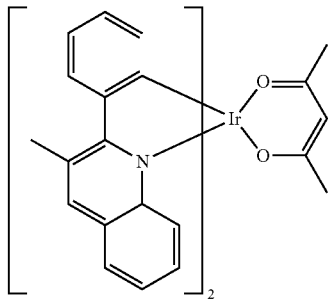

[Chemical Formula 692]

(EMH-1)

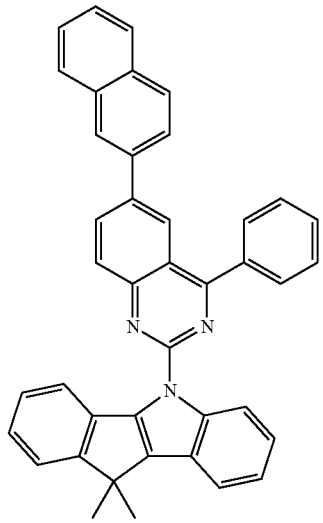

[Chemical Formula 693]

(6b-1)

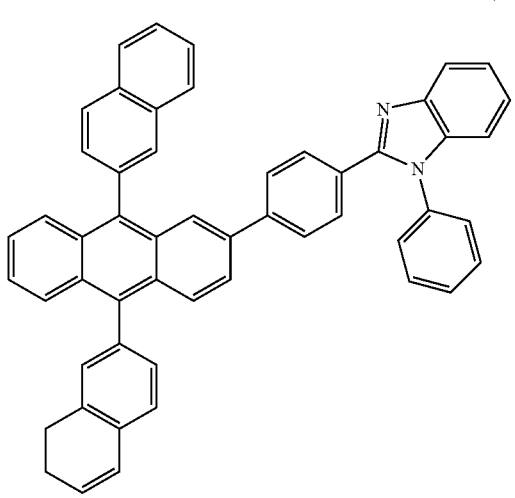

[Chemical Formula 694]

(ETM-1)

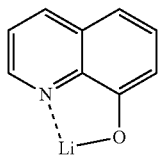

Example 16

An organic EL device was fabricated under the same conditions as those of Example 15, except that the compound (6b-1) having an anthracene ring structure was replaced with the compound (6c-28) having an anthracene ring structure as the material of the electron transport layer 7, and the layer was formed in a film thickness of 30 nm by dual vapor deposition of the compound (6c-28) and the compound ETM-1 of the above structural formula at a vapor deposition rate ratio of the compound (6c-28):ETM-1=50:50. The characteristics of the organic EL device thus fabricated were measured in the atmosphere at an ordinary temperature. Table 1 summarizes the results of measurement of emission characteristics when applying a DC voltage to the fabricated organic EL device.

[Chemical Formula 695]

(6c-28)

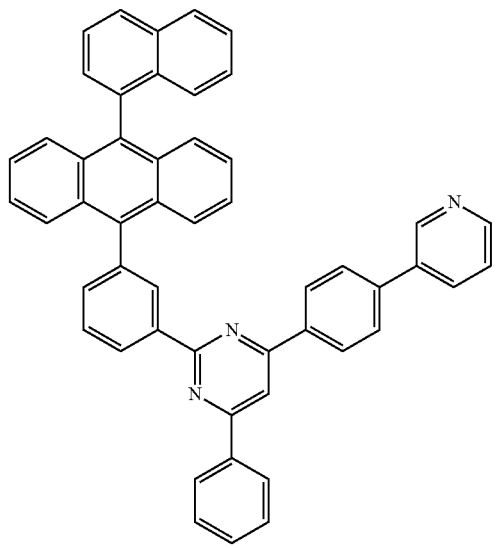

Example 17

An organic EL device was fabricated under the same conditions as those of Example 15, except that the compound (6b-1) having an anthracene ring structure was replaced with the compound (7-126) having a pyrimidine ring structure as the material of the electron transport layer 7, and the layer was formed in a film thickness of 30 nm by dual vapor deposition of the compound (7-126) and the compound ETM-1 of the above structural formula at a vapor deposition rate ratio of the compound (7-126):ETM-1=50:50. The characteristics of the organic EL device thus fabricated were measured in the atmosphere at an ordinary temperature. Table 1 summarizes the results of measurement of emission characteristics when applying a DC voltage to the fabricated organic EL device.

[Chemical Formula 696]

(7-126)

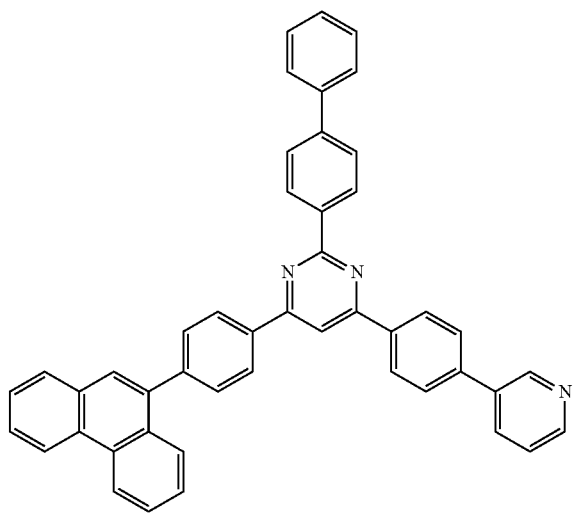

Example 18

An organic EL device was fabricated under the same conditions as those of Example 15, except that the compound (6b-1) having an anthracene ring structure was replaced with the compound (9-112) having a benzotriazole ring structure as the material of the electron transport layer 7, and the layer was formed in a film thickness of 30 nm by dual vapor deposition of the compound (9-112) and the compound ETM-1 of the above structural formula at a vapor deposition rate that satisfies a vapor deposition rate ratio of the compound (9-112):ETM-1=50:50. The characteristics of the organic EL device were measured in the atmosphere at ordinary temperature. Table 1 summarizes the results of measurement of emission characteristics when applying a DC voltage to the fabricated organic EL device.

[Chemical Formula 697]

(9-112)

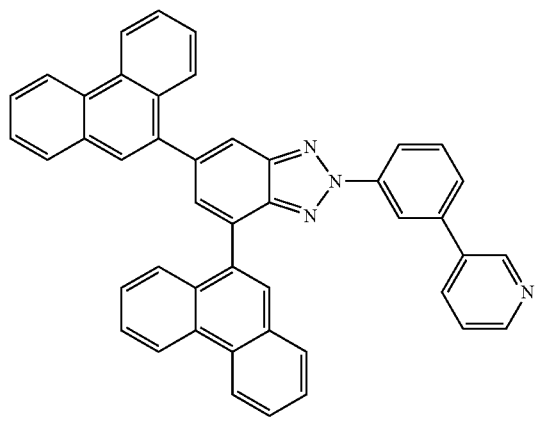

Example 19

An organic EL device was fabricated under the same conditions as those of Example 15, except that the compound (5-62) of Example 9 was replaced with the compound (5-56) of Example 8 as the material of the second hole transport layer 5, and the layer was formed in a film thickness of 60 nm. The characteristics of the organic EL device were measured in the atmosphere at ordinary temperature. Table summarizes the results of measurement of emission characteristics when applying a DC voltage to the fabricated organic EL device.

[Chemical Formula 698]

(5-56)

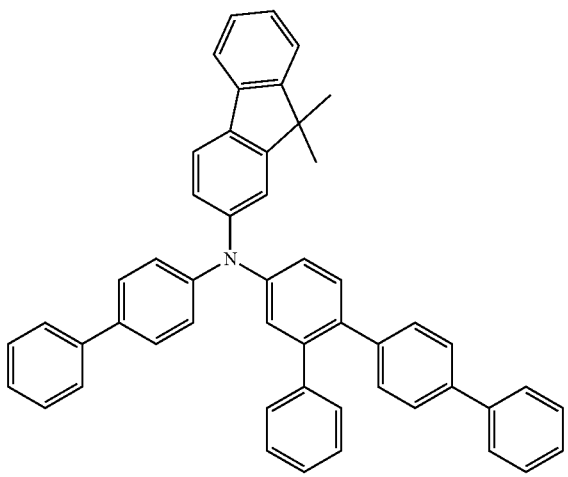

Example 20

An organic EL device was fabricated under the same conditions as those of Example 19, except that the compound (6b-1) having an anthracene ring structure was replaced with the compound (6c-28) having an anthracene ring structure as the material of the electron transport layer 7, and the layer was formed in a film thickness of 30 nm by dual vapor deposition of the compound (6c-28) and the compound ETM-1 of the above structural formula at a vapor deposition rate that satisfies a vapor deposition rate ratio of the compound (6c-28):ETM-1=50:50. The characteristics of the organic EL device were measured in the atmosphere at ordinary temperature. Table 1 summarizes the results of measurement of emission characteristics when applying a DC voltage to the fabricated organic EL device.

Example 21

An organic EL device was fabricated under the same conditions as those of Example 19, except that the compound (6b-1) having an anthracene ring structure was replaced with the compound (7-126) having a pyrimidine ring structure as the material of the electron transport layer 7, and the layer was formed in a film thickness of 30 nm by dual vapor deposition of the compound (7-126) and the compound ETM-1 of the above structural formula at a vapor deposition rate that satisfies a vapor deposition rate ratio of the compound (7-126):ETM-1=50:50. The characteristics of the organic EL device were measured in the atmosphere at ordinary temperature. Table 1 summarizes the results of measurement of emission characteristics when applying a DC voltage to the fabricated organic EL device.

Example 22

An organic EL device was fabricated under the same conditions as those of Example 19, except that the compound (6b-1) having an anthracene ring structure was replaced with the compound (9-112) having a benzotriazole ring structure as the material of the electron transport layer 7, and the layer was formed in a film thickness of 30 nm by dual vapor deposition of the compound (9-112) and the compound ETM-1 of the above structural formula at a vapor deposition rate that satisfies a vapor deposition rate ratio of the compound (9-112):ETM-1=50:50. The characteristics of the organic EL device were measured in the atmosphere at ordinary temperature. Table 1 summarizes the results of measurement of emission characteristics when applying a DC voltage to the fabricated organic EL device.

Comparative Example 1

For comparison, an organic EL device was fabricated under the same conditions as those of Example 15, except that the compound (5-62) of Example 9 was replaced with the compound (1-1) of the above structural formula as the material of the second hole transport layer 5, and the layer was formed in a film thickness of 60 nm. The characteristics of the organic EL device were measured in the atmosphere at ordinary temperature. Table 1 summarizes the results of measurement of emission characteristics when applying a DC voltage to the fabricated organic EL device.

Comparative Example 2

For comparison, an organic EL device was fabricated under the same conditions as those of Example 16, except that the compound (5-62) of Example 9 was replaced with the compound (1-1) of the above structural formula as the material of the second hole transport layer 5, and the layer was formed in a film thickness of 60 nm. The characteristics of the organic EL device were measured in the atmosphere at ordinary temperature. Table 1 summarizes the results of measurement of emission characteristics when applying a DC voltage to the fabricated organic EL device.

Comparative Example 3

For comparison, an organic EL device was fabricated under the same conditions as those of Example 17, except that the compound (5-62) of Example 9 was replaced with the compound (1-1) of the above structural formula as the material of the second hole transport layer 5, and the layer was formed in a film thickness of 60 nm. The characteristics of the organic EL device were measured in the atmosphere at ordinary temperature. Table 1 summarizes the results of measurement of emission characteristics when applying a DC voltage to the fabricated organic EL device.

Comparative Example 4

For comparison, an organic EL device was fabricated under the same conditions as those of Example 18, except that the compound (5-62) of Example 9 was replaced with the compound (1-1) of the above structural formula as the material of the second hole transport layer 5, and the layer was formed in a film thickness of 60 nm. The characteristics of the organic EL device were measured in the atmosphere at ordinary temperature. Table 1 summarizes the results of measurement of emission characteristics when applying a DC voltage to the fabricated organic EL device.

Table 1 summarizes the results of measurement of a device lifetime using the organic EL devices fabricated in Examples 15 to 22 and Comparative Examples 1 to 4. The device lifetime was measured as a time elapsed until the emission luminance of 7,000 cd/m$^2$ (initial luminance) at the start of emission was attenuated to 6,790 cd/m$^2$ (corresponding to 97% when taking the initial luminance as 100%: Attenuation to 97%) when carrying out constant current driving.

TABLE 1

| | Hole injection layer | First hole transport layer | Second hole transport layer | Light emitting layer | Electron transport layer | Voltage [V] (@ 10 mA/cm2) |
|---|---|---|---|---|---|---|
| Example 15 | Compound 1-1/ Acceptor-1 | Compound 1-1 | Compound 5-62 | EMD-1/ EMH-1 | Compound 6b-1/ ETM-1 | 3.80 |
| Example 16 | Compound 1-1/ Acceptor-1 | Compound 1-1 | Compound 5-62 | EMD-1/ EMH-1 | Compound 6c-28/ ETM-1 | 3.57 |
| Example 17 | Compound 1-1/ Acceptor-1 | Compound 1-1 | Compound 5-62 | EMD-1/ EMH-1 | Compound 7-126/ ETM-1 | 3.83 |
| Example 18 | Compound 1-1/ Acceptor-1 | Compound 1-1 | Compound 5-62 | EMD-1/ EMH-1 | Compound 9-112/ ETM-1 | 3.67 |
| Example 19 | Compound 1-1/ Acceptor-1 | Compound 1-1 | Compound 5-56 | EMD-1/ EMH-1 | Compound 6b-1/ ETM-1 | 3.97 |
| Example 20 | Compound 1-1/ Acceptor-1 | Compound 1-1 | Compound 5-56 | EMD-1/ EMH-1 | Compound 6c-28/ ETM-1 | 3.67 |
| Example 21 | Compound 1-1/ Acceptor-1 | Compound 1-1 | Compound 5-56 | EMD-1/ EMH-1 | Compound 7-126/ ETM-1 | 3.94 |
| Example 22 | Compound 1-1/ Acceptor-1 | Compound 1-1 | Compound 5-56 | EMD-1/ EMH-1 | Compound 9-112/ ETM-1 | 3.80 |
| Comparative Example 1 | Compound 1-1/ Acceptor-1 | Compound 1-1 | Compound 1-1 | EMD-1/ EMH-1 | Compound 6b-1/ ETM-1 | 3.99 |
| Comparative Example 2 | Compound 1-1/ Acceptor-1 | Compound 1-1 | Compound 1-1 | EMD-1/ EMH-1 | Compound 6c-28/ ETM-1 | 3.67 |
| Comparative Example 3 | Compound 1-1/ Acceptor-1 | Compound 1-1 | Compound 1-1 | EMD-1/ EMH-1 | Compound 7-126/ ETM-1 | 3.95 |
| Comparative Example 4 | Compound 1-1/ Acceptor-1 | Compound 1-1 | Compound 1-1 | EMD-1/ EMH-1 | Compound 9-112/ ETM-1 | 3.72 |

| | Luminance [cd/m2] (@ 10 mA/cm2) | Luminous efficiency [cd/A] (@ 10 mA/cm2) | Power efficiency [lm/W] (@ 10 mA/cm2) | Lifetime of device, attenuation to 0.97% |
|---|---|---|---|---|
| Example 15 | 2679 | 26.82 | 22.18 | 546 hours |
| Example 16 | 2787 | 27.90 | 24.55 | 275 hours |
| Example 17 | 2620 | 26.25 | 21.53 | 510 hours |

TABLE 1-continued

| | | | | |
|---|---|---|---|---|
| Example 18 | 2686 | 26.90 | 23.03 | 505 hours |
| Example 19 | 2804 | 28.06 | 22.21 | 600 hours |
| Example 20 | 2861 | 28.63 | 24.51 | 350 hours |
| Example 21 | 2871 | 28.73 | 22.91 | 613 hours |
| Example 22 | 2812 | 28.15 | 23.27 | 590 hours |
| Comparative Example 1 | 2195 | 22.00 | 17.32 | 204 hours |
| Comparative Example 2 | 2393 | 24.06 | 20.60 | 62 hours |
| Comparative Example 3 | 2286 | 22.90 | 18.22 | 165 hours |
| Comparative Example 4 | 2356 | 23.61 | 19.94 | 175 hours |

As shown in Table 1, it was understood as follows in the comparison of Example 15, Example 19, and Comparative Example 1 having the same combination of materials of the electron transport layer. The luminous efficiency upon passing an electric current with a current density of 10 mA/cm$^2$ was 22.00 cd/A for the organic EL device of Comparative Example 1, whereas high efficiencies of 26.82 and 28.06 cd/A were obtained for the organic EL devices of Example 15 and Example 19. The power efficiency was 17.32 lm/W for the organic EL device of Comparative Example 1, whereas high efficiencies of 22.18 and 22.21 lm/W were obtained for the organic EL devices of Example 15 and Example 19. The lifetime of device (attenuation to 97%) was 204 hours for the organic EL device of Comparative Example 1, whereas was 546 and 600 hours were obtained for the organic EL devices of Example 15 and Example 19, which indicates largely increased lifetimes.

As shown in Table 1, it was understood as follows in the comparison of Example 16, Example 20, and Comparative Example 2 having the same combination of materials of the electron transport layer. The luminous efficiency upon passing an electric current with a current density of 10 mA/cm$^2$ was 24.06 cd/A for the organic EL device of Comparative Example 2, whereas high efficiencies of 27.90 and 28.63 cd/A were obtained for the organic EL devices of Example 16 and Example 20. The power efficiency was 20.60 lm/W for the organic EL device of Comparative Example 2, whereas high efficiencies of 24.55 and 24.51 lm/W were obtained for the organic EL devices of Example 16 and Example 20. The lifetime of device (attenuation to 97%) was 62 hours for the organic EL device of Comparative Example 2, whereas 275 and 350 hours were obtained for the organic EL devices of Example 16 and Example 20, which indicates largely increased lifetimes.

As shown in Table 1, it was understood as follows in the comparison of Example 17, Example 21, and Comparative Example 3 having the same combination of materials of the electron transport layer. The luminous efficiency upon passing an electric current with a current density of 10 mA/cm$^2$ was 22.90 cd/A for the organic EL device of Comparative Example 3, whereas high efficiencies of 26.25 and 28.73 cd/A were obtained for the organic EL devices of Example 17 and Example 21. The power efficiency was 18.22 lm/W for the organic EL device of Comparative Example 3, whereas high efficiencies of 21.53 and 22.91 lm/W were obtained for the organic EL devices of Example 17 and Example 21. The lifetime of device (attenuation to 97%) was 165 hours for the organic EL device of Comparative Example 3, whereas 510 and 613 hours were obtained for the organic EL devices of Example 17 and Example 21, which indicates largely increased lifetimes.

As shown in Table 1, it was understood as follows in the comparison of Example 18, Example 22, and Comparative Example 4 having the same combination of materials of the electron transport layer. The luminous efficiency upon passing an electric current with a current density of 10 mA/cm$^2$ was 23.61 cd/A for the organic EL device of Comparative Example 4, whereas high efficiencies of 26.90 and 28.15 cd/A were obtained for the organic EL devices of Example 18 and Example 22. The power efficiency was 19.94 lm/W for the organic EL device of Comparative Example 4, whereas high efficiencies of 23.03 and 23.27 lm/W were obtained for the organic EL devices of Example 18 and Example 22. The lifetime of device (attenuation to 97%) was 175 hours for the organic EL device of Comparative Example 4, whereas was 505 and 590 hours were obtained for the organic EL devices of Example 18 and Example 22, which indicates largely increased lifetimes.

It has been found that in the organic EL devices of the present invention, for injecting and transporting holes efficiently from the anode, the particular arylamine compound (having the particular structure) doped with an electron acceptor is used as the material of the hole injection layer, the hole transport layer is formed of two layers including the first hole transport layer and the second hole transport layer, the particular arylamine compounds (having the particular structures) that are not doped with an electron acceptor are combined for the materials of the two layers, and furthermore the compound having an anthracene ring structure having the particular structure, the compound having a pyrimidine ring structure having the particular structure, or the compound having a benzotriazole ring structure having the particular structure is used as the material of the electron transport layer, thereby improving the carrier balance in the organic EL device, and consequently, it is possible to achieve an organic EL device having a higher luminous efficiency and a longer lifetime than the conventional organic EL devices.

INDUSTRIAL APPLICABILITY

The organic EL device of the present invention using the particular arylamine compound (having the particular structure) doped with an electron acceptor as the material of the hole injection layer, and having the combination of the particular arylamine compound (having the particular structure) with the compound having an anthracene ring structure having the particular structure, the compound having a pyrimidine ring structure having the particular structure, or the compound having a benzotriazole ring structure having the particular structure has an improved luminous efficiency and an improved durability of the organic EL device, and can be applied, for example, to home electric appliances and illuminations.

REFERENCE SIGNS LIST

1 Glass substrate
2 Transparent anode
3 Hole injection layer
4 First hole transport layer
5 Second hole transport layer
6 Light emitting layer
7 Electron transport layer
8 Electron injection layer
9 Cathode

The invention claimed is:

1. An organic electroluminescent device comprising at least an anode, a hole injection layer, a first hole transport layer, a second hole transport layer, a light emitting layer, an electron transport layer, and a cathode in this order, wherein the hole injection layer comprises an arylamine compound of the following general formula (1) and an electron acceptor:

[Chemical Formula 1]

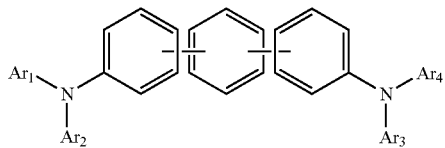

(1)

wherein $Ar_1$ to $Ar_4$ may be the same or different, and represent a substituted or unsubstituted aromatic hydrocarbon group, a substituted or unsubstituted aromatic heterocyclic group, or a substituted or unsubstituted condensed polycyclic aromatic group.

2. The organic electroluminescent device according to claim 1, wherein the electron acceptor is an electron acceptor selected from trisbromophenylaminehexachloroantimony, tetracyanoquinodimethane (TCNQ), 2,3,5,6-tetrafluoro-tetracyano-1,4-benzoquinodimethane (F4TCNQ), and a radialene derivative.

3. The organic electroluminescent device according to claim 1, wherein the electron acceptor is a radialene derivative of the following general formula (2):

[Chemical Formula 2]

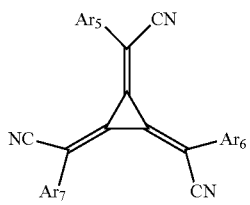

(2)

wherein $Ar_5$ to $Ar_7$ may be the same or different, and represent an aromatic hydrocarbon group, an aromatic heterocyclic group, or a condensed polycyclic aromatic group, having an electron acceptor group as a substituent.

4. The organic electroluminescent device according to claim 1, wherein the first hole transport layer or the second hole transport layer comprises only a hole transporting arylamine compound.

5. The organic electroluminescent device according to claim 1, wherein the first hole transport layer and the second hole transport layer comprise only a hole transporting arylamine compound.

6. The organic electroluminescent device according to claim 4, wherein the first hole transport layer contains an arylamine compound having a structure in which two to six triphenylamine structures are joined within a molecule via a single bond or a divalent group that does not contain a heteroatom.

7. The organic electroluminescent device according to claim 6, wherein the arylamine compound having a structure in which two to six triphenylamine structures are joined within a molecule via a single bond or a divalent group that does not contain a heteroatom is an arylamine compound of the following general formula (3):

[Chemical Formula 3]

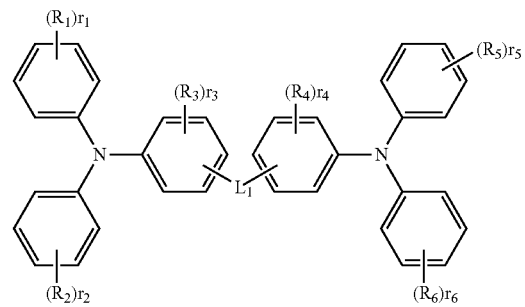

(3)

wherein $R_1$ to $R_6$ represent a deuterium atom, a fluorine atom, a chlorine atom, cyano, nitro, linear or branched alkyl of 1 to 6 carbon atoms that may have a substituent, cycloalkyl of 5 to 10 carbon atoms that may have a substituent, linear or branched alkenyl of 2 to 6 carbon atoms that may have a substituent, linear or branched alkyloxy of 1 to 6 carbon atoms that may have a substituent, cycloalkyloxy of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, or substituted or unsubstituted aryloxy; $r_1$ to $r_6$ may be the same or different, $r_1$, $r_2$, $r_5$, and $r_6$ representing an integer of 0 to 5, and $r_3$ and $r_4$ representing an integer of 0 to 4, where when $r_1$, $r_2$, $r_5$, and $r_6$ are an integer of 2 to 5, or when $r_3$ and $r_4$ are an integer of 2 to 4, $R_1$ to $R_6$, a plurality of which bind to the same benzene ring, may be the same or different and may bind to each other via a single bond, substituted or unsubstituted methylene, an oxygen atom, or a sulfur atom to form a ring; and $L_1$ represents a divalent linking group or a single bond.

8. The organic electroluminescent device according to claim 6, wherein the arylamine compound having a structure in which two to six triphenylamine structures are joined within a molecule via a single bond or a divalent group that does not contain a heteroatom is an arylamine compound of the following general formula (4):

[Chemical Formula 4]

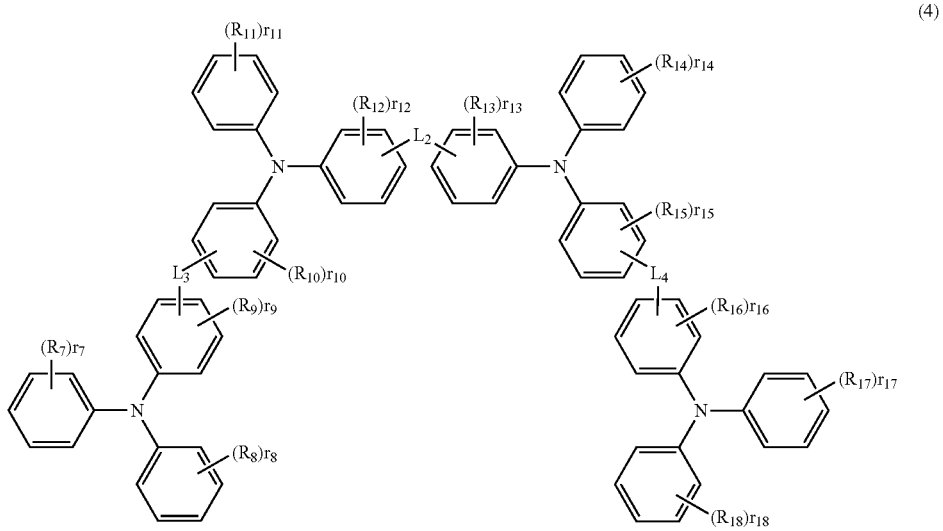

(4)

wherein $R_7$ to $R_{18}$ represent a deuterium atom, a fluorine atom, a chlorine atom, cyano, nitro, linear or branched alkyl of 1 to 6 carbon atoms that may have a substituent, cycloalkyl of 5 to 10 carbon atoms that may have a substituent, linear or branched alkenyl of 2 to 6 carbon atoms that may have a substituent, linear or branched alkyloxy of 1 to 6 carbon atoms that may have a substituent, cycloalkyloxy of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, or substituted or unsubstituted aryloxy; $r_7$ to $r_{18}$ may be the same or different, $r_7$, $r_8$, $r_{11}$, $r_{14}$, $r_{17}$, and $r_{18}$ representing an integer of 0 to 5, and $r_9$, $r_{10}$, $r_{12}$, $r_{13}$, $r_{15}$, and $r_{16}$ representing an integer of 0 to 4, where when $r_7$, $r_8$, $r_{11}$, $r_{14}$, $r_{17}$, and $r_{18}$ are an integer of 2 to 5, or when $r_9$, $r_{10}$, $r_{12}$, $r_{13}$, $r_{15}$, and $r_{16}$ are an integer of 2 to 4, $R_7$ to $R_{18}$, a plurality of which bind to the same benzene ring, may be the same or different and may bind to each other via a single bond, substituted or unsubstituted methylene, an oxygen atom, or a sulfur atom to form a ring; and $L_2$, $L_3$, and $L_4$ may be the same or different, and represent a divalent linking group or a single bond.

9. The organic electroluminescent device according to claim 4, wherein the second hole transport layer comprises an arylamine compound of the general formula (5):

[Chemical Formula 5]

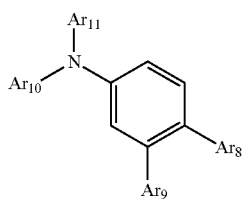

(5)

wherein $Ar_8$ to $Ar_{11}$ may be the same or different, and represent a substituted or unsubstituted aromatic hydrocarbon group, a substituted or unsubstituted aromatic heterocyclic group, or a substituted or unsubstituted condensed polycyclic aromatic group.

10. The organic electroluminescent device according to claim 1, wherein the electron transport layer comprises a compound having a LUMO level of 2.9 to 3.4 eV.

11. The organic electroluminescent device according to claim 1, wherein the electron transport layer comprises a compound having an anthracene ring structure of the following general formula (6):

[Chemical Formula 6]

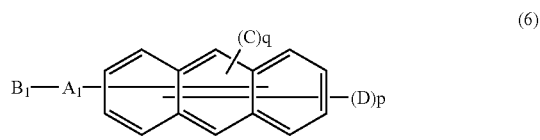

(6)

wherein $A_1$ represents a divalent group of a substituted or unsubstituted aromatic hydrocarbon, a divalent group of a substituted or unsubstituted aromatic heterocyclic ring, a divalent group of a substituted or unsubstituted condensed polycyclic aromatic, or a single bond; $B_1$ represents a substituted or unsubstituted aromatic heterocyclic group; C represents a substituted or unsubstituted aromatic hydrocarbon group, a substituted or unsubstituted aromatic heterocyclic group, or a substituted or unsubstituted condensed polycyclic aromatic group; D may be the same or different, and represents a hydrogen atom, a deuterium atom, a fluorine atom, a chlorine atom, a cyano group, a trifluoromethyl group, a linear or branched alkyl group of 1 to 6 carbon atoms, a substituted or unsubstituted aromatic hydrocarbon group, a substituted or unsubstituted aromatic heterocyclic group, or a substituted or unsubstituted condensed polycyclic aromatic group; and while p and q maintain a relationship that the sum of p and q is 9, p represents 7 or 8, and q represents 1 or 2.

12. The organic electroluminescent device according to claim 1, wherein the electron transport layer comprises a compound having a pyrimidine ring structure of the following general formula (7):

[Chemical Formula 7]

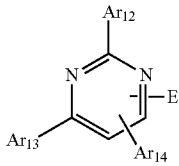

(7)

wherein $Ar_{12}$ represents a substituted or unsubstituted aromatic hydrocarbon group or a substituted or unsubstituted condensed polycyclic aromatic group; $Ar_{13}$ and $Ar_{14}$ may be the same or different, and represent a hydrogen atom, a substituted or unsubstituted aromatic hydrocarbon group, or a substituted or unsubstituted condensed polycyclic aromatic group; and E represents a monovalent group of the following structural formula (8), provided that $Ar_{13}$ and $Ar_{14}$ are not simultaneously a hydrogen atom:

[Chemical Formula 8]

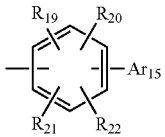

(8)

wherein $Ar_{15}$ represents a substituted or unsubstituted aromatic heterocyclic group; $R_{19}$ to $R_{22}$ may be the same or different, and represent a hydrogen atom, a deuterium atom, a fluorine atom, a chlorine atom, a cyano group, a trifluoromethyl group, a linear or branched alkyl group of 1 to 6 carbon atoms, a substituted or unsubstituted aromatic hydrocarbon group, a substituted or unsubstituted aromatic heterocyclic group, or a substituted or unsubstituted condensed polycyclic aromatic group.

13. The organic electroluminescent device according to claim 1, wherein the electron transport layer comprises a compound having a benzotriazole ring structure of the following general formula (9):

[Chemical Formula 9]

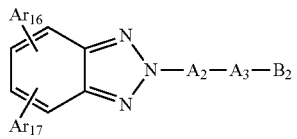

(9)

wherein $Ar_{16}$ represents a substituted or unsubstituted aromatic hydrocarbon group, a substituted or unsubstituted aromatic heterocyclic group, or a substituted or unsubstituted condensed polycyclic aromatic group; $Ar_{17}$ represents a hydrogen atom, a deuterium atom, a substituted or unsubstituted aromatic hydrocarbon group, a substituted or unsubstituted aromatic heterocyclic group, or a substituted or unsubstituted condensed polycyclic aromatic group; $A_2$ represents a divalent group of a substituted or unsubstituted aromatic hydrocarbon, a divalent group of a substituted or unsubstituted aromatic heterocyclic ring, a divalent group of a substituted or unsubstituted condensed polycyclic aromatic, or a single bond; $A_3$ represents a divalent group of a substituted or unsubstituted condensed polycyclic aromatic or a single bond; and $B_2$ represents a substituted or unsubstituted aromatic heterocyclic group.

14. The organic electroluminescent device according to claim 1, wherein the light emitting layer contains a phosphorescent light-emitting material.

15. The organic electroluminescent device according to claim 14, wherein the phosphorescent light-emitting material is a metal complex that contains iridium or platinum.

16. The organic electroluminescent device according to claim 14, wherein the phosphorescent light-emitting material is a red light emitting dopant.

17. The organic electroluminescent device according to claim 1, wherein the light emitting layer contains a quinazoline derivative.

18. The organic electroluminescent device according to claim 17, wherein the light emitting layer contains a host material, which is a quinazoline derivative.

19. The organic electroluminescent device according to claim 2, wherein the first hole transport layer or the second hole transport layer comprises only a hole transporting arylamine compound.

20. The organic electroluminescent device according to claim 2, wherein the first hole transport layer and the second hole transport layer comprise only a hole transporting arylamine compound.

* * * * *